US009579373B2

(12) United States Patent
Jordan et al.

(10) Patent No.: US 9,579,373 B2
(45) Date of Patent: Feb. 28, 2017

(54) PORCINE REPRODUCTIVE AND RESPIRATORY SYNDROME VIRUS, COMPOSITIONS, VACCINE AND METHODS OF USE

(71) Applicants: Dianna M. Murphy Jordan, Ames, IA (US); Brian Thomas Martinson, Duncombe, IA (US); Michael B. Roof, Ames, IA (US); Eric Martin Vaughn, Ames, IA (US); Joseph Gilbert Victoria, Ames, IA (US)

(72) Inventors: Dianna M. Murphy Jordan, Ames, IA (US); Brian Thomas Martinson, Duncombe, IA (US); Michael B. Roof, Ames, IA (US); Eric Martin Vaughn, Ames, IA (US); Joseph Gilbert Victoria, Ames, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 0 days.

(21) Appl. No.: 14/206,283

(22) Filed: Mar. 12, 2014

(65) Prior Publication Data
US 2014/0271698 A1 Sep. 18, 2014

Related U.S. Application Data

(60) Provisional application No. 61/791,504, filed on Mar. 15, 2013.

(51) Int. Cl.
| *A61K 39/12* | (2006.01) |
| *C07K 14/005* | (2006.01) |
| *C07K 16/10* | (2006.01) |
| *C12N 7/00* | (2006.01) |
| *A61K 39/00* | (2006.01) |

(52) U.S. Cl.
CPC ............ *A61K 39/12* (2013.01); *C07K 14/005* (2013.01); *C07K 16/10* (2013.01); *C12N 7/00* (2013.01); *A61K 2039/5252* (2013.01); *A61K 2039/5254* (2013.01); *A61K 2039/552* (2013.01); *C12N 2770/10021* (2013.01); *C12N 2770/10022* (2013.01); *C12N 2770/10034* (2013.01); *C12N 2770/10064* (2013.01)

(58) Field of Classification Search
None
See application file for complete search history.

(56) References Cited

U.S. PATENT DOCUMENTS

| 3,080,291 | A | 3/1963 | Sinha et al. |
| 3,137,631 | A | 6/1964 | Soloway |
| 3,959,457 | A | 5/1976 | Speaker et al. |
| 4,015,100 | A | 3/1977 | Gnanamuthu et al. |
| 4,122,167 | A | 10/1978 | Buynak et al. |
| 4,205,060 | A | 5/1980 | Monsimer et al. |
| 4,224,412 | A | 9/1980 | Dorofeev et al. |
| 4,452,747 | A | 6/1984 | Gersonde et al. |
| 4,468,346 | A | 8/1984 | Paul et al. |
| 4,554,159 | A | 11/1985 | Roizman et al. |
| 4,606,940 | A | 8/1986 | Frank et al. |
| 4,636,485 | A | 1/1987 | van der Smissen |
| 4,744,933 | A | 5/1988 | Rha et al. |
| 4,753,884 | A | 6/1988 | Kit et al. |
| 4,810,493 | A | 3/1989 | Patrick et al. |
| 4,921,706 | A | 5/1990 | Roberts et al. |
| 4,927,637 | A | 5/1990 | Morano et al. |
| 4,944,948 | A | 7/1990 | Uster et al. |
| 5,008,050 | A | 4/1991 | Cullis et al. |
| 5,009,956 | A | 4/1991 | Baumann |
| 5,132,117 | A | 7/1992 | Speaker et al. |
| 5,206,163 | A | 4/1993 | Renard et al. |
| 5,213,759 | A | 5/1993 | Castberg et al. |
| 5,419,907 | A | 5/1995 | Paul et al. |
| 5,476,778 | A | 12/1995 | Chladek et al. |
| 5,510,258 | A | 4/1996 | Sanderson et al. |
| 5,587,164 | A | 12/1996 | Sanderson et al. |
| 5,597,721 | A | 1/1997 | Brun et al. |
| 5,620,691 | A | 4/1997 | Wensvoort et al. |
| 5,674,500 | A | 10/1997 | Peeters et al. |
| 5,677,429 | A | 10/1997 | Benfield |
| 5,683,865 | A | 11/1997 | Collins et al. |

(Continued)

FOREIGN PATENT DOCUMENTS

| CA | 2103460 A1 | 12/1992 |
| DE | 145705 A1 | 1/1981 |

(Continued)

OTHER PUBLICATIONS

Meulenberg et al., "Infectious Transcripts from Cloned Genome-Length cDNA of Porcine Reproductive and Respiratory Syndrome Virus". Journal of Virology, vol. 72, No. 1, Jan. 1998, pp. 380-387.
Meulenberg et al., "Lelystad Virus, the Causative Agent of Porcine Epidemic Abortion and Respiratory Syndrome (PEARS), is Related to LDV and EAV". Virology, vol. 192, 1993, pp. 62-72.
Meulenberg et al., "Localization and Fine Mapping of Antigenic Sites on the Nucleocapsid Protein N of Porcine Reproductive and Respiratory Syndrome Virus with Monoclonal Antibodies". Virology, vol. 252, 1998, pp. 106-114.
Meulenberg et al., "Molecular characterization of Lelystad virus". Veterinary Microbiology, vol. 55, 1997, pp. 197-202.
Meulenberg et al., "Nucleocapsid Protein N of Lelystad Virus: Expression by Recombinant Baculovirus, Immunological Properties, and Suitability for Detection of Serum Antibodies". Clinical and Diagnostic Laboratory Immunology, vol. 2, No. 6, Nov. 1995, pp. 652-656.

(Continued)

Primary Examiner — Benjamin P Blumel
(74) Attorney, Agent, or Firm — Michael P. Morris; Joyce L. Morrison

(57) ABSTRACT

The present invention relates to Porcine Reproductive and Respiratory Syndrome Virus (PRRSV) mutant strains having increased stability; compositions containing the strains or antigens derived therefrom; vaccines containing the strains, including killed, attenuated or subunit vaccines; nucleic acids encoding PRRSV polypeptides, polypeptides encoded by the nucleic acids, including antigenic fragments thereof; antibodies which specifically bind to said polypeptides, and methods making and using thereof.

8 Claims, 27 Drawing Sheets

(56) References Cited

U.S. PATENT DOCUMENTS

| | | |
|---|---|---|
| 5,690,940 A | 11/1997 | Joo |
| 5,695,766 A | 12/1997 | Paul et al. |
| 5,698,203 A | 12/1997 | Visser et al. |
| 5,789,388 A | 8/1998 | Visser et al. |
| 5,840,563 A | 11/1998 | Chladek et al. |
| 5,846,805 A | 12/1998 | Collins et al. |
| 5,858,729 A | 1/1999 | Van Woensel et al. |
| 5,866,401 A | 2/1999 | Hesse |
| 5,888,513 A | 3/1999 | Plana Duran et al. |
| 5,910,310 A | 6/1999 | Heinen et al. |
| 5,925,359 A | 7/1999 | Van Woensel et al. |
| 5,968,525 A | 10/1999 | Fitzgerald et al. |
| 5,976,537 A | 11/1999 | Mengeling et al. |
| 5,989,563 A | 11/1999 | Chladek et al. |
| 5,998,601 A | 12/1999 | Murtaugh et al. |
| 6,001,370 A | 12/1999 | Burch et al. |
| 6,015,663 A | 1/2000 | Wesley et al. |
| 6,042,830 A | 3/2000 | Chladek et al. |
| 6,080,570 A | 6/2000 | Chladek et al. |
| 6,110,467 A | 8/2000 | Paul et al. |
| 6,110,468 A | 8/2000 | Collins et al. |
| 6,149,917 A | 11/2000 | Fanget et al. |
| 6,194,210 B1 | 2/2001 | Leu et al. |
| 6,197,310 B1 | 3/2001 | Wensvoort et al. |
| 6,241,990 B1 | 6/2001 | Collins et al. |
| 6,251,397 B1 | 6/2001 | Paul et al. |
| 6,251,404 B1 | 6/2001 | Paul et al. |
| 6,268,199 B1 | 7/2001 | Meulenberg et al. |
| 6,380,376 B1 | 4/2002 | Paul et al. |
| 6,391,314 B1 | 5/2002 | Allan et al. |
| 6,455,245 B1 | 9/2002 | Wensvoort et al. |
| 6,495,138 B1 | 12/2002 | van Nieuwstadt et al. |
| 6,498,008 B2 | 12/2002 | Collins et al. |
| 6,500,662 B1 | 12/2002 | Calvert et al. |
| 6,592,873 B1 | 7/2003 | Paul et al. |
| 6,641,819 B2 | 11/2003 | Mengeling et al. |
| 6,660,513 B2 | 12/2003 | Mengeling et al. |
| 6,773,908 B1 | 8/2004 | Paul et al. |
| 6,806,086 B2 | 10/2004 | Wensvoort et al. |
| 6,841,364 B2 | 1/2005 | Yuan et al. |
| 6,855,315 B2 | 2/2005 | Collins et al. |
| 6,982,160 B2 | 1/2006 | Collins et al. |
| 7,018,638 B2 | 3/2006 | Chu et al. |
| 7,081,342 B2 | 7/2006 | Mengeling et al. |
| 7,109,025 B1 | 9/2006 | Eloit et al. |
| 7,122,347 B2 | 10/2006 | Verheije et al. |
| 7,132,106 B2 | 11/2006 | Calvert et al. |
| 7,169,394 B2 | 1/2007 | Chu et al. |
| 7,211,379 B2 | 5/2007 | Ellis et al. |
| 7,232,680 B2 | 6/2007 | Calvert et al. |
| 7,264,804 B2 | 9/2007 | Collins et al. |
| 7,273,617 B2 | 9/2007 | Yuan et al. |
| 7,312,030 B2 | 12/2007 | van Rijn et al. |
| 7,335,361 B2 | 2/2008 | Liao et al. |
| 7,335,473 B2 | 2/2008 | Wensvoort et al. |
| 7,368,117 B2 | 5/2008 | Fetzer et al. |
| 7,618,797 B2 | 11/2009 | Calvert et al. |
| 7,632,636 B2 | 12/2009 | Roof et al. |
| 7,691,389 B2 | 4/2010 | Calvert et al. |
| 7,722,878 B2 | 5/2010 | Vaughn et al. |
| 7,897,343 B2 | 3/2011 | Wensvoort et al. |
| 2002/0012670 A1 | 1/2002 | Elbers et al. |
| 2002/0098573 A1 | 7/2002 | Meulenberg et al. |
| 2002/0172690 A1 | 11/2002 | Calvert et al. |
| 2003/0049274 A1 | 3/2003 | Meulenberg et al. |
| 2003/0118608 A1 | 6/2003 | Wensvoort et al. |
| 2003/0157689 A1 | 8/2003 | Calvert et al. |
| 2003/0219732 A1 | 11/2003 | van Rijn et al. |
| 2004/0009190 A1 | 1/2004 | Elbers et al. |
| 2004/0132014 A1 | 7/2004 | Wensvoort et al. |
| 2004/0197872 A1 | 10/2004 | Meulenberg et al. |
| 2004/0213805 A1 | 10/2004 | Verheije |
| 2004/0224327 A1 | 11/2004 | Meulenberg et al. |
| 2004/0253270 A1 | 12/2004 | Meng et al. |
| 2006/0063151 A1 | 3/2006 | Roof et al. |
| 2006/0205033 A1 | 9/2006 | Meulenberg et al. |
| 2006/0240041 A1 | 10/2006 | Meulenberg et al. |
| 2006/0286123 A1 | 12/2006 | Fetzer et al. |
| 2007/0003570 A1 | 1/2007 | Murtaugh et al. |
| 2007/0042000 A1 | 2/2007 | Mengeling et al. |
| 2009/0148474 A1 | 6/2009 | Roof et al. |
| 2010/0003278 A1 | 1/2010 | Roof et al. |
| 2010/0028860 A1 | 2/2010 | Roof et al. |
| 2010/0129398 A1 | 5/2010 | Klinge et al. |
| 2011/0104201 A1 | 5/2011 | Mengeling et al. |
| 2011/0117129 A1 | 5/2011 | Roof et al. |
| 2011/0195088 A1 | 8/2011 | Roof et al. |
| 2012/0189655 A1 | 7/2012 | Wu et al. |
| 2013/0183329 A1 | 7/2013 | Zhang et al. |

FOREIGN PATENT DOCUMENTS

| | | |
|---|---|---|
| EP | 208672 A1 | 1/1987 |
| EP | 0440219 A1 | 8/1991 |
| EP | 0529584 A2 | 3/1993 |
| EP | 587780 A1 | 3/1994 |
| EP | 0595436 A2 | 5/1994 |
| EP | 0610250 A1 | 8/1994 |
| EP | 676467 A2 | 10/1995 |
| EP | 732340 A2 | 9/1996 |
| EP | 0835929 A1 | 4/1998 |
| EP | 0835930 A1 | 4/1998 |
| EP | 0839912 A1 | 5/1998 |
| EP | 1018557 A2 | 7/2000 |
| FR | 2602791 A1 | 2/1988 |
| GB | 2282811 A | 4/1995 |
| GB | 2289279 A | 11/1995 |
| JP | 62/198626 A | 9/1987 |
| WO | 8803410 A1 | 5/1988 |
| WO | 8908701 A1 | 9/1989 |
| WO | 9221375 A1 | 12/1992 |
| WO | 9303760 A1 | 3/1993 |
| WO | 9306211 A1 | 4/1993 |
| WO | 9307898 A1 | 4/1993 |
| WO | 9314196 A1 | 7/1993 |
| WO | 9418311 A1 | 8/1994 |
| WO | 9528227 A1 | 10/1995 |
| WO | 9531550 A1 | 11/1995 |
| WO | 9604010 A1 | 2/1996 |
| WO | 9606619 A1 | 3/1996 |
| WO | 9636356 A1 | 11/1996 |
| WO | 9640932 A1 | 12/1996 |
| WO | 9700696 A1 | 1/1997 |
| WO | 9731651 A1 | 9/1997 |
| WO | 9731652 A1 | 9/1997 |
| WO | 9818933 A1 | 5/1998 |
| WO | 9835023 A1 | 8/1998 |
| WO | 9850426 A1 | 11/1998 |
| WO | 9855625 A1 | 12/1998 |
| WO | 9855626 A2 | 12/1998 |
| WO | 0053787 A1 | 9/2000 |
| WO | 0065032 A1 | 11/2000 |
| WO | 0159077 A1 | 8/2001 |
| WO | 0190363 A1 | 11/2001 |
| WO | 02060921 A2 | 8/2002 |
| WO | 02095040 A1 | 11/2002 |
| WO | 03062407 A1 | 7/2003 |
| WO | 2006002193 A2 | 1/2006 |
| WO | 2006034319 A2 | 3/2006 |
| WO | 2006074986 A2 | 7/2006 |
| WO | 2007064742 A2 | 6/2007 |
| WO | 2008109237 A2 | 9/2008 |
| WO | 2008121958 A2 | 10/2008 |
| WO | 2010025109 A1 | 3/2010 |
| WO | 2011128415 A1 | 10/2011 |
| WO | 2014150822 A2 | 9/2014 |

OTHER PUBLICATIONS

Meulenberg et al., "Posttranslational Processing and Identification of a Neutralization Domain of the GP4 Protein Encoded by ORF4 of Lelystad Virus". Journal of Virology, vol. 71, No. 8, Aug. 1997, pp. 6061-6067.

(56) References Cited

OTHER PUBLICATIONS

Meulenberg et al., "Subgenomic RNAs of Lelystad virus contain a conserved leader-body junction sequence". Journal of General Virology, vol. 74, 1993, pp. 1697-1701.
Miller et al., "Interferon type I response in porcine reproductive and respiratory syndrome virus-infected MARC-145 cells". Archives of Virology, vol. 149, 2004, pp. 2453-2463.
Morozov et al., "Sequence analysis of open reading frames (ORFs) 2 to 4 of a U.S. isolate of porcine reproductive and respiratory syndrome virus". Archives of Virology, vol. 140, No. 7, 1995, pp. 1313-1319.
Morrison et al., "Brief Communications Serologic evidence incriminating a recently isolated virus (ATCC VR-2332) as the cause of swine infertility and respiratory syndrome (SIRS)". Journal of Veterinary Diagnostic Investigation, vol. 4, No. 2, Apr. 1992, pp. 186-188.
Morrison et al., "Sero-epidemiologic Investigation of Swine Infertility and Respiratory Syndrome (SIRS)". 72st Annual Meeting of the Conference of Research Workers in Animal Disease, Chicago, IL, Nov. 11-12, 1991, p. 55, Abstract No. 309.
Murtaugh et al., "Comparison of the structural protein coding sequences of the VR-2332 and Lelystad virus strains of the PRRS virus". Archives of Virology, vol. 140, No. 8, 1995, pp. 1451-1460.
Murtaugh et al., "Genetic Variation in the PRRS Virus". Coronaviruses and Arteriviruses, Plenum Press, New York, 1998, pp. 787-794.
Murtaugh et al., "Immunological Responses of Swine to Porcine Reproductive and Respiratory Syndrome Virus Infection". Viral Immunology, vol. 15, No. 4, 2002, pp. 533-547.
Murtaugh et al., "Role of Viral Proteases in PRRS Immunity, Project Period Sep. 1, 1997-Dec. 31, 2002, no cost extension Jan. 1, 2003-Jun. 30, 2003". Final Report: Aug. 30, 2003, Department of Veterinary Pathology, University of Minnesota, St. Paul, MN and Boehringer Ingelheim Vetmedica, Inc., Ames, IA, 2003, pp. 1-38.
Murtaugh, "Allen D Lehman Swine Conference: the Evolution of the Swine veterinary profession: The PRRS Virus". University of Minnesota, Veterinary Continuing Education and Extension, vol. 20, 1993, pp. 43-47.
NCBI: Accession No. AF046869. "Porcine reproductive and respiratory syndrome virus isolate 16244B, Feb. 18, 1997 (Nebraska) pass.3, complete genome." Mar. 17, 1999.
NCBI: Accession No. AF066183. "Porcine reproductive and respiratory syndrome virus RespPRRS MLV, complete genome." Feb. 22, 2001.
NCBI: Accession No. AF159149. "Porcine reproductive and respiratory syndrome virus isolate MLV RespPRRS/Repro, complete genome." Aug. 28, 2000.
NCBI: Accession No. AF176348. "Porcine reproductive and respiratory syndrome virus isolate PA8 complete genome." Sep. 3, 2002.
NCBI: Accession No. AF184212. "Porcine reproductive and respiratory syndrome virus strain SP, complete genome." Sep. 28, 2000.
NCBI: Accession No. AF325691. "Porcine reproductive and respiratory syndrome virus isolate NVSL 977985 IA 1-4-2, complete genome." Feb. 11, 2001.
NCBI: Accession No. AF331831. "Porcine reproductive and respiratory syndrome virus BJ-4, complete genome." Jan. 15, 2001.
NCBI: Accession No. M96262. "Lelystad virus, complete genome." Nov. 8, 2000.
NCBI: Accession No. M96262.2. "Lelystad virus, complete genome." Nov. 8, 2000.
NCBI: Accession No. NC_001639. Lactate dehydrogenase-elevating virus, complete genome. Dec. 8, 2008.
NCBI: Accession No. NC_001961. "Porcine reproductive and respiratory syndrome virus, complete genome." Jan. 12, 2004.
NCBI: Accession No. NC_002533. "Lelystad virus, complete genome." Nov. 11, 2000.
NCBI: Accession No. NC_002534. "Lactate dehydrogenase-elevating virus, complete genome." Dec. 29, 2003.
NCBI: Accession No. U15146. "Lactate dehydrogenase-elevating virus Plagemann strain, complete genome." Jan. 26, 1996.
NCBI: Accession No. U87392 AF030244 U00153. "Porcine reproductive and respiratory syndrome virus strain VR-2332, complete genome." Nov. 17, 2000.
Nelsen et al., "Porcine Reproductive and Respiratory Syndrome Virus Comparison: Divergent Evolution on Two Continents". Journal of Virology, vol. 73, No. 1, Jan. 1999, pp. 270-280.
Nelson et al., "Differentiation of U.S. and European Isolates of Porcine Reproductive and Respiratory Syndrome Virus by Monoclonal Antibodies". Journal of Clinical Microbiology, vol. 31, No. 12, Dec. 1993, pp. 3184-3189.
Nelson et al., "High affinity interaction between nucleocapsid protein and leader/intergenic sequence of mouse hepatitis virus RNA". Journal of General Virology, vol. 81, 2000, pp. 181-188.
Nielsen et al., "Generation of an Infectious Clone of VR-2332, a Highly Virulent North American-Type Isolate of Porcine Reproductive and Respiratory Syndrome Virus". Journal of Virology, vol. 77, No. 6, Mar. 2003, pp. 3702-3711.
Nodelijk et al., "A quantitative assessment of the effectiveness of PRRSV vaccination in pigs under experimental conditions". Vaccine, vol. 19, 2000, pp. 3636-3644.
Oleksiewicz et al., "Semen from Boars Infected with Porcine Reproductive and Respiratory Syndrome Virus (PRRSV) Contains Antibodies Against Structural as Well as Nonstructural Viral Proteins". Veterinary Microbiology, vol. 81, 2001, pp. 109-125.
Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, Dec. 2002, pp. 11837-11844.
Opriessnig et al., "Use of an Experimental Model to Test the Efficacy of Planned Exposure to Live Porcine Reproductive and Respiratory Syndrome Virus". Clinical and Vaccine Immunology, vol. 14, No. 12, Dec. 2007, pp. 1572-1577.
Ostrowski et al., "Identification of Neutralizing and Nonneutralizing Epitopes in the Porcine Reproductive and Respiratory Syndrome Virus GP5 Ectodomain". Journal of Virology, vol. 76, No. 9, May 2002, pp. 4241-4250.
Pesch et al., "New insights into the genetic diversity of European porcine reproductive and respiratory syndrome virus (PRRSV)". Veterinary Microbiology, vol. 107, 2005, pp. 31-48.
Polson, DD, "Answers to Your Questions on PRRS". NOBL Laboratories, 1993, 18 Pages.
Polson, DD, "RespPRRS a PRRS Vaccine Review", NOBL Laboratories, 1993, 22 pages.
Porcine Reproductive and Respiratory Syndrome: A Report on the Seminar Held in Brussels on Nov. 4-5, 1991 and Organized by the European Commission.
Quaife, T. "Mystery Agent Isolated! Isolation of the etiological agent behind mystery swine disease is a major breakthrough". Swine Practitioner, Mystery Disease: Part 8, Nov. 1991, pp. 4-7.
Roof et al., "Efficacy of Modified Live Virus Porcine Reproductive and Respiratory Virus Vaccines Against Heterologous Respiratory Challenge". 4th International Symposium on Emerging and Re-emerging Pig Diseases, Rome, Jun. 28-Jul. 2, 2003, pp. 117-118.
Ropp et al., "Characterization of Emerging European-Like Porcine Reproductive and Respiratory Syndrome Virus Isolates in the United States"., Journal of Virology, vol. 78, No. 7, Apr. 2004, pp. 3684-3703.
Rossow et al., "Experimental porcine reproductive and respiratory syndrome virus infection in one-, four-, and 10-week-old pigs". Journal of Veterinary Diagnostic Investigation, vol. 6, 1993, pp. 3-12.
Rossow, K.D., "Porcine Reproductive and Respiratory Syndrome". Veterinary Pathology, vol. 35, 1998, pp. 1-20.
Rovira et al., "Experimental Inoculation of Conventional Pigs with Porcine Reproductive and Respiratory Syndrome virus and Porcine Circovirus 2", J. Virol, jApr. 2002, vol. 76, No. 7, pp. 3232-3239.
Brockmeier et al., "Genomic sequence and virulence comparison of four Type 2 porcine reproductive and respiratory syndrome virus strains". Virus Research, vol. 169, No. 1, 2012, pp. 212-221.

(56) References Cited

OTHER PUBLICATIONS

Charerntantanakul et al., "Porcine reproductive and respiratory syndrome virus vaccines: Immunogenicity, efficacy and safety aspects". World Journal of Virology, vol. 1, No. 1, Feb. 2012, pp. 23-30.
Collins et al., "Laboratory diagnosis of porcine reproductive and respiratory syndrome (PRRS) virus infection". Swine Health and Production, vol. 4, No. 1, Feb. 1996, pp. 33-35.
Database EMBL Accession No. EF488739, "Porcine respiratory and reproductive syndrome virus isolate MN184C, complete genome". Apr. 19, 2007, pp. 1-4.
Database EMBL Accession No. EU759247, "Porcine respiratory and reproductive syndrome virus isolate PRRSV2000000079 envelope glycoprotein gene, complete cds". Aug. 10, 2008, 1 page.
Huang et al., "Novel strategies and approaches to develop the next generation of vaccines against porcine reproductive and respiratory syndrome virus (PRRSV)". Virus Research, vol. 154, 2010, pp. 141-149.
Leng et al., "Evaluation of the Efficacy of an Attenuated Live Vaccine against Highly Pathogenic Porcine Reproductive and Respiratory Syndrome Virus in Young Pigs". Clinical and Vaccine Immunology, vol. 19, No. 8, Aug. 2012, pp. 1199-1206.
UniProt: Accession No. B4ZUF3. "SubName: Full=Envelope glycoprotein". Sep. 23, 2008, 1 page.
UniProt: Accession No. J9QHK0. "SubName: Full=Nucleocapsid protein". Nov. 28, 2012, 1 page.
UniProt: Accession No. J9QII1. "SubName: Full=Unglycosylated membrane protein". Nov. 28, 2012, 1 page.
UniProt: Accession No. J9QIW4. "SubName: Full=Polyprotein lab". Nov. 28, 2012, pp. 1-3.
Halbur et al., "Comparative pathogenicity of nine US porcine reproductive and respiratory syndrome virus (PRRSV) isolates in a five-week-old cesarean-derived, colostrum-deprived pig model". Journal of Veterinary Diagnostic Investigation, vol. 8, 1996, pp. 11-20.
Halbur et al., "Effects of different US isolates of porcine reproductive and respiratory syndrome virus (PRRSV) on blood and bone marrow parameters of experimentally infected pigs". Veterinary Record, vol. 151, 2002, pp. 344-348.
Halbur et al., "Variable Pathogenicity of Nine Porcine Reproductive and Respiratory Syndrome Virus (PRRSV) Isolates". Conference of Research Workers in Animal Diseases, Abstracts of Papers, Chicago, Illinois, paper #222, Nov. 1993.
Halbur et al., "Viral Pneumonia in Neonatal and Nursery pigs. Experimental Work with SIRS Agent and Evidence of Another New Viral Agent". Agri-Practice, vol. 12, No. 1, Jan.-Feb. 1991, pp. 23-34.
Hao et al., "Polymorphic genetic characterization of the ORF7 gene of porcine reproductive and respiratory syndrome virus (PRRSV) in China". Virology Journal, vol. 8, No. 73, 2011, pp. 1-9.
Haynes et al., "Temporal and Morphologic Characterization of the Distribution of Porcine Reproductive and Respiratory Syndrome Virus (PRRSV) by In Situ Hybridization in Pigs Infected with Isolates of PRRSV that Differ in Virulence". Veterinary Pathology, vol. 34, 1997, pp. 39-43.
Johnson et al., "Pathogenic and humoral immune responses to porcine reproductive and respiratory syndrome virus (PRRSV) are related to viral load in acute infection". Veterinary Immunology and Immunopathology, vol. 102, No. 3, PRRS Immunology and Immunopathology Special Issue, Dec. 2004, pp. 233-247.
Kapur et al., "Genetic variation in porcine reproductive and respiratory syndrome virus isolates in the midwestern United States". Journal of General Virology, vol. 77, 1996, pp. 1271-1276.
Katz et al., "Antigenic differences between European and American isolates of porcine reproductive and respiratory syndrome virus (PRRSV) are encoded by the carboxyterminal portion of viral open reading frame 3". Veterinary Microbiology, vol. 44, No. 1, Apr. 1995, pp. 65-76.

Key et al., "Genetic variation and phylogenetic analyses of the ORF5 gene of acute porcine reproductive and respiratory syndrome virus isolates". Veterinary Microbiology, vol. 83, 2001, pp. 249-263.
Kim et al., "Different Biological Characteristics of Wild-Type Porcine Reproductive and Respiratory Syndrome Viruses and Vaccine Viruses and Identification of the Corresponding Genetic Determinants". Journal of Clinical Microbiology, vol. 46, No. 5, May 2008, pp. 1758-1768.
Kim et al., "Enhanced replication of porcine reproductive and respiratory syndrome (PRRS) virus in a homogeneous subpopulation of MA-104 cell line". Archives of Virology, vol. 133, 1993, pp. 477-483.
Kim et al., "Modulation of type I interferon induction by porcine reproductive and respiratory syndrome virus and degradation of CREB-binding protein by non-structural protein 1 in MARC-145 and HeLa cells". Virology, vol. 402, 2010, pp. 315-326.
Kimman et al., "Challenges for porcine reproductive and respiratory syndrome virus (PRRSV) vaccinology". Vaccine, vol. 27, No. 28, Jun. 2009, pp. 3704-3718.
Klinge et al, "Age-dependent resistance to Porcine reproductive and respiratory syndrome virus replication in swine". Virology Journal, vol. 6, No. 177, Oct. 2009.
Klinge et al., "PRRSV replication and subsequent immune responses in swine of various ages". Abstract of Poster No. 56, International Porcine Reproductive and Respiratory Syndrome (PRRS) Symposium, PRRS and PRRSV-Related Diseases: Prevention and Control Strategies, Chicago, IL, Nov. 30-Dec. 1, 2007.
Kreutz, L.C., "Cellular membrane factors are the major determinants of porcine reproductive and respiratory syndrome virus tropism". Virus Research, vol. 53, 1998, pp. 121-128.
Kroese et al., "The nsp1a and nsp1b papain-like autoproteinases are essential for porcine reproductive and respiratory syndrome virus RNA synthesis". Journal of General Virology, vol. 89, 2008, pp. 494-499.
Kwang et al., "Cloning, expression, and sequence analysis of the ORF4 gene of the porcine reproductive and respiratory syndrome virus MN-1b". Journal of Veterinary Diagnostic Investigation, vol. 6, No. 3, Jul. 1994, pp. 293-296.
Labarque et al., "Effect of cellular changes and onset of humoral immunity on the replication of porcine reproductive and respiratory syndrome virus in the lungs of pigs". Journal of General Virology, vol. 81, 2000, pp. 1327-1334.
Labarque et al., "Respiratory tract protection upon challenge of pigs vaccinated with attenuated porcine reproductive and respiratory syndrome virus vaccines". Veterinary Microbiology, vol. 95, 2003, pp. 187-197.
Li et al., "Emergency vaccination alleviates highly pathogenic porcine reproductive and respiratory syndrome virus infection after contact exposure". BMC Veterinary Research, vol. 9, No. 26, 2013, pp. 1-6.
Li et al., "The cysteine protease domain of porcine reproductive and respiratory syndrome virus non-structural protein 2 antagonizes interferon regulatory factor 3 activation". Journal of General Virology, vol. 91, 2010, pp. 2947-2958.
Liesner et al., "Efficacy of Ingelvac® PRRS MLV against highly pathogenic PRRSV: a summary of three challenge trials". Virology & Viral Diseases—PRRS, 22nd International Pig Veterinary Society Congress, Korea, 2012, p. 958.
Lopez et al., "Role of neutralizing antibodies in PRRSV protective immunity". Veterinary Immunology and Immunopathology, vol. 102, 2004, pp. 155-163.
Loula, T., "Clinical Presentation of Mystery Pig Disease in the Breeding Herd and Suckling Piglets". Proceedings of the Mystery Swine Disease Committee Meeting, Denver, CO, Oct. 6, 1990, pp. 37-40.
Loula, T., "Mystery Pig Disease", Agri-Practice, vol. 12, No. 1, Jan.-Feb. 1991, pp. 29-34.
Luo et al., "Antiviral activity of type I and type III interferons against porcine reproductive and respiratory syndrome virus (PRRSV)". Antiviral Research, vol. 91, 2011, pp. 91-101.

(56) References Cited

OTHER PUBLICATIONS

Lv et al., "An infectious cDNA clone of a highly pathogenic porcine reproductive and respiratory syndrome virus variant associated with porcine high fever syndrome". Journal of General Virology, vol. 89, 2008, pp. 2075-2079.

Mardassi et al., "Identification of major differences in the nucleocapsid protein genes of a Québec strain and European strains of porcine reproductive and respiratory syndrome virus". vol. 75, No. 3, Mar. 1994, pp. 681-685.

Mardassi et al., "Molecular analysis of the ORFs 3 to 7 of porcine reproductive and respiratory syndrome virus, Québec reference strain". Archives of Virology, vol. 140, No. 8, 1995, pp. 1405-1418.

Mardassi et al., "Structural Gene Analysis of a Quebec Reference Strain of Porcine Reproductive and Respiratory Syndrome Virus (PRRSV)". Corona- and Related Viruses, Edited by P.J. Talbot and G.A. Levy, Plenum Press, New York, 1995, pp. 277-281.

Matanin et al., "Purification of the major envelop protein GP5 of porcine reproductive and respiratory syndrome virus (PRRSV) from native virions". Journal of Virological Methods, vol. 147, 2008, pp. 127-135.

McCullough et al., "9. Experimental Transmission of Mystery Swine Disease", The New Pig Disease Porcine Respiration and Reproductive Syndrome, A report on the seminar/workshop held in Brussels on Apr. 29-30, 1991, pp. 46-52.

Meier et al., "Gradual development of the interferon-g response of swine to porcine reproductive and respiratory syndrome virus infection or vaccination". Virology, vol. 309, 2003, pp. 18-31.

Meng et al., "Characterization of a High-Virulence US Isolate of Porcine Reproductive and Respiratory Syndrome Virus in a Continuous Cell Line, ATCC CRL11171". Journal of Veterinary Diagnostic Investigation, vol. 8, No. 3, Jul. 1996, pp. 374-381.

Meng et al., "Molecular cloning and nucleotide sequencing of the 3'-terminal genomic RNA of the porcine reproductive and respiratory syndrome virus". Journal of General Virology, vol. 75, 1994, pp. 1795-1801.

Meng et al., "Phylogenetic analyses of the putative M (ORF 6) and N (ORF 7) genes of porcine reproductive and respiratory syndrome virus (PRRSV): implication for the existence of two genotypes of PRRSV in the U.S.A. and Europe". Archives of Virology, vol. 140, No. 4, 1995, pp. 745-755.

Meng, X.J., "Heterogeneity of porcine reproductive and respiratory syndrome virus: implications for current vaccine efficacy and future vaccine development". Veterinary Microbiology, vol. 74, 2000, pp. 309-329.

Mengeling et al., "An update of research at the National Animal Disease Center on current field strains of Porcine Reproductive and Respiratory Syndrome (PRRS) virus". Allen D. Leman Swine Conference, 1997, pp. 138-145.

Mengeling et al., "Clinical consequences of exposing pregnant gilts to strains of porcine reproductive and respiratory syndrome (PRRS) virus isolated from field cases of "atypical" PRRS". American Journal of Veterinary Research, vol. 59, No. 12, Dec. 1998, pp. 1540-1544.

Mengeling et al., "Clinical Effects of porcine reproductive and respiratory syndrome virus on pigs during the early postnatal interval". American Journal of Veterinary Research, vol. 59, No. 1, Jan. 1998, pp. 52-55.

Mengeling et al., "Comparative safety and efficacy of attenuated single-strain and multi-strain vaccines for porcine reproductive and respiratory syndrome". Veterinary Microbiology, vol. 93, 2003, pp. 25-38.

Mengeling et al., "Comparison among strains of porcine reproductive and respiratory syndrome virus for their ability to cause reproductive failure". American Journal of Veterinary Research, vol. 57, No. 6, Jun. 1996, pp. 834-839.

Mengeling et al., "Mystery Pig Disease: Evidence and Considerations for its Etiology". Proceedings of the Mystery Swine Disease Committee Meeting, Oct. 6, 1990, Denver, Colorado, Livestock Conservation Institute, Madison, WI, USA, pp. 88-90.

Mengeling et al., "Strain specificity of the immune response of pigs following vaccination with various strains of porcine reproductive and respiratory syndrome virus". Veterinary Microbiology, vol. 93, 2003, pp. 13-24.

Meredith, MJ, "Porcine Reproductive and Respiratory Syndrome (PRRS)", Pig Disease Information Center, 1st North American Edition, University of Cambridge, Aug. 1994, pp. 1-57.

Meulenberg et al., "An infectious cDNA clone of Porcine Reproductive and Respiratory Syndrome Virus". Coronaviruses and Arteriviruses (Advances in Experimental Medicine and Biology, vol. 440), Ch. 24, 1998, pp. 199-206.

Meulenberg et al., "Characterization of Proteins Encoded by ORFs 2 to 7 of Lelystad Virus". Virology, vol. 206, No. 1, Jan. 1995, pp. 155-163.

Meulenberg et al., "Identification and Characterization of a Sixth Structural Protein of Lelystad Virus: The Glycoprotein GP2Encoded by ORF2 is Incorporated in Virus Particles". Virology, vol. 225, No. 1, Nov. 1996, pp. 44-51.

"Dutch Team Isolates Mystery Pig Disease Agent", Animal Pharm, vol. 230, Abstract No. 00278268, Jun. 21, 1991, p. 21.

Albina et al., "Immune responses in pigs infected with porcine reproductive and respiratory syndrome virus (PRRSV)". Veterinary Immunology and Immunopathology, vol. 61, 1998, pp. 49-66.

Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.

Allende et al., "Mutations in the genome of porcine reproductive and respiratory syndrome virus responsible for the attenuated phenotype". Archives of Virology, vol. 145, No. 6, Jun. 2000, pp. 1149-1161.

Allende et al., "North American and European porcine reproductive and respiratory syndrome viruses differ in non-structural protein coding regions". Journal of General Virology, vol. 80, 1999, pp. 307-315.

Allende et al., "Porcine Reproductive and Respiratory Syndrome Virus: Description of Persistence in Individual Pigs upon Experimental Infection†". Journal of Virology, vol. 74, No. 22, Nov. 2000, pp. 10834-10837.

Andreyev et al., "Genetic variation and phylogenetic relationships of 22 porcine reproductive and respiratory syndrome virus (PRRSV) field strains based on sequence analysis of open reading frame 5". Archives of Virology, vol. 142, 1997, pp. 993-1001.

Ansari et al., "Influence of N-Linked Glycosylation of Porcine Reproductive and Respiratory Syndrome Virus GP5 on Virus Infectivity, Antigenicity, and Ability to Induce Neutralizing Antibodies." Journal of Virology, vol. 80, No. 8, Apr. 2006, pp. 3994-4004.

Barfoed et al., "DNA vaccination of pigs with open reading frame 1-7 of PRRS virus". Vaccine, vol. 22, 2004, pp. 3628-3641.

Bautista et al., "Comparison of Porcine Alveolar Macrophages and CL 2621 for the Detection of Porcine Reproductive and Respiratory Syndrome (PRRS) Virus and Anti-PRRS Antibody". Journal of Veterinary Diagnostic Investigation, vol. 5, No. 2, Apr. 1993, pp. 163-165.

Bautista et al., "Serologic Survey for Lelystad and VR-2332 Strains of Porcine Respiratory and Reproductive Syndrome (PRRS) Virus in US Swine Herds". Journal of Veterinary Diagnostic Investigation, vol. 5, No. 4, Oct. 1992, pp. 612-614.

Benfield et al., "Characterization of swine infertility and respiratory syndrome (SIRS) virus (isolate ATCC VR-2332)". Journal of Veterinary Diagnostic Investigation, vol. 4, 1992, pp. 127-133.

Benfield et al., "Etiologic Agent of Swine Infertility and Respiratory Syndrome in the United States". 72st Annual Meeting of the Conference of Research Workers in Animal Disease, Chicago, IL, Nov. 11-12, 1991, p. 48, Abstract No. 268.

Benfield et al., "Properties of SIRS Virus Isolate ATCC VR-2332 in the United States and Preliminary Characterization of a Monoclonal Antibody to this Virus". American Association of Swine Practitioners Newsletter, vol. 4, No. 4, Jul./Aug. 1992, pp. 19-21.

Beura et al., "Porcine Reproductive and Respiratory Syndrome Virus Nonstructural Protein 1β Modulates Host Innate Immune Response by Antagonizing IRF3 Activation". Journal of Virology, Volo. 84, No. 3, Feb. 2010, pp. 1574-1584.

(56) References Cited

OTHER PUBLICATIONS

Bilodeau et al., "'Porcine Reproductive and Respiratory Syndrome' in Quebec". The Veterinary Record, Aug. 3, 1991, p. 102.
Bramel-Verheije et al., "Expression of a Foreign Epitope by Porcine Reproductive and Respiratory Syndrome Virus". Virology, vol. 278, 2000, pp. 380-389.
Buddaert et al., "In Vivo and In Vitro Interferon (IFN) Studies with the Porcine Reproductive and Respiratory Syndrome Virus (PRRSV)". Coronaviruses and Arteriviruses: Advances in Experimental Medicine and Biology, vol. 440, Plenum Press, New York, 1998, pp. 461-467.
Cano et al., "Impact of a modified-live porcine reproductive and respiratory syndrome virus vaccine intervention on a population of pigs infected with a heterologous isolate". Vaccine, vol. 25, 2007, pp. 4382-4391.
Chang et al., "Evolution of Porcine Reproductive and Respiratory Syndrome Virus during Sequential Passages in Pigs". Journal of Virology, vol. 76, No. 10, May 2002, pp. 4750-4763.
Chen et al., "Synthetic B- and T-cell epitope peptides of porcine reproductive and respiratory syndrome virus with Gp96 as adjuvant induced humoral and cell-mediated immunity". Vaccine, vol. 31, 2013, pp. 1838-1847.
Christianson et al., "Experimental Reproduction of a Newly Described Viral Disease, Swine Infertility and Respiratory Syndrome (SIRS), in Pregnant Sows". 72nd Annual Meeting of the Conference of Research Workers in Animal Disease, Chicago, IL, Nov. 11 & 12, 1991, p. 48, Abstract No. 269.
Christianson et al., "Experimental reproduction of swine infertility and respiratory syndrome in pregnant sows". American Journal of Veterinary Research, vol. 53, No. 4, Apr. 1992, pp. 485-488.
Christianson et al., "Porcine reproductive and respiratory syndrome: A review"., Journal of Swine Health and Production, vol. 2, No. 2, Mar. and Apr. 1994, pp. 10-28.
Christianson et al., "Swine Infertility and Respiratory Syndrome". Pig Veterinary Journal, vol. 27, No. 9, Apr. 1991, pp. 9-12.
Collins et al., "Experimental Transmission of Swine Reproductive Failure Syndrome (Mystery Swine Disease) in Gnotobiotic Piglets". 71st Annual Meeting of the Conference of Research Workers in Animal Disease, Chicago, IL, Nov. 5-6, 1990, Abstract No. 2.
Collins et al., "Isolation of swine infertility and respiratory syndrome virus (isolate ATCC VR-2332) in North America and experimental reproduction of the disease in gnotobiotic pigs". Journal of Veterinary Diagnostic Investigation, vol. 4, 1992, pp. 117-126.
Collins et al., "Production of infectious human respiratory syncytial virus from cloned cDNA confirms an essential role for the transcription elongation factor from the 5' proximal open reading frame of the M2 mRNA in gene expression and provides a capability for vaccine development". Proceedings of the National Academy of Sciences, vol. 92, Dec. 1995, pp. 11563-11567.
Collins et al., "Respiratory Disease in a Swine Herd Experiencing a Reproductive Failure Syndrome". Minnesota Swine Conference for Veterinarians, Sep. 16-18, 1990, pp. 206-207.
Collins et al., "Swine Diagnostic Pathology". Allen D. Leman Swine Conference, College of Veterinary Medicine, University of Minnesota, Sep. 18-22, 1998, pp. 1-4.
Collins et al., "Swine Infertility and Respiratory Syndrome (Mystery Swine Disease)". Minnesota Swine Conference for Veterinarians, St. Paul, MN, Sep. 15-17, 1991, pp. 200-205.
Collins, J.E., "Newly Recognized Respiratory Syndromes in North American Swine Herds". American Association of Swine Practitioners Newsletter, vol. 3, No. 7, Sep.-Oct. 1991, pp. 7, 10-11.
Conzelmann et al., "Molecular Characterization of Porcine Reproductive and Respiratory Syndrome Virus, a Member of the Arterivirus Group". Virology, vol. 193, 1993, pp. 329-339.
Cooper et al., "Porcine Reproductive and Respiratory Syndrome: NEB-1 PRRSV Infection did not Potentiate Bacterial Pathogens". Journal of Veterinary Diagnostic Investigation, vol. 7, No. 3, Jul. 1995, pp. 313-320.

Darwich et al., "Genetic and immunobiological diversities of porcine reproductive and respiratory syndrome genotype I strains". Veterinary Microbiology, vol. 150, 2011, pp. 49-62.
Dea et al., "Antigenic Variability among North American and European Strains of Porcine Reproductive and Respiratory Syndrome Virus as Defined by Monoclonal Antibodies to the Matrix Protein". Journal of Clinical Microbiology, vol. 34, No. 5, Jun. 1996, pp. 1488-1493.
Dea et al., "Antigenic variant of swine influenza virus causing proliferative and necrotizing pneumonia in pigs". Journal of Veterinary Diagnostic Investigation, vol. 4, No. 4, 1992, pp. 380-392.
Dea et al., "Current knowledge on the structural proteins of porcine reproductive and respiratory syndrome (PRRS) virus: comparison of the North American and European isolate". Archives of Virology, vol. 145, No. 4, Apr. 2000, pp. 659-688.
Dea et al., "Swine reproductive and respiratory syndrome in Quebec: Isolation of an enveloped virus serologically-related to Lelystad virus". Canadian Veterinary Journal, vol. 33, No. 12, Dec. 1992, pp. 801-808.
Dea et al., "Virus Isolations from Farms in Quebec Experiencing Severe Outbreaks of Respiratory and Reproductive Problems". Proceedings of the Mystery Swine Disease Committee Meeting, Denver, CO, Oct. 6, 1990, pp. 67-72.
Drew, T., "Porcine Reproductive and Respiratory Syndrome Virus: A Review". Apr. 1996, 3 pages.
Duan et al., "Identification of a putative Receptor for Porcine Reproductive and Respiratory Syndrome Virus on Porcine Alveolar Macrophages". Journal of Virology, vol. 72, No. 5, May 1998, pp. 4520-4523.
Duran et al. "Recombinant Baculovirus Vaccines Against Porcine Reproductive and Respiratory Syndrome (PRRS)". Abstracts PRRS, Aug. 9 to 10, 1995, Copenhagen, Denmark, 2 pages.
Fang et al., "Heterogeneity in nsp2 of European-like porcine reproductive and respiratory syndrome viruses isolated in the United States". Virus Research, vol. 100, 2004, pp. 229-235.
Foss et al., "Adjuvant Danger Signals Increase the Immune Response to Porcine Reproductive and Respiratory Syndrome Virus". Viral Immunology, vol. 15, No. 4, 2002, pp. 557-566.
Gao et al., "Genomic characterization of two Chinese isolates of Porcine respiratory and reproductive syndrome virus*". Archives of Virology, vol. 149, 2004, pp. 1341-1351.
Gorcyca et al., RespPRRS: A new tool for the prevention and control of PRRS in pigs. Proceedings of the American Association of Swine Practitioners, Omaha, Nebraska, Mar. 1995, pp. 1-22.
Goyal, S., "Porcine Reproductive and Respiratory Syndrome", Journal of Veterinary Diagnostic Investigation, vol. 5, No. 4, 1993, pp. 656-664.
Grebennikova et al., "Genomic characterization of virulent, attenuated, and revertant passages of a North American porcine reproductive and respiratory syndrome virus strain". Virology, vol. 321, 2004, pp. 383-390.
Greiner et al., "Quantitative Effect of Porcine Reproductive Respiratory Syndrome Virus on Pig Growth and Immune Response"., 1999, Swine Research Report, Paper 5, 1998, 4 pages.
International Search Report and Written Opinion for PCT/US2014/024321 mailed Oct. 24, 2014.
NCBI: Accession No. B4ZWR2. "Porcine reproductive and respiratory syndrome virus (PRRSV)." May 2008, 1 page.
Wensvoort et al., "Lelystad virus, the cause of porcine epidemic abortion and respiratory syndrome: a review of mystery swine disease research in Lelystad". Veterinary Microbiology, vol. 33, Nos. 1-4, Nov. 1992, pp. 185-193.
Wensvoort et al., "The Porcine Reproductive and Respiratory Syndrome; Characteristics and diagnosis of the causative virus". Veterinary Biotechnology Newsletter, vol. 3, 1993, pp. 113-120.
Wesley et al., "Differentiation of a porcine reproductive and respiratory syndrome virus vaccine strain from North American field strains by restrction fragment length polymorphism analysis of ORF 5". Journal of Veterinary Diagnostic Investigation, vol. 10, 1998, pp. 140-144.

(56) References Cited

OTHER PUBLICATIONS

Wesley et al., "Differentiation of vaccine (strain RespPRRS) and field strains of porcine reproductive and respiratory syndrome virus by restriction enzyme analysis". Proceedings of the American Association on Swine Practitioners, Nashville, TN, USA, 1996, pp. 141-143.
Wieczorek-Krohmer et al., "Porcine reproductive and respiratory syndrome virus (PRRSV): Monoclonal antibodies detect common epitopes on two viral proteins of European and U.S. isolates". Veterinary Microbiology, vol. 51, Nos. 3-4, Aug. 1996, pp. 257-266.
Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, Jun. 21-24, 1999, pp. 37-38.
Xiao et al., "The Level of Virus-Specific T-Cell and Macrophage Recruitment in Porcine Reproductive and Respiratory Syndrome Virus Infection in Pigs is Independent of Virus Load". Journal of Virology, vol. 78, No. 11, Jun. 2004, pp. 5923-5933.
Xue et al., "The Crystal Structure of Porcine Reproductive and Respiratory Syndrome Virus Nonstructural Protein Nsp1b Reveals a Novel Metal-Dependent NucleaseŇ". Journal of Virology, vol. 84, No. 13, Jul. 2010, pp. 6461-6471.
Yang et al., "Comparative sequence analysis of open reading frames 2 to 7 of the modified live vaccine virus and other North American isolates of the porcine reproductive and respiratory syndrome virus". Archives of Virology, vol. 143, 1998, pp. 601-612.
Yoon et al., "Failure to Consider the Antigenic Diversity of Porcine Reproductive and Respiratory Syndrome (PRRS) Virus Isolates May Lead to Misdiagnosis". Journal of Veterinary Diagnostic Investigation, vol. 7, Jul. 1995, pp. 386-387.
Yoon et al., "Isolation of a Cytopathic Virus from Weak Pigs on Farms with a History of Swine Infertility and Respiratory Syndrome". Journal of Veterinary Diagnostic Investigation, vol. 4, Apr. 1992 pp. 139-143.
Yu et al., "Genomic Sequencing Reveals Mutations Potentially Related to the Overattenuation of a Highly Pathogenic Porcine Reproductive and Respiratory Syndrome Virus". Clinical and Vaccine Immunology, vol. 20, No. 4, Apr. 2013, pp. 613-619.
Yuan et al., "Complete genome comparison of porcine reproductive and respiratory syndrome virus parental and attenuated strains". Virus Research, vol. 74, 2001, pp. 99-110.
Yuan et al., "Erratum to 'Complete genome comparison of porcine reproductive and respiratory syndrome virus parental and attenuated strains' [Virus Research 74 (2001) 99-110]". Virus Research, vol. 79, 2001, p. 187.
Yuan et al., American Society for Virology, 16th Annual Meeting, Bozeman, Montana, Jul. 19-23, 1997, Abstract P29-5, p. 229.
Zimmerman et al., "General overview of PRRSV: A perspective from the United States". Veterinary Microbiology, vol. 55, Nos. 1-4, Apr. 1997, pp. 187-196.
Scott, F.W., "Immunization against feline coronaviruses". Advances in Experimental Medicine and Biology, vol. 218, 1987, pp. 569-576.
Shen et al., "Determination of the complete nucleotide sequence of a vaccine strain of porcine reproductive and respiratory syndrome virus and identification of the Nsp2 gene with a unique insertion". Archives of Virology, vol. 145, No. 5, May 2000, pp. 871-883.
Shi et al., "Endoribonuclease activities of porcine reproductive and respiratory syndrome virus nsp11 was essential for nsp11 to inhibit IFN-β induction". Molecular Immunology, vol. 48, 2011, pp. 1568-1572.
Shi et al., "Porcine reproductive and respiratory syndrome virus (PRRSV) could be sensed by professional beta interferon-producing system and had mechanisms to inhibit this action in MARC-145 cells". Virus Research, vol. 153, 2010, pp. 151-156.
Shi et al., "The Nonstructural Protein 1 Papain-Like Cysteine Protease Was Necessary for Porcine Reproductive and Respiratory Syndrome Virus Nonstructural Protein 1 to Inhibit Interferon-β Induction". DNA and Cell Biology, vol. 30, No. 6, 2011, pp. 355-362.

Snijder et al., "Identification of a Novel Structural Protein of Arteriviruses". Journal of Virology, vol. 73, No. 8, Aug. 1999, pp. 6335-6345.
Snijder et al., "Non-structural proteins 2 and 3 interact to modify host cell membranes during the formation of the arterivirus replication complex". Journal of General Virology, vol. 83, 2001, pp. 985-994.
Snijder et al., "Proteolytic Processing of the Replicase ORF1a Protein of Equine Arteritis Virus". Journal of Virology, vol. 68, No. 9, Sep. 1994, pp. 5755-5764.
Snijder et al., "The molecular biology of arteriviruses". Journal of General Virology, vol. 79, 1998, pp. 961-979.
Song et al., "Nonstructural protein 1? subunit-based inhibition of NF-?B activation and suppression of interferon-? production by porcine reproductive and respiratory syndrome virus". Virology, vol. 407, 2010, pp. 268-280.
Stevenson et al., "Endemic Porcine Reproductive and Respiratory Syndrome Virus Infection of Nursery Pigs in Two Swine Herds without Current Reproductive Failure". Journal of Veterinary Diagnostic Investigation, vol. 5, 1993, pp. 432-434.
Suarez et al., "Direct detection of the porcine reproductive and respiratory syndrome (PRRS) virus by reverse polymerase chain reaction (RT-PCR)". Archives of Virology, vol. 135, No. 1-2, 1994, pp. 89-99.
Sumiyoshi et al., "Infectious Japanese Encephalitis Virus RNA Can Be Synthesized from In Vitro-Ligated cDNA Templates". Journal of Virology, vol. 66, No. 9, Sep. 1992, pp. 5425-5431.
Sun et al., "Crystal Structure of Porcine Reproductive and Respiratory Syndrome Virus Leader Protease Nsp1aŇ". Journal of Virology, vol. 83, No. 21, Nov. 2009, pp. 10931-10940.
Thanawongnuwech et al., "Effects of Low (Modified-live Virus Vaccine) and High (VR-2385)-Virulence Strains of Porcine Reproductive and Respiratory Syndrome Virus on Pulmonary Clearance of Copper Particles in Pigs". Veterinary Pathology, vol. 35, 1998, pp. 398-406.
Tian et al., "An attenuated live vaccine based on highly pathogenic porcine reproductive and respiratory syndrome virus (HP-PRRSV) protects piglets against HP-PRRS". Veterinary Microbiology, vol. 138, 2009. pp. 34-40.
Tian et al., "Emergence of Fatal PRRSV Variants: Unparalleled Outbreaks of Atypical PRRS in China and Molecular Dissection of the Unique Hallmark". PLoS One, vol. 2, No. 6, e526, 2007, pp. 1-10.
Van Alstine, W.G., "Past Diagnostic Approaches and Findings and Potentially Useful Diagnostic Strategies". Proceedings Mystery Swine Disease Committee Meeting, Oct. 6, 1990, pp. 52-58.
Van Der Linden et al., "Virological kinetics and immunological responses to a porcine reproductive and respiratory syndrome virus infection of pigs at different ages". Vaccine, vol. 21, 2003, pp. 1952-1957.
Van Der Meer et al., "ORF1a-Encoded Replicase Subunits are Involved in the Membrane Association of the Arterivirus Replication Complex". Journal of Virology, vol. 72, No. 8, 1998, pp. 6689-6698.
Van Dinten et al., "An infectious arterivirus cDNA clone: Identification of a replicase point mutation that abolished discontinuous mRNA transcription". Proceedings of the National Academy of Sciences, vol. 94, Feb. 1997, pp. 997-996.
Van Dinten et al., "Processing of the Equine Arteritis Virus Replicase ORF1b Protein: Identification of Cleavage Products Containing the Putative Viral Polymerase and Helicase Domains". Journal of Virology, vol. 70, No. 10, Oct. 1996, pp. 6625-6633.
Van Dinten et al., "Proteolytic Processing of the Open Reading Frame 1b-Encoded Part of Arterivirus Replicase is Mediated by nsp4 Serine Protease and is Essential for Virus Replication". Journal of Virology, vol. 73, No. 3, Mar. 1999, pp. 2027-2037.
Van Marle et al., "Arterivirus discontinuous mRNA transcription is guided by base pairing between sense and antisense transcription-regulating sequences". Proceedings of the National Academy of Sciences, vol. 96, 1999, pp. 12056-12061.
Van Marle et al., "Characterization of an Equine Arteritis Virus Replicase Mutant Defective in Subgenomic mRNA Synthesis". Journal of Virology, vol. 73, No. 7, Jul. 1999, pp. 5274-5281.

(56) References Cited

OTHER PUBLICATIONS

Van Marle et al., "Regulation of Coronavirus mRNA Transcription". Journal of Virology, vol. 69, No. 12, Dec. 1995, pp. 7851-7856.
Van Nieuwstadt et al., "Infection with porcine respiratory coronavirus does not fully protect pigs against intestinal transmissable gastroenteritis virus". The Veterinary Record, vol. 125, No. 3, 1989, pp. 58-60.
Van Nieuwstadt et al., "Proteins Encoded by Open Reading Frames 3 and 4 of the Genome of Lelystad Virus (Arteriviridae) are Structural Proteins of the Virion". Journal of Virology, vol. 70, No. 7, Jul. 1996, pp. 4767-4772.
Van Nieuwstadt et al., "Use of two enzyme-linked immunosorbent assays to monitor antibody responses in swine with experimentally induced infection with porcine epidemic diarrhea virus". American Journal of Veterinary Research, vol. 42, Jul. 1991, pp. 1044-1050.
Van Zijl et al., "Live Attenuated Pseudorabies Virus Expressing Envelope Glycoprotein E1 of Hog Cholera Virus Protects Swine Against Both Pseudorabies and Hog Cholera". Journal of Virology, vol. 65, No. 5, May 1991, pp. 2761-2765.
Vennema et al., "Nucleocapsid-independent assembly of coronavirus-like particles by co-expression of viral envelope protein genes". The EMBO Journal, vol. 15, No. 8, 1996, pp. 2020-2028.
Verheije et al., "Kissing Interaction between 3' Noncoding and Coding Sequences Is Essential for Porcine Arterivirus RNA Replication". Journal of Virology, vol. 76, No. 3, Feb. 2002, pp. 1521-1526.
Verheije et al., "Safety and protective efficacy of porcine reproductive and respiratory syndrome recombinant virus vaccines in young pigs". Vaccine, vol. 21, 2003, pp. 2556-2563.
Veterinary Bulletin, vol. 58, No. 11, 1988, Nos. 6903-6909, p. 932.
Veterinary Bulletin, vol. 60, No. 3, 1990, Nos. 1536-1551, pp. 255-256.
Vieira et al., "New pUC-derived cloning vectors with different selectable markers and DNA replication origins". Gene, vol. 100, 1991, pp. 189-194.
VIIIth International Symposium on Nidoviruses (Corona and Arteriviruses), May 20-25, 2000, 32 pages.
Visser, Nicolaas, "Declaration of Dr. N. Visser". Nov. 14, 1995, pp. 1-11.
Von Busse, F.W., Epidemiologic Studies on Porcine Reproductive and Respiratory Syndrome (PRRS). Tierarztliche Umschau, Dec. 1991, pp. 708-717 (Abstract in English p. 711).
Von Ohlinger et al., "Der Seuchenhafte Spatabort beim Schwein Ein Beitrag zur Atiologie des Porcine Reproductive and Respiratory Syndrome (PRRS)". Tierarztl, vol. 46, 1991, pp. 703-708.
Waltner-Toews et al., "A Field Trial to Evaluate the Efficacy of a Combined Rotavirus-Coronavirus/*Escherichia coli* vaccine in Dairy Cattle"., Canadian Journal of Comparative Medicine, vol. 49, No. 1, 1985, pp. 1-9.
Wang et al., "Attenuation of porcine reproductive and respiratory syndrome virus strain MN184 using chimeric construction with vaccine sequence". Virology, vol. 371, 2008, pp. 418-429.
Wang et al., "Immune responses in piglets infected with highly pathogenic porcine reproductive and respiratory syndrome virus". Veterinary Immunology and Immunopathology, vol. 142, 2011, pp. 170-178.
Ward et al., "Efficiency of human rotavirus propagation in cell culture". Journal of Clinical Microbiology, vol. 19, No. 6, Jun. 1984, pp. 748-753.
Wardley et al., "The Host Response to African Swine Fever Virus". Progress of Medical Virology, vol. 34, 1987, pp. 180-192.
Wassenaar et al., "Alternative Proteolytic Processing of the Arterivirus Replicase ORF1a Polyprotein: Evidence that NSP2 Acts as a Cofactor for the NSP4 Serine Protease". Journal of Virology, vol. 71, No. 12, Dec. 1997, pp. 9313-9322.
Webster et al., "Chemotherapy and Vaccination: a Possible Strategy for the Control of Highly Virulent Influenza Virus". Journal of Virology, vol. 55, No. 1, 1985, pp. 173-176.
Welch et al., "Construction and evaluation of genetically engineered replication-defective porcine reproductive and respiratory syndrome virus vaccine candidates". Veterinary Immunology and Immunopathology, vol. 102, 2004, pp. 277-290.
Wensvoort et al., "'Lelystad agent'—the cause of abortus blauw (mystery swine disease)". Tijdschr Diergeneeskd, vol. 116, No. 13, Jul. 1991, pp. 675-676.
Wensvoort et al., "Antigenic Comparison of Lelystad Virus and Swine Infertility and Respiratory Syndrome (SIRS) Virus". Journal of Veterinary Diagnostic Investigation, vol. 4, 1992, pp. 134-138.

FIG. 5

```
SID_1    1  GGGTGTTGGCTCTATGCCACGACATTTGTATTGTCAGCAGCTGTGACCACTGGCACAGCC   60
            ||||||||||||||||||||||||||||||||| |||||||||||||||||||||||||
SID_2    1  GGGTGTTGGCTCTATGCCACGACATTTGTATTGTCAGGAGCTGTGACCACTGGCACAGCC   60

SID_1   61  CAAAACTTGCTGCACGGGAACACCCTCCTGTGACGGCCTCCTTCAGGGAAGTTTAGGGGT  120
            ||||||||||||||||||||||||||||||||||||||||||||||||||||||||||||
SID_2   61  CAAAACTTGCTGCACGGGAACACCCTCCTGTGACGGCCTCCTTCAGGGAAGTTTAGGGGT  120

SID_1  121  TTGTCCCTAACACCTTGTTTCCGGAGTTGCACTGCTTTACGGTCTCTCCACTCCTTTAAC  180
            ||||||||||||||||||||||||||||||||||||||||||||||||||||||||||||
SID_2  121  TTGTCCCTAACACCTTGTTTCCGGAGTTGCACTGCTTTACGGTCTCTCCACTCCTTTAAC  180

SID_1  181  CATGTCTGGGATTCTTGATCGGTGCACGTGTACCCCAATGCCAGGGTGTTTGTGGCAGA  240
            ||||||||||||||||||||||||||||||||||||||||||||||||||||||||||||
SID_2  181  CATGTCTGGGATTCTTGATCGGTGCACGTGTACCCCAATGCCAGGGTGTTTGTGGCAGA  240

SID_1  241  CGGCCAGGTCTACTGCACACGATGTCTCAGTGCACGGACCCTCCTTCCCCTGAATCTCCA  300
            ||||||||||||||||||||||||||||||||||||||||||||||||||||||||||||
SID_2  241  CGGCCAGGTCTACTGCACACGATGTCTCAGTGCACGGACCCTCCTTCCCCTGAATCTCCA  300

SID_1  301  AGTCTCTGAACTTGGGGTGTTGGGCTTGTTCTACAGGCCCGAAGAGCCACTCCGGTGGAC  360
            ||||||||||||||||||||||||||||||||||||||||||||||||||||||||||||
SID_2  301  AGTCTCTGAACTTGGGGTGTTGGGCTTGTTCTACAGGCCCGAAGAGCCACTCCGGTGGAC  360

SID_1  361  GTTGCCGCGCGCATTCCCCACTGTTGAGTGCTCCCCTGCTGGAGCTTGTTGGCTTTCTGC  420
            ||||||||||||||||||||||||||||||||||||||||||||||||||||||||||||
SID_2  361  GTTGCCGCGCGCATTCCCCACTGTTGAGTGCTCCCCTGCTGGAGCTTGTTGGCTTTCTGC  420

SID_1  421  GATTTTCCAATTGCACGAATGACCAGTGGAAACCTGAACTTCCAACAAAGGATAGTACG  480
            ||||||||||||||||||||||||||||||||||||||||||||||||||||||||||||
SID_2  421  GATTTTCCAATTGCACGAATGACCAGTGGAAACCTGAACTTCCAACAAAGGATAGTACG  480

SID_1  481  GGTTGCAGCTGAGATTTACAGAGTCGGCCAACTCACCCCCACAGTCTTGAAGAACCTACA  540
            ||||||||||||||||||||||||||||||||||||||||||||||||||||||||||||
SID_2  481  GGTTGCAGCTGAGATTTACAGAGTCGGCCAACTCACCCCCACAGTCTTGAAGAACCTACA  540

SID_1  541  AGTCTATGAACGGGGTTGCCGCTGGTACCCCATCGTCGGACCTGTCCCTGGAGTTGCCGT  600
            ||||||||||||||||||||||||||||||||||||||||||||||||||||||||||||
SID_2  541  AGTCTATGAACGGGGTTGCCGCTGGTACCCCATCGTCGGACCTGTCCCTGGAGTTGCCGT  600

SID_1  601  TTACGCTAACTCCCTACATGTGAGTGATAAACCTTTCCCGGGGGCTACTCACGTGCTAAC  660
            ||||||||||||||||||||||||||||||||||||||||||||||||||||||||||||
SID_2  601  TTACGCTAACTCCCTACATGTGAGTGATAAACCTTTCCCGGGGGCTACTCACGTGCTAAC  660

SID_1  661  CAACCTGCCGCTCCCGCAGAGACCTAAGCCTGAAGATTTTTGCCCCTTTGAGTGTGCGAT  720
            ||||||||||||||||||||||||||||||||||||||||||||||||||||||||||||
SID_2  661  CAACCTGCCGCTCCCGCAGAGACCTAAGCCTGAAGATTTTTGCCCCTTTGAGTGTGCGAT  720

SID_1  721  GGCTGTCGTCTATGACATTGGTCATGACGCTGTTATGTATGTGGCCAAAGAGAGGGTCTC  780
            ||||||||||||||||||||||||||||||||||||||||||||||||||||||||||||
SID_2  721  GGCTGTCGTCTATGACATTGGTCATGACGCTGTTATGTATGTGGCCAAAGAGAGGGTCTC  780

SID_1  781  CTGGGCTCCGCGTGGTGGAGAAAAGGGAAAATTCGAAACTGTTCCAGAGGAGTTGAGGTT  840
            ||||||||||||||||||||||||||||||||||||||||||||||||||||||||||||
SID_2  781  CTGGGCTCCGCGTGGTGGAGAAAAGGGAAAATTCGAAACTGTTCCAGAGGAGTTGAGGTT  840

SID_1  841  GGTTGCAGAGCAACTTTTTACCTCCTTCCCGCCTCACCACGTGGTAGACATGTCGAAGTT  900
            ||||||||||||||||||||||||||||||||||||||||||||||||||||||||||||
```

FIG. 5 (cont)

```
SID_2   841   GGTTGCAGAGCAACTTTTTACCTCCTTCCCGCCTCACCACGTGGTAGACATGTCGAAGTT   900

SID_1   901   CATCTTCACAGCCCCTGATTGTGGAGCTTCCATGCGGGTCGAACGCCAGTATGGCTGCCT   960
              |||||||||||||||||||||||||||||| |||||||||||||||||||||||||||||
SID_2   901   CATCTTCACAGCCCCTGATTGTGGAGCTTCTATGCGGGTCGAACGCCAGTATGGCTGCCT   960

SID_1   961   CCCCGCTGGCACTGTCCCTGACGGTAATTGCTGGTGGAGCTTGTTTAGCTCACTCCCACC   1020
              ||||||||||||||||||||||||||||||||||||||||||||||||||||||||||||
SID_2   961   CCCCGCTGGCACTGTCCCTGACGGTAATTGCTGGTGGAGCTTGTTTAGCTCACTCCCACC   1020

SID_1   1021  GGAAGTTCAGTGTAGAGAAATTCGCCGCGCCACCCAATTTGGCTACCAAACCAAGCATGG   1080
              ||||||||||||||||||||||||||||||||||||||||||||||||||||||||||||
SID_2   1021  GGAAGTTCAGTGTAGAGAAATTCGCCGCGCCACCCAATTTGGCTACCAAACCAAGCATGG   1080

SID_1   1081  CGTTGCTGGCAAGTACCTACAGCGGAGGCTGCAAGCCAATGGTCTCCGAGCAGTGGTTGA   1140
              ||||||||||||||||||||||||||||||||||||||||||||||||||||||||||||
SID_2   1081  CGTTGCTGGCAAGTACCTACAGCGGAGGCTGCAAGCCAATGGTCTCCGAGCAGTGGTTGA   1140

SID_1   1141  CTCAAATGGACCTATCGTCATACAGTATTTCTCCGTTAAGGAGAGCTGGATCCGCCACGT   1200
              |||||| |||||||||||||||||||||||||||||||||||||||||||||||||||||
SID_2   1141  CTCAAACGGACCTATCGTCATACAGTATTTCTCCGTTAAGGAGAGCTGGATCCGCCACGT   1200

SID_1   1201  GAAACTGGCGGGAGAGCCCTGCTATCCCGGGTTTGAGGATCTCCTCAGGATAAGAGTCGA   1260
              ||||||||||||||||||||||||||||||||||||||||||||||||||||||||||||
SID_2   1201  GAAACTGGCGGGAGAGCCCTGCTATCCCGGGTTTGAGGATCTCCTCAGGATAAGAGTCGA   1260

SID_1   1261  GCCCAACACGTTGCCATTGTCCGACAAGGGCGACAAAGTCTTCCGGTTTGGCGGGCACAA   1320
              ||||||||||||||||||||||||||||||||||||||||||||||||||||||||||||
SID_2   1261  GCCCAACACGTTGCCATTGTCCGACAAGGGCGACAAAGTCTTCCGGTTTGGCGGGCACAA   1320

SID_1   1321  GTGGTACGGCGCTGGGAAGAGGGCAAGGAGATCACGTGCAGGTGCTGCCACTACAGTTGC   1380
              ||||||||||||||||||||||||||||||||||||||||||||||||||||||||||||
SID_2   1321  GTGGTACGGCGCTGGGAAGAGGGCAAGGAGATCACGTGCAGGTGCTGCCACTACAGTTGC   1380

SID_1   1381  CGGTCACGCCTCGCCTGTTCGCGAAACTCAACAGGCCAAGAAGCACGAGGCTGCTAGCGC   1440
              ||||||||||||||||||||||||||||||||||||||||||||||||||||||||||||
SID_2   1381  CGGTCACGCCTCGCCTGTTCGCGAAACTCAACAGGCCAAGAAGCACGAGGCTGCTAGCGC   1440

SID_1   1441  CAACAAGGCTGAGCTCCTTGAGCGCTACTCCCCGCCTGCTCAAGGGAACTGCGGCTGGCA   1500
              |||||||||||||||||||||||||||||||||||||||| ||| |||||||||||||||
SID_2   1441  CAACAAGGCTGAGCTCCTTGAGCGCTACTCCCCGCCTGCTGAAGGGAACTGCGGCTGGCA   1500

SID_1   1501  CTGCATCTCTGCCATTGTCAACCGAATGGTAAATTCCAAGTTTGAAACTGCCCTTCCTGA   1560
              ||||||||||||||||||||||||||||||||||||||||||||||||||||||||||||
SID_2   1501  CTGCATCTCTGCCATTGTCAACCGAATGGTAAATTCCAAGTTTGAAACTGCCCTTCCTGA   1560

SID_1   1561  AAAAGTGAGACCCCAGAAGATTGGGCCACTGATGAGGATCTTGTGAACACTATCCAAAT   1620
              ||||||||||||||||||||||||||||||||||||||||||||||||||||||||||||
SID_2   1561  AAAAGTGAGACCCCAGAAGATTGGGCCACTGATGAGGATCTTGTGAACACTATCCAAAT   1620

SID_1   1621  TCTCAGGCTCCCTGCGGCCTTGGACAGGAACGGCGTCTGCGCAAGCGCCAAGTACGTCCT   1680
              ||||||||||||||||||||||||||||||||||||||||||||||||||||||||||||
SID_2   1621  TCTCAGGCTCCCTGCGGCCTTGGACAGGAACGGCGTCTGCGCAAGCGCCAAGTACGTCCT   1680

SID_1   1681  TAAACTGGAGGGTGAACATTGGACTGTTTCAGTGACTCCCGGAATGCCTCCTTCCTTGCT   1740
              ||||||||||||||||||||||||||||||||||||||||||||||||||||||||||||
SID_2   1681  TAAACTGGAGGGTGAACATTGGACTGTTTCAGTGACTCCCGGAATGCCTCCTTCCTTGCT   1740
```

FIG. 5 (cont)

```
SID_1  1741  CCCCCTTGAATGCGTTCAAGGTTGTTGTGAGCACAAGGGCAGTCTTCGTTCTCCAGATGC  1800
             ||||||||||||||||||||||||||||||||||||||||||||||||||||||||||||
SID_2  1741  CCCCCTTGAATGCGTTCAAGGTTGTTGTGAGCACAAGGGCAGTCTTCGTTCTCCAGATGC  1800

SID_1  1801  GGTCGAAGTTTCCGGATTCGACCCTGCCAGCCTTGATCGACTCGCCGGGGTGATGCATCT  1860
             ||||||||||||||||||||||||||||||||||||||||||||||||||||||||||||
SID_2  1801  GGTCGAAGTTTCCGGATTCGACCCTGCCAGCCTTGATCGACTCGCCGGGGTGATGCATCT  1860

SID_1  1861  GCCCAGCAGTGCCATCCCAGCCGCCCTGGCTGAGTTGTCTGGCGACCCTGATCGTCCAGT  1920
             ||||||||||||||||||||||||||||||||||||||||||||||||||||||||||||
SID_2  1861  GCCCAGCAGTGCCATCCCAGCCGCCCTGGCTGAGTTGTCTGGCGACCCTGATCGTCCAGT  1920

SID_1  1921  TTCCCGGCCACCACTGCGTGGACTGTCTCGCAGTTTTATGCTCGCCATAGTGGCGGAGA  1980
             ||||||||||||||||||||||||||||||||||||||||||||||||||||||||||||
SID_2  1921  TTCCCGGCCACCACTGCGTGGACTGTCTCGCAGTTTTATGCTCGCCATAGTGGCGGAGA  1980

SID_1  1981  GCATCCTGACCAAAAGTACTTAAGAAAAATCATCAGCCTCTGCGAGGTGATCGAGAGCTG  2040
             ||||||||||||||||||||||||||||||||||||||||||||||||||||||||||||
SID_2  1981  GCATCCTGACCAAAAGTACTTAAGAAAAATCATCAGCCTCTGCGAGGTGATCGAGAGCTG  2040

SID_1  2041  CTGCTGTTCCCAGAATAAAATCAACCTGGTCACTCCGGAAGAGGTTAAAACAAAAATTGA  2100
             ||||||  ||||||||||||||||||||||||||||||||||||||||||||||||||||
SID_2  2041  CTGCTGCTCCCAGAATAAAATCAACCTGGTCACTCCGGAAGAGGTTAAAACAAAAATTGA  2100

SID_1  2101  CCAATACCTCAGTGGTGCAGCAAGTCTTGAAGAATGCTTGGCCAGGCTTGAGAAGGCTCG  2160
             |||||||||||||||||||||||||||||||||||||||  |||||||||||||||||||
SID_2  2101  CCAATACCTCAGTGGTGCAGCAAGTCTTGAAGAATGTTTGGCCAGGCTTGAGAAGGCTCG  2160

SID_1  2161  CCCGCCAAGCGTGTTGGACACCTCCTTTGATTGGGATGTTGTGCTCCCTGGTGTTGGGGC  2220
             ||||||||||||||||||||||||||||||||||||||||||||||||||||||||||||
SID_2  2161  CCCGCCAAGCGTGTTGGACACCTCCTTTGATTGGGATGTTGTGCTCCCTGGTGTTGGGGC  2220

SID_1  2221  GGCTGTTCGAGCAGCGAAACTGCCCCTCGCCAATCAGTGTCACGCTCCAGTCACTGTTGT  2280
             ||||||||||||||||||||||||||||||||||||||||||||||||||||||||||||
SID_2  2221  GGCTGTTCGAGCAGCGAAACTGCCCCTCGCCAATCAGTGTCACGCTCCAGTCACTGTTGT  2280

SID_1  2281  GACCCAAAGGCCTTCGTTGAAATTTCAGCCTCGAAAAGCGGAATCTGTCAAGAGCTTACC  2340
             ||||||||||||||||||||||||||||||||||||||||||||||||||||||||||||
SID_2  2281  GACCCAAAGGCCTTCGTTGAAATTTCAGCCTCGAAAAGCGGAATCTGTCAAGAGCTTACC  2340

SID_1  2341  AGAGAGCAGGCCTCTTCCTGCCCCGCGCAGGAAGATTAGGTCCAGGTGTGGTAGTCTGAC  2400
             ||||||||||||||||||||||||||||||||||||||||||||||||||||||||||||
SID_2  2341  AGAGAGCAGGCCTCTTCCTGCCCCGCGCAGGAAGATTAGGTCCAGGTGTGGTAGTCTGAC  2400

SID_1  2401  TTCATTGGACGGCAACTTCCCTGACAGCTGGGAAGACTTGGCCGGTGGTCCCTTCCATTT  2460
             ||||||||||||||||||||||||||||||||||||||||||||||||||||||||||||
SID_2  2401  TTCATTGGACGGCAACTTCCCTGACAGCTGGGAAGACTTGGCCGGTGGTCCCTTCCATTT  2460

SID_1  2461  CCCGACCCTACCTGAGCCGACGACACGTCCGGGTGAGCCTGTGCCTGTCCCTGCACCGCG  2520
             ||||||||||||||||||||||||||||||||||||||||||||||||||||||||||||
SID_2  2461  CCCGACCCTACCTGAGCCGACGACACGTCCGGGTGAGCCTGTGCCTGTCCCTGCACCGCG  2520

SID_1  2521  CAAGACTGTGCCCCGATTGGTGTCGTCACTGATAGTGTCAGTCCCTGTGCCCGCACCACG  2580
             ||||||||||||||||||||||||||||||||||||||||||||||||||||||||||||
SID_2  2521  CAAGACTGTGCCCCGATTGGTGTCGTCACTGATAGTGTCAGTCCCTGTGCCCGCACCACG  2580

SID_1  2581  ACGTGGGATTCGACAGGCGGAGGGAATGAATTTGGTGGCAGTGACTCCAGCGTGCCAGGA  2640
             ||||||||||||||||||||||||||||||||||||||||||||||||||||||||||||
```

FIG. 5 (cont)

```
SID_2  2581  ACGTGGGATTCGACAGGCGGAGGGAATGAATTTGGTGGCAGTGACTCCAGCGTGCCAGGA  2640

SID_1  2641  CGAGCTCCTCGATTTATCTGAATCCTCGCAGGCTGAGCATGGGGCTCCCTCCTTGGCATT  2700
             ||||||||||||||||||||||||||||||||||||||||||||||||||||||||||||
SID_2  2641  CGAGCTCCTCGATTTATCTGAATCCTCGCAGGCTGAGCATGGGGCTCCCTCCTTGGCATT  2700

SID_1  2701  GCCGCGGAGTGAGGATGCCCTGGCGGTGGGGAGACGAGAAGCTGAAGAAGTTCTGAGCGA  2760
             ||||||||||||||||||||||||||||||||||||||||||||||||||||||||||||
SID_2  2701  GCCGCGGAGTGAGGATGCCCTGGCGGTGGGGAGACGAGAAGCTGAAGAAGTTCTGAGCGA  2760

SID_1  2761  AATCTCGGGCATGCCAGATGACATTAGATTGGTGCCCGTGTCATCAAGCAGCTCCCTGTC  2820
             ||||||||||||||||||||||||||||||||||||||||||||||||||||||||||||
SID_2  2761  AATCTCGGGCATGCCAGATGACATTAGATTGGTGCCCGTGTCATCAAGCAGCTCCCTGTC  2820

SID_1  2821  AAGCGTAGAGATTACACGCCCAAAGTACTCAGCTCAAGCCATCATTGACTCAGGTGGGCC  2880
             ||||||||||||||||||||||||||||||||||||||||||||||||||||||||||||
SID_2  2821  AAGCGTAGAGATTACACGCCCAAAGTACTCAGCTCAAGCCATCATTGACTCAGGTGGGCC  2880

SID_1  2881  CTGTTGTGGGCACCTCCAAGAGGTAAAAGAGAAATACCTCAATGTGATGCGTGAGGCATG  2940
             |||||||||||||||||||||||||||||||||||| |||||||||||||||||||||||
SID_2  2881  CTGTTGTGGGCACCTCCAAGAGGTAAAAGAGAAATGCCTCAATGTGATGCGTGAGGCATG  2940

SID_1  2941  TGATGCGACCAAGCTTGATGACCCTGCCACACGAGAATGGCTTTCCCGTATGTGGGACAG  3000
             ||||||||||||||||||||||||||||||||||||||||||||||||||||||||||||
SID_2  2941  TGATGCGACCAAGCTTGATGACCCTGCCACACGAGAATGGCTTTCCCGTATGTGGGACAG  3000

SID_1  3001  GGTAGACATGCTAACCTGGCGCAACACGTCCATTTTTCAGGCGCCTTTCACTTTGGCTGA  3060
             |||||||||| |||||||||||||||||||||||||||||||||||||||||||||||||
SID_2  3001  GGTAGACATGTTAACCTGGCGCAACACGTCCATTTTTCAGGCGCCTTTCACTTTGGCTGA  3060

SID_1  3061  CAAGTTCAAGCTCCTCCCGAAGATGATACTCGAAACACCGCCGCCCTACCCTTGCGGGTT  3120
             ||||||||||||||||||||||||||||||||||||||||||||||||||||||||||||
SID_2  3061  CAAGTTCAAGCTCCTCCCGAAGATGATACTCGAAACACCGCCGCCCTACCCTTGCGGGTT  3120

SID_1  3121  TGTAATGATGCCCCGCACACCTGCACCTTCTGTGGGTGCGGAGAGCGACCTCACCGTTGG  3180
             ||||||||||||||||||||||||||||||||||||||||||||||||||||||||||||
SID_2  3121  TGTAATGATGCCCCGCACACCTGCACCTTCTGTGGGTGCGGAGAGCGACCTCACCGTTGG  3180

SID_1  3181  TTCAGTTGCTACTGAGGATGTTCCGCGCATTCTCGGGAAGGTGCAAGGTGTTTGCAAAAC  3240
             ||||||||||||||||||||||||||||||||||||||||||||||||||||||||||||
SID_2  3181  TTCAGTTGCTACTGAGGATGTTCCGCGCATTCTCGGGAAGGTGCAAGGTGTTTGCAAAAC  3240

SID_1  3241  AACCGTCCATGAACCCTTAGCACCTTTCGCAGATGGACCGACAGATGGCCAACCTGCTAG  3300
             ||||||||||||||||||||||||||||||||||||||||||||||||||||||||||||
SID_2  3241  AACCGTCCATGAACCCTTAGCACCTTTCGCAGATGGACCGACAGATGGCCAACCTGCTAG  3300

SID_1  3301  AGAACCCCGAACACAAACTCCTCCCGCAGGCACAGGTGGCGTTGGCTTAGTTTTGGATTC  3360
             ||||||||||||||||||||||||||||||||||||||||||||||||||||||||||||
SID_2  3301  AGAACCCCGAACACAAACTCCTCCCGCAGGCACAGGTGGCGTTGGCTTAGTTTTGGATTC  3360

SID_1  3361  TGAAGGATCGCCGGAGCTCACTGATTCGCCGCCTCCAAACGGTACAGACGCGAGCGGAGG  3420
             ||||||||||||||||||||||||||||||||||||||||||||||||||||||||||||
SID_2  3361  TGAAGGATCGCCGGAGCTCACTGATTCGCCGCCTCCAAACGGTACAGACGCGAGCGGAGG  3420

SID_1  3421  GGGACCGTTATACACAGTCAAGAAGAAGGCTGAGAGGTGCTTTGACCAGCTGAGCCGACG  3480
             ||||||||||||||||||||||||||||| ||||||||||||||||||||||||||||||
SID_2  3421  GGGACCGTTATACACAGTCAAGAAGAAGGTTGAGAGGTGCTTTGACCAGCTGAGCCGACG  3480
```

FIG. 5 (cont)

```
SID_1  3481  GGTTTTTGACATCGTCTCCCATCTCCCTGTTTTCTTCTCACGCCTTTTCAAGTCTGACGG  3540
              ||||||||||||||||||||||||||||||||||||||||||||||||||||||||||||
SID_2  3481  GGTTTTTGACATCGTCTCCCATCTCCCTGTTTTCTTCTCACGCCTTTTCAAGTCTGACGG  3540

SID_1  3541  TCATTATGCTCCGGGTGATTGGGGTTTTGCAGCTTTTACTTTATTGTGCCTCTTTCTGTG  3600
              ||||||||||||||||||||||||||||||||||||||||||||||||||||||||||||
SID_2  3541  TCATTATGCTCCGGGTGATTGGGGTTTTGCAGCTTTTACTTTATTGTGCCTCTTTCTGTG  3600

SID_1  3601  TTACAGTTACCCGGCGTTCGGTGTGGTTCCCCTATTGGGTGTATTTTCTGGGTCTTCTCG  3660
              ||||||||||||||||||||||||||||||||||||||||||||||||||||||||||||
SID_2  3601  TTACAGTTACCCGGCGTTCGGTGTGGTTCCCCTATTGGGTGTATTTTCTGGGTCTTCTCG  3660

SID_1  3661  GCGCGTCCGCATGGGGGTTTTTGGTTGTTGGTTGGCTTTCGCTGTTAGTTTGTTCAAGCC  3720
              ||||||||||||||||||||||||||||||||||||||||||||||||||||||||||||
SID_2  3661  GCGCGTCCGCATGGGGGTTTTTGGTTGTTGGTTGGCTTTCGCTGTTAGTTTGTTCAAGCC  3720

SID_1  3721  TGCTCCCGACCCAGTCGGTACTGCTTGTGAGTTTGACTCGCCAGAGTGTAGAGACATCCT  3780
              ||||||||||||||||||||||||||||||||||||||||||||||||||||||||||||
SID_2  3721  TGCTCCCGACCCAGTCGGTACTGCTTGTGAGTTTGACTCGCCAGAGTGTAGAGACATCCT  3780

SID_1  3781  TCATTCTTTTGAGCTTCTGCAACCTTGGGACCCTGTTCGCAGCCTTGTGGTGGGCCCCGT  3840
              ||||||||||||||||||||||||||||||||||||||||||||||||||||||||||||
SID_2  3781  TCATTCTTTTGAGCTTCTGCAACCTTGGGACCCTGTTCGCAGCCTTGTGGTGGGCCCCGT  3840

SID_1  3841  CGGTCTCGGTCTTGCCATTCTTGGCAGGTACTGGGCGGGGCACGCTACGTCTGGTTGTT  3900
              |||||||||||||||||||||||||||||||||||||||||||||||||||||||| ||||
SID_2  3841  CGGTCTCGGTCTTGCCATTCTTGGCAGGTACTGGGCGGGGCACGCTACGTCTGGCTGTT  3900

SID_1  3901  TTTGCTTAGGCTTGGCATCGTTTCAGACTGTATCTTGGCTGGAGCCTATGTGCTTTCGCA  3960
              ||||||||||||||||||||||||||||||||||||||||||||||||||||||||||||
SID_2  3901  TTTGCTTAGGCTTGGCATCGTTTCAGACTGTATCTTGGCTGGAGCCTATGTGCTTTCGCA  3960

SID_1  3961  AGGTAGGTGTAAAAAGTGTTGGGGATCTTGTATAAGAACTGCTCCCAGTGAGGTCGCCTT  4020
              ||||||||||||||||||||||||||||||||||||||||||||||||||||||||||||
SID_2  3961  AGGTAGGTGTAAAAAGTGTTGGGGATCTTGTATAAGAACTGCTCCCAGTGAGGTCGCCTT  4020

SID_1  4021  CAATGTGTTTCCCTTCACACGCGCAACCAGATCGTCACTTATTGACCTGTGCGACCGGTT  4080
              ||||||||||||||||||||||||||||||||||||||||||||||||||||||||||||
SID_2  4021  CAATGTGTTTCCCTTCACACGCGCAACCAGATCGTCACTTATTGACCTGTGCGACCGGTT  4080

SID_1  4081  CTGCGCGCCCAAAGGCATGGACCCCATCTTCCTCGCTACTGGATGGCGTGGATGCTGGGC  4140
              ||||||||||||||||||||||||||||||||||||||||||||||||||||||||||||
SID_2  4081  CTGCGCGCCCAAAGGCATGGACCCCATCTTCCTCGCTACTGGATGGCGTGGATGCTGGGC  4140

SID_1  4141  CGGTCAGAGCCCCATTGAGCAACCCACTGAGAAACCCATTGCGTTCGCCCAGTTGGATGA  4200
              ||||||||||||||||||||||||||||||||||||||||||||||||||||||||||||
SID_2  4141  CGGTCAGAGCCCCATTGAGCAACCCACTGAGAAACCCATTGCGTTCGCCCAGTTGGATGA  4200

SID_1  4201  GAAGAAAATCACTGCTAAAACTGTGGTTGCCCAGCCTTATGACCCCAACCAAGCTGTGAA  4260
              ||||||||||||||||||||||||||||||||||||||||||||||||||||||||||||
SID_2  4201  GAAGAAAATCACTGCTAAAACTGTGGTTGCCCAGCCTTATGACCCCAACCAAGCTGTGAA  4260

SID_1  4261  GTCCTTACGAGTCCTCCAGGCGGGCGGGCCGATGGTGGCTGAGGCGATTCCAAAAGTAGT  4320
              || |||||||||||||||||||||| ||||||||||||||| |||||||||||||||||||
SID_2  4261  GTGCTTACGAGTCCTGCAGGCGGGCGGGGCGATGGTGGCTGAGGCGATTCCAAAAGTAGT  4320

SID_1  4321  CAAAGTTTCTGCTATCCCATTTCGAGCTCCCTTCTTCCCTGTCGGAGTGAAAGTTGATCC  4380
              ||||||||||||||||||||||||||||||||||||||||||||||||||||||||||||
```

FIG. 5 (cont)

```
SID_2  4321  CAAAGTTTCTGCTATCCCATTTCGAGCTCCCTTCTTCCCTGTCGGAGTGAAAGTTGATCC  4380

SID_1  4381  TGAATGCAGGGTCGTGGTTGACTCTGACACCTTCACAACTGCTCTCCGGTCCGGCTACTC  4440
             ||||||||||||||||||||||||||||||||||||||||||||||||||||||||||||
SID_2  4381  TGAATGCAGGGTCGTGGTTGACTCTGACACCTTCACAACTGCTCTCCGGTCCGGCTACTC  4440

SID_1  4441  CACCACAAACCTCATTCTTGGTGTGGGGATTTGCCCAGCTGAATGGGTTGAAAATCAG   4500
             ||||||||||||||||||||||||||||||||||||||||||||||||||||||||||||
SID_2  4441  CACCACAAACCTCATTCTTGGTGTGGGGATTTGCCCAGCTGAATGGGTTGAAAATCAG   4500

SID_1  4501  GCAAATTTCCAAGCCTTCGGGAGGAGGTCCACACATCATGGCGGCCTTACATGTCGCTTG  4560
             ||||||||||||||||||||||||||||||||||||||||||||||||||||||||||||
SID_2  4501  GCAAATTTCCAAGCCTTCGGGAGGAGGTCCACACATCATGGCGGCCTTACATGTCGCTTG  4560

SID_1  4561  CTCGATGGCTTTGCACATGCTCGTTGGGATTTACGTCACTACGGTGGGTTCTTGTGGTTC  4620
             ||||||||||||||||||||||||||||||||||||||||||||||||||||||||||||
SID_2  4561  CTCGATGGCTTTGCACATGCTCGTTGGGATTTACGTCACTACGGTGGGTTCTTGTGGTTC  4620

SID_1  4621  TGGCACTAACGACCCGTGGTGCACTAACCCGTTTGCCGTCCCTGTCTACGGACCTGGCTC  4680
             ||||||||||||||||||||||||||||||||||||||||||||||||||||||||||||
SID_2  4621  TGGCACTAACGACCCGTGGTGCACTAACCCGTTTGCCGTCCCTGTCTACGGACCTGGCTC  4680

SID_1  4681  TCTTTGCACCTCCAGGTTGTGCATCTCCCAGCATGGCCTTACTCTGCCCTTAACAGCGCT  4740
             ||||||||||||||||||||||||||||||||||||||||||||||||||||||||||||
SID_2  4681  TCTTTGCACCTCCAGGTTGTGCATCTCCCAGCATGGCCTTACTCTGCCCTTAACAGCGCT  4740

SID_1  4741  TGTGGCGGGGTTTGGCATTCAGGAAGTTGCCTTGGTGGTTTTAATCTTTGTTTCCATCGG  4800
             ||||||||||||||||||||||||||||||||||||||||||||||||||||||||||||
SID_2  4741  TGTGGCGGGGTTTGGCATTCAGGAAGTTGCCTTGGTGGTTTTAATCTTTGTTTCCATCGG  4800

SID_1  4801  AGGTATGGCTCACAGATTAAGTTGCAAGGCTGATGTACTGTGTATTCTGCTTGCGATTGC  4860
             ||||||||||||||||||||||||||||||||||||||||||||||||||||||||||||
SID_2  4801  AGGTATGGCTCACAGATTAAGTTGCAAGGCTGATGTACTGTGTATTCTGCTTGCGATTGC  4860

SID_1  4861  CAGCTATGTTTGGTTACCCCTCACCTGGTTGCTCTGTGTGTTTCCTTGCTGGTTACGTTG  4920
             ||||||||||||||||||||||||||||||||||||||||||||||||||||||||||||
SID_2  4861  CAGCTATGTTTGGTTACCCCTCACCTGGTTGCTCTGTGTGTTTCCTTGCTGGTTACGTTG  4920

SID_1  4921  GTTTTCTTTGCATCCCCTCACCGTTACATGGTTGGTGTTTTTCTTGATTTCTGTAAACAT  4980
             ||||||||||||||||||||||||||||||||||||||||||||||||||||||||||||
SID_2  4921  GTTTTCTTTGCATCCCCTCACCGTTACATGGTTGGTGTTTTTCTTGATTTCTGTAAACAT  4980

SID_1  4981  GCCCTCAGGAGTCTTGGCCTTGGTGTTGTTAATCTCTCTCTGGCTCCTTGGCCGCTATAC  5040
             ||||||||||||||||||||||||||||||||||||||||||||||||||||||||||||
SID_2  4981  GCCCTCAGGAGTCTTGGCCTTGGTGTTGTTAATCTCTCTCTGGCTCCTTGGCCGCTATAC  5040

SID_1  5041  CAATGTCGCAGGTCTTGTCACTCCTTATGACATTCACCATTACACCAACGGCCCCCGTGG  5100
             ||||||||||||||||||||||||||||||||||||||||||||||||||||||||||||
SID_2  5041  CAATGTCGCAGGTCTTGTCACTCCTTATGACATTCACCATTACACCAACGGCCCCCGTGG  5100

SID_1  5101  CGTTGCCGCCTTGGCCACTGCACCGGATGGGACCTACTTGGCTGCTGTCCGCCGCGCTGC  5160
             ||||||||||||||||||||||||||||||||||||||||||||||||||||||||||||
SID_2  5101  CGTTGCCGCCTTGGCCACTGCACCGGATGGGACCTACTTGGCTGCTGTCCGCCGCGCTGC  5160

SID_1  5161  GCTGACTGGTCGTACCATGCTGTTTACCCCGTCCCAGCTTGGGTCACTCCTTGAGGGTGC  5220
             ||||||||||||||||||||||||||||||||||||||||||||||||||||||||||||
SID_2  5161  GCTGACTGGTCGTACCATGCTGTTTACCCCGTCCCAGCTTGGGTCACTCCTTGAGGGTGC  5220
```

FIG. 5 (cont)

```
SID_1  5221  CTTTAGAACCCAAAAGCCTACACTGAATACCGTCAATGTGGTCGGGTCCTCTATGGGCTC  5280
             ||||||||||||||||||||||||||||||||||||||||||||||||||||||||||||
SID_2  5221  CTTTAGAACCCAAAAGCCTACACTGAATACCGTCAATGTGGTCGGGTCCTCTATGGGCTC  5280

SID_1  5281  CGGCGGGGTGTTCACCATTGACGGGAAAATCAAGTGCGTGACAGCAGCGCATATTCTCAC  5340
             ||||||||||||||||||||||||||||||||||||||||||||||||||||||||||||
SID_2  5281  CGGCGGGGTGTTCACCATTGACGGGAAAATCAAGTGCGTGACAGCAGCGCATATTCTCAC  5340

SID_1  5341  AGGCAACTCTGCCAGGGTCTCCGGGGTCGGCTTCAATCAAATGTTGGATTTCGATGTGAA  5400
             ||||||||||||||||||||||||||||||||||||||||||||||||||||||||||||
SID_2  5341  AGGCAACTCTGCCAGGGTCTCCGGGGTCGGCTTCAATCAAATGTTGGATTTCGATGTGAA  5400

SID_1  5401  AGGGGATTTTGCCATAGCCGATTGTCCGGATTGGCAAGGAGTCGCTCCCAAGTCCCAGTT  5460
             ||||||||||||||||||||||||||||||||||||||||||||||||||||||||||||
SID_2  5401  AGGGGATTTTGCCATAGCCGATTGTCCGGATTGGCAAGGAGTCGCTCCCAAGTCCCAGTT  5460

SID_1  5461  CTGTGAGGATGGGTGGACTGGCCGCGCTTATTGGCTAACATCCTCTGGCGTCGAACCCGG  5520
             ||||||||||||||||||||||||||||||||||||||||||||||||||||||||||||
SID_2  5461  CTGTGAGGATGGGTGGACTGGCCGCGCTTATTGGCTAACATCCTCTGGCGTCGAACCCGG  5520

SID_1  5521  CGTCATCGGGAGGGATTTGCCTTTTGTTTCACCGCGTGCGGCGATTCCGGGTCCCCAGT  5580
             ||||||||||||||||||||||||||||||||||||||||||||||||||||||||||||
SID_2  5521  CGTCATCGGGAGGGATTTGCCTTTTGTTTCACCGCGTGCGGCGATTCCGGGTCCCCAGT  5580

SID_1  5581  GATCACCGAGGCCGGAGAACTTGTCGGTGTCCACACGGGATCAAACAAACAAGGAGGAGG  5640
             |||||||||||||||||||||||||||||||||||||||||||||| |||||||||||||
SID_2  5581  GATCACCGAGGCCGGAGAACTTGTCGGTGTCCACACGGGATCAAATAAACAAGGAGGAGG  5640

SID_1  5641  CATTGTCACGCGCCCTTCAGGCCAGTTTTGTAATGTGACACCCACCAAATTAAGTGAATT  5700
             ||||||||||||||||||||||||||||||||||||||||||||||||||||||||||||
SID_2  5641  CATTGTCACGCGCCCTTCAGGCCAGTTTTGTAATGTGACACCCACCAAATTAAGTGAATT  5700

SID_1  5701  GAGTGAATTCTTCGCTGGACCCAGGGTCCCGCTTGGCGATGTGAAGGTCGGCAACCACAT  5760
             |||||||||||| |||||||||||||||||||||||||||||||||||||||||||||||
SID_2  5701  GAGTGAATTCTTTGCTGGACCCAGGGTCCCGCTTGGCGATGTGAAGGTCGGCAACCACAT  5760

SID_1  5761  AATCAAAGACACAAATGAGGTGCCCTCAGATCTTTGCGCCTTGCTCGCTGCCAAACCCGA  5820
             |||||||||||||||||||||||||||||||||||| |||||||||||||||||||||||
SID_2  5761  AATCAAAGACACAAATGAGGTGCCCTCAGATCTTTGTGCCTTGCTCGCTGCCAAACCCGA  5820

SID_1  5821  GTTGGAAGGAGGTCTCTCCACCGTTCAACTTTTGTGCGTGTTTTCCTCCTATGGAGAAT  5880
             ||||||||||||||||||||||||||||||||||||||||||||||||||||||||||||
SID_2  5821  GTTGGAAGGAGGTCTCTCCACCGTTCAACTTTTGTGCGTGTTTTCCTCCTATGGAGAAT  5880

SID_1  5881  GATGGGACATGCCTGGACGCCTTTGGTTGCTGTTGGTTTTTCGTTTTGAACGAAATCCT  5940
             ||||||||||||||||||||||||||||||||||||||||||||||||||||||||||||
SID_2  5881  GATGGGACATGCCTGGACGCCTTTGGTTGCTGTTGGTTTTTCGTTTTGAACGAAATCCT  5940

SID_1  5941  CCCAGCGGTTCTGGTCCGGAGTGTTTTCTCCTTTGGAATGTTCGCACTGTCTTGGTTCAC  6000
             ||||||||||||||||||||||||||||||||||||||||||||||||||||||||||||
SID_2  5941  CCCAGCGGTTCTGGTCCGGAGTGTTTTCTCCTTTGGAATGTTCGCACTGTCTTGGTTCAC  6000

SID_1  6001  ACCGTGGTCTGCACAAATTCTAATGATCAGGCTTCTAACAGCAGCTCTTAACAGAAACAG  6060
             ||||||||||||||||||||||||||||||||||||||||||||||||||||||||||||
SID_2  6001  ACCGTGGTCTGCACAAATTCTAATGATCAGGCTTCTAACAGCAGCTCTTAACAGAAACAG  6060

SID_1  6061  ATGGTCACTTGCCTTTTACAGCCTTGGTGCACTAACTGGATTTGCTGCAGACCTTGCAAT  6120
             ||||||||||||||||||||||||||||||||||||||||||||||||||||||||||||
```

FIG. 5 (cont)

```
SID_2  6061  ATGGTCACTTGCCTTTTACAGCCTTGGTGCACTAACTGGATTTGCTGCAGACCTTGCAAT  6120

SID_1  6121  TAATCAGGGGCACTCGCTGCACGTGGCCATGAATTTTAGCACCTATGCATTCCTACCTCG  6180
             ||||||||||||||||||||||||||||||||||||||||||||||||||||||||||||
SID_2  6121  TAATCAGGGGCACTCGCTGCACGTGGCCATGAATTTTAGCACCTATGCATTCCTACCTCG  6180

SID_1  6181  TGCAATGGCCGTGACCTCACCAGTCCCAACGATTGCGTGTGGTGTTGTGCACTTGCTTGC  6240
             ||||||||||||||||||||||||||||||||||||||||||||||||||||||||||||
SID_2  6181  TGCAATGGCCGTGACCTCACCAGTCCCAACGATTGCGTGTGGTGTTGTGCACTTGCTTGC  6240

SID_1  6241  TATTGTTTTGTACTTGTTCAAGTACCGCAGCCTGCATACCGTCTTGGTCGGCGATGGAGC  6300
             ||||||||||||||||||||||||||||||||||||||||||||||||||||||||||||
SID_2  6241  TATTGTTTTGTACTTGTTCAAGTACCGCAGCCTGCATACCGTCTTGGTCGGCGATGGAGC  6300

SID_1  6301  GTTTTCCGCAGCTTTCTTTTTGCGATACTTTGCGGAGGGAAAACTGAGGGAAGGGGTGTC  6360
             ||||||||||||||||||||||||||||||||||||||||||||||||||||||||||||
SID_2  6301  GTTTTCCGCAGCTTTCTTTTTGCGATACTTTGCGGAGGGAAAACTGAGGGAAGGGGTGTC  6360

SID_1  6361  GCAGTCTTGCGGCATGAATCATGAGTCACTGACTGGTGCCATCGCCATCAGACTCGACGA  6420
             ||||||||||||||||||||||||||||||||||||||||||||||||||||||||||||
SID_2  6361  GCAGTCTTGCGGCATGAATCATGAGTCACTGACTGGTGCCATCGCCATCAGACTCGACGA  6420

SID_1  6421  CGAGGACCTGGATTTCCTTATAAAACTGACTGATTTTAAGTGCTTTGTTTCCGCGTCCAA  6480
             |||||||||||||||||||||||||||||| |||||||||||||||||||||||||||||
SID_2  6421  CGAGGACCTGGATTTCCTTATAAAACTGTCTGATTTTAAGTGCTTTGTTTCCGCGTCCAA  6480

SID_1  6481  CATGAGGAATGCGGCAGGCCAGTTCATCGAGGCCGCTTATGCCAAAGCACTTAGGGTGGA  6540
             ||||||||||||||||||||||||||||||||||||||||||||||||||||||||||||
SID_2  6481  CATGAGGAATGCGGCAGGCCAGTTCATCGAGGCCGCTTATGCCAAAGCACTTAGGGTGGA  6540

SID_1  6541  ACTTGCTCAGTTAGTGCAGGTTGACAAGGTCCGTGGTGTCTTAGCTAAGCTTGAAGCATT  6600
             ||||||||||||||||||||||||||||||||||||||||||||||||||||||||||||
SID_2  6541  ACTTGCTCAGTTAGTGCAGGTTGACAAGGTCCGTGGTGTCTTAGCTAAGCTTGAAGCATT  6600

SID_1  6601  TGCTGACACTGCGACGCCCCAACTCTCACCTGGCGACATTGTTGTTGCTCTTGGCCATAC  6660
             ||||||||||||||||||||||||||||||||||||||||||||||||||||||||||||
SID_2  6601  TGCTGACACTGCGACGCCCCAACTCTCACCTGGCGACATTGTTGTTGCTCTTGGCCATAC  6660

SID_1  6661  GCCTGTTGGCAGTATCTTCGACTTGAAAGTGGGCAGCACCAAGCATACCCTACAAGCCAT  6720
             ||||||||||||||||||||||||||||||||||||||||||||||||||||||||||||
SID_2  6661  GCCTGTTGGCAGTATCTTCGACTTGAAAGTGGGCAGCACCAAGCATACCCTACAAGCCAT  6720

SID_1  6721  CGAGACCAGAGTCCTCGCTGGGTCCAGAATGACCGTGGCGCGCGTCGTTGATCCGACTCC  6780
             |||||||||||||||||||||||||||||||||||||||||||||||||  ||| |||||
SID_2  6721  CGAGACCAGAGTCCTCGCTGGGTCCAGAATGACCGTGGCGCGCGTCGTAGATCCGACTCC  6780

SID_1  6781  CGCACCTCCACCCGTGCCCGTGCCCATTCCTCTCCCGCCGAAAGTTTTAGAGAACGGCCC  6840
             ||||||||||||||||||||||||||||||||||||||||||||||||||||||||||||
SID_2  6781  CGCACCTCCACCCGTGCCCGTGCCCATTCCTCTCCCGCCGAAAGTTTTAGAGAACGGCCC  6840

SID_1  6841  CCGTGCCTGGGAGGACGAGGACCGTCTGAACAAAAGAGGCGGCGCAAAATGGAAGCCGT  6900
             |||||||||||||||||||||||||||||||||||||||||||||||||||||||||||
SID_2  6841  CCGTGCCTGGGAGGACGAGGACCGTCTGAACAAAAGAGGCGGCGCAAAATGGAAGCCGT  6900

SID_1  6901  TGGCATTTATGTCATGGACGGGAAAAAGTACCAAAAATTTGGGATAAGAATTCTGGTGA  6960
             |||||||||||||||||||||||||||||||||||||||||||||| ||| |||||||||
SID_2  6901  TGGCATTTATGTCATGGACGGGAAAAAGTACCAAAAATTTGGGATCAGAATTCTGGTGA  6960
```

FIG. 5 (cont)

```
SID_1  6961  TGTGTTCTATGAGGAAGTCCACGATAACACAGACGCGTGGGAATGCCTCAGAACTGACGA  7020
             ||||||||||||||||||||||||||||||||||||||||||||||||||||||||||||
SID_2  6961  TGTGTTCTATGAGGAAGTCCACGATAACACAGACGCGTGGGAATGCCTCAGAACTGACGA  7020

SID_1  7021  CCCTGCCGACTTGGATCCTGAGAAGGGGACTTTGTGTGGGCACCTCACCATAGAGAATAG  7080
             ||||||||||||||||||||||||||||||||||||||||||||||||||||||||||||
SID_2  7021  CCCTGCCGACTTGGATCCTGAGAAGGGGACTTTGTGTGGGCACCTCACCATAGAGAATAG  7080

SID_1  7081  ACCTTACCATGTTTACGCCTCCCCTTCCGGTAGGAAGTTCCTGGTCCCTGCCAACCCAGA  7140
             ||||||||||||||||||||||||||||||||||||||||||||||||||||||||||||
SID_2  7081  ACCTTACCATGTTTACGCCTCCCCTTCCGGTAGGAAGTTCCTGGTCCCTGCCAACCCAGA  7140

SID_1  7141  GAGTGGGAAAGCCCAGTGGGAAGCTGCAAGGCTTTCCATAGAGCAGGCCCTTGGCATGAT  7200
             ||||||||||||||||||||||||||||||||||||||||||||||||||||||||||||
SID_2  7141  GAGTGGGAAAGCCCAGTGGGAAGCTGCAAGGCTTTCCATAGAGCAGGCCCTTGGCATGAT  7200

SID_1  7201  GAACGTCGACGGCGAGTTGACCGCCAAGGAGGTAGAGAAACTGAAGAGAATAATTGACAA  7260
             ||||||||||||||||||||||||||||||||||||||||||||||||||||||||||||
SID_2  7201  GAACGTCGACGGCGAGTTGACCGCCAAGGAGGTAGAGAAACTGAAGAGAATAATTGACAA  7260

SID_1  7261  ACTCCAGGGCCTGACTAAGGAGCAGTGTTAAACTACTAGCCGCCAGCGGCTTGACCCGC  7320
             ||||||||||||||||||||||||||||||||||||||||||||||||||||||||||||
SID_2  7261  ACTCCAGGGCCTGACTAAGGAGCAGTGTTAAACTACTAGCCGCCAGCGGCTTGACCCGC  7320

SID_1  7321  TGTGGTCGCGGCGGCTTGGTTATTACTGAGACAGCGGTGAAAATAGTCAGATTCCACAGT  7380
             |||||||||||||||||||||||| |||||||||||||||||||||||||||||||||||
SID_2  7321  TGTGGTCGCGGCGGCTTGGTTATTGCTGAGACAGCGGTGAAAATAGTCAGATTCCACAGT  7380

SID_1  7381  CGGACCTTTACCCTGGGGCCTGTGAATTTGAAAGTGGCTAGCGAGGTTGAGTTGAAAGAC  7440
             ||||||||||||||||||||||||||||||||||||||||||||||||||||||||||||
SID_2  7381  CGGACCTTTACCCTGGGGCCTGTGAATTTGAAAGTGGCTAGCGAGGTTGAGTTGAAAGAC  7440

SID_1  7441  GCCGTCGAGCACAACCAACACCCAATTGCAAGACCAGTTGACGGTGGCGTTGTGCTCCTG  7500
             ||||||||||||||||||||||||||||||||||||||||||||||||||||||||||||
SID_2  7441  GCCGTCGAGCACAACCAACACCCAATTGCAAGACCAGTTGACGGTGGCGTTGTGCTCCTG  7500

SID_1  7501  CGCTCTGCAGTTCCTTCGCTCATAGACGTCTTGATCTCCGGGGCCGACGCATCCCCTCAG  7560
             ||||||||||||||||||||||||||||||||||||||||||||||||||||||||||||
SID_2  7501  CGCTCTGCAGTTCCTTCGCTCATAGACGTCTTGATCTCCGGGGCCGACGCATCCCCTCAG  7560

SID_1  7561  TTACTCGCCCATCATGGGCCAGGAAACACCGGGATTGATGGCACGCTCTGGGATTTTGAG  7620
             |||||||||||||||||||||||||||||||||||||||| |||||||||||||||||||
SID_2  7561  TTACTCGCCCATCATGGGCCAGGAAACACCGGGATTGATGGTACGCTCTGGGATTTTGAG  7620

SID_1  7621  TCCGTAGCCACTAAAGAGGAAGTCACACTTAGTGCACAGATAATACAGGCTTGTGGCATT  7680
             ||||||||||||||||||||||||||||||||||||||||||||||||||||||||||||
SID_2  7621  TCCGTAGCCACTAAAGAGGAAGTCACACTTAGTGCACAGATAATACAGGCTTGTGGCATT  7680

SID_1  7681  AGGCGCGGCGATGCTCCTGAGATCGGCCTCCCTTACAAACTGCACCCTGTTAGGGGCAAC  7740
             ||||||||||||||||||||||||||||||||||||||||||||||||||||||||||||
SID_2  7681  AGGCGCGGCGATGCTCCTGAGATCGGCCTCCCTTACAAACTGCACCCTGTTAGGGGCAAC  7740

SID_1  7741  CCTGAACGTGTAAAAGGGGTTTTGAAGAACACAAGGTTTGGGGACATACCTTACAAGACC  7800
             ||||||||||||||||||||||||||||||||||||||||||||||||||||||||||||
SID_2  7741  CCTGAACGTGTAAAAGGGGTTTTGAAGAACACAAGGTTTGGGGACATACCTTACAAGACC  7800

SID_1  7801  CCTAGTGACACTGGGAGCCCTGTACATGCGGCCGCCTGTCTTACGCCTAATGCCACCCCG  7860
             ||||||||||||||||||||||||||||||||||||||||||||||||||||||||||||
```

FIG. 5 (cont)

```
SID_2  7801  CCTAGTGACACTGGGAGCCCTGTACATGCGGCCGCCTGTCTTACGCCTAATGCCACCCCG  7860

SID_1  7861  GTGACTGACGGGCGCTCCGTCTTGGCCACGACCATGCCCTCCGGGTTTGAGTTGTATGTG  7920
             ||||||||||||||||||||||||||||||||||||||||||||||||||||||||||||
SID_2  7861  GTGACTGACGGGCGCTCCGTCTTGGCCACGACCATGCCCTCCGGGTTTGAGTTGTATGTG  7920

SID_1  7921  CCGACCATTCCAGCATCTGTCCTTGATTACCTTGATTCCAGGCCAGACTGCCCTAAACAG  7980
             ||||||||||||||||||||||||||||||||||||||||||||||||||||||||||||
SID_2  7921  CCGACCATTCCAGCATCTGTCCTTGATTACCTTGATTCCAGGCCAGACTGCCCTAAACAG  7980

SID_1  7981  TTGACGGAGCACGGGTGTGAAGATGCTGCATTGAGAGATCTCTCCAAATATGACTTGTCC  8040
             ||||||||||||||||||||||||||||||||||||||||||||||||||||||||||||
SID_2  7981  TTGACGGAGCACGGGTGTGAAGATGCTGCATTGAGAGATCTCTCCAAATATGACTTGTCC  8040

SID_1  8041  ACCCAAGGTTTTGTTTTGCCCGGGGTCCTCCGCCTCGTACGGAAATATTTATTTGCCCAC  8100
             ||||||||||||||||||||||||||||||||||||||||||||||||||||||||||||
SID_2  8041  ACCCAAGGTTTTGTTTTGCCCGGGGTCCTCCGCCTCGTACGGAAATATTTATTTGCCCAC  8100

SID_1  8101  GTGGGCAAGTGCCCGCCTGTCCATCGGCCCTCCACCTACCCGGCCAAGAATTCCATGGCT  8160
             ||||||||||||||||||||||||||||||||||||||||||||||||||||||||||||
SID_2  8101  GTGGGCAAGTGCCCGCCTGTCCATCGGCCCTCCACCTACCCGGCCAAGAATTCCATGGCT  8160

SID_1  8161  GGAATAAACGGGAATAGGTTCCCAACCAAGGACATTCAGAGCATTCCTGAGATCGACGTT  8220
             ||||||||||||||||||||||||||||||||||||||||||||||||||||||||||||
SID_2  8161  GGAATAAACGGGAATAGGTTCCCAACCAAGGACATTCAGAGCATTCCTGAGATCGACGTT  8220

SID_1  8221  CTATGTGCACAGGCTGTACGAGAGAACTGGCAAACTGTTACCCCTTGCACCCTCAAGAAG  8280
             ||||||||||||||||||||||||||||||||||||||||||||||||||||||||||||
SID_2  8221  CTATGTGCACAGGCTGTACGAGAGAACTGGCAAACTGTTACCCCTTGCACCCTCAAGAAG  8280

SID_1  8281  CAGTATTGCGGGAAGAAGAAAACCAGGACCATACTCGGTACCAATAACTTTATCGCGCTG  8340
             ||||||||||||||||||||||||||||||||||||||||||||||||||||||||||||
SID_2  8281  CAGTATTGCGGGAAGAAGAAAACCAGGACCATACTCGGTACCAATAACTTTATCGCGCTG  8340

SID_1  8341  GCCCACCGGGCAGCGCTGAGTGGTGTCACCCAGGGCTTCATGAAAAAGGCATTTAACTCG  8400
             |||||||||||||||||||||||||||| |||||||||||||| ||||||||||||||||
SID_2  8341  GCCCACCGGGCAGCGCTGAGTGGAGTCACCCAGGGCTTTATGAAAAAGGCATTTAACTCG  8400

SID_1  8401  CCCATTGCCCTCGGGAAGAATAAATTCAAGGAGCTACAAACTCCGGTCCTGGGCAGGTGC  8460
             ||||||||||||||||||||||||||||||||||||||||||||||||||||||||||||
SID_2  8401  CCCATTGCCCTCGGGAAGAATAAATTCAAGGAGCTACAAACTCCGGTCCTGGGCAGCTGC  8460

SID_1  8461  CTTGAGGCTGATCTTGCATCTTGCGATCGATCCACTCCCGCGATTGTCCGCTGGTTTGCC  8520
             ||||||||||||||||||||||||||||||||||||||||||||||||||||||||||||
SID_2  8461  CTTGAGGCTGATCTTGCATCTTGCGATCGATCCACTCCCGCGATTGTCCGCTGGTTTGCC  8520

SID_1  8521  GCCCATCTCCTTTATGAACTTGCCTGCGCTGAAGAGCACCTACCGTCATATGTCTGAAC  8580
             ||||||||||||||||||||||||||||||||||||||||||||||||||||||||||||
SID_2  8521  GCCCATCTCCTTTATGAACTTGCCTGCGCTGAAGAGCACCTACCGTCATATGTCTGAAC  8580

SID_1  8581  TGCTGTCATGACCTATTGGTCACGCAATCCGGTGCGGTGACTAAGAGAGGTGGCCTGTCA  8640
             ||||||||||||||||||||||||||||||||||||||||||||||||||||||||||||
SID_2  8581  TGCTGTCATGACCTATTGGTCACGCAATCCGGTGCGGTGACTAAGAGAGGTGGCCTGTCA  8640

SID_1  8641  TCTGGTGATCCGATCACCTCTGTGTCCAACACCATTTACAGTCTGGTGATTTACGCGCAG  8700
             ||||||||||||||||||||||||||||||||||||||||||||||||||||||||||||
SID_2  8641  TCTGGTGATCCGATCACCTCTGTGTCCAACACCATTTACAGTCTGGTGATTTACGCGCAG  8700
```

FIG. 5 (cont)

```
SID_1  8701  CACATGGTGCTCAGTTACTTTAAAAGTGGTCACCCACATGGTCTCTTGTTCCTTCAGGAC  8760
              ||||||||||||||||||||||||||||||||||||||||||||||||||||||||||||
SID_2  8701  CACATGGTGCTCAGTTACTTTAAAAGTGGTCACCCACATGGTCTCTTGTTCCTTCAGGAC  8760

SID_1  8761  CAGCTAAAGTTTGAGGACATGCTCAAGGTTCAACCCCTGATTGTCTACTCGGACGATCTT  8820
              ||||||||||||||||||||||||||||||||||||||||||||||||||||||||||||
SID_2  8761  CAGCTAAAGTTTGAGGACATGCTCAAGGTTCAACCCCTGATTGTCTACTCGGACGATCTT  8820

SID_1  8821  GTGCTGTATGCCGAGTCTCCCACCATGCCAAACTACCATTGGTGGGTTGAGCACCTGAAT  8880
              ||||||||||||||||||||||||||||||||||||||||||||||||||||||||||||
SID_2  8821  GTGCTGTATGCCGAGTCTCCCACCATGCCAAACTACCATTGGTGGGTTGAGCACCTGAAT  8880

SID_1  8881  TTGATGTTAGGGTTTCAGACGGACCCGAAGAAAACAACCATTACTGACTCGCCGTCTTTC  8940
              ||||||||||||||||||||||||||||||||||||||||||||||||||||||||||||
SID_2  8881  TTGATGTTAGGGTTTCAGACGGACCCGAAGAAAACAACCATTACTGACTCGCCGTCTTTC  8940

SID_1  8941  CTGGGCTGCAGGATAATGAATGGGTGTCAGCTAGTCCCAAACCGTGACAGGATTCTCGCA  9000
              ||||||||||||||||||||||||||||||||||||||||||||||||||||||||||||
SID_2  8941  CTGGGCTGCAGGATAATGAATGGGTGTCAGCTAGTCCCAAACCGTGACAGGATTCTCGCA  9000

SID_1  9001  GCTCTTGCCTACCACATGAAGGCGAATAATGTTTCTGAGTACTACGCCTCCGCCGCTGCA  9060
              ||||||||||||||||||||||||||||||||||||||||||||||||||||||||||||
SID_2  9001  GCTCTTGCCTACCACATGAAGGCGAATAATGTTTCTGAGTACTACGCCTCCGCCGCTGCA  9060

SID_1  9061  ATACTCATGGACAGTTGTGCTTGTCTGGAGTACGACCCTGAATGGTTTGAAGAACTTGTG  9120
              ||||||||||||||||||||||||||||||||||||||||||||||||||||||||||||
SID_2  9061  ATACTCATGGACAGTTGTGCTTGTCTGGAGTACGACCCTGAATGGTTTGAAGAACTTGTG  9120

SID_1  9121  GTAGGAATGGCGCAATGCGCTCGCAAGGACGGCTATAGCTTCCCCGGCCCGCCGTTCTTC  9180
              ||||||||||||||||||||||||||||||||||||||||||||||||||||||||||||
SID_2  9121  GTAGGAATGGCGCAATGCGCTCGCAAGGACGGCTATAGCTTCCCCGGCCCGCCGTTCTTC  9180

SID_1  9181  CTATCCATGTGGGAGAAACTCAGGTCTAATTATGAGGGGAAGAGGTCAAGGGTGTGTGGG  9240
              ||||||||||||||||||||||||||||||||||||||||||||||||||||||||||||
SID_2  9181  CTATCCATGTGGGAGAAACTCAGGTCTAATTATGAGGGGAAGAGGTCAAGGGTGTGTGGG  9240

SID_1  9241  TACTGCGGAGCTTCAGCCCCGTATGCCACTTCCTGTGGTCTTGATGTCTGTGTTTACCAC  9300
              ||||||||||||||||||||||||||||||||||||||||||||||||||||||||||||
SID_2  9241  TACTGCGGAGCTTCAGCCCCGTATGCCACTTCCTGTGGTCTTGATGTCTGTGTTTACCAC  9300

SID_1  9301  ACTCACTTCCACCAGCATTGTCCAGTCATAATCTGGTGTGGCCACCCGGCGGGTTCTGGG  9360
              ||||||||||||||||||||||||||||||||||||||||||||||||||||||||||||
SID_2  9301  ACTCACTTCCACCAGCATTGTCCAGTCATAATCTGGTGTGGCCACCCGGCGGGTTCTGGG  9360

SID_1  9361  TCCTGTGATGATTGCAAATCTCCCACAGGGAAAGATACAAACCCCCTGGATGAGGTCTTA  9420
              ||||||||||||||||||||||||||||||||||||||||||||||||||||||||||||
SID_2  9361  TCCTGTGATGATTGCAAATCTCCCACAGGGAAAGATACAAACCCCCTGGATGAGGTCTTA  9420

SID_1  9421  AAACAAGTCCCATATAAGCCTCCACGGACTGTCCTCATGCATGTGGAGCAGGGCCTCACC  9480
              ||||||||||||||||||||||||||||||||||||||||||||||||||||||||||||
SID_2  9421  AAACAAGTCCCATATAAGCCTCCACGGACTGTCCTCATGCATGTGGAGCAGGGCCTCACC  9480

SID_1  9481  CCCCTTGACCCAGGCAGATATCAGACCCGTCGTGGGTTGGTTGCCGTTAGGCGCGGGATC  9540
              ||||||||||||||||||||||||||||||||||||||||||||||||||||||||||||
SID_2  9481  CCCCTTGACCCAGGCAGATATCAGACCCGTCGTGGGTTGGTTGCCGTTAGGCGCGGGATC  9540

SID_1  9541  AGGGGAAATGAAGTCGACCTACCAGATGGTGATTATGCCAGCACCGCGTTACTCCCAACT  9600
              ||||||||||||||||||||||||||||||||||||||||||||||||||||||||||||
```

FIG. 5 (cont)

```
SID_2   9541   AGGGGAAATGAAGTCGACCTACCAGATGGTGATTATGCCAGCACCGCGTTACTCCCAACT   9600

SID_1   9601   TGTAAAGAGATCAACATGGTCGCTGTTGCTTCCAATGTATTGCGCAGTAGATTTATCATC   9660
               ||||||||||||||||||||||||||||||||||||||||||||||||||||||||||||
SID_2   9601   TGTAAAGAGATCAACATGGTCGCTGTTGCTTCCAATGTATTGCGCAGTAGATTTATCATC   9660

SID_1   9661   GGTCCACCCGGTGCTGGAAAAACACACTGGCTCCTTCAACAGGTTCAGGATGGTGATGTC   9720
               ||||||||||||||||||||||||||||||||||||||||||||||||||||||||||||
SID_2   9661   GGTCCACCCGGTGCTGGAAAAACACACTGGCTCCTTCAACAGGTTCAGGATGGTGATGTC   9720

SID_1   9721   ATTTATACACCGACCCACCAGACCATGCTCGACATGATTAAAGCTTTGGGGACGTGTCGA   9780
               ||||||||||||||||||||||||||||||||||||||||||||||||||||||||||||
SID_2   9721   ATTTATACACCGACCCACCAGACCATGCTCGACATGATTAAAGCTTTGGGGACGTGTCGA   9780

SID_1   9781   TTTAACGTTCCGGCAGGTACAACGCTGCAATTCCCCGCCCCTTCCCGCACTGGCCCGTGG   9840
               ||||||||||||||||||||||||||||||||||||||||||||||||||||||||||||
SID_2   9781   TTTAACGTTCCGGCAGGTACAACGCTGCAATTCCCCGCCCCTTCCCGCACTGGCCCGTGG   9840

SID_1   9841   GTTCGCATCCTGGCTGGCGGGTGGTGTCCTGGCAAAAATTCATTCCTGGACGAAGCTGCG   9900
               ||||||||||||||||||||||||||||||||||||||||||||||||||||||||||||
SID_2   9841   GTTCGCATCCTGGCTGGCGGGTGGTGTCCTGGCAAAAATTCATTCCTGGACGAAGCTGCG   9900

SID_1   9901   TATTGCAACCATCTTGATGTCTTGAGGCTCCTTAGCAAAACTACTCTCACCTGTTTGGGA   9960
               |||||||||||||||||||||||||||||||||||||||||||||||||||||||| |||
SID_2   9901   TATTGCAACCATCTTGATGTCTTGAGGCTCCTTAGCAAAACTACTCTCACCTGTTTAGGA   9960

SID_1   9961   GACTTCAAACAACTCCACCCGGTGGGTTTTGATTCTCACTGCTATGTCTTTGACATCATG   10020
               ||||||||||||||||||||||||||||||||||||||||||||||||||||||||||||
SID_2   9961   GACTTCAAACAACTCCACCCGGTGGGTTTTGATTCTCACTGCTATGTCTTTGACATCATG   10020

SID_1   10021  CCTCAAACTCAACTGAAGACTATCTGGAGGTTTGGACAGAATATCTGTGATGCCATTCAA   10080
               ||||||||||||||||||||||||||||||||||||||||| ||||||||||||||||||
SID_2   10021  CCTCAAACTCAACTGAAGACTATCTGGAGGTTTGGACACAATATCTGTGATGCCATTCAA   10080

SID_1   10081  CCAGATTACAGGGACAAGCTTATGTCCATGGTCAACACAACTCGTGTAACCTATGTGGAA   10140
               ||||||||||||||||||||||||||||||||||||||||||||||||||||||||||||
SID_2   10081  CCAGATTACAGGGACAAGCTTATGTCCATGGTCAACACAACTCGTGTAACCTATGTGGAA   10140

SID_1   10141  AAGCCCGTCAAATATGGGCAAGTCCTCACCCCTTACCATAGGGACCGAGAGGATGGCGCC   10200
               ||||||||||||||||||||||||||||||||||||||||||||||||||||||||||||
SID_2   10141  AAGCCCGTCAAATATGGGCAAGTCCTCACCCCTTACCATAGGGACCGAGAGGATGGCGCC   10200

SID_1   10201  ATTACCATTGACTCCAGTCAAGGTGCCACATTTGATGTGGTTACACTGCATTTGCCCACG   10260
               ||||||||||||||||||||||||||||||||||||||||||||||||||||||||||||
SID_2   10201  ATTACCATTGACTCCAGTCAAGGTGCCACATTTGATGTGGTTACACTGCATTTGCCCACG   10260

SID_1   10261  AAAGATTCACTCAACAAACAAAGGGCCCTTGTTGCTATCACCAGGGCAAGACATGCCATC   10320
               ||||||||||||||||||||||||||||||||||||||||||||||||||||||||||||
SID_2   10261  AAAGATTCACTCAACAAACAAAGGGCCCTTGTTGCTATCACCAGGGCAAGACATGCCATC   10320

SID_1   10321  TTTGTGTATGACCCATATAGGCAACTGCAGAGCTTATTTGATCTTCCTGCAAAAAGCACG   10380
               |||||||||||||||||||||||||||||||||||||||||| |||||||||||||||||
SID_2   10321  TTTGTGTATGACCCATATAGGCAACTGCAGAGCTTATTTGGTCTTCCTGCAAAAAGCACG   10380

SID_1   10381  CCCGTCAACCTGGCCGTGCACCGCGATGGGCAACTGATTGTGCTAGACAGAAATAATAAA   10440
               ||||||||||||||||||||||||||||||||||||||||||||||||||||||||||||
SID_2   10381  CCCGTCAACCTGGCCGTGCACCGCGATGGGCAACTGATTGTGCTAGACAGAAATAATAAA   10440
```

FIG. 5 (cont)

```
SID_1  10441  GAATGCACGGTTGCCCAGGCTCTGGGCAATGGTGACAAATTCAGAGCTACAGATAAGCGC  10500
              ||||||||||||||||||||||||||||||||||||||||||||||||||||||||||||
SID_2  10441  GAATGCACGGTTGCCCAGGCTCTGGGCAATGGTGACAAATTCAGAGCTACAGATAAGCGC  10500

SID_1  10501  GTTGTAGATTCTCTTCGCGCCATTTGTGCTGACCTGGAAGGGTCGAGCTCGCCGCTTCCC  10560
              ||||||||||||||||||||||||||||||||||||||||||||||||||||||||||||
SID_2  10501  GTTGTAGATTCTCTTCGCGCCATTTGTGCTGACCTGGAAGGGTCGAGCTCGCCGCTTCCC  10560

SID_1  10561  AAGGTTGCACATAACTTGGGGTTTTATTTCTCACCTGATTTGACACAGTTTGCCAAGCTT  10620
              ||||||||||||||||||||||||||||||||||||||||||||||||||||||||||||
SID_2  10561  AAGGTTGCACATAACTTGGGGTTTTATTTCTCACCTGATTTGACACAGTTTGCCAAGCTT  10620

SID_1  10621  CCAATAGAACTTGCACCACATTGGCCAGTGGTGACGACCCAAAATAATGAGAACTGGCCT  10680
              ||||||||||||||||||||||||||||||||||||||||||||||||||||||||||||
SID_2  10621  CCAATAGAACTTGCACCACATTGGCCAGTGGTGACGACCCAAAATAATGAGAACTGGCCT  10680

SID_1  10681  GATCGACTGGTTGCCAGCCTACGCCCCATTCACAAATATAGCCGTGCATGTATCGGTGCC  10740
              ||||||||||||||||||||||||||||||||||||||||||||||||||||||||||||
SID_2  10681  GATCGACTGGTTGCCAGCCTACGCCCCATTCACAAATATAGCCGTGCATGTATCGGTGCC  10740

SID_1  10741  GGCTATATGGTGGGCCCCTCGGTGTTTTAGGCACCCCTGGGGTAGTATCATACTATCTC   10800
              ||||||||||||||||||||||||||||||||||||||||||||||||||||||||||||
SID_2  10741  GGCTATATGGTGGGCCCCTCGGTGTTTTAGGCACCCCTGGGGTAGTATCATACTATCTC   10800

SID_1  10801  ACAAAATTTGTCAAAGGCGAGGCTCAGGTGCTTCCAGAAACGGTCTTCAGCACTGGCCGA  10860
              ||||||||||||||||||||||||||||||||||||||||||||||||||||||||||||
SID_2  10801  ACAAAATTTGTCAAAGGCGAGGCTCAGGTGCTTCCAGAAACGGTCTTCAGCACTGGCCGA  10860

SID_1  10861  ATTGAGGTGGACTGCCGAGAGTACCTTGATGATCGGGAGCGGGAAGTCGCAGCGTCCCTC  10920
              |||||||||||||||||||||||||||||||||||| |||||||||||||||||||||||
SID_2  10861  ATTGAGGTGGACTGCCGAGAGTACCTTGATGATTGGGAGCGGGAAGTCGCAGCGTCCCTC  10920

SID_1  10921  CCGCATGCCTTTATCGGCGACGTCAAAGGCACTACTGTGGGAGGGTGTCACCATGTCACC  10980
              ||||||||||||||||||||||||||||||||||||||||||||||||||||||||||||
SID_2  10921  CCGCATGCCTTTATCGGCGACGTCAAAGGCACTACTGTGGGAGGGTGTCACCATGTCACC  10980

SID_1  10981  TCTAAATATCTCCCGCGCTTCCTCCCCAAGGAATCAGTCGCGGTGGTCGGGGTTTCAAGC  11040
              ||||||||||||||||||||||||||||||||||||||||||||||||||||||||||||
SID_2  10981  TCTAAATATCTCCCGCGCTTCCTCCCCAAGGAATCAGTCGCGGTGGTCGGGGTTTCAAGC  11040

SID_1  11041  CCCGGGAAAGCCGCAAAAGCAGTGTGCACATTGACGGATGTGTACCTCCCAGACCTTGAG  11100
              ||||||||||||||||||||||||||||||||||||||||||||||||||||||||||||
SID_2  11041  CCCGGGAAAGCCGCAAAAGCAGTGTGCACATTGACGGATGTGTACCTCCCAGACCTTGAG  11100

SID_1  11101  GCCTACCTCCATCCTGTGACCCAGTCCAAGTGCTGGAAAATGATGTTGGACTTTAAAGAA  11160
              ||||||||||||||||||||||||||||||||||||||||||||||||||||||||||||
SID_2  11101  GCCTACCTCCATCCTGTGACCCAGTCCAAGTGCTGGAAAATGATGTTGGACTTTAAAGAA  11160

SID_1  11161  GTTCGACTGATGGTTTGGAAGGACAAGACGGCCTATTTCCAACTCGAAGGTCGTCATTTC  11220
              ||||||||||||||||||||||||||||||||||||||||||||||||||||||||||||
SID_2  11161  GTTCGACTGATGGTTTGGAAGGACAAGACGGCCTATTTCCAACTCGAAGGTCGTCATTTC  11220

SID_1  11221  ACCTGGTATCAGCTTGCTAGCTTTGCTTCGTACATCCGTGTTCCTGTAAATTCCACGGTG  11280
              ||||||||||||||||||||||||||||||||||||||||||||||||||||||||||||
SID_2  11221  ACCTGGTATCAGCTTGCTAGCTTTGCTTCGTACATCCGTGTTCCTGTAAATTCCACGGTG  11280

SID_1  11281  TACCTGGACCCCTGCATGGGCCCCGCCCTTTGCAACAGGAAAGTCGTTGGGTCCCCTCAT  11340
              ||||||||||||||||||||||||||||||||||||||||||||||||||||||||||||
```

FIG. 5 (cont)

```
SID_2  11281  TACCTGGACCCCTGCATGGGCCCCGCCCTTTGCAACAGGAAAGTCGTTGGGTCCCCTCAT  11340

SID_1  11341  TGGGGAGCTGACCTCGCAGTCACCCCTTATGATTATGGAGCTAGAAAAATTTTGTCCAGT  11400
              ||||||||||||||||||||||||||||||||||||||||||||||||||||||||||||
SID_2  11341  TGGGGAGCTGACCTCGCAGTCACCCCTTATGATTATGGAGCTAGAAAAATTTTGTCCAGT  11400

SID_1  11401  GCATATCATGGTGAGATGCCTCCTGGGTACAAGATTCTGGCGTGCGCAGAGTTCTCGCTA  11460
              ||||||||||||||||||||||||||||||||||||||||||||||||||||||||||||
SID_2  11401  GCATATCATGGTGAGATGCCTCCTGGGTACAAGATTCTGGCGTGCGCAGAGTTCTCGCTA  11460

SID_1  11461  GACGACCCAGTCAGATACAAGCATACTTGGGGGTTCGAGTCGGATACAGCGTACTTGTAC  11520
              ||||||||||||||||||||||||||||||||||||||||||||||||||||||||||||
SID_2  11461  GACGACCCAGTCAGATACAAGCATACTTGGGGGTTCGAGTCGGATACAGCGTACTTGTAC  11520

SID_1  11521  GAGTTCACTGGAAACGGCGAGGACTGGGAGGATTACAACGACGCGTTTCGTGCGCGACAG  11580
              ||||||||||||||||||||||||||||||||||||||||||||||||||||||||||||
SID_2  11521  GAGTTCACTGGAAACGGCGAGGACTGGGAGGATTACAACGACGCGTTTCGTGCGCGACAG  11580

SID_1  11581  AAAGGAAAAATTTATAAGGCCACTGCCACCAGCCTGAAGTTCCATTTCCCTCCGGGTCAC  11640
              ||||||||||||||||||||||||||||||||||||||||||||||||||||||||||||
SID_2  11581  AAAGGAAAAATTTATAAGGCCACTGCCACCAGCCTGAAGTTCCATTTCCCTCCGGGTCAC  11640

SID_1  11641  ATCGTTGAACCAACTTTGGGCCTGAACTGAAATGAGATGGGAGCCGCACAGAGCCTTTTT  11700
              ||||||||||||||||||||||||||||||||||||||||||||||||||||||||||||
SID_2  11641  ATCGTTGAACCAACTTTGGGCCTGAACTGAAATGAGATGGGAGCCGCACAGAGCCTTTTT  11700

SID_1  11701  GACAAAATTGGTCAACTTTTTGTTGATGCCTTCACGGAGTTCTTGGTGTCTATTGTTGAT  11760
              ||||||||||||||||||||||||||||||||||||||||||||||||||||||||||||
SID_2  11701  GACAAAATTGGTCAACTTTTTGTTGATGCCTTCACGGAGTTCTTGGTGTCTATTGTTGAT  11760

SID_1  11761  ATCATCATATTTTTGGCCATTTGTTCGGCTTCACCATCGCCGGTTGGCTGGTGGTCTTT  11820
              ||||||||||||||||||||||||||||||||||||||||||||||||||||||||||||
SID_2  11761  ATCATCATATTTTTGGCCATTTGTTCGGCTTCACCATCGCCGGTTGGCTGGTGGTCTTT  11820

SID_1  11821  TGCATCAGATTGGTTTTCTCCGCGATACTCCGTGCGCGCCCTACCGTTCACTCTGAGCAA  11880
              ||||||||||||||||||||||||||||||||||||||||||||||||||||||||||||
SID_2  11821  TGCATCAGATTGGTTTTCTCCGCGATACTCCGTGCGCGCCCTACCGTTCACTCTGAGCAA  11880

SID_1  11881  TTACAGAAGATCCTATGAGGCCTACCTCTCCCAGTGCCAGGTGGACATTCCTGCCTGGGG  11940
              ||||||||||||||||||||||||||||||||||||||||||||||||||||||||||||
SID_2  11881  TTACAGAAGATCCTATGAGGCCTACCTCTCCCAGTGCCAGGTGGACATTCCTGCCTGGGG  11940

SID_1  11941  GACTAAACACCCTTTGGGGATGATCTGGCACCACAAGGTGTCGACCCTAATTGATGAAAT  12000
              |||||||||||||||||||||||||||||||||||||||| |||||||||||||||||||
SID_2  11941  GACTAAACACCCTTTGGGGATGATCTGGCACCACAGGGTGTCGACCCTAATTGATGAAAT  12000

SID_1  12001  GGTGTCGCGTCGGATGTACCGCACCATGGAACAAGCAGGGCAGGCTGCCTGGAAACAGGT  12060
              ||||||||||||||||||||||||||||||||||||||||||||||||||||||||||||
SID_2  12001  GGTGTCGCGTCGGATGTACCGCACCATGGAACAAGCAGGGCAGGCTGCCTGGAAACAGGT  12060

SID_1  12061  GGTGACCGAGGCAACGCTGTCTCGTATTAGTAGTTTGGATGTGGTGGCTCATTTCCAGCA  12120
              ||||||||||||||||||||||||||||||||||||||||||||||||||||||||||||
SID_2  12061  GGTGACCGAGGCAACGCTGTCTCGTATTAGTAGTTTGGATGTGGTGGCTCATTTCCAGCA  12120

SID_1  12121  TCTTGCCGCCATAGAAGCCGAGACTTGTAAATACTTGGCCTCCCGGCTGCCAATGCTACA  12180
              ||||||||||||||||||||||||||||||||||||||||||||||||||||||||||||
SID_2  12121  TCTTGCCGCCATAGAAGCCGAGACTTGTAAATACTTGGCCTCCCGGCTGCCAATGCTACA  12180
```

FIG. 5 (cont)

```
SID_1  12181  CAACCTGCGCTTGACAGGGTCAAATGTAACCATAGTGTATAATAGCTCCCTGGACCGGGT  12240
              ||||||||||||||||||||||||||||||||||||||||||||||||||||||||||||
SID_2  12181  CAACCTGCGCTTGACAGGGTCAAATGTAACCATAGTGTATAATAGCTCCCTGGACCGGGT  12240

SID_1  12241  GTTTGCTGTTTTCCCGACCTCCAGTTCCCGGCCAAAGCTTCATGATTTTCGGCAATGGCT  12300
              ||||||||||||||||||||||||||||||||||||||||||||||||||||||||||||
SID_2  12241  GTTTGCTGTTTTCCCGACCTCCAGTTCCCGGCCAAAGCTTCATGATTTTCGGCAATGGCT  12300

SID_1  12301  AATAGCTGTGCATTCCTCCATATTCTCCTCTGTTGCGGCTTCTTGTACCCTTTCGTCGT  12360
              ||||||||||||||||||||||||||||||||||||||||||||||||||||||||||||
SID_2  12301  AATAGCTGTGCATTCCTCCATATTCTCCTCTGTTGCGGCTTCTTGTACCCTTTCGTCGT  12360

SID_1  12361  ACTGTGGTTGCGGCTTCCAATAATACGTACTGTTTTGGTTTCCGCTGGTTAGGGGCAAT  12420
              ||||||||||||||||||||||||||||||||||||||||||||||||||||||||||||
SID_2  12361  ACTGTGGTTGCGGCTTCCAATAATACGTACTGTTTTGGTTTCCGCTGGTTAGGGGCAAT  12420

SID_1  12421  TTTTCTTTCGAGCTCACAGTGAATTACACGGTATGTCCTCCCTGCCTCACCCGGCAAGCG  12480
              ||||||||||||||||||||||||||||||||||||||||||||||||||||||||||||
SID_2  12421  TTTTCTTTCGAGCTCACAGTGAATTACACGGTATGTCCTCCCTGCCTCACCCGGCAAGCG  12480

SID_1  12481  GCTTCAGAGATCTACGAACCCAGCAGATCTCTTTGGTGTAGGATAGGGCAAGATCGATGT  12540
              ||||||||||||||||||||||||||||||||||||||||||||||||||||||||||||
SID_2  12481  GCTTCAGAGATCTACGAACCCAGCAGATCTCTTTGGTGTAGGATAGGGCAAGATCGATGT  12540

SID_1  12541  ACAGAGAGCGATCACGATGAGCTAGGTTTCCTGGTGCCGCCTGGCCTCTCTAACGAAGGC  12600
              ||||||||||||||||||||||||||||||||||||||||||||||||||||||||||||
SID_2  12541  ACAGAGAGCGATCACGATGAGCTAGGTTTCCTGGTGCCGCCTGGCCTCTCTAACGAAGGC  12600

SID_1  12601  CATTTAATTAGTGTCTACGCCTGGCTGGCGTTCCTATCCTTCAGTTACACGTCGCAGTTC  12660
              ||||||||||||||||||||||||||||||||||||||||||||||||||||||||||||
SID_2  12601  CATTTAATTAGTGTCTACGCCTGGCTGGCGTTCCTATCCTTCAGTTACACGTCGCAGTTC  12660

SID_1  12661  CATCCCGAAATATTCGGCATAGGGAATGTGAGCGAGGTCTATGTCGACATCAAGCACCAA  12720
              ||||||||||||||||||||||||||||||||||| ||||||||||||||||||||||||
SID_2  12661  CATCCCGAAATATTCGGCATAGGGAATGTGAGTGAGGTCTATGTCGACATCAAGCACCAA  12720

SID_1  12721  TTTATTTGTGCTGTTCATGATGGGCAGAACACCACCTTGCCTCGCCATGACAACATCACG  12780
              ||||||||||||||||||||||||||||||||||||||||||||||||||||||||||||
SID_2  12721  CTTATTTGTGCTGTTCATGATGGGCAGAACACCACCTTGCCTCGCCATGACAACATCACG  12780

SID_1  12781  GCCGTGTACCAGACGTATTATCAACACCAGGTTGATGGCGGCAACTGGTTTCACCTGGAA  12840
              ||||||||||||||||||||||||||||||||||||||||||||||||||||||||||||
SID_2  12781  GCCGTGTACCAGACGTATTATCAACACCAGGTTGATGGCGGCAACTGGTTTCACCTGGAA  12840

SID_1  12841  TGGCTGCGTCCCTTCTTTTCTTCTTGGTTGGTTTTGAATGTTTCATGGTTTCTCAGGCGT  12900
              ||||||||||||||||||||||||||||||||||||||||||||||||||||||||||||
SID_2  12841  TGGCTGCGTCCCTTCTTTTCTTCTTGGTTGGTTTTGAATGTTTCATGGTTTCTCAGGCGT  12900

SID_1  12901  TCGCCTGCAAGCCGTGTTTCAGTTCGAGTCTTTCAGACATCAAAACCAACACCACCGCAG  12960
              ||||||||||||||||||||||||||||||||||||||||||||||||||||||||||||
SID_2  12901  TCGCCTGCAAGCCGTGTTTCAGTTCGAGTCTTTCAGACATCAAAACCAACACCACCGCAG  12960

SID_1  12961  CTGCAGGCTTTGCTGTCCTCCAAGACATCAGCTGTCTTAGGCATGGCGACTCGTCCTCTG  13020
              |||||||  |||||||||||||||||||||||||||||||||||| ||||||||||||||
SID_2  12961  CTGCAGGTTTTGCTGTCCTCCAAGACATCAGCTGTCTTAGGCATGGCGACTCGTCCTCTG  13020

SID_1  13021  AGGCGACTCGCAAAAGCCGCCAATGCCGTACGGCGATAGGGACGCCCGTATACATTACTG  13080
              ||||||||||||||||||||||||||||||||||||||||||||||||||||||||||||
```

FIG. 5 (cont)

```
SID_2  13021  AGGCGACTCGCAAAAGCCGCCAATGCCGTACGGCGATAGGGACGCCCGTATACATTACTG  13080

SID_1  13081  TCACAGCCAACGTGACAGATGAGAATTATTTGCATTCCTCTGACCTTCTCATGCTTTCTT  13140
              ||||||||||||||||||||||||||||||||||||||||||||||||||||||||||||
SID_2  13081  TCACAGCCAACGTGACAGATGAGAATTATTTGCATTCCTCTGACCTTCTCATGCTTTCTT  13140

SID_1  13141  CTTGCCTTTTCTACGCTTCTGAGATGAGTGAAAAGGGATTCAAGGTGATATTTGGCAATG  13200
              ||||||||||||||||||||||||||||||||||||||||||||||||||||||||||||
SID_2  13141  CTTGCCTTTTCTACGCTTCTGAGATGAGTGAAAAGGGATTCAAGGTGATATTTGGCAATG  13200

SID_1  13201  TGTCAGGCATCGTGGCTGTTTGTGTCAACTTCACCAGCTATGTCCAACATGTTAAGGAAT  13260
              ||||||||||||||||||||||||||||||||||||||||||||||||||||||||||||
SID_2  13201  TGTCAGGCATCGTGGCTGTTTGTGTCAACTTCACCAGCTATGTCCAACATGTTAAGGAAT  13260

SID_1  13261  TTACCCGACGCTCCTTGGTAGTCGATCATGTACGACTACTACATTTCATGACACCTGAGA  13320
              ||||||||||||||||||||||||||||||||||||||||||||||||||||||||||||
SID_2  13261  TTACCCGACGCTCCTTGGTAGTCGATCATGTACGACTACTACATTTCATGACACCTGAGA  13320

SID_1  13321  CTATCAGCTGGGCAACAGTTTTAGCCTGTCTTTTTGCCATCCTATTGGCAATTTGAATGT  13380
              ||||| |||||||||||||||||||||||||||||||||||||||||||||||||||||
SID_2  13321  CTATGAGGTGGGCAACAGTTTTAGCCTGTCTTTTTGCCATCCTATTGGCAATTTGAATGT  13380

SID_1  13381  TCAGGTATGTTGGGGAAATGCTTGACCGCGGGCTGTTGCTCGCAGTTGC     GTGG  13440
              |||||||||||||||| || |||||||||||||||||||||||||||||       ||||
SID_2  13381  TCAGGTATGTTGGGGAATTGCTTGACCGCGGGCTGTTGCTCGCAGTTGCTTTTTTGTGG  13440

SID_1  13441  TGTATCGTGCCGTTCTGTTTTGTTGCGCTCGTCAACGCCAACAACAGCAGCAGCTCCCAT  13500
              ||||||||||||||||||||||||||||||||||||||||||||||||||||||||||||
SID_2  13441  TGTATCGTGCCGTTCTGTTTTGTTGCGCTCGTCAACGCCAACAACAGCAGCAGCTCCCAT  13500

SID_1  13501  TTACAGTTAATTTATAACCTGACGATATGTGAGCTGAATGGCACAGATTGGCTAAATAGA  13560
              ||||||||||||||||||||||||||||||||||||||||||||||||||||||||||||
SID_2  13501  TTACAGTTAATTTATAACCTGACGATATGTGAGCTGAATGGCACAGATTGGCTAAATAGA  13560

SID_1  13561  AAATTCGACTGGGCAGTGGAGACCTTTGTCATCTTCCAGTATTGACTCACATCGTCTCC  13620
              ||||||||||||||||||||||||||||||||||||||||||||||||||||||||||||
SID_2  13561  AAATTCGACTGGGCAGTGGAGACCTTTGTCATCTTCCAGTATTGACTCACATCGTCTCC  13620

SID_1  13621  TATGGTGCCCTCACCACCAGCCATTTCCTTGACACAGTCGGTTTGGTCACCGTGTCCACC  13680
              ||||||||||||||||||||||||||||||||||||||||||||||||||||||||||||
SID_2  13621  TATGGTGCCCTCACCACCAGCCATTTCCTTGACACAGTCGGTTTGGTCACCGTGTCCACC  13680

SID_1  13681  GCCGGATACTACCACAGGCGGTATGTCCTGAGTAGCATTTACGCTGTCTGCGCCCTGGCC  13740
              ||||||||||||||||||||||||||||||||||||||||||||||||||||||||||||
SID_2  13681  GCCGGATACTACCACAGGCGGTATGTCCTGAGTAGCATTTACGCTGTCTGCGCCCTGGCC  13740

SID_1  13741  GCGCTGATTTGCTTCGCCATCAGGCTGACAAAAAACTGCATGTCCTGGCGCTACTCATGC  13800
              ||||||||||||||||||||||||||||||||||||||||||||||||||||||||||||
SID_2  13741  GCGCTGATTTGCTTCGCCATCAGGCTGACAAAAAACTGCATGTCCTGGCGCTACTCATGC  13800

SID_1  13801  ACTAGATATACTAATTTTCTTCTAGACACCAAGGGCAAACTCTATCGTTGGCGGTCTCCC  13860
              ||||||||||||||||||||||||||||||||||||||||||||||||||||||||||||
SID_2  13801  ACTAGATATACTAATTTTCTTCTAGACACCAAGGGCAAACTCTATCGTTGGCGGTCTCCC  13860

SID_1  13861  GTCATTATAGAGAAAGGGGGAAAAATCGAGGTTAACGGTCACTTGATCGACCTCAAGAGA  13920
              |||||||||||||||||||| |||||||||||||||||||||||||||||||||||||||
SID_2  13861  GTCATTATAGAGAAAGGGGGAAAAATCGAGGTTAACGGTCACTTGATCGACCTCAAGAGA  13920
```

FIG. 5 (cont)

```
SID_1  13921  GTTGTGCTTGATGGTTCCGCAGCAACCCCTGTAACCAAAGTTTCAGCGGAACAATGGGGA  13980
              ||||||||||||||||||||||||||||||||||||||||| ||||||||||||||||||
SID_2  13921  GTTGTGCTTGATGGTTCCGCAGCAACCCCTGTAACCAAAGTTTTAGCGGAACAATGGGGA  13980

SID_1  13981  CGTCCTTAGATGACTTTTGCAATGACAGCACGGCTCCACAAAAGGTGCTTTTGGCGTTTT  14040
              ||||||||||||||||||||||||||||||||||||||||||||||||||||||||||||
SID_2  13981  CGTCCTTAGATGACTTTTGCAATGACAGCACGGCTCCACAAAAGGTGCTTTTGGCGTTTT  14040

SID_1  14041  CCATTACCTATACGCCAATAATGATATATGCCCTGAAGGTAAGTCGCGGCCGATTGTTAG  14100
              |||||||||||||||||||||||||||||||||||||||||||||||||||||||||| |
SID_2  14041  CCATTACCTATACGCCAATAATGATATATGCCCTGAAGGTAAGTCGCGGCCGATTGTCAG  14100

SID_1  14101  GGCTTCTACACCTTTTGATTTTCTTGAATTGTGCTTTTACCTTCGGGTACATGACATTCG  14160
              ||||||||||||||||||||||||||||||||||||||||||||||||||||||||||||
SID_2  14101  GGCTTCTACACCTTTTGATTTTCTTGAATTGTGCTTTTACCTTCGGGTACATGACATTCG  14160

SID_1  14161  CGCATTTTCGCAGCACGAACAAGGTCGCGCTCACTATGGGAGCAGTAGTTGCACTCCTTT  14220
              ||||||||||||||||||||||||||||||||||||||||||||||||||||||||||||
SID_2  14161  CGCATTTTCGCAGCACGAACAAGGTCGCGCTCACTATGGGAGCAGTAGTTGCACTCCTTT  14220

SID_1  14221  GGGGGGTGTATTCAGCCATAGAAACCTGGAGATTCATCACCTCCAGATGCCGGTTGTGCT  14280
              ||||||||||||||||||||||||||||||||||||||||||||||||||||||||||||
SID_2  14221  GGGGGGTGTATTCAGCCATAGAAACCTGGAGATTCATCACCTCCAGATGCCGGTTGTGCT  14280

SID_1  14281  TGCTAGGCCGCAGGTACATTCTGGCCCCTGCCCACCACGTTGAAAGTGTCGCAGGCTTTC  14340
              ||||||||||||||||||||||||||||||||||||||||||||||||||||||||||||
SID_2  14281  TGCTAGGCCGCAGGTACATTCTGGCCCCTGCCCACCACGTTGAAAGTGTCGCAGGCTTTC  14340

SID_1  14341  ATCCGATAACGGCAAGTGATAACCACGCATTTGTCGTTCGGCGTCCCGGCTCCACTACAG  14400
              ||||||||||||||||||||||||||||||||||||||||||||||||||||||||||||
SID_2  14341  ATCCGATAACGGCAAGTGATAACCACGCATTTGTCGTTCGGCGTCCCGGCTCCACTACAG  14400

SID_1  14401  TCAACGGCACATTGGTGCCCGGGTTGAAAAGCCTCGTGTTGGGTGGCAGAAGAGCTGTTA  14460
              ||||||||||||||||||||||||||||||||||||||||||||||||||||||||||||
SID_2  14401  TCAACGGCACATTGGTGCCCGGGTTGAAAAGCCTCGTGTTGGGTGGCAGAAGAGCTGTTA  14460

SID_1  14461  AACGAGGAGTGGTGAACCTTGTCAAATATGCCAAATAACAACGGCAAGCAGCAGAAAAGA  14520
              ||||||||||||||||||||||||||||||||||||||||||||||||||||||||||||
SID_2  14461  AACGAGGAGTGGTGAACCTTGTCAAATATGCCAAATAACAACGGCAAGCAGCAGAAAAGA  14520

SID_1  14521  AAAAGGGGATGGCCAGCCAGTCAATCAGCTGTGCCAGATGCTGGGCAGGATCATCGCCC   14580
              ||||||||||||||||||||||||||||||||||||||||||||||||||||||||||||
SID_2  14521  AAAAGGGGATGGCCAGCCAGTCAATCAGCTGTGCCAGATGCTGGGCAGGATCATCGCCC   14580

SID_1  14581  AGCAAAACCAGCCCAGAGGTAAGGGACCGGGAAAAAGGAATAAGAAGAAAAGCCCGGAGA  14640
              ||||||||||||||||||||||||||||||||||||||||||||||||||||||||||||
SID_2  14581  AGCAAAACCAGCCCAGAGGTAAGGGACCGGGAAAAAGGAATAAGAAGAAAAGCCCGGAGA  14640

SID_1  14641  AGCCCCATTTTCCTCTGGCGACTGAAGATGACGTTAGACATCACTTCACCCCTAGTGAGC  14700
              ||||||||||||||||||||||||||||||||||||||||||||||||||||||||||||
SID_2  14641  AGCCCCATTTTCCTCTGGCGACTGAAGATGACGTTAGACATCACTTCACCCCTAGTGAGC  14700

SID_1  14701  GACAACTGTGTCTGTCGTCAATCCAAACTGCCTTTAACCAAGGCGCTGGAACTTGCACCC  14760
              ||||||||||||||||||||||||||||||||||||||||||||||||||||||||||||
SID_2  14701  GACAACTGTGTCTGTCGTCAATCCAAACTGCCTTTAACCAAGGCGCTGGAACTTGCACCC  14760

SID_1  14761  TGTCAGACTCGGGTAGGGTGAGTTATGCAGTGGAGTTTAGTTTGCCTACGCATCATACTG  14820
              ||||||||||||||||||||||||||||||||||||||||||||||||||||||||||||
```

FIG. 5 (cont)

```
SID_2  14761  TGTCAGACTCGGGTAGGGTGAGTTATGCAGTGGAGTTTAGTTTGCCTACGCATCATACTG  14820

SID_1  14821  TGCGCCTGATTCGTGCCACAACATCACCCTCAGCATGATGAGCTGGCATTCTTGAGACAT  14880
              ||||||||||||||||||||||||||||||||||||||||||||||||||||||||||||
SID_2  14821  TGCGCCTGATTCGTGCCACAACATCACCCTCAGCATGATGAGCTGGCATTCTTGAGACAT  14880

SID_1  14881  CCCAGTGTTTGAATTGGAAGTGTGTGTGGTGAATGGCACTGATTGACATTGTGCCTCTAA  14940
              ||||||||||||||||||||||||||||||||||||||||||||||||||||||||||||
SID_2  14881  CCCAGTGTTTGAATTGGAAGTGTGTGTGGTGAATGGCACTGATTGACATTGTGCCTCTAA  14940

SID_1  14941  GTCACCTATTCAATTAGGGCGAC  14963
              |||||||||||||||||||||||
SID_2  14941  GTCACCTATTCAATTAGGGCGAC  14963
```

PORCINE REPRODUCTIVE AND RESPIRATORY SYNDROME VIRUS, COMPOSITIONS, VACCINE AND METHODS OF USE

SEQUENCE LISTING

This application contains a sequence listing which has been submitted electronically in ASCII format in accordance with 37 C.F.R. 1.821-1.825. Said ASCII copy, created on Jan. 29, 2014, is named 10-0145-US-2-SEQ.txt and is 124,818 bytes in size. The sequence listing accompanying this application is hereby incorporated by reference in its entirety.

BACKGROUND OF THE INVENTION

A. Field of the Invention

The present invention relates to Porcine Reproductive and Respiratory Syndrome Virus (PRRSV) compositions and associated methods.

B. Description of the Related Art

The swine industry continues to experience major economic losses due to PRRSV despite major efforts aimed at pathogen elimination and control strategies. PRRSV is an enveloped single-strand positive sense RNA virus classified under the order Nidovirales, family Arteriviridae and genus Arterivirus. The virus causes Porcine Reproductive and Respiratory Syndrome (PRRS), and has also been known as the Mystery Swine Disease and SIR. The symptoms of PRRS include reproductive failure in breeding females and respiratory disease in growing swine. The reproductive failure is associated with mid to late term abortions, increased numbers of mummified fetuses and weak born piglets and fewer healthy born piglets. PRRSV is also characterized by anorexia, fever and respiratory disease typically seen microscopically as interstitial pneumonia. Thus infection with PRRSV can have a significant negative effect on the productivity of a herd. It has been estimated that PRRSV costs the US swine industry around 560 million U.S. dollars a year. Compounding the situation is the fact that PRRSV is endemic in most swine producing countries and has a similar economic effect elsewhere.

Current control strategies to prevent the spread of the virus within and between herds include: the proper management of breeding animals, removal of infected individuals, strict biosecurity measures including air filtration systems, serum inoculation, and the use of vaccines. Both inactivated and modified (attenuated) live vaccines are commercially available. Inactivated vaccines produce a high level of safety but are generally considered as ineffective or as conveying a very limited degree of efficacy. Attenuated live vaccines have been widely used to reduce the transmission and clinical disease cause by wild type PRRS viruses. While modified live vaccine efficacy may vary against heterologous isolates, they remain the best vaccination option available to combat the disease.

Attenuated vaccines do carry some risk as several instances of suspected reversion to virulence have been reported. Therefore, new vaccines need to be capable of providing sufficient immunological protection to reduce transmission and clinical disease while also exhibiting a high degree of safety and resistance to genetic changes.

To increase genetic stability, viruses with cell passaged derived deletions in the nsp2 (nonstructural protein 2) region have been developed. The nsp2 protein is the largest PRRSV protein, is highly antigenic and possesses the highest genetic diversity of the PRRSV genome. The value of deletion mutants stems from the increased stability they confer. Shorter sequences result in less potential for reversion to virulence. Deleted portions would require insertions to revert back to its original state which is much less likely to occur than a simple substitution back to the original virulent form.

SUMMARY OF THE INVENTION

The present invention provides immunogenic compositions, vaccines, and related methods that overcome deficiencies in the art. The compositions and methods provide, inter alia, immunogenic deletion mutants of PRRSV which are genetically stable, from which vaccines, including attenuated whole virus vaccines and polypeptide subunit vaccines can be made, wherein said vaccines confer immunity from, protective resistance to, reduce transmission of and/or reduce clinical disease caused by infections with PRRSV.

Exemplary immunogenic compositions of the invention comprise any one of the polypeptide sequences encoded by the nucleotide sequence of SEQ ID NO: 1 (pre-attenuated Wetzel isolate of a PRRSV) and SEQ ID NO: 2 (an attenuated form of the Wetzel isolate), or fragments thereof, in particular fragments that are biologically or functionally, e.g., immunologically, active, with similar immunogenic specificity as compared to the full length PRRSV protein from which it is derived. Preferably those polypeptides are immunogenic and induce an immunoreactive response to the PRRS virus in animals to which the polypeptides are administered, which response is immunoprotective to PRRSV.

In another aspect the invention provides nucleic acid sequences, including both DNA and RNA sequences, that encode one or more polypeptides, antibody constructs, or antibody conjugates. The gene sequences coding for the polypeptides comprise a nucleic acid sequence that is at least 95%, 90%, 85%, or even 80% homologous to and/or identical with the nucleic acid sequence of Wetzel p3 ORF1a (SEQ ID NO:3), Wetzel p3 ORF1b (SEQ ID NO:4), Wetzel p3 GP2 (SEQ ID NO:5), Wetzel p3 GP3 (SEQ ID NO:6), Wetzel p3 GP4 (SEQ ID NO:7), Wetzel p3 GP5 (SEQ ID NO:8), Wetzel p3 M (SEQ ID NO:9), Wetzel p3 N (SEQ ID NO:10), Wetzel p41 ORF1a (SEQ ID NO:11), Wetzel p41 ORF1b (SEQ ID NO:12), Wetzel p41 GP2 (SEQ ID NO:13), Wetzel p41 GP3 (SEQ ID NO:14), Wetzel p41 GP4 (SEQ ID NO:7—identical to the p3 GP4 sequence), Wetzel p41 GP5 (SEQ ID NO:15), Wetzel p3 M (SEQ ID NO:9—identical to the p3 M sequence) and Wetzel p3 N (SEQ ID NO:10—identical to the p3 N sequence), or fragments thereof that are immunoreactive to or immunogenic for Porcine Reproductive and Respiratory Syndrome Virus (PRRSV). Complementary nucleic acid sequences to the above sequences are a further aspect of the invention.

Moreover a polypeptide of the invention as used herein includes but is not limited to a polypeptide that comprises:
i) a polypeptide comprising an amino acid sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14 or SEQ ID NO:15;
ii) a polypeptide that is at least 95% homologous to and/or identical with a polypeptide of i);
iii) a fragment of the polypeptides of i) and/or ii);
iv) a polypeptide of i) or ii), or a fragment of iii) comprising an amino acid motif or immunogenic epitope of any one of the polypeptides of i);

v) a fragment of iii) or iv) comprising at least 5, preferably 8, more preferably 10, even more preferably 15 or more contiguous amino acids included in the sequences of i);

vi) a polypeptide that is encoded by a polynucleotide comprising the sequence of SEQ ID NO:1 (pre-attenuated Wetzel) or SEQ ID NO:2 (attenuated Wetzel);

vii) a polypeptide that is encoded by a polynucleotide that is at least 95% homologous to or identical with polynucleotide of vi); or viii) a protein fragment that is encoded by a polynucleotide that comprises at least 15, preferably 24, more preferably 30, even more preferably 45 contiguous nucleotides or more, included in the sequences of SEQ ID NO:1 or SEQ ID NO:2.

Immunogenic compositions of the invention which comprise at least one or more PRRSV polypeptides as defined herein, killed or attenuated virus, or DNA- or RNA-based vaccines, e.g., encoding such immunogens, may further comprise a physiologically-acceptable vehicle such as a pharmaceutically or veterinarily acceptable carrier, adjuvant, or combination thereof.

Any of the PRRSV polypeptides provided herewith or any immunogenic compositions comprising one or more of these PRRSV polypeptides provided herewith can be used as a medicament, preferably as a vaccine or immunogenic composition, most preferably for the prophylaxis or treatment of a subject against a PRRS infection.

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include veterinary-acceptable carriers, diluents, isotonic agents, stabilizers, or adjuvants.

Methods of the invention include, but are not limited to, a method of provoking an immune response against a PRRSV infection in a subject comprising the step of administering to the subject an immunogenic composition comprising one or more PRRSV polypeptides as defined herein. Preferably, the immune response is provoked against more than one serotype or strain of PRRSV. Compositions of the invention may be used to treat or alternatively to prevent a PRRSV infection. Preferably, such immune response reduces the incidence of or severity of one or more clinical signs associated with or caused by the infection with one or more PRRSV serotypes.

Herein, suitable subjects and subjects in need to which compositions of the invention may be administered include animals in need of either prophylactic or treatment for a viral, microbial, parasitic, protozoan, bacterial, or fungal associated infection, disease, or condition. Animals in which the immune response is stimulated by use of compositions or methods of the invention include livestock, such as swine, bovines, poultry (e.g. chickens, ducks, geese, or turkeys) goats, and sheep, and domestic animals, such as mice, rabbits, dogs, cats, and horses. Preferred animals include porcines.

The invention also provides a method of reducing the incidence of or severity of one or more clinical signs associated with or caused by PRRSV infection, comprising the step of administering an immunogenic composition of the invention that comprises one or more PRRSV peptides as provided herewith and preferably a carrier molecule, such that the incidence of or the severity of a clinical sign of the PRRSV infection is reduced by at least 10%, preferably at least 20%, even more preferred at least 30%, even more preferred at least 50%, even more preferred at least 70%, most preferred at least 100% relative to a subject that has not received the immunogenic composition as provided herewith. Such clinical signs include reproductive failure in breeding females and respiratory disease in growing swine. The reproductive failure is associated with mid to late term abortions, increased numbers of mummified fetuses and weak born piglets and fewer health born piglets. PRRSV is also characterized by anorexia, fever and respiratory disease typically seen microscopically as interstitial pneumonia.

According to a further aspect, the present invention also relates to a method for the prophylaxis of a PRRSV infection, wherein said PRRSV infection may be caused by serotype PRRSV or any other serotype of PRRSV, comprising the step of administering an immunogenic composition of the invention that comprises one or more PRRSV peptides as provided herewith.

The invention also provides a method of preparing any of the immunogenic compositions provided herewith that method comprises mixing one or more PRRSV peptides as provided herewith with a carrier molecule, preferably such that the one or more PRRSV peptides and carrier molecule are covalently coupled or conjugated to one another. Such conjugates may be multivalent or univalent. Multivalent compositions or vaccines include an immuno-conjugation of multiple PRRSV peptides with a carrier molecule. In a further aspect, the invention provides a method of producing one or more PRRSSSV peptides that method comprises transforming a host cell, preferably a prokaryotic cell such as *E. coli* with a nucleic acid molecule that codes for any of the PRRSV peptides as provided herewith. Alternatively, the host cell may be a eukaryotic cell such as an animal cell, protist cell, plant cell, or fungal cell. Preferably the eukaryotic cell is a mammalian cell such as CHO, BHK or COS, or a fungal cell such as *Saccharomyces cerevisiae*, or an insect cell such as Sf9.

Another aspect of the invention provides a method of producing one or more PRRSV peptides that induce an immune response against at least one serotype of PRRSV, and more preferably two or more serotypes of PRRSV. This comprises culturing a transformed expression vector coding for and expressing one or more PRRSV peptides disclosed herein. The expressed proteins are either retained by the expression organism or secreted into the culture medium. Expression is conducted under conditions sufficient to produce a PRRSV peptide a capable of inducing an immune response to PRRSV.

A still further aspect of the invention is compositions comprising and methods of making and administering DNA- and/or RNA-based vaccines, including nucleic acids (or polynucleotides) that encode for immunity-conferring polypeptides (immunogenic polypeptides") or wherein the nucleic acid is itself the immunogen. Methods of making and using such DNA- and/or RNA-based vaccines are well known in the art.

Methods of making compositions of the invention may further comprise admixing the conjugate of one or more PRRSV antigens and a carrier molecule with a physiologically-acceptable vehicle such as a pharmaceutically- or veterinary-acceptable carrier, adjuvant, or combination thereof. Those of skill in the art will recognize that the choice of vehicle, adjuvant, or combination will be determined by the delivery route, personal preference, and animal species among others.

In another aspect, the invention provides a method of diagnosing a PRRSV infection in a subject. That method comprises providing one or more PRRSV peptides; contacting the one or more PRRSV peptides with a sample obtained from the subject; and identifying the subject as having a PRRSV infection if an antibody capable of binding the one or more PRRSV peptides is detected in the sample.

In another respect, the invention provides a method of ascertaining that a subject has been previously exposed to a PRRSV infection and is able to express an immune response to PRRSV. That method comprises providing one or more PRRSV peptides; contacting the one or more PRRSV peptides with a sample obtained from the subject; and identifying the subject as having a PRRSV infection if an antibody capable of binding the one or more PRRSV peptides is detected in the sample.

The invention also provides kits that comprise an immunogenic composition that comprises one or more PRRSV peptides, preferably together with a carrier molecule; a container for packaging the immunogenic composition; a set of printed instructions; and a dispenser capable of administering the immunogenic composition to an animal. Optionally, the one or more PRRSV peptides and the carrier molecule may be packaged as a conjugate or as separate compounds. When supplied separately, a means of conjugating the one or more PRRSV peptides and carrier molecule, as well as appropriate printed instructions, is also supplied.

The invention also provides kits for vaccinating an animal comprising a set of printed instructions; a dispenser capable of administering the immunogenic composition provided herewith comprising one or more PRRSV peptides to an animal; and wherein at least one of PRRSV peptides effectively immunizes the animal against at least one disease associated with PRRSV infection. Preferably, the one or more PRRSV peptides are selected from those provided herewith. Kits of the invention may further comprise a veterinary acceptable carrier, adjuvant, or combination thereof.

The dispenser in a kit of the invention is capable of dispensing its contents as droplets; and the immunogenic composition comprises the PRRSV peptides as provided herewith included in the kit is capable of reducing the severity of at least one clinical sign of a PRRSV infection when administered intranasally, orally, intradermally, or intramuscularly to an animal. Preferably, the severity of a clinical sign is reduced by at least 10% preferably by at least 20%, even more preferred by at least 30%, even more preferred by at least 50%, even more preferred by at least 70%, most preferred by at least 100% as compared to an untreated, infected animal.

Methods for the treatment or prophylaxis of infections caused by PRRSV are also disclosed. The method comprises administering an effective amount of the immunogenic composition of the present invention to a subject, wherein said treatment or prophylaxis is selected from the group consisting of reducing signs of PRRSV infection, reducing the severity of or incidence of clinical signs of PRRSV infection, reducing the mortality of subjects from PRRSV infection, and combinations thereof.

Compositions of the invention further comprise a veterinarily acceptable carrier, adjuvant, or combination thereof. Such compositions may be used as a vaccine and comprise an attenuated vaccine, an inactivated vaccine, or combinations thereof. Such vaccines elicit a protective immunological response against at least one disease associated with PRRSV.

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include pharmaceutical- or veterinary-acceptable carriers, diluents, isotonic agents, stabilizers, or adjuvants.

Methods of the invention may also comprise admixing a composition of the invention with a veterinarily acceptable carrier, adjuvant, or combination thereof. Those of skill in the art will recognize that the choice of carrier, adjuvant, or combination will be determined by the delivery route, personal preference, and animal species among others.

The invention also provides a method of reducing the severity of a PRRSV infection in an animal comprising administrating to the animal a composition that comprises an isolate from a viral culture selected from the group consisting of a non-virulent, killed or attenuated immunologically-effective antigen of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14 and SEQ ID NO:15, including a fragment thereof, and/or combinations thereof.

Methods for the treatment or prophylaxis of infections caused by PRRSV are also disclosed. The method comprises administering an effective amount of the immunogenic composition of the present invention to an animal, wherein said treatment or prophylaxis is selected from the group consisting of reducing signs of PRRSV infection, reducing the severity of or incidence of clinical signs of PRRSV infection, reducing the mortality of animals from PRRSV infection, and combinations thereof.

Preferred routes of administration include intranasal, oral, intradermal, and intramuscular. Administration in drinking water, most preferably in a single dose, is preferred. The skilled artisan will recognize that compositions of the invention may also be administered in one or two or more doses, as well as, by other routes of administration. For example, such other routes include subcutaneously, intracutaneously, intravenously, intravascularly, intraarterially, intraperitoneally, intrathecally, intratracheally, intracutaneously, intracardially, intralobally, intramedullarly, intrapulmonarily, or intravaginally. Depending on the desired duration and effectiveness of the treatment, the compositions according to the invention may be administered once or several times, also intermittently, for instance on a daily basis for several days, weeks or months and in different dosages.

The invention also provides kits for vaccinating an animal comprising a set of printed instructions; a dispenser capable of administering a vaccine to an animal; and at least one isolate from a viral culture of a PRRSV or immunogenic composition that effectively immunizes the animal against at least one disease associated with PRRSV. Kits of the invention may further comprise a veterinarily acceptable carrier, adjuvant, or combination thereof.

The dispenser in a kit of the invention is capable of dispensing its contents as droplets; and the isolate included in the kit is capable of reducing the severity of at least one clinical sign of a PRRSV infection when administered intranasally, orally, intradermally, or intramuscularly to an animal. In some kits, the isolate is also capable of reducing the severity of at least one clinical sign of a PRRSV infection. Preferably, the severity of a clinical sign is reduced by at least 10% as compared to an untreated, infected animal.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5 is a comparison of the nucleotide sequences (DNA equivalent of the RNA viral sequences) of SEQ ID NO: 1 (pre-attenuated Wetzel p3) and SEQ ID NO: 2 (attenuated Wetzel p41).

DETAILED DESCRIPTION

Figure 1:
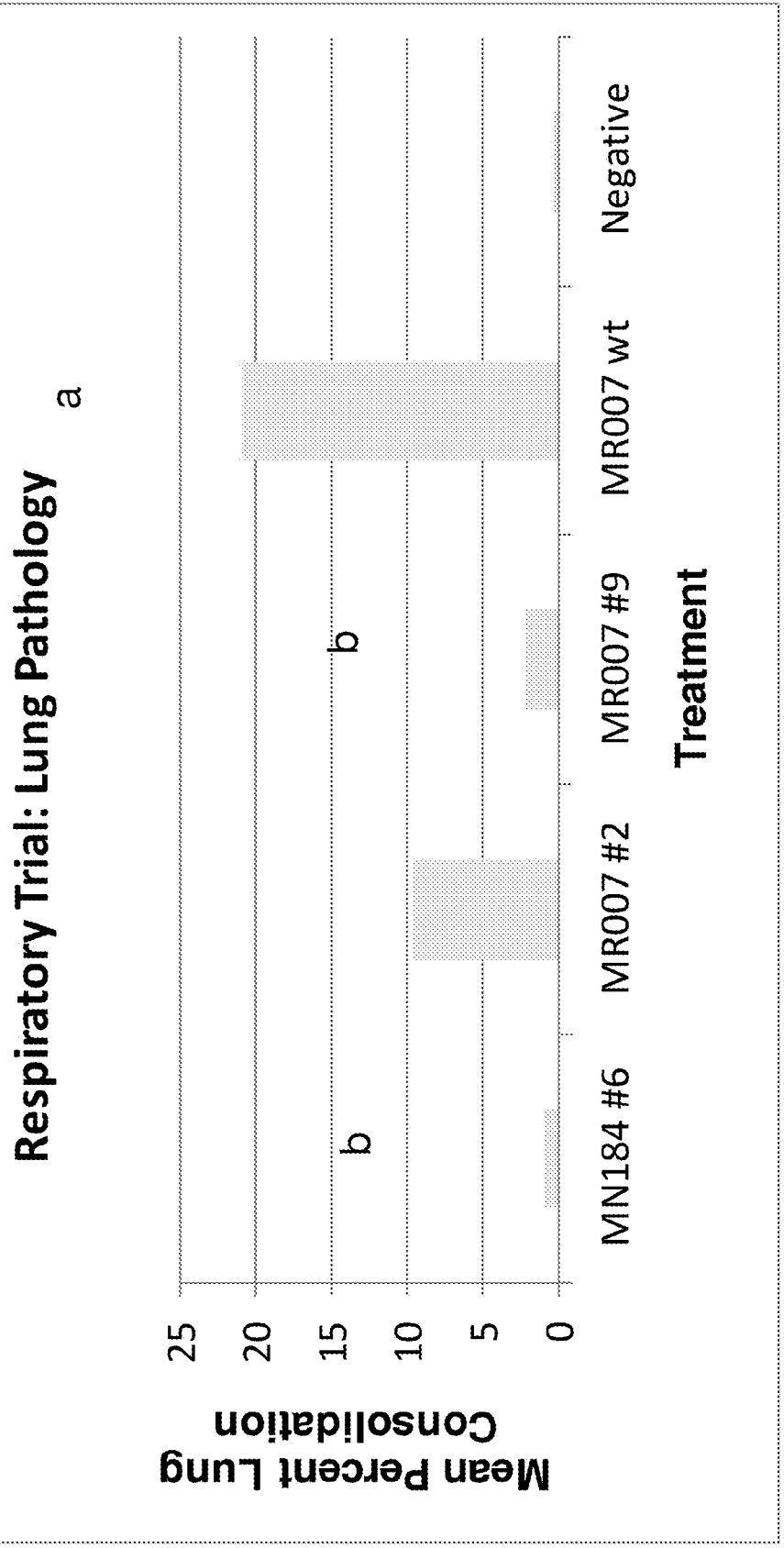
FIG. 1 is a chart of the Lung Pathology from the respiratory trial of Example 1. Pig safety study average lung scores as collected on day 14. The letter 'a' indicates the average lung score was higher than the negative control group while the letter 'b' indicates the scores were lower than the Isolate X wild type group.

The invention provides attenuated PRRSV strains having enhanced stability. Specifically polypeptides of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14 or SEQ ID NO:15, and fragments thereof (including but not limited at least 5, preferably 8, more preferably 10, even more preferably 15 contiguous amino acids included in the above described sequences) are disclosed. In addition, polypeptides which are at least 95% homologous to and/or identical with the above-described polypeptides. Further, associated polynucleotides of the above described polypeptides are also disclosed.

The practice of the present invention will employ, unless otherwise indicated, conventional techniques of molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens; reference to "an excipient" includes mixtures of two or more excipients, and the like.

A. Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

"Protection against disease", "protective immunity", "functional immunity" and similar phrases, means a response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection is lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of malaria. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent, preferably a PRRSV, respectively, in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably at least 20%, more preferably at least 30%, even more preferably at least 50%, and even more preferably at least 70% lower than in the non-vaccinated control group after the challenge the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

An "immunogenic or immunological composition" or "vaccine" refers to a composition of matter that comprises at least one PRRSV, or immunogenic portion thereof, that elicits an immunological response in the host of a cellular or antibody-mediated immune response to the composition. In a preferred embodiment of the present invention, an immunogenic composition induces an immune response and, more preferably, confers protective immunity against one or more of the clinical signs of a PRRSV infection. The term thus encompasses both subunit immunogenic compositions, as described below, as well as compositions containing whole killed, or attenuated, and/or inactivated PRRSV.

The term "subunit immunogenic composition" or "subunit vaccine" as used herein refers to a composition containing at least one immunogenic polypeptide or antigen, but not all antigens, derived from or homologous to an antigen from PRRSV. Such a composition is substantially free of intact PRRSV. Thus, a "subunit immunogenic composition" or "subunit vaccine" is prepared from at least partially purified or fractionated (preferably substantially purified) immunogenic polypeptides from PRRSV, or recombinant analogs thereof. A subunit immunogenic composition can comprise the subunit antigen or antigens of interest substantially free of other antigens or polypeptides from PRRSV, or in fractionated form. A preferred immunogenic subunit composition comprises PRRSV proteins or fragments thereof, e.g., those which are incorporated into the envelope of the virus, e.g., gp2, gp4, gp5 and/or matrix ("M") proteins. Also included are subunit immunogenic compositions which are modified analogs of the PRRSV virus, wherein the amino acid sequences of the antigen have been modified to enhance stability or immunogenicity.

An "immunogenic" PRRSV polypeptide, or "antigen," as used herein refer to a polypeptide or protein that elicits an immunological response as described herein. An "immunogenic" PRRSV protein or polypeptide includes the full-length sequence of any of the PPRSV identified herein or analogs or immunogenic fragments thereof. The term "immunogenic fragment" or "immunogenic portion" refers to a fragment or truncated and/or substituted form of a PRRSV that includes one or more epitopes and thus elicits the immunological response described herein. In general, such truncated and/or substituted forms, or fragments will comprise at least six contiguous amino acids from the full-length PRRSV protein. More preferably, the truncated or substituted forms, or fragments will have at least 10, more preferably at least 15, and still more preferably at least 19 or more contiguous amino acids from the full-length PRRSV protein. Analogs include modifications to the antigen which confer enhanced properties to the molecule such as stability or immunogenicity.

The term "epitope" means a segment or fragment of a composition of matter, e.g., a protein or polypeptide, which is recognized by the immune system, specifically by antibodies, B cells, or T cells. In the present invention, the epitope is generally a fragment or fragments of a polypeptide sequence of a viral protein.

Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. U.S Pat No. 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, June 28-Jul. 3, 1998. (The teachings and content of which are all incorporated by reference herein.)

An "immune response" or "immunological response" means, but is not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

Herein, "specifically immunoreactive" refers to an immunoreactive protein or polypeptide that recognizes an antigen characteristic of PRRSV infection but does not react with an antigen characteristic of a strict challenge control. To determine the specificity of a potential PRRSV immunoreactive protein or other polypeptide, various immunoassays (ELISA, IFA, WesternBlot) would be used to test the protein against animal sera containing genetically similar viruses. The protein would also be tested in various immunoassays against material containing proteins related to the expression method (Baculovirus, Sf9 cells, etc.).

As used herein, "a pharmaceutically- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed.Stewart-Tull, D. E. S.), John Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Pharmeuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with allyl sucrose or with allyl pentaerythritol. Among them, there may be mentioned CARBOPOL® 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Safety" refers to the absence of adverse consequences in a vaccinated animal following vaccination, including but not limited to: potential reversion of a bacterium-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—an immune response in the animal against PRRSV.

"Mortality", in the context of the present invention, refers to death caused by PRRSV infection, and includes the situation where the infection is so severe that an animal is euthanized to prevent suffering and provide a humane ending to its life.

"Attenuation" means reducing the virulence of a pathogen. In the present invention "attenuation" is synonymous with "avirulent." In the present invention, an attenuated virus is one in which the virulence has been reduced so that it does not cause clinical signs of a PRRSV infection but is capable of inducing an immune response in the target mammal, but may also mean that the clinical signs are reduced in incidence or severity in animals infected with the attenuated PRRSV in comparison with a "control group" of animals infected with non-attenuated PRRSV and not receiving the attenuated bacterium. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent PRRSV strain is one that suitable for incorporation into an immunogenic composition comprising a modified live PRRSV virus.

"Killed" or "inactivated" means treated with a physical or chemical agent which renders the PRRSV virus dead and/or otherwise incapable of reproduction. PRRSV may be killed by conventional means, such as, for example, heat, radiation or psoralen in the presence of ultraviolet light. PRRSV can be inactivated by conventional means such as, for example, through chemical inactivation using one or more chemical inactivating agents including, but not limited to, one or more of binary ethyleneimine (BEI), beta-propiolactone, formalin, gluteraldehyde, and/or sodium dodecyl sulfate. Methods of attenuating virulent strains of these viruses and methods of making an inactivated viral preparation are known in the art and are described in, e.g., U.S. Pat. Nos. 4,567,042 and 4,567,043. Antigens from PRRSV for use in the vaccine compositions of the present invention can thus be in the form of a whole virus which is a modified and/or attenuated live viral preparation or a killed or inactivated viral preparation, inter alia.

"Antibodies" as used herein includes anti-PRRSV antibodies, e.g., monoclonal and polyclonal antibodies, single chain antibodies, chimeric antibodies, humanized, human, porcine, and CDR-grafted antibodies, including compounds which include CDR sequences which specifically recognize a PRRSV polypeptide of the invention. The term "specific for" indicates that the variable regions of the antibodies of the invention recognize and bind a PRRSV polypeptide exclusively (i.e., are able to distinguish a single PRRSV polypeptide from related polypeptides despite sequence identity, homology, or similarity found in the family of polypeptides), and which are permitted (optionally) to interact with other proteins (for example, S. aureus protein A or other antibodies in ELISA techniques) through interactions with sequences outside the variable region of the antibodies, and in particular, in the constant region of the antibody molecule. Screening assays to determine binding specificity of an antibody of the invention are well known and routinely practiced in the art. For a comprehensive discussion of such assays, see Harlow et al. (Eds), Antibodies A Laboratory Manual: Cold Spring Harbor Laboratory; Cold Spring Harbor, N.Y. (1988), Chapter 6. Antibodies that recognize and bind fragments of the PRRSV polypeptides of the invention are also contemplated, provided that the antibodies are first and foremost specific for, as defined above, a PPRSV polypeptide of the invention from which the fragment was derived. For the purposes of clarity, "antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions. Antibodies can exist in a variety of forms including, for example, as functionally active fragments such as Fv, Fab', F(ab')2, as well as in single chains, and include synthetic polypeptides that contain all or part of one or more antibody single chain polypeptide sequences. Genetic constructs and methods for making antibodies of the invention, including cloning vectors, host cells transformed with cloning vectors and hybridomas, are well-known in the art.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount refers to colony forming units (CFU) per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

The term "immunoreactive to PRRSV" as used herein means that the peptide or fragment elicits the immunological response against PRRSV.

As used herein, "complementary" means a nucleic acid molecule has a sequence which complements a reference template sequence, whereby the two sequences can specifically hybridize. Preferably, the term refers to exact complementarity, e.g., as is found between the two strands of a nucleotide sequence in a naturally-occurring DNA-encoded gene.

"Sequence identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences, with gaps introduced if necessary. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A.M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988); the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and BLASTX (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, at least 85%, preferably at least 90%, even more preferably at least 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably at least 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology" as used herein refers to a method of determining the relatedness of two sequences. To determine sequence homology, two or more sequences are optimally aligned, and gaps are introduced if necessary. However, in contrast to "sequence identity," conservative amino acid substitutions are also counted as a match when determining sequence homology. In other words, to obtain a polypeptide having 95% sequence homology with a reference sequence, 85%, preferably 90%, even more preferably 95% of the amino acid residues in the reference sequence must match or comprise a conservative substitution with another amino acid, or a number of amino acids up to 15%, preferably up to 10%, even more preferably up to 5% of the total amino acid residues, not including conservative substitutions, in the reference sequence may be inserted into the reference sequence. Preferably the homologous sequence comprises at least a stretch of 50, even more preferred of 100, even more preferred of 250, even more preferred of 500 nucleotides encoding homologous amino acids.

A "conservative substitution" refers to the substitution of an amino acid residue with another amino acid residue having similar characteristics or properties including size, hydrophobicity, etc., such that the overall functionality does not change significantly. It can also mean a nucleotide substitution which results in a conservative amino acid substitution.

B. Carriers Molecules

The carrier molecules to which the PRRSV peptides of the invention can be conjugated or covalently linked are preferably those described above. Preferred carriers for animal use are bovine serum albumin and Keyhole Limpet Hemocyanin. Protein carriers suitable for human use but which may also be used in animals include tetanus toxoid, diphtheria toxoid, acellular pertussis vaccine (LPF toxoid), cross-reacting materials (CRM's) which are antigenically similar to bacterial toxins but are non-toxic by means of mutation. For example, CRM 197 obtained according to Pappenheimer, et al, Immunochemistry, 9, 891-906 (1972), and other bacterial protein carriers, for example meningococcal outer membrane protein may be used. Preferably, the carrier protein itself is an immunogen.

The PRRSV peptides of the invention may be covalently coupled to the carrier by any convenient method known to the art. While use of a symmetric linker such as adipic acid dihydrazide, as described by Schneerson et al, J. Experimental Medicine, 152, 361-376 (1980), or a heterobifunctional linker such as N-succinimidyl 3-(2-pyridyldithio) propionate as described by Fattom et al, Infection and Immunity, 56, 2292-2298 (1988), all incorporated by reference, are within the scope of the invention, it is preferred to avoid the use of any linker but instead couple a S. suis peptide of the invention directly to the carrier molecule. Such coupling may be achieved by means of reductive amination as described by Landi et al J. Immunology, 127, 1011-1019 (1981), expressly incorporated by reference herein.

The size of the immunogenic composition, as defined by average molecular weight, is variable and dependent upon the chosen PRRSV peptide(s) and the method of coupling of the PRRSV peptide(s) to the carrier. Therefore, it can be as small as 1,000 daltons ($10^3$) or greater than $10^6$ daltons. With the reductive amination coupling method, the molecular weight of the PRRSV peptide(s) is usually within the range of 5,000 to 500,000, for example 300,000 to 500,000, or for example 5,000 to 50,000 daltons.

Carrier molecules, i.e. peptides, derivatives and analogs thereof, and peptide mimetics that specifically bind a PRRSV peptide of the invention can be produced by various methods known in the art, including, but not limited to solid-phase synthesis or by solution (Nakanishi et al., 1993, Gene 137:51-56; Merrifield, 1963, J. Am. Chem. Soc. 15:2149-2154; Neurath, H. et al., Eds., The Proteins, Vol II, 3d Ed., p. 105-237, Academic Press, New York, N.Y. (1976), all incorporated herein by reference in their entirety).

The PRRSV peptides of the invention or the antibodies or binding portions thereof of the present invention may be administered in injectable dosages by solution or suspension of in a diluent with a pharmaceutical or veterinary carrier.

Safety and efficacy of such molecules are determined by standard procedures in cell cultures or experimental animals as described and regulated by the Center for Veterinary Biologics (CVB). Toxicity and therapeutic efficacy of such molecules can be determined by standard pharmaceutical procedures in cell cultures or experimental animals, e.g., for determining the $LD_{50}$ (the dose lethal to 50% of the population).

The vaccines of the invention may be multivalent or univalent. Multivalent vaccines are made from immunoconjugation of multiple PRRSV peptides with a carrier molecule.

In one aspect, the PRRSV peptide compositions comprise an effective immunizing amount of the immunogenic conjugate, preferably in combination with an immunostimulant; and a physiologically acceptable vehicle. As used in the present context, "immunostimulant" is intended to encompass any compound or composition which has the ability to enhance the activity of the immune system, whether it is a specific potentiating effect in combination with a specific antigen, or simply an independent effect upon the activity of one or more elements of the immune response. Immunostimulant compounds include but are not limited to mineral gels, e.g., aluminum hydroxide; surface active substances such as lysolecithin, pluronic polyols; polyanions; peptides; oil emulsions; alum, and MDP. Methods of utilizing these materials are known in the art, and it is well within the ability of the skilled artisan to determine an optimum amount of stimulant for a given vaccine. More than one immunostimulant may be used in a given formulation. The immunogen may also be incorporated into liposomes, or conjugated to polysaccharides and/or other polymers for use in a vaccine formulation.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a mammal, especially a pig. Associated with such container(s) can be a notice in the form prescribed by a governmental agency regulating the manufacture, use or sale of pharmaceuticals or biological products, which notice reflects approval by the agency of manufacture, use or sale for administration.

C. Adjuvants

In order to further increase the immunogenicity of the immunogenic compositions provided herewith, and which contain one or more PRRSV peptides may also comprise one or more adjuvants.

The adjuvant may be purified by any of the techniques described previously or known in the art. The preferred purification technique is silica gel chromatography, in particular the "flash" (rapid) chromatographic technique, as described by W. Clark Still et al, J. Organic Chemistry, 43, 2923-2925 (1978). However, other chromatographic methods, including HPLC, may be used for purification of the adjuvant. Crystallization may also be used to purify the adjuvant. In some cases, no purification is required as a product of analytical purity is obtained directly from the synthesis.

The vaccine compositions of the invention are prepared by physically mixing the adjuvant with the PRRSV peptide(s) under appropriate sterile conditions in accordance with known techniques to produce the adjuvanted composition. Complexation of the PRSV peptide(s) and the adjuvant is facilitated by the existence of a net negative charge on the conjugate which is electrostatically attracted to the positive charge present on the long chain alkyl compound adjuvant.

It is expected that an adjuvant can be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01% to 75%, preferably at a concentration of about 2% to 30%, more preferably at a concentration of about 5% to 25%, still more preferably at a concentration of about 7% to 22%, and most preferably at a concentration of 10% to 20% by volume of the final product.

D. Physiologically-Acceptable Vehicles

The vaccine compositions of this invention may be formulated using techniques similar to those used for other pharmaceutical polypeptide compositions. Thus, the adjuvant and PRRSV peptide(s), preferably conjugated to carrier molecule and/or admixed with an adjuvant may be stored in lyophilized form and reconstituted in a physiologically acceptable vehicle to form a suspension prior to administration. Alternatively, the adjuvant and conjugate may be stored in the vehicle. Preferred vehicles are sterile solutions, in particular, sterile buffer solutions, such as phosphate buffered saline. Any method of combining the adjuvant and the conjugate in the vehicle such that improved immunological effectiveness of the immunogenic composition is appropriate.

The volume of a single dose of the vaccine of this invention may vary but will be generally within the ranges commonly employed in conventional vaccines. The volume of a single dose is preferably between about 0.1 ml and about 3 ml, preferably between about 0.2 ml and about 1.5 ml, more preferably between about 0.2 ml and about 0.5 ml at the concentrations of conjugate and adjuvant noted above.

The vaccine compositions of the invention may be administered by any convenient means.

E. Formulation

Immunogenic conjugates comprising a PRRSV peptide(s) coupled to a carrier molecule can be used as vaccines for immunization against one or more serotypes of PRRSV. The vaccines, comprising the immunogenic conjugate in a physiologically acceptable vehicle, are useful in a method of immunizing animals, preferably swine, for treatment or prevention of infections by PRRSV.

Antibodies generated against immunogenic conjugates of the present invention by immunization with an immunogenic conjugate can be used in passive immunotherapy and generation of antiidiotypic antibodies for treating or preventing infections of PRRSV.

The subject to which the composition is administered is preferably an animal, including but not limited to cows, horses, sheep, pigs, poultry (e.g. chickens), goats, cats, dogs, hamsters, mice and rats; most preferably the mammal is a swine.

The formulations of the invention comprise an effective immunizing amount of one or more immunogenic compositions or antibodies thereto and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

F. Effective Dose

The compounds described herein can be administered to a subject at therapeutically effective doses to treat PRRSV-associated diseases. The dosage will depend upon the host receiving the vaccine as well as factors such as the size, weight, and age of the host.

The precise amount of immunogenic conjugate or antibody of the invention to be employed in a formulation will depend on the route of administration and the nature of the subject (e.g., species, age, size, stage/level of disease), and should be decided according to the judgment of the practitioner and each subject's circumstances according to standard clinical techniques. An effective immunizing amount is that amount sufficient to treat or prevent a PRRSV infectious disease in a subject. Effective doses may also be extrapolated from dose-response curves derived from animal model test systems and can vary from 0.001 mg/kg to 100 mg/kg.

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in animals, especially swine. The dosage of such compounds lies preferably within a range of circulating concentrations that include the $ED_{50}$ with little or no toxicity. The dosage can vary within this range depending upon the dosage form employed and the route of administration utilized. For any compound used in the methods of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in subjects. Levels in plasma can be measured, for example, by high performance liquid chromatography.

Immunogenicity of a composition can be determined by monitoring the immune response of test subjects following immunization with the composition by use of any immunoassay known in the art. Generation of a humoral (antibody) response and/or cell-mediated immunity may be taken as an indication of an immune response. Test subjects may include animals such as pigs, mice, hamsters, dogs, cats, rabbits, cows, horses, sheep, and poultry (e.g. chickens, ducks, geese and turkeys).

The immune response of the test subjects can be analyzed by various approaches such as: the reactivity of the resultant immune serum to the immunogenic conjugate, as assayed by known techniques, e.g., enzyme linked immunosorbent assay (ELISA), immunoblots, immunoprecipitations, etc.; or, by protection of immunized hosts from infection by the pathogen and/or attenuation of symptoms due to infection by the pathogen in immunized hosts as determined by any method known in the art, for assaying the levels of an infectious disease agent, e.g., the bacterial levels (for example, by culturing of a sample from the subject), or other technique known in the art. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective.

The therapeutics of the invention can be tested in vitro for the desired therapeutic or prophylactic activity, prior to in vitro use in animals. For example, in vitro assays that can be used to determine whether administration of a specific therapeutic is indicated include in vitro cell culture assays in which appropriate cells from a cell line or cells cultured from a subject having a particular disease or disorder are exposed to or otherwise administered a therapeutic, and the effect of the therapeutic on the cells is observed.

Alternatively, the therapeutic may be assayed by contacting the therapeutic to cells (either cultured from a subject or from a cultured cell line) that are susceptible to infection by the infectious disease agent but that are not infected with the infectious disease agent, exposing the cells to the infectious disease agent, and then determining whether the infection rate of cells contacted with the therapeutic was lower than the infection rate of cells not contacted with the therapeutic. Infection of cells with an infectious disease agent may be assayed by any method known in the art.

In addition, the therapeutic can be assessed by measuring the level of the molecule against which the antibody is directed in the animal model at suitable time intervals before, during, or after therapy. Any change or absence of change in the amount of the molecule can be identified and correlated with the effect of the treatment on the subject. The level of the molecule can be determined by any method known in the art.

After vaccination of an animal to a PRRSV using the methods and compositions of the present invention, any binding assay known in the art can be used to assess the binding between the resulting antibody and the particular molecule. These assays may also be performed to select antibodies that exhibit a higher affinity or specificity for the particular antigen.

G. Detection And Diagnostic Methods

Antibodies, or binding portions thereof, resulting from the use of PRRSV peptides of the present invention are useful for detecting in a sample the presence of PRRSV. This detection method comprises the steps of providing an isolated antibody or binding portion thereof raised against an PRRSV peptide of the invention, adding to the isolated antibody or binding portion thereof a sample suspected of containing a quantity of PRRSV, and detecting the presence of a complex comprising the isolated antibody or binding portion thereof bound to PRRSV.

The antibodies or binding portions thereof of the present invention are also useful for detecting in a sample the presence of a PRRSV peptide. This detection method comprises the steps of providing an isolated antibody or binding portion thereof raised against a PRRSV peptide, adding to the isolated antibody or binding portion thereof a sample suspected of containing a quantity of the PRRSV peptide, and detecting the presence of a complex comprising the isolated antibody or binding portion thereof bound to the PRRSV peptide.

Immunoglobulins, particularly antibodies, (and functionally active fragments thereof) that bind a specific molecule that is a member of a binding pair may be used as diagnostics and prognostics, as described herein. In various embodiments, the present invention provides the measurement of a member of the binding pair, and the uses of such measurements in clinical applications. The immunoglobulins in the present invention may be used, for example, in the detection of an antigen in a biological sample whereby subjects may be tested for aberrant levels of the molecule to which the immunoglobulin binds, and/or for the presence of abnormal forms of such molecules. By "aberrant levels" is meant increased or decreased relative to that present, or a standard level representing that present, in an analogous sample from a portion of the body or from a subject not having the disease. The antibodies of this invention may also be included as a reagent in a kit for use in a diagnostic or prognostic technique.

In one aspect, an antibody of the invention that immunospecifically binds to a PRRSV peptide may be used to diagnose, prognose or screen for a PRRSV infection.

In another aspect, the invention provides a method of diagnosing or screening for the presence of a PRRSV infection or immunity thereto, comprising measuring in a subject the level of immunospecific binding of an antibody to a sample derived from the subject, in which the antibody immunospecifically binds a PRRSV peptide in which an increase in the level of said immunospecific binding, relative to the level of said immunospecific binding in an analogous sample from a subject not having the infectious disease agent, indicates the presence of PRRSV.

Examples of suitable assays to detect the presence of PRRSV peptides or antagonists thereof include but are not limited to ELISA, radioimmunoassay, gel-diffusion precipitation reaction assay, immunodiffusion assay, agglutination assay, fluorescent immunoassay, protein A immunoassay, or immunoelectrophoresis assay.

Immunoassays for the particular molecule will typically comprise incubating a sample, such as a biological fluid, a tissue extract, freshly harvested cells, or lysates of cultured cells, in the presence of a detectably labeled antibody and detecting the bound antibody by any of a number of techniques well-known in the art.

The binding activity of a given antibody may be determined according to well-known methods. Those skilled in the art will be able to determine operative and optimal assay conditions for each determination by employing routine experimentation.

An additional aspect of the present invention relates to diagnostic kits for the detection or measurement of PRRSV. Kits for diagnostic use are provided, that comprise in one or more containers an anti-PRRSV peptide antibody, and, optionally, a labeled binding partner to the antibody. Alternatively, the anti-PRRSV peptide antibody can be labeled (with a detectable marker, e.g., a chemiluminescent, enzymatic, fluorescent, or radioactive moiety). Accordingly, the present invention provides a diagnostic kit comprising, an anti-PRRSV peptide antibody and a control immunoglobulin. In a specific embodiment, one of the foregoing compounds of the container can be detectably labeled. A kit can optionally further comprise in a container a predetermined amount of a PRRSV peptide recognized by the antibody of the kit, for use as a standard or control.

H. Administration To A Subject

Preferred routes of administration include but are not limited to intranasal, oral, intradermal, and intramuscular. Administration in drinking water, most preferably in a single dose, is desirable. The skilled artisan will recognize that compositions of the invention may also be administered in one, two or more doses, as well as, by other routes of administration. For example, such other routes include subcutaneously, intracutaneously, intravenously, intravascularly, intraarterially, intraperitnoeally, intrathecally, intratracheally, intracutaneously, intracardially, intralobally, intramedullarly, intrapulmonarily, and intravaginally. Depending on the desired duration and effectiveness of the treatment, the compositions according to the invention may be administered once or several times, also intermittently, for instance on a daily basis for several days, weeks or months and in different dosages.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The entire disclosures of all applications, patents and publications, cited herein are expressly incorporated by reference herein.

EXAMPLES

The strains of the invention used in the examples are SEQ ID NO: 1 (Wetzel p3 (pre-attenuated)) and SEQ ID NO: 2 (Wetzel p41 (attenuated)).

Example 1

Respiratory and Reproductive Safety of Cell Passage-Attenuated PRRS Virus

The following disclosure relates to experiments performed on different PRRSV isolates; however, similar methods were used to prepare the Wetzel isolates of the present invention, and can be used by one of skill in the art to prepare these and similar attenuated isolates.

Cell Passage

With the goal of creating isolates with naturally occurring deletions, a unique passage process was used. A 96 well cell culture plates were planted with MA-104 cells (ATCC CRL2621) and incubated with minimum essential medium (EMEM, SAFC Biosciences M56416) with 10% fetal bovine serum (Invitrogen) and 5% $CO_2$ at 37° C. Once cells had incubated for 3 days, 100 μL of parent virus, either MN184 (MN/01/A2) or Isolate X, were added to each well of an entire row on the culture plate. Each well was then used to make four 1/10 dilutions down each column. After dilution, 100 μL of fresh media was added over the top of each well. Plates were incubated for 3-8 days prior to being checked for cytopathic effect. After reading the plates, the highest positive dilution of each column was passed to another plate with 3 day old MA-104 cells. On this new plate four 1/10 dilutions were performed, media was overlayed, and plates were again incubated. This process was performed continuously through in vitro cell passage 51. Occasionally, if a column would display no growth the lowest dilution was passed in an attempt to harbor enough virus to maintain the passing infection. Subsequently, if there were still no signs of CPE on the next plate another column was used to plant the next plate.

Isolate X is an isolated virulent field virus from a 2007 PRRS outbreak that exhibits an ORFS 1-7-4 RFLP pattern and has a JA-142 like nsp2 region. MN184 is a very pathogenic isolate that appeared in North America in 2002 causing high mortality and severe reproductive disorders. This isolate has a 131 amino acid deletion in the nsp2 region as compared to VR-2332, the type 2 prototype strain. Furthermore, MN184 has been found to have the shortest PRRS genome found to date at 15,019 kb [12] [16]. Deletion mutants created through the passage process were referred to as 96 well deletion mutants while Isolate X-9, related to Isolate X, contained no significant deletions in the nsp2 region but was selected for comparison purposes.

Nucleotide Sequence Analysis

Nucleotide sequence analysis was performed from both in vitro cell cultures and from study animal serum samples. For the in vitro samples, QIAamp Viral RNA Mini kit (Qiagen Inc, Valencia, Calif.) was used for the ribonucleic acid (RNA) extractions while the Total Nucleic Acid MagNA Pure kit (Roche Applied Science) was used to extract from the collected swine serum. SUPERSCRIPT® III First-Strand Synthesis (Invitrogen Corp, Carlsbad, Calif.) was used to create complementary deoxyribonucleic acid (cDNA) per the manufacturer's recommendations. The cDNA product then underwent polymerase chain reaction (PCR) in a GENEAMP® PCR System 9700 (Applied Biosystems) 96 well machine with the following configuration: an initializing step for 5 minutes (min.) at 95° C., 35 cycles of a denaturation step at 95° C. for 30 seconds (sec.) an annealing step at 53° C. for 30 sec. followed by an extension step at 72° C. for 150 sec., and finally a single elongation step at 72° C. for 5 min. Samples were held at 4° C. until removal from the thermocycler. Each PCR well was set up accordingly: 25 µL, of 2×AmpliTaq Gold Mastermix (Applied Biosystems), 21 µL, DEPC Water (EMD Chemicals, Gibbstown, N.J.), 2 µL, of cDNA template, and 1 µL, of each respective primer (see Table 1).

TABLE 1

Primers used in preparation of PRRSV isolates

| Primer | Target | Sequence | SEQ ID NO: |
|---|---|---|---|
| PCR Amplification of cDNA | | | |
| NamNsp2U | Nsp2 | CTGCGGCCTTRGACAGGAACGG | 16 |
| NamNsp2L | Nsp2 | TGTCHACCCKATCCCACATGCG | 17 |
| PRRS-Out1 | ORF5 | GTACGGCGATAGGGACACC | 18 |
| PRRS-Out2 | ORF5 | CCAGAATGTACTTGCGGCC | 19 |

Letter Key:
A - Adenosine;
T - Thymidine;
K - G or T;
G - Guanosine;
R - A or G;
Y - C or T;
C - Cytidine;
H - A, C or T The PCR products were then purified with the WIZARD® DNA Clean-Up System (Promega, Madison Wis.) per the manufacturer's recommendations. Samples were then placed into a Savant Speedvac DNA 110 (Global Medical Instrumentation, Ramsey, Minn.) at medium speed for 10 min. to remove any residual isopropanol. Samples were then mixed with 10 µL of loading dye and loaded onto a 1.5% agarose gel. Electrophoresis was performed by applying 120 volts for 45 min. Bands of the appropriate size were visualized and underwent purification with the WIZARD® SV Gel and PCR Clean-Up System (Promega).

Samples were then sent to Iowa State University (ISU) DNA Facility for sequence analysis where the sequencing reactions were set up with the appropriate primers. At ISU an Applied Biosystems 3730×1 DNA Analyzer was used. Sequences were analyzed with GeneTool Version 2.0 (BioTools Inc.). The ORFS sequences were classified according to their restriction fragment length polymorphism cut pattern as outlined by the University of Minnesota Veterinary Diagnostic Laboratory.

Respiratory Safety Trial

For this study, twenty-five 3 week old commercial crossbred pigs naïve to PRRSV were randomly split by weight into groups of 5 for a 14 day respiratory safety trial. All animals were housed at a research facility and blinded to all individuals working with the animals throughout the study. Each animal within a study group, with the exception of the negative controls, received a 2 mL intramuscular (IM) injection in the neck that contained either an attenuated clone of MN184 (Isolate Y) (4.86 logs delivered), Isolate X-2 (another attenuated isolate of Isolate X) (6.13 logs delivered), Isolate X-9 (6.31 logs delivered), or wild type Isolate X (3.59 logs delivered). Viral titers were determined by $TCID_{50}$/ml (Johnson W, Roof M, Vaughn E, Christopher-Hennings J, Johnson C R, Murtaugh M P. *Pathogenic and humoral immune responses to porcine reproductive and respiratory syndrome virus (PRRSV) are related to viral load in acute infection*. Vet Immunol Immunopathol 2004 December. 8; 102(3):233-47 [17] and Reed L J, Muench H. *A simple method of estimating fifty percent end-points*. Amer J Hyg 1938; 27:493-7 [18], both hereby incorporated by reference).

The study concluded at day 14 upon which all animals underwent humane euthanasia and necropsy by a licensed veterinarian. Blood samples were collected prior to treatment administration on study day 0 as well as on day 7, and 14.

Reproductive Safety Trial

The reproductive safety trial included 16 PRRS ELISA negative commercial crossbred gilts at 90±4 days of gestation housed in a research facility and blinded to all animal caretakers and investigators. Animals were randomly divided into four treatment groups consisting of the same three cell passaged test articles from the respiratory trial and one negative control group. The study officially began at day 0 when the females were inoculated intranasally with 2.0 mL per nostril with one of the following: Isolate Y, Isolate X-2, Isolate X-9, or phosphate buffered saline (PBS). All viruses were diluted with minimum essential medium (MEM; Sigma, St. Louis, Mo.) containing 2% fetal bovine serum (FBS) (Sigma, St. Louis, Mo.) in order to deliver a target of 5.00 logs of virus in 4 ml to each animal. Viral titers were determined by $TCID_{50}$/dose. The study ended for each gilt and her piglets 21 days after their respective day of farrowing (DOF). All gilts had blood drawn at day 0, 7, 14, 21, day of farrowing (DOF), 7 days after farrowing (DOF+7), 14 days after farrowing (DOF+14), and 21 days after farrowing (DOF+21). In addition, live piglets had blood collected on DOF, DOF+7, DOF+14, and DOF+21 while dead piglets had blood or thoracic fluid collected immediately upon examination regardless of study day.

Respiratory Safety Trial Clinical Lung Evaluation

The lungs of all animals in the pig safety study were evaluated at necropsy for percent consolidation consistent with PRRSV infection. Lungs were scored for each individual lobe and total gross lung pathology using a standardized scoring system. See, Halbur P G, Miller L D, Paul P S, Meng X J, Huffman E L, Andrews J J. *Immunohistochemical identification of porcine reproductive and respiratory syndrome virus (PRRSV) antigen in the heart and lymphoid system of three-week-old colostrum-deprived pigs.* Vet Pathol 1995 March; 32(2):200-4 [19]. The final observation score equaled the weighted sum of all the individual lobe scores.

Reproductive Safety Trial Reproductive Performance

Abortions and farrowing data were recorded for each female. The day of farrowing was defined as the day the first live born pig of the litter is delivered. Gilts were observed periodically from at least 6:00 AM to 10:00 PM daily. Litter observations included the number of abortions, stillbirths, mummies, live piglets, and weak born live piglets for each female. Piglets found dead due to being crushed by the dam were recorded and confirmed with a necropsy.

Serology

Whole blood (5-10 mL) was collected from each animal via venipuncture. Samples were returned to the laboratory for separation from the clot by centrifugation. Serum was then decanted into screw-cap cryogenic vials and stored for a maximum of 24 hours at 4° C. or frozen at −70° C. until testing could be performed. Serum samples were analyzed for PRRSV specific antibody using the IDEXX HERD-CHEK® PRRS ELISA 2XR (IDEXX Laboratories Inc, Westbrook, Me.). All tests were performed as described by the manufacturer's instructions. Samples were considered positive for PRRSV antibodies if the sample-to-positive (S/P) ratio was at least 0.4.

Average Daily Weight Gain

As another parameter to gauge the health status of study animals, average daily weight gain (ADWG) was recorded. Animal weights were recorded on a scale that was calibrated prior to each use. For the respiratory safety study, animals were weighed 3 days prior to vaccination (Day −3), and at necropsy (Day 14) for average daily weight gain analysis. For the reproductive safety study, all piglets delivered were weighed within 8 hours of farrowing and all remaining live piglets were again weighed 21 days later for analysis.

Reproductive Safety Trial Viremia

Both gilt and piglet serum was tested via reverse transcriptase polymerase chain reaction (RT-PCR) for the presence of PRRSV nucleic acid. Serum was extracted by the Roche MagNA pure extraction robot with the Total Nucleic Acid MagNA Pure kit (Roche Applied Science). The RT-PCR was performed with the AgPath-ID™ NA and EU PRRSV Multiplex (Applied Biosystems) per the manufacturer's instructions. The reactions were run on a Roche Lightcycler 480 96 well machine with the following configuration: an annealing step at 45° C. for 10 min., denaturation at 95° C. for 10 min., and 40 cycles of denaturation at 97° C. for 2 sec. followed by an annealing step at 60° C. for 40 sec., and finally a cooling step at 40° C. for 40 seconds.

Reproductive Safety Study Animal Clinical Observations

All study animals were observed daily for overall health and clinical signs associated with PRRS. Each animal was evaluated for respiration, behavior, and cough with scores assigned for each category. Possible scores ranged from 0 (normal) to 1 (abnormal). Abnormal behaviors were defined as abnormal respiration, abnormal behavior such as lethargy, and the presence of a cough. A total daily score was recorded based on the sum of the 3 individual scores. Any dead piglets were assigned a score of 3 and then were weighed and subsequently had a necropsy performed to determine the likely cause of death. In addition to the daily observations, gilt rectal temperatures were taken periodically beginning with the day prior to treatment (day −1) through study termination (DOF+21).

Statistics/Biometrics

All data for the respiratory safety and reproductive safety studies were imported into SAS version 9.1 for management and analysis. Summary statistics by treatment group including mean, median, standard deviation, standard error, minimum, maximum, coefficient of variation, and frequency distributions were generated for all variables, where appropriate. All parameters were compared between groups (pairwise) 1-4 vs. 5 for both the pig and reproductive studies and groups 1-3 vs. 4 for the respiratory study. In compliance with the methods recommended by APHIS, only two-sided results were reported and all comparisons were at $\alpha=0.05$. The specific methods used to analyze data are shown in Table 2.

TABLE 2

Statistical methods of analysis for each parameter evaluated

| Safety Study | Parameter | Specific Evaluation To Be Conducted | Statistical Method of Analysis |
| --- | --- | --- | --- |
| Respiratory | Mean Lung Scores | Mean lung scores for each group | ANOVA |
| Respiratory and Reproductive | Serology | Number of animals in each group serologically positive/total number of animals in each group | Fisher's Exact Test |
| Respiratory and Reproductive | Weights and ADWG | Mean Data | ANOVA ANCOVA |
| Reproductive | Gilt Reproductive Performance | 1. Total Piglets 2. Stillborn 3. Healthy Live Piglets 4. Weak Live Piglets 5. Mummies 6. Live Pigs at DOF 21 | 1-6. Kurskal-Wallis/Wilcoxon Two Sample Test |
| Reproductive | Gilt and Piglet Clinical Observations | Gilts/Piglets with score >0 for at least one day | Fisher's Exact Test |
| Reproductive | Gilt Rectal Temperatures | Mean Data Pyrexia | 1. ANOVA Fisher's Exact Test |
| Reproductive | Gilt/Piglet Viremia | Animals positive | Fisher's Exact Test |

Results:
Sequence Analysis

The viruses undergoing continuous cell passage had genomic sequence analysis performed at approximately every 10 passages on the nsp2 region and on the ORF5 region at passage 50. As expected, several isolates had natural deletions occur throughout the process. At cell passage 50 Isolate Y had a continuous 6 nucleotide deletion in the nsp2 region, expected to result in the loss of 2 amino acids. Isolate X-2 at cell passage 50 exhibited a continuous 63 nucleotide deletion in the nsp2 region which results in the loss of a continuous 21 amino acid sequence. Isolate X-9 remained similar to JA-142 and had no large deletions in the nsp2 region. Results of sequencing of the ORF5 region displayed that the MN184 isolates still had a 1-8-4 RFLP cut pattern while the Isolate X isolates maintained a 1-7-4 RFLP cut pattern.

Samples from the reproductive safety trial also underwent sequence analysis to determine how stable the viruses were in vitro. All PCR positive piglet blood samples, from the final day of the study (DOF+21), underwent attempted sequence analysis and at least one sequence was successfully attained from each vaccinate group. All viruses remained relatively stable after in vitro replication. The nsp2 region sequencing from each individual animal revealed only a few substitutions for each virus. Substitutions resulting in amino acid changes are summarized in Table 3 and are described in comparison to MN184A and JA142 AY424271. The ORF5 regions were also sequenced and all isolates maintained their original cut pattern.

TABLE 3

Nsp2 mutations which resulted in corresponding amino acid changes from positive piglets at three weeks after farrowing.

| Isolate | | Nucleotide Change |
|---|---|---|
| | MN184A Position* | |
| Isolate Y | A | A → G |
| Isolate Y | B | A → G |
| Isolate Y | C | T → C |
| Isolate Y | D | A → G |
| | JA142 AY424271 Position* | |
| Isolate X-2 | Position | A → G |
| Isolate X-2 | F | G → A |
| Isolate X-9 | G | G → A |
| Isolate X-9 | H | C → T |
| Isolate X-9 | I | T → G |
| Isolate X-9 | J | G → A |

Respiratory Safety Trial Lung Pathology

Upon completion of the study on day 14, all animals were necropsied and assessed for lung pathology (FIG. 1). Using ANOVA to compare group mean lung scores, only the wild type Isolate X group had a statistically significant increase in clinical lung scores as compared to the negative control group. The Isolate Y group and Isolate X-9 group had statistically significant lower lung scores than the Isolate X wild type group. The lung scores indicate that the cell passage process has indeed significantly reduced the virulence of the Isolate Y and Isolate X-9 isolates while Isolate X-2 may still be capable of causing some degree of respiratory disease.

Average Daily Weight Gain

For the respiratory safety study, average daily weight gain analysis via ANOVA revealed that there were no statistically significant differences for either group mean initial body weight or average daily gain for the duration of the study amongst all treatment groups. The wild type Isolate X treatment had a slightly higher mean initial body weight than the other groups which may account for the lack of statistical differences in ADWG as compared to the other groups.

For the reproductive safety study, ANOVA analysis revealed piglets in the Isolate X-2 group had a statistically significant lower mean body weight at farrowing than the negative control group. Interestingly, piglets in all treatment groups had a statistically significant lower ADWG as compared to the negative control group. However, with the use of another statistical test, ANCOVA, it was determined that initial piglet mean body weight and the initial piglet mean body weight—treatment group interaction were significant contributors to piglet ADWG while the treatment group each piglet belonged to was not a significant contributor to ADWG.

Herdchek® Elisa

Figure 2:
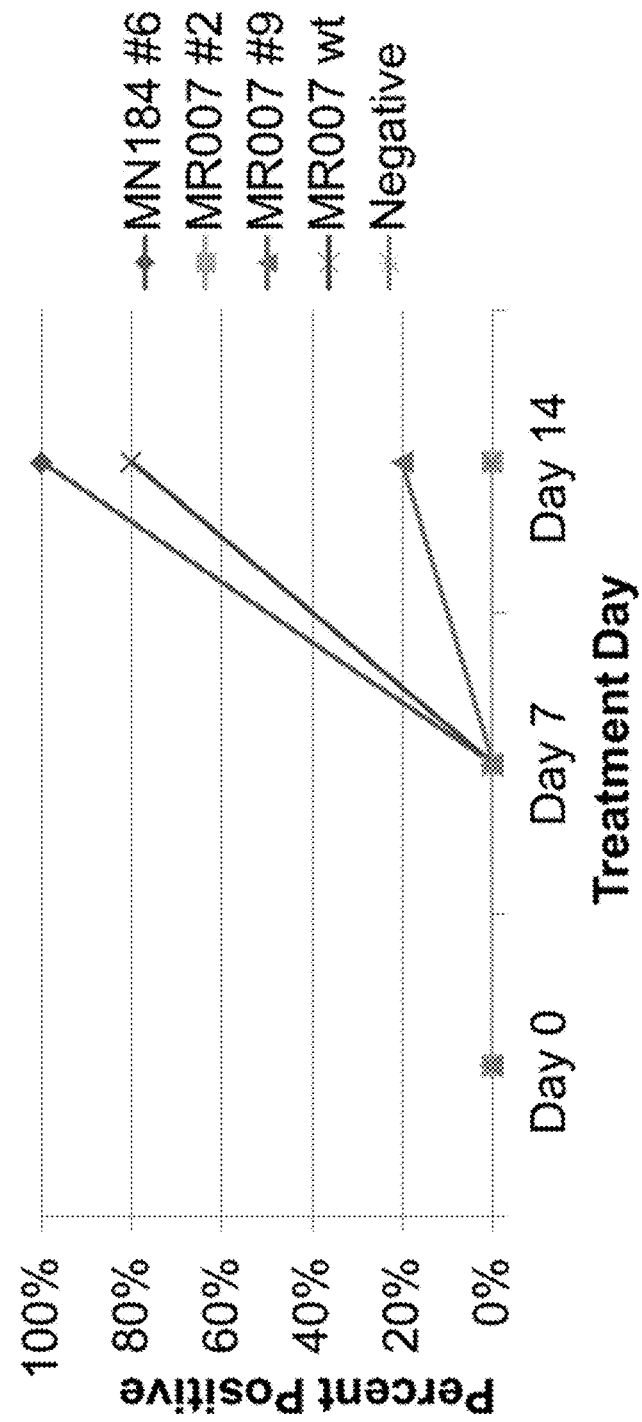
FIG. 2 is a graph of the IDEXX ELISA from the respiratory trial of Example 1. Samples are considered positive for PRRSV specific antibodies if (S/P) ratio was at least 0.4.

For the respiratory safety study, on day 0 and 7 all animals were negative via the IDEXX HERDCHEK® PRRS ELISA 2XR. However, on day 14 all animals in the Isolate Y group and most animals in group 4 (wild type Isolate X) had seroconverted while the treatment groups administered Isolates X-2 and X-9, after about 50 passages, displayed poor seroconversion (FIG. 2). Fisher's Exact Test was used to compare the number of animals that had seroconverted in each group. The results indicated that only the Isolate Y group and the wild type Isolate X group had significantly higher numbers of animals positive by ELISA as compared to the negative control group. The wild type Isolate X treatment group was statistically different from animals in the Isolate X-2 group, but not the Isolate X-9 group.

For the reproductive safety study, all animals were again negative on days 0 and 7. However, by day 21 nearly all gilts that received virus as a treatment were positive. Gilts in the MN184 treatment group all remained positive by ELISA for the duration of the study. All treatment groups had a statistically significant increase in positive animals as compared to the negative control group at day 21, DOF 0, and DOF+14.

The piglets from the reproductive safety study were found to have a considerable amount of PRRSV specific antibody. The Isolate X-9 and Isolate Y groups displayed statistically significant increases in positive ELISA tests as compared to the piglets belonging to the negative control group for all sample collection dates. The Isolate X-2 treatment group piglets were found to only be statistically distinct from the negative control group at DOF+7.

ELISA findings for both studies echoed the same results. While all isolates proved to be capable of inducing a PRRSV specific antibody response as detected by the HERDCHEK® PRRS ELISA 2XR, the onset and duration of antibody detected in the MN184 treatment group seemed to be earlier and longer lasting than the response of the Isolate X treatment groups. Within the Isolate X isolates, the Isolate X-9 groups consistently had more animals test positive than the groups that received Isolate X-2.

Gilt Reproductive Performance

All females included in the study farrowed relatively normal and healthy litters as outlined in Table 4.

TABLE 4

Mean gilt reproductive performance per litter

| | Total Piglets Farrowed | Stillborn | Healthy Live Piglets | Weak Live Piglets | Mummies | Live Pigs at DOF 21 |
|---|---|---|---|---|---|---|
| Isolate X-9 | 11.25 | 0.25 | 9.5 | 1 | 0.5 | 9.75 |
| Isolate Y | 9 | 1.75 | 6.25 | 0.25 | 0.5 | 6.5 |
| Isolate X-2 | 8.25 | 2.5 | 5.75 | 0 | 0 | 5.25 |
| Negative | 8.25 | 1.25 | 6.5 | 0 | 0.25 | 6.5 |

Due to facility and labor limitations, only 4 gilts were used for each isolate. There were no dramatic signs of virulence in any of the tested isolates. For statistical analysis, a Wilcoxon two sample test was used to make comparisons between each treatment group and the negative control group. The number of total piglets born, stillborns, healthy live piglets, weak live piglets, mummies, and pigs still alive 21 days after farrowing were compared to the negative control group. No statistical differences were found for any of the reproductive performance variables. These findings suggest that the described attenuation process has been successful in reducing the amount of reproductive failure caused by each isolate.

Mortality of Piglets, Pigs, and Gilts

For the respiratory safety study no animals were lost during the study. However, for the reproductive safety study 6 piglets were lost from the DOF 0 to DOF+21. These losses still fall within the expected range of piglet mortality prior to weaning. One gilt in the Isolate X-2 treatment group was euthanized due to illness resulting from a retained placenta. This gilt delivered just 3 stillborn piglets so no piglet performance data was compromised.

Viremia

Figure 3:
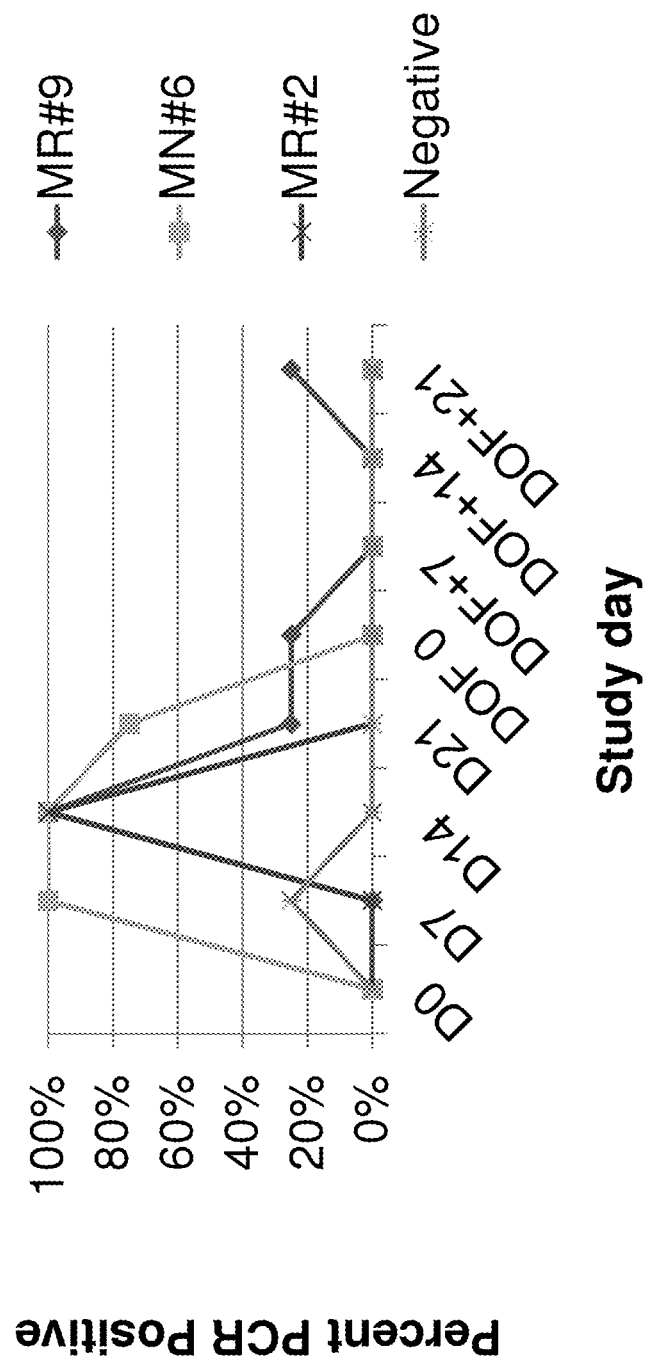
FIG. 3 is a graph of the Gilt Viremia of the reproductive trial as determined by RT-PCR via the AgPath-ID™ NA and EU PRRSV Multiplex kit with relatively short period of viremia detected of Example 1.

Gilt viremia as detected by RT-PCR was relatively short for most groups (FIG. 3). Each treatment group was compared to the negative control group using Fischer's exact test for statistical analysis. The Isolate X-9 group, Isolate Y group, and Isolate X-2 group had a statistically significant increase in animals positive for PRRS RNA at study day 14 while the Isolate Y group was also statistically distinct at day 7. The negative control group had 1 animal test positive at DOF+7. This was likely the result of sample contamination sometime along processing as this was the only positive test out of this group.

Figure 4:
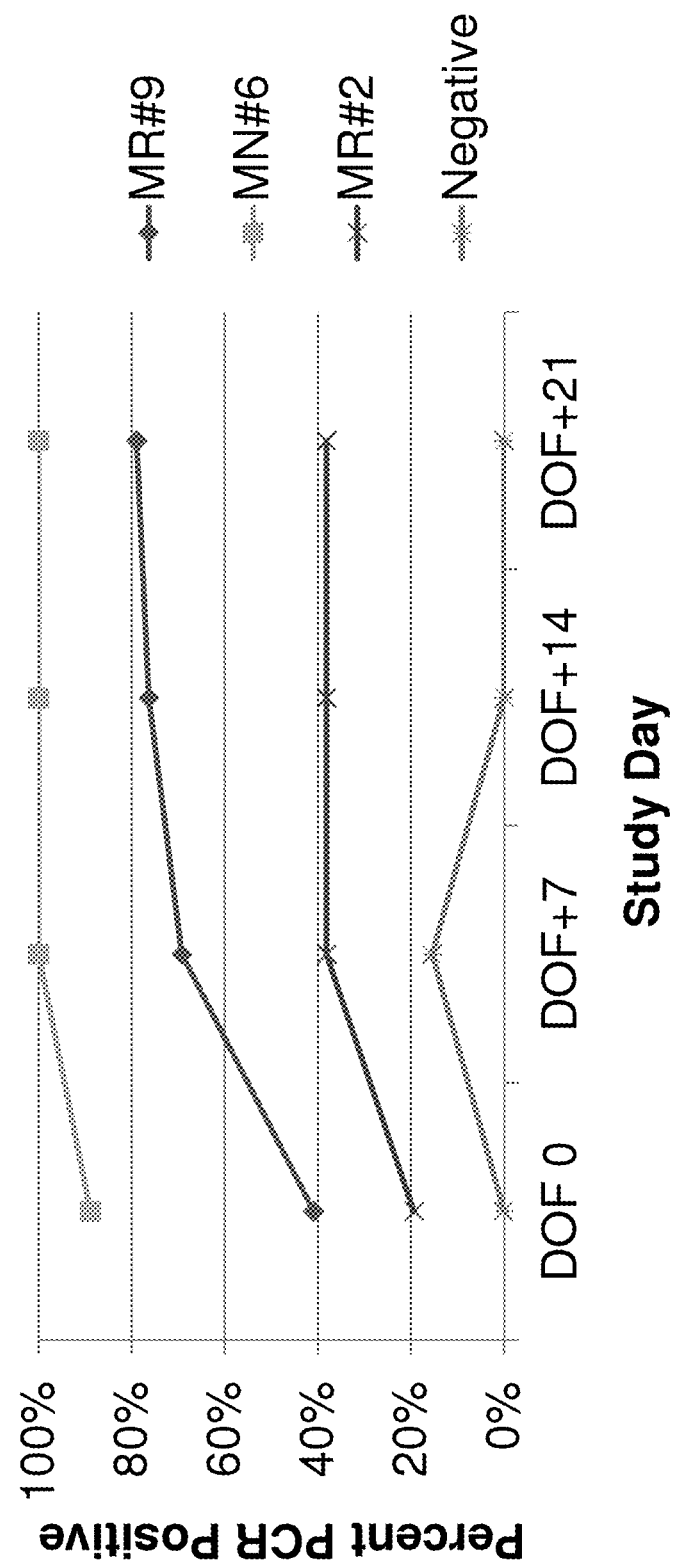
FIG. 4 is a graph of the piglet viremia as determined by RT-PCR via the AgPath-ID™ NA and EU PRRSV Multiplex kit. Variably levels of piglet viremia at birth followed by horizontal transmission within litters from the reproductive trial of Example 1.

An important safety indicator for PRRS is transplacental transfer from dam to piglet. For the Isolate X treatment groups, the majority of the piglets were negative on the day of farrowing. However, by DOF+21 most piglets belonging to the Isolate X-9 and Isolate Y treatment groups were positive, presumably due to horizontal transmission of virus. Fisher's exact test was used for statistical analysis. All treatment groups exhibited a statistically significant increase in the number of piglets testing positive for PRRS RNA, with the exception of Isolate X-2 at DOF+7 which lost significance due to 4 out of the 26 piglets in the negative control group testing positive on that day. The negative control positive samples were likely the results of contamination somewhere along the line of sample collection, handling, and processing as no other negative control group samples were PCR positive prior to or after DOF+7 (FIG. 4).

Reproductive Safety Study Clinical Observations

Clinical observations were recorded for the reproductive safety study as supporting data for remaining isolate virulence. With the exception of the euthanized gilt, only a few isolated events of abnormal scores of 1 were documented. No groups were statistically different than the negative control group when using Fisher's exact test to compare the number of animals per group with a clinically abnormal score for at least one day. Also, mean gilt group rectal temperatures were collected and compared to the negative control group using ANOVA. Statistically significant higher mean rectal temperatures were noted at day 7 (Isolate X-9 and Isolate X-2) and day 14 (Isolate Y). Body temperatures for gilts in all treatment groups remained normal for the duration of the study.

For the piglet clinical observation scores there were statistically significant increases in piglet clinical abnormalities in the Isolate X-9 and Isolate X-2 treatment groups as compared to the negative control group. Piglets in the Isolate Y treatment group had a P value of 0.0547 which is approaching statistical significance but is above the 0.05 cutoff used for all statistical analysis for this study. As previously mentioned 8 piglets (4 from the Isolate X-9 group, 1 from each MN184 group, and 2 from the Isolate X-2 group) were found dead throughout the study. No piglets in the negative control group were found dead during the study. All other clinically abnormal animals were not severally affected and no abnormalities compromised the outcome of the study.

In this study, a passage process is described in which single isolates were passed multiple times by limiting dilution. Frequent sequence analysis was used as a selection tool to test individual clones in vitro for vaccine potential. Genomic deletions within the nsp2 gene were targeted, as these isolates are believed to be more genomically stable in the animal host while also capable of providing sufficient immunological protection against wild type virus. The selected isolates were screened for genomic stability and safety through the use of both a respiratory and reproductive animal model.

The results of this trial serve as evidence that all isolates are attenuated to some degree. When compared to the negative control group, all cell passage isolates had no statistical differences for lung pathology or average daily weight gain. Furthermore, the wild type Isolate X group had statistically significant higher scores for lung pathology than the Isolate Y and the Isolate X-9 group. A wild type MN184 was not used in this study, but has been tested previously [17]. Johnson et al. inoculated ten 2-3 week old pigs with MN184 at cell culture passage 1 and documented the death of 2 pigs in that group by the first 14 days of the study. Lung pathology was not collected for the MN184 group, but the group mortality rate speaks for the general virulence of the parent wild type isolate. Here, in the pig respiratory trial, no animals were lost for any treatment group over the course of the study. Clearly, the ability to cause respiratory disease has been decreased with all isolates, but perhaps less so with Isolate X-2 group. This group's lung scores were not statistically different when compared to the wild type Isolate X treatment group.

Results for the reproductive safety trial mimicked those from the respiratory trial. When compared to the negative control group, all reproductive performance parameters and gilt clinical observations had no statistical differences for any of the tested isolates. ELISA results for both trials indicated all isolates are capable of inducing the production of PRRSV specific antibodies by day 21 in the gilts, although seroconversion in the MN184 group seems to be more consistent and longer lasting than that in the Isolate X groups. Viremia detected by RT-PCR showed that the virus attained detectable levels within the blood for only short periods of time in the gilts while there was transplacental transmission of virus with subsequent horizontal spread to littermates in all groups. While congenital transmission of virus with the transmission to littermates did occur, it didn't negatively affect the performance of all groups. The Isolate Y group had no statistical differences in piglet clinical observations when compared to the negative control group which is a phenomenon that has been previously described with currently available attenuated vaccines See, Mengeling W L, Lager K M, Vorwald A C. *Clinical effects of porcine reproductive and respiratory syndrome virus on pigs during the early postnatal interval.* Am J Vet Res 1998 January; 59(1):52-5 [20], hereby incorporated by reference. With the rising concern of modified live vaccines possibly reverting back to virulent forms, increased and proven stability of vaccine isolates will become increasingly important. Our genomic stability data indicates these isolates appear to be sufficiently stable with relatively few changes in both the nsp2 and ORF 5 regions which are to be expected and especially so with PRRS. See, Wesley R D, Mengeling W L, Lager K M, Vorwald A C, Roof M B. *Evidence for divergence of restriction fragment length polymorphism patterns following in vitro replication of porcine reproductive and respiratory syndrome virus.* Am J Vet Res 1999 April; 60(4):463-7 [21], hereby incorporated by reference.

The given results indicate the isolates are capable of inducing seroconversion in vitro and are much less virulent than the parent viruses, yet may still be capable of causing some disease or losses in production. Therefore, these isolates can be further passed in cell culture in an attempt to further attenuate and stabilize the genome. The 96 well deletion passage process is an effective and efficient method to develop novel modified live vaccines with increased efficacy and genomic stability.

Example 2

Safety of Cell Passage-Attenuated PRRS Virus in 5 Week Old Piglets

In this study, three PRRSV clones were evaluated for safety: Isolate X-6, Wetzel Clone 3 p51, and Wetzel Clone 9 p48. A 2 mL dose of each clone was administered intramuscularly (IM) to one of three groups of 6 cesarean delivered-colostrum deprived (CD-CD) pigs at 5 weeks of age. A fourth group of 5 pigs received a placebo and served as controls. The safety of the clones was evaluated based on PRRSV seroconversion, viremia and PRRSV-associated lung lesions.

On Day 0 (D0) of the study, twenty-three (23) healthy 5-week old CD-CD piglets, susceptible to PRRSV (serologically negative; <0.4, for PRRSV antibodies by ELISA), were inoculated with PRRSV Isolate X-6 (Group T1), Wetzel Clone 3 p51 (Group T2), Wetzel Clone 9 p48 (Group T3), or a placebo (Group C).

Serum samples were collected on D0, 7 and 14 from all pigs. On D14, all pigs were euthanized at which time gross pathological examinations and lung lesion scoring was performed.

Clinical observations were made daily from D-1 to D14 for overall health and signs associated with PRRS disease, specifically, respiration, behavior, and cough. No clinical signs were observed in any pig throughout the entire study. Additionally, no lung lesions (score=0) were observed in any pig at necropsy.

Polymerase Chain Reaction (PCR) testing for the presence of PRRSV viremia was completed on all serum samples. PCR results for pigs in all groups were negative on D0 indicating a lack of exposure to PRRSV at the time of inoculation. Results on the remaining time points for the control Group C were also negative indicating a lack of environmental exposure to PRRSV during the study. On D7, all pigs in Group T1 (6/6, 100%) and T2 (6/6, 100%) were PCR positive while all pigs in Group T3 (0/6, 0.0%) were negative. On D14, Group T1 (6/6, 100%) and T2 (6/6, 100%) remained at the same levels, while Group T3 (2/6, 33.3%) showed two pigs positive for PRRS viremia. To verify that PRRSV in these last two pigs was the clone they received at inoculation, ORF 5 sequence analysis was performed with results matching Wetzel Clone 9 p48 indicating no cross contamination and/or environmental infection.

Antibody titers for PRRSV were determined by IDEXX® ELISA. All pigs were sero-negative (<0.4) on D0. This indicates a lack of maternal antibodies at the time of inoculation. All pigs remained negative on D7. On D14, Group T1, T2, and T3 had 4/6 (66.7%), 5/6 (83.3%), and 1/6 (16.7%) positive pigs, respectively. Controls remained negative at D14 showing a lack of exposure to PRRSV.

Despite the fact that piglets developed viremia by Day 14, the data indicates that the PRRSV clones used in this study caused no lung lesions and/or clinical signs of PRRSV infection. These clones are deemed to be safe in 5-week old piglets.

In this study, three clones were evaluated for safety: Isolate X-6, Wetzel Clone 3 p51, and Wetzel Clone 9 p48. A 2 mL dose of each clone was administered intramuscularly (IM) to one of three groups of 6 cesarean delivered-colostrum deprived (CDCD) pigs at 5 weeks of age. A fourth group of 5 pigs received a placebo and served as controls. The safety of the clones was evaluated based on PRRSV seroconversion, viremia and PRRSV-associated lung lesions to help determine the feasibility of their use as a MLV candidate.

The objective of this study was to evaluate the safety of the PRRSV clones Isolate X-6, Wetzel Clone 3 p51, and Wetzel Clone 9 p48 in 5-week old piglets. Clinical evaluation of all piglets was conducted daily from Day-1 to 14. Evaluations included incidence of mortality, clinical scores (respiratory distress, lethargy, behavior, and cough), viremia, lung lesions, sero-status, and virus isolation (VI). A schedule of events is shown in Table 5.

TABLE 5

Schedule of events

| Day | Event | Samples | Testing |
|---|---|---|---|
| 0 | Pigs to be 5 weeks old +/− 5 d Clinical Evaluations, Serum collection, Inoculate with IVP's | Serum | PCR, ELISA, VI |
| 1-14 | Clinical evaluation | None | None |
| 7 | Serum Collection | Serum | PCR, ELISA, VI |
| 14 | Necropsy, serum collection, lavage collection | Serum, Lung Scores, Lavages | PCR, ELISA, VI |

Study Design:

Twenty-three (23) PRRS-susceptible (ELISA <0.4), CD-CD study animals were purchased, transported, and then housed together 1 week prior to vaccination at Veterinary Resources, Inc.'s (VR1) Cambridge, Iowa facility. The test animals were individually identified and examined by the study investigator for overall health.

Piglets were randomly divided into four groups as shown in Table 6.

TABLE 6

Treatment Groups

| Group | Number of Animals | Treatment | Dose/Route |
|---|---|---|---|
| T1 | 6 | PRRSV Isolate X-6 | 2 mL/IM |
| T2 | 6 | PRRSV Wetzel Clone 3 p51 | 2 mL/IM |
| T3 | 6 | PRRSV Wetzel Clone 9 p48 | 2 mL/IM |
| C | 5 | Control (Sterile PBS Placebo) | 2 mL/IM |

Randomization Method

For randomization, a roster of all animals included in the study was prepared by the study investigator prior to study initiation. A computer random number generator (Microsoft Excel) was used to assign each animal a unique random number. Animals were sorted into weight blocks (experimental blocks). Within experimental blocks, the animal with the lowest random number was assigned to the first treatment group. Assignment continued by increasing random number until all animals had been assigned to a treatment group. See Attachment 7 for group assignments.

Methods of Blinding

The study was blinded as to eliminate bias in laboratory sample testing. The person conducting the laboratory testing of study samples was not the same person administering treatment or making daily observations. See Table 7 for inclusion criteria.

TABLE 7

Inclusion Criteria

| | |
|---|---|
| a) Species: | Porcine |
| b) Breed: | Commercial cross |
| c) Age Requirements: | 5 weeks ± 5 days of age |
| d) Weight Range: | Uniform for age |
| e) Sex: | Both female and neutered males |
| f) Number: | 23 |
| g) Source of test animal and ownership: | Commercial Class A Dealer; Boehringer Ingelheim Vetmedica, Inc. |
| h) Special Requirements: | Cesarean delivered and colostrum deprived (CD/CD) |
| i) Serological Status: | Seronegative to PRRSV (S/P < 0.400) |

Exclusion Policy

No animals were excluded from the study prior to completion of the animal phase.

Identification of Test Animals

All test animals were identified by duplicated ear tags not associated with treatment group.

Animal Management and Housing

Animals were housed in the facilities at Veterinary Resources, Inc. according to their standard operating procedures.

Animal Care

The animals were deemed to be in good health and nutritional status before the study was initiated. The investigator conducted a health examination prior to the randomization procedure.

Due to the susceptibility of CD/CD animals, all piglets received one dose of Pfizer EXCEDE® on six days prior to inoculation (D-6) as per label instructions. Additionally, piglets were fed PURINA® Mills Senior Medicated feed from D-6 through D0. From D1 through the end of the study, piglets received PURINA® Mills Senior feed.

Management of Food and Water

Feed rations were appropriate for the age, condition, and species of test animal according to facility standard operating procedure. Water was provided ad libitum throughout the study.

Investigational veterinary products (IVP)

The PRRSV clones were prepared by infection of AK MA-104 cells in modified Minimum Essential Media (mMEM) with 2% FBS. The cultures were allowed to incubate at 37° C. until CPE was ≥80% at which time they were placed at −70° C. On the day of inoculation (D0), flasks were removed from the freezer and allowed to thaw at room temperature. Each clones' suspension was then transferred to a plastic, stopper-topped vaccine bottle and labeled with T1, T2, or T3 (see Table 1). They were then delivered directly on ice to the study site. All clone preparations were tested and quantified by the $TCID_{50}$ assay pre- and post-inoculation. For the control Group C, 1×PBS was used as a placebo. The pigs were administered 2.0 mL IM of the appropriate IVP or placebo on D0. Any remaining IVP's were returned to BIVI-Ames after inoculation. See Tables 8, 9, and 10 for details of the PRRSV clone IVP's.

TABLE 8

Investigational Veterinary Products, PRRSV Isolate Y-6

| | |
|---|---|
| Generic Product Name: | PRRSV "Isolate Y-6" |
| Manufacturer: | Boehringer Ingelheim Vetmedica, Inc. |
| Lot or Serial Number: | 250-071-MRC6P81 |
| Expiration Date: | N/A |
| Storage Requirements | −70° C. |
| Testing | On the day of challenge, a $TCID_{50}$ assay was performed pre- and post-challenge resulting in respective titers of 6.23 and 6.66 with an overall average of 6.45 $\log_{10}$ $TCID_{50}$/mL. |
| Test Article Transfer | The required doses of IVP were transferred by the Study Monitor to the study site just prior to inoculation and kept on ice. |
| Test Article Retention: | Any unused IVP was disposed of by autoclaving. |
| Applied Dose: | 2.0 mL of the PRRSV Isolate 6 was administered IM on Day 0 to each pig in Group T1. |

TABLE 9

Investigational Veterinary Products, PRRSV Wetzel Clone 3 p51

| | |
|---|---|
| Generic Product Name: | PRRSV Wetzel Clone 3 p51 |
| Manufacturer: | Boehringer Ingelheim Vetmedica, Inc. |
| Lot or Serial Number: | 250-096-WC3P51 |
| Expiration Date: | N/A |
| Storage Requirements | −70° C |
| Testing | On the day of challenge, a $TCID_{50}$ assay was performed pre- and post-challenge resulting in respective titers of 6.29 and 6.72 with an overall average of 6.51 $\log_{10}$ $TCID_{50}$/mL. |
| Test Article Transfer | The required doses of IVP were transferred by the Study Monitor to the study site just prior to inoculation and kept on ice. |
| Test Article Retention: | Any unused IVP was disposed of by autoclaving. |
| Applied Dose: | 2.0 mL of the PRRSV Wetzel Clone 3 p51 was administered IM on Day 0 to each pig in Group T2. |

TABLE 10

Investigational Veterinary Products, PRRSV Wetzel Clone 9 p48

| | |
|---|---|
| Generic Product Name | PRRSV Wetzel Clone 9 p48 |
| Manufacturer Lot or Serial Number | Boehringer Ingelheim Vetmedica, Inc. 250-046-WC9P48 |
| Expiration Date | N/A |
| Storage Requirements | −70° C. |
| Testing | On the day of challenge, a $TCID_{50}$ assay was performed pre- and post-challenge resulting in respective titers of 6.98 and 6.91 with an overall average of 6.95 $\log_{10}$ $TCID_{50}$/mL. |
| Test Article Transfer | The required doses of IVP were transferred by the Study Monitor to the study site just prior to inoculation and kept on ice. |
| Test Article Retention | Any unused IVP was disposed of by autoclaving. |
| Applied Dose | 2.0 mL of the PRRSV Wetzel Clone 9 p48 was administered IM on Day 0 to each pig in Group T3. |

Carcasses of all euthanized study pigs were disposed of by rendering. No test animals were removed from the study after inoculation or prior to necropsy. After all of the doses of the Investigational Veterinary Products were administered, the remaining IVP's were returned to the Study Monitor for appropriate disposal.

Evaluation of CLONE Safety

The safety of the clones was evaluated based on seroconversion to PRRSV, viremia and presence/severity of PRRSV-associated lung lesions. A single occurrence of viremia at any time point following inoculation classified a pig as positive for viremia. Percentage pathology for each animal's lungs was calculated according to the procedure described in section 12.3.1. Results from each Test Group were compared to those of the Control Group. Pigs were also assessed for the isolation of PRRSV in serum and lung lavage fluid, clinical observations/scores, and mortality.

No more than 10 mL of venous whole blood was collected via the anterior vena cava from each pig using a sterile 18-20g×1 inch (2.54 cm) to 1.5 inch (3.81 cm)1-1½" VACCUTAINER® needle, a VACCUTAINER® needle holder and 13 mL serum separator tubes (SST) by the Study the Investigator or a designee. Blood was collected prior to inoculation and on Day 7 and 14. Each blood tube was labeled with the animal's ID number, the study number, the date of collection, the study day and the sample type.

Serum samples were tested for PRRSV viremia by PCR and for PRRSV antibodies using a commercially available test—IDEXX® PRRS ELISA. Serum samples were also tested for the presence of PRRSV by virus isolation (VI). Every animal was PRRS sero-negative (ELISA S/P ratio of <0.4) prior to vaccination indicating a valid study. Virus isolation results were reported as positive or negative.

Clinical Observations

Pigs were observed for overall health and clinical signs associated with PRRS disease by the Investigator or designee daily from Day −1 to Day 14. Specifically, pigs were examined each day for respiration, behavior, and cough with each category rated 0 for normal and 1 for abnormal (See Table 11). A total daily score for each pig was the summation of its Respiratory Score, Behavior Score and Cough Score for that particular day. No deaths occurred during the study.

Respiration, Behavior, Cough, and Observation Scores were scored as follows: Respiration Score: 0=Normal Respiration, 1=Abnormal Respiration; Behavior Score: 0=Normal Behavior, 1=Abnormal Behavior; Cough Score: 0=No Coughing Noted, 1=Cough Present.

On the day of necropsy, after data and samples were collected, each pig was euthanized and necropsied by the Investigator or designee. Following euthanasia, the Investigator or designee removed the lungs and trachea intact, with a clamp placed across the trachea to prevent blood cross contamination. A general description of lung pathology was observed and the percentage of pathology in each lung lobe was recorded. Total % lung pathology was determined for each pig by summation of percent lung pathology for each lung lobe.

After the lungs were evaluated for pathology, a lung lavage sample was collected from each set of lungs by the Investigator or designee. Each sample was labelled with the animal number, study number, sample type, date of collection and study day. No lung tissue samples were collected for this study.

Results:

ELISA results were negative (S/P<0.400) for all pigs on Day 0, indicating a lack of maternal antibodies present at the time of inoculation. Day 0 averages for group T1, T2, T3, and C are −0.070, −0.042, −0.037, and −0.032, respectively. All pigs remained negative on Day 7 with averages for group T1, T2, T3, and C at −0.069, −0.038, −0.023, and −0.053, respectively. On Day 14, there were four positive pigs (4/6, 66.7%) in Group Ti, five positive pigs (5/6, 83.3%) in Group T2, and one positive pig (1/6, 16.7%) in Group T3. However, Group C remained all negative (0/5, 0.0%). Averages for Day 14 were 1.122, 1.024, 0.247, and −0.045 for Group T1, T2, T3, and C, respectively. ELISA data can be seen in Table 11.

TABLE 11

PRRSV IDEXX ® ELISA Sample to Positive Ratios

| Pig ID | Group | D0 | D7 | D14 |
|---|---|---|---|---|
| 9 | T1 | −0.013 | −0.079 | 0.305 |
| 23 | | 0.002 | −0.024 | 2.007* |
| 31 | | −0.007 | −0.045 | 1.626* |
| 32 | | −0.385 | −0.241 | 0.083 |
| 33 | | −0.018 | −0.009 | 1.333* |
| 36 | | 0.002 | −0.016 | 1.380* |
| Average S/P | | −0.070 | −0.069 | 1.122 |
| # of Positive Pigs (%) | | 0/6 (0.0%) | 0/6 (0.0%) | 4/6 (66.7%) |
| 60 | T2 | −0.049 | −0.049 | 0.187 |
| 61 | | −0.016 | 0.002 | 0.447* |
| 62 | | −0.005 | −0.040 | 2.490* |
| 65 | | −0.131 | −0.089 | 1.281* |
| 76 | | −0.022 | −0.011 | 1.020* |
| 80 | | −0.029 | −0.040 | 0.720* |
| Average S/P | | −0.042 | −0.038 | 1.024 |
| # of Positive Pigs (%) | | 0/6 (0.0%) | 0/6 (0.0%) | 5/6 (83.3%) |
| 70 | T3 | −0.018 | −0.029 | 0.031 |
| 81 | | −0.163 | −0.054 | 0.246 |
| 88 | | −0.007 | −0.022 | 0.107 |
| 90 | | −0.016 | −0.005 | 0.241 |
| 95 | | −0.017 | −0.016 | −0.014 |
| 97 | | −0.002 | −0.011 | 0.869* |
| Average S/P | | −0.037 | −0.023 | 0.247 |
| # of Positive Pigs (%) | | 0/6 (0.0%) | 0/6 (0.0%) | 1/6 (16.7%) |
| 57 | C | −0.022 | −0.033 | −0.040 |
| 84 | | −0.020 | −0.033 | −0.052 |
| 91 | | −0.025 | −0.047 | −0.045 |
| 92 | | −0.061 | −0.074 | −0.059 |
| 94 | | −0.032 | −0.080 | −0.028 |
| Average S/P | | −0.032 | −0.053 | −0.045 |
| # of Positive Pigs (%) | | 0/5 (0.0%) | 0/5 (0.0%) | 0/5 (0.0%) |

*Positive Sample = S/P > 0.400

All pigs were PCR negative on Day 0 indicating a lack of exposure to PRRSV at the time of inoculation. On Day 7, all pigs in Group T1 (6/6, 100%) and T2 (6/6, 100%) were positive, while Group T3 (0/6, 0.0%) and C (0/5, 0.0%) had all negative pigs. The number of positive pigs per group for Day 14 was T1 6/6 (100%), T2 6/6 (100%), T3 2/6 (33.3%), and C 0/5 (0.0%). The lack of positive pigs throughout the study in the control Group C indicates that there was no environmental exposure to PRRSV. PCR totals can be seen in Table 12.

TABLE 12

NA-PRRSV Multiplex PCR Results

| Pig ID | Group | D0 | D7 | D14 |
|---|---|---|---|---|
| 9 | T1 | Neg | Pos | Pos |
| 23 | | Neg | Pos | Pos |

TABLE 12-continued

NA-PRRSV Multiplex PCR Results

| Pig ID | Group | D0 | D7 | D14 |
|---|---|---|---|---|
| 31 | | Neg | Pos | Pos |
| 32 | | Neg | Pos | Pos |
| 33 | | Neg | Pos | Pos |
| 36 | | Neg | Pos | Pos |
| # of Positive Pigs (%) | | 0/6 (0.0%) | 6/6 (100%) | 6/6 (100%) |
| 60 | T2 | Neg | Pos | Pos |
| 61 | | Neg | Pos | Pos |
| 62 | | Neg | Pos | Pos |
| 65 | | Neg | Pos | Pos |
| 76 | | Neg | Pos | Pos |
| 80 | | Neg | Pos | Pos |
| # of Positive Pigs (%) | | 0/6 (0.0%) | 6/6 (100%) | 6/6 (100%) |
| 70 | T3 | Neg | Neg | Neg |
| 81 | | Neg | Neg | Neg |
| 88 | | Neg | Neg | Pos |
| 90 | | Neg | Neg | Neg |
| 95 | | Neg | Neg | Neg |
| 97 | | Neg | Neg | Pos |
| # of Positive Pigs (%) | | 0/6 (0.0%) | 0/6 (0.0%) | 2/6 (33.3%) |
| 57 | C | Neg | Neg | Neg |
| 84 | | Neg | Neg | Neg |
| 91 | | Neg | Neg | Neg |
| 92 | | Neg | Neg | Neg |
| 94 | | Neg | Neg | Neg |
| # of Positive Pigs (%) | | 0/5 (0.0%) | 0/5 (0.0%) | 0/5 (0.0%) |

*Neg = negative, Pos = positive

Due to the fact that Group T3 did not show any PCR positive pigs until Day 14, sequencing was performed to verify that pigs #88 and 97 were infected with Wetzel Clone 9. ORF 5 sequences were compared between the PRRSV isolated from the above listed pigs and the three PRRSV clones used in this study. Results from pigs 88 and 97 were homologous with Wetzel clone 9. Sequence results can be seen in FIG. 5.

Virus isolation on serum samples was similar to PCR results. All pigs were negative by CPE and FA on Day 0. Positive pigs per group on Day 7 were 6/6 (100%), 6/6 (100%), 2/6 (33.3%), and 0/5 (0.0%) for Group T1, T2, T3, and C, respectively, for both CPE and FA. Positive pigs per group on Day 14 were 5/6 (83.3%), 2/6 (33.3%), 5/6 (83.3%), and 0/5 (0.0%) for Group T1, T2, T3, and C, respectively, for both CPE and FA. Again, control Group C remained negative for the entire study showing lack of exposure to PRRSV. See Table for Virus Isolation-Serum results. Virus isolation was also performed on bronchial-alveolar lavage samples taken at the time of necropsy. Results show 2/6 (33.3%), 3/6 (50.0%), 1/6 (16.7%), and 0/5 (0.0%) positive pigs for Group T1, T2, T3, and C, respectively. See Table 14 for Virus Isolation-Lavage results.

TABLE 13

Virus Isolation-Serum

| Pig ID | Group | D0 CPE/FA | D7 CPE/FA | D14 CPE/FA |
|---|---|---|---|---|
| 9 | T1 | Neg/Neg | Pos/Pos | Pos/Pos |
| 23 | | Neg/Neg | Pos/Pos | Pos/Pos |
| 31 | | Neg/Neg | Pos/Pos | Pos/Pos |
| 32 | | Neg/Neg | Pos/Pos | Pos/Pos |
| 33 | | Neg/Neg | Pos/Pos | Pos/Pos |
| 36 | | Neg/Neg | Pos/Pos | Neg/Neg |
| # of Positive Pigs (%) | | 0/6 (0.0%) | 6/6 (100%) | 5/6 (83.3%) |
| 60 | T2 | Neg/Neg | Pos/Pos | Neg/Neg |
| 61 | | Neg/Neg | Pos/Pos | Pos/Pos |
| 62 | | Neg/Neg | Pos/Pos | Pos/Pos |
| 65 | | Neg/Neg | Pos/Pos | Neg/Neg |
| 76 | | Neg/Neg | Pos/Pos | Neg/Neg |
| 80 | | Neg/Neg | Pos/Pos | Neg/Neg |
| # of Positive Pigs (%) | | 0/6 (0.0%) | 6/6 (100%) | 2/6 (33.3%) |
| 70 | T3 | Neg/Neg | Neg/Neg | Pos/Pos |
| 81 | | Neg/Neg | Neg/Neg | Neg/Neg |
| 88 | | Neg/Neg | Pos/Pos | Pos/Pos |
| 90 | | Neg/Neg | Neg/Neg | Pos/Pos |
| 95 | | Neg/Neg | Neg/Neg | Pos/Pos |
| 97 | | Neg/Neg | Pos/Pos | Pos/Pos |
| # of Positive Pigs (%) | | 0/6 (0.0%) | 2/6 (33.3%) | 5/6 (83.3%) |
| 57 | C | Neg/Neg | Neg/Neg | Neg/Neg |
| 84 | | Neg/Neg | Neg/Neg | Neg/Neg |
| 91 | | Neg/Neg | Neg/Neg | Neg/Neg |
| 92 | | Neg/Neg | Neg/Neg | Neg/Neg |
| 94 | | Neg/Neg | Neg/Neg | Neg/Neg |
| # of Positive Pigs (%) | | 0/5 (0.0%) | 0/5 (0.0%) | 0/5 (0.0%) |

*Neg = negative, Pos = positive; CPE = cytopathic effect, FA = fluorescent antibody

TABLE 14

Virus Isolation-Lavages

| Pig ID | Group | Lavage CPE/FA |
|---|---|---|
| 9 | T1 | Pos/Pos |
| 23 | | Neg/Neg |
| 31 | | Neg/Neg |
| 32 | | Pos/Pos |
| 33 | | Neg/Neg |
| 36 | | Neg/Neg |
| # of Positive Pigs (%) | | 2/6 (33.3%) |
| 60 | T2 | Pos/Pos |
| 61 | | Neg/Neg |
| 62 | | Pos/Pos |
| 65 | | Neg/Neg |
| 76 | | Neg/Neg |
| 80 | | Pos/Pos |
| # of Positive Pigs (%) | | 3/6 (50.0%) |
| 70 | T3 | Pos/Pos |
| 81 | | Neg/Neg |
| 88 | | Neg/Neg |
| 90 | | Neg/Neg |
| 95 | | Neg/Neg |
| 97 | | Neg/Neg |
| # of Positive Pigs (%) | | 1/6 (16.7%) |
| 57 | C | Neg/Neg |
| 84 | | Neg/Neg |
| 91 | | Neg/Neg |
| 92 | | Neg/Neg |
| 94 | | Neg/Neg |
| # of Positive Pigs (%) | | 0/5 (0.0%) |

*Neg = negative, Pos = positive; CPE = cytopathic effect, FA = fluorescent antibody Clinical Observations All pigs had a clinical score of 0, meaning there were no observed abnormal clinical respiratory signs, abnormal behavior, or cough. See Table 15 for Observation Scores.

TABLE 15

Clinical Observation Scores

| Pig ID | Group | D-1 | D0 | D1 | D2 | D3 | D4 | D5 | D6 | D7 | D8 | D9 | D10 | D11 | D12 | D13 | D14 | Total Score |
|---|---|---|---|---|---|---|---|---|---|---|---|---|---|---|---|---|---|---|
| 9 | T1 | 0 | 0 | 0 | 0 | 0 | 0 | 0 | 0 | 0 | 0 | 0 | 0 | 0 | 0 | 0 | 0 | 0 |
| 23 | | 0 | 0 | 0 | 0 | 0 | 0 | 0 | 0 | 0 | 0 | 0 | 0 | 0 | 0 | 0 | 0 | 0 |
| 31 | | 0 | 0 | 0 | 0 | 0 | 0 | 0 | 0 | 0 | 0 | 0 | 0 | 0 | 0 | 0 | 0 | 0 |
| 32 | | 0 | 0 | 0 | 0 | 0 | 0 | 0 | 0 | 0 | 0 | 0 | 0 | 0 | 0 | 0 | 0 | 0 |
| 33 | | 0 | 0 | 0 | 0 | 0 | 0 | 0 | 0 | 0 | 0 | 0 | 0 | 0 | 0 | 0 | 0 | 0 |
| 36 | | 0 | 0 | 0 | 0 | 0 | 0 | 0 | 0 | 0 | 0 | 0 | 0 | 0 | 0 | 0 | 0 | 0 |
| Average Score | | 0 | 0 | 0 | 0 | 0 | 0 | 0 | 0 | 0 | 0 | 0 | 0 | 0 | 0 | 0 | 0 | 0 |
| 60 | T2 | 0 | 0 | 0 | 0 | 0 | 0 | 0 | 0 | 0 | 0 | 0 | 0 | 0 | 0 | 0 | 0 | 0 |
| 61 | | 0 | 0 | 0 | 0 | 0 | 0 | 0 | 0 | 0 | 0 | 0 | 0 | 0 | 0 | 0 | 0 | 0 |
| 62 | | 0 | 0 | 0 | 0 | 0 | 0 | 0 | 0 | 0 | 0 | 0 | 0 | 0 | 0 | 0 | 0 | 0 |
| 65 | | 0 | 0 | 0 | 0 | 0 | 0 | 0 | 0 | 0 | 0 | 0 | 0 | 0 | 0 | 0 | 0 | 0 |
| 76 | | 0 | 0 | 0 | 0 | 0 | 0 | 0 | 0 | 0 | 0 | 0 | 0 | 0 | 0 | 0 | 0 | 0 |
| 80 | | 0 | 0 | 0 | 0 | 0 | 0 | 0 | 0 | 0 | 0 | 0 | 0 | 0 | 0 | 0 | 0 | 0 |
| Average Score | | 0 | 0 | 0 | 0 | 0 | 0 | 0 | 0 | 0 | 0 | 0 | 0 | 0 | 0 | 0 | 0 | 0 |
| 70 | T3 | 0 | 0 | 0 | 0 | 0 | 0 | 0 | 0 | 0 | 0 | 0 | 0 | 0 | 0 | 0 | 0 | 0 |
| 81 | | 0 | 0 | 0 | 0 | 0 | 0 | 0 | 0 | 0 | 0 | 0 | 0 | 0 | 0 | 0 | 0 | 0 |
| 88 | | 0 | 0 | 0 | 0 | 0 | 0 | 0 | 0 | 0 | 0 | 0 | 0 | 0 | 0 | 0 | 0 | 0 |
| 90 | | 0 | 0 | 0 | 0 | 0 | 0 | 0 | 0 | 0 | 0 | 0 | 0 | 0 | 0 | 0 | 0 | 0 |
| 95 | | 0 | 0 | 0 | 0 | 0 | 0 | 0 | 0 | 0 | 0 | 0 | 0 | 0 | 0 | 0 | 0 | 0 |
| 97 | | 0 | 0 | 0 | 0 | 0 | 0 | 0 | 0 | 0 | 0 | 0 | 0 | 0 | 0 | 0 | 0 | 0 |
| Average Score | | 0 | 0 | 0 | 0 | 0 | 0 | 0 | 0 | 0 | 0 | 0 | 0 | 0 | 0 | 0 | 0 | 0 |
| 57 | C | 0 | 0 | 0 | 0 | 0 | 0 | 0 | 0 | 0 | 0 | 0 | 0 | 0 | 0 | 0 | 0 | 0 |
| 84 | | 0 | 0 | 0 | 0 | 0 | 0 | 0 | 0 | 0 | 0 | 0 | 0 | 0 | 0 | 0 | 0 | 0 |
| 91 | | 0 | 0 | 0 | 0 | 0 | 0 | 0 | 0 | 0 | 0 | 0 | 0 | 0 | 0 | 0 | 0 | 0 |
| 92 | | 0 | 0 | 0 | 0 | 0 | 0 | 0 | 0 | 0 | 0 | 0 | 0 | 0 | 0 | 0 | 0 | 0 |
| 94 | | 0 | 0 | 0 | 0 | 0 | 0 | 0 | 0 | 0 | 0 | 0 | 0 | 0 | 0 | 0 | 0 | 0 |
| Average Score | | 0 | 0 | 0 | 0 | 0 | 0 | 0 | 0 | 0 | 0 | 0 | 0 | 0 | 0 | 0 | 0 | 0 |

All pigs had a % lung lobe pathology score of 0, meaning no lesions were seen on any of the lung lobes upon gross pathological examination. See Table 16 for Lung Lesion Scores and Table 17 for IVP Titration.

TABLE 16

Lung Lesion Scores

| Pig ID | Group | RA | RC | RD | LA | LC | LD | Int | Total Score |
|---|---|---|---|---|---|---|---|---|---|
| 9 | T1 | 0 | 0 | 0 | 0 | 0 | 0 | 0 | 0 |
| 23 | | 0 | 0 | 0 | 0 | 0 | 0 | 0 | 0 |
| 31 | | 0 | 0 | 0 | 0 | 0 | 0 | 0 | 0 |
| 32 | | 0 | 0 | 0 | 0 | 0 | 0 | 0 | 0 |
| 33 | | 0 | 0 | 0 | 0 | 0 | 0 | 0 | 0 |
| 36 | | 0 | 0 | 0 | 0 | 0 | 0 | 0 | 0 |
| Average Score | | 0 | 0 | 0 | 0 | 0 | 0 | 0 | 0 |
| 60 | T2 | 0 | 0 | 0 | 0 | 0 | 0 | 0 | 0 |
| 61 | | 0 | 0 | 0 | 0 | 0 | 0 | 0 | 0 |
| 62 | | 0 | 0 | 0 | 0 | 0 | 0 | 0 | 0 |
| 65 | | 0 | 0 | 0 | 0 | 0 | 0 | 0 | 0 |
| 76 | | 0 | 0 | 0 | 0 | 0 | 0 | 0 | 0 |
| 80 | | 0 | 0 | 0 | 0 | 0 | 0 | 0 | 0 |
| Average Score | | 0 | 0 | 0 | 0 | 0 | 0 | 0 | 0 |
| 70 | | 0 | 0 | 0 | 0 | 0 | 0 | 0 | 0 |
| 81 | | 0 | 0 | 0 | 0 | 0 | 0 | 0 | 0 |
| 88 | | 0 | 0 | 0 | 0 | 0 | 0 | 0 | 0 |
| 90 | | 0 | 0 | 0 | 0 | 0 | 0 | 0 | 0 |
| 95 | | 0 | 0 | 0 | 0 | 0 | 0 | 0 | 0 |
| 97 | | 0 | 0 | 0 | 0 | 0 | 0 | 0 | 0 |
| Average Score | | 0 | 0 | 0 | 0 | 0 | 0 | 0 | 0 |
| 57 | | 0 | 0 | 0 | 0 | 0 | 0 | 0 | 0 |
| 84 | | 0 | 0 | 0 | 0 | 0 | 0 | 0 | 0 |
| 91 | | 0 | 0 | 0 | 0 | 0 | 0 | 0 | 0 |
| 92 | | 0 | 0 | 0 | 0 | 0 | 0 | 0 | 0 |
| 94 | | 0 | 0 | 0 | 0 | 0 | 0 | 0 | 0 |
| Average Score | | 0 | 0 | 0 | 0 | 0 | 0 | 0 | 0 |

*RA = right apical lobe, RC = right cardiac lobe, RD = right diaphragmatic lobe, LA = left apical lobe, LC = left cardiac lobe, LD = left diaphragmatic lobe, Int = intermediate lobe

TABLE 17

IVP Titration Results

| | Pre-Inoculation Titers | | | | | |
|---|---|---|---|---|---|---|
| PRRSV Clone | 1 | 2 | 3 | 4 | 5 | Ave[1] |
| Isolate X-6 | 6.25 | 6.25 | 6.40 | 6.50 | 5.75 | 6.23 |
| Wetzel Clone 3 p51 | 5.70 | 6.16 | 6.50 | 6.88 | 6.22 | 6.29 |
| Wetzel Clone 9 p48 | 7.00 | 6.60 | 7.16 | 7.16 | 7.00 | 6.98 |

| | Post-Inoculation Titers | | | | | |
|---|---|---|---|---|---|---|
| | 1 | 2 | 3 | 4 | 5 | Ave[2] |
| Isolate X-6 | 6.50 | 6.60 | 6.75 | 6.69 | 6.76 | 6.66 |
| Wetzel Clone 3 p51 | 7.36 | 6.84 | 6.45 | 6.36 | 6.60 | 6.72 |
| Wetzel Clone 9 p48 | 6.70 | 6.75 | 6.60 | 7.50 | 7.00 | 6.91 |

| Average Total (Ave[1] + Ave[2]) | |
|---|---|
| Isolate X-6 | 6.45 |
| Wetzel Clone 3 p51 | 6.51 |
| Wetzel Clone 9 p48 | 6.95 |

*Titer expressed as $\log_{10}$ TCID$_{50}$/mL

CONCLUSION

The objective of this study was to evaluate the safety of the PRRSV clones Isolate Y-6, Wetzel Clone 3 p51, and Wetzel Clone 9 p48 in 5-week old piglets to determine their viability as vaccine candidates. Although no lung lesions were visible 14 days post-inoculation, for two clones (Isolate Y-6 and Wetzel Clone 3 p51) PRRS viremia was present by Day 7. Two piglets inoculated with the third clone (Wetzel Clone 9 p48) tested PCR positive at Day 14. Additionally, no PRRSV antibodies were detected in any of the IVP piglets until Day 14, one week after the presence of viremia. Despite the fact that piglets developed viremia by Day 14, the data indicates that the PRRSV clones used in this study caused no lung lesions and/or clinical signs of PRRSV infection. These clones are deemed to be safe in 5-week old piglets. Future studies should include vaccination-challenge models to determine these clones' abilities to reduce lung lesions after virulent challenge with PRRSV.

Example 3

Efficacy of Attenuated PRRS Virus (Wetzel Attenuated) in a Respiratory Challenge Model The objective of this study was to evaluate the efficacy of INGELVAC PRRS® MLV and an experimental vaccine against a recent NA-PRRSV challenge isolate in a respiratory challenge model. Evaluations included mortality, clinical scores (respiratory distress, behavior, cough, etc.), viremia, lung lesions, serology, virus isolation, average daily gain, and rectal temperature.

The objective of this study was to evaluate the efficacy of INGELVAC PRRS® MLV and an experimental vaccine against a recent NA-PRRSV challenge isolate in a respiratory challenge model. Evaluations included mortality, clinical scores (respiratory distress, behavior, cough, etc.), viremia, lung lesions, serology, virus isolation, average daily gain, and rectal temperature. Schedule of events is provided in Table 18.

Sixty-five PRRS-susceptible study pigs were individually identified and examined by the Investigator and were deemed healthy for enrollment. Pigs were randomly divided into four groups as shown in Table 19.

TABLE 19

Treatment Groups

| Group | # of Pigs | Room Vx phase | Day 0-Vaccine | Room Challenge Phase | Day 22- Challenge Isolate |
|---|---|---|---|---|---|
| 1 | 20 | CC2 | Placebo (Diluent) | CC2 | 1-4-4 |
| 2 | 20 | CA5 | INGELVAC PRRS ® MLV | CC2 | 1-4-4 |
| 3 | 20 | CC1 | W96117 #9 p42 | CC1 | 1-4-4 |
| SC | 5 | CC2 | NA | NA | NA |

On Day 00n Day 0 (D0) of the study, Groups 2 and 3 were vaccinated with INGELVAC PRRS® MLV per label instructions or 2.0 mL of the experimental vaccine, 1M, respectively. Groups 1 received an equivalent dose of a placebo in the same manner. Group SC served as strict controls and received no treatment. Pigs were vaccinated at >3 weeks of age. On D22, Groups 1, 2, and 3 were challenged with the 1-4-4 isolate. Only two rooms were available during the challenge period. Group 1 and 2 were housed together and Group 3 remained in its original room. Challenge route and dose was 1.0 ml intranasal (0.5 mL/nostril). The challenge virus was titrated for potency on the day of challenge, results indicated a delivered dose of 5.13 log/dose. Fourteen days following challenge (D36), all pigs were euthanized and necropsied. The lungs and trachea were removed and a general description of lung pathology was observed. The percentage of pathology in each lung lobe was recorded. After scoring, lung lavages were collected. Individual lung lavage fluid was tested for presence of PRRSV by PCR.

Rectal temperatures were taken and animal observations were performed from one day prior to challenge (D21) through the day of necropsy (D36); observations were for mortality, respiratory distress, behavior, and cough. Serum

TABLE 18

SCHEDULE OF EVENTS

| Day | Event | Samples | Testing |
|---|---|---|---|
| −2 or before | Transportation to study site | None | None |
| | Health examination | None | None |
| 0 | Sample collection (all) | Blood (SST) | ELISA, PCR, VI |
| | Weight (all) | None | None |
| | Vaccination (V1, V2, C1) | Retention | Titration (TCID$_{50}$) |
| 7, 14, 22 | Sample collection (all) | Blood (SST) | ELISA, PCR, VI |
| 22 | Necropsy strict controls | % lung pathology, lavage; lung; other tissues if necessary | VI, Histopathology (if necessary) |
| 22 | Sample collection (all) | Blood (SST) | ELISA, PCR, VI |
| | Weight (all) & move V1 and C1 to the same room, separate pens | None | None |
| | Challenge (V1, V2, C1) | Retention | Titration (TCID$_{50}$) |
| 29 | Sample collection (all) | Blood (SST) | ELISA, PCR, VI |
| 21-36 | Clinical observations, temp (all) | None | None |
| 36 | Sample collection (all) | Blood (SST) | ELISA, PCR, VI |
| | Weight (all) | None | None |
| | Necropsy (all) | % lung pathology, lavage; lung; other tissues if necessary | VI, Histopathology (if necessary) | was collected prior to vaccination on D0, and at D7, 14, 21, D28, and D35. Serum samples were individually tested for PRRSV antibodies by IDEXX® ELISA and viremia by PCR, qPCR and VI. In addition, fixed lung tissue was collected and retained for histopathological testing, if necessary. Animals were weighed at the beginning of the study (Day 0), at challenge (Day 22) and just prior to necropsy (Day 36).Sixty-five, mixed breed, mixed sexed, individually identified pigs were used in the study that were PRRSV antibody and viremia negative prior to allotment in the study. Animals were housed in a BSL2 facility in accordance with the appropriate SOP(s). To eliminate the possibility of shedding across groups, vaccinates were housed separately from controls for the duration of the study, see Table 1. Also, Group SC remained with non-vaccinated Group 1 until the day of challenge and was necropsied on Day 22.

Animal space was appropriate for the size and number of pigs in accordance with acceptable animal husbandry practices for these regions. Feed rations were appropriate for the age, condition, and species of test animal according to facility standard operating procedure. Water was provided ad libitum throughout the study. No extra-protocol biologicals or pharmaceuticals were administered to the pigs during the study.

Vaccine, Placebo, and Challenge Virus

See Table 20, 21, 22, and 23 for vaccine, placebo, and challenge virus that were used in this study.

TABLE 20

| Vaccine, INGELVAC PRRS ® MLV | |
|---|---|
| Vaccine: | INGELVAC PRRS ® MLV, reconstituted with Diluent. |
| Formulation: | Released serial formulated according to Outline of Production. |
| Manufacturer: | Boehringer Ingelheim Vetmedica, Inc. |
| Lot/Serial Number: | Lot 245-C29; Diluent Item #180460 |
| Storage: | Lyophilized: 2-8° C. Reconstituted: On ice and protected from light |
| Testing: | Potency titration results: 6.0 log/dose (5.71 $Log_{10}$ $TCID_{50}$/mL) |
| Dose/Route: | 2.0 mL/intramuscular (IM) injection; Groups 2 |

TABLE 21

| Experimental Vaccine | |
|---|---|
| Vaccine: | W96117#9 p42 |
| Formulation: | Frozen cell culture preparation. The virus was propagated twice in AKMA-104 cells p78 from Wetzel#9 p41 Lot#262-132. T-75 flasks of cells were used and inoculated with 200 ul of virus. The flasks were incubated at 37 C. with CO2 for seven days, then frozen. The two sets were thawed, combined and harvested. (N288-029 through N288-039) |
| Manufacturer: | Boehringer Ingelheim Vetmedica, Inc. |
| Lot/Serial Number: | Lot #N288-038 |
| Storage: | Frozen, thaw in lukewarm water bath; hold on ice during use |
| Testing: | Potency titration results: 6.6 log/dose (6.29 $Log_{10}$ $TCID_{50}$/mL) |
| Dose/Route: | 2.0 mL/intramuscular (IM) injection; Group 3 |

TABLE 22

| Placebo, Diluent Only | |
|---|---|
| Placebo: | Diluent, Sterile water for injection |
| Formulation: | Formulated according to Outline of Production. |
| Manufacturer: | Boehringer Ingelheim Vetmedica, Inc. |
| Lot/Serial Number: | Item #180460 |
| Storage: | Room temperature. |
| Testing: | After vaccination, any remaining diluent was frozen at <−40° C. and checked for sterility. |
| Dose/Route: | 2.0 mL/intramuscular (IM) injection; Groups 1 |

TABLE 23

| Challenge Virus, North American PRRSV (NA-PRRSV) Challenge Isolates | |
|---|---|
| Virus: | NA-PRRSV, 109866 (144 or 1-4-4) |
| Formulation: | Isolate 109866 (144) was used (200 ul) to inoculate a T-75 flask of AKMA-104 cells, incubated at 37 C. with CO2 for five days, and was then frozen. The material was thawed and aliquoted to individual vials. The necessary number of vials of tissue culture harvest was removed from the freezer, thawed, combined, transferred to vaccine bottles and put on ice. |
| Manufacturer: | Boehringer Ingelheim Vetmedica, Inc. |
| Lot/Serial Number: | Lot N191-154, preparation N288-136 |
| Storage: | Long term: frozen −70 ± 10° C. Frozen, thaw in lukewarm water bath; put on ice during use. |
| Testing: | Potency testing: 5.13 log/dose |
| Dose/Route: | 1.0 mL/intranasal (IN) at 0.5 mL/nostril; Groups 1, 2, 3. |

Assessment of Effectiveness

Vaccine efficacy was assessed based on reduction of PRRSV viremia and percentage of total PRRSV-associated lung lesions. A single occurrence of viremia at any time point following vaccination classified a pig as positive for viremia. Percentage pathology for each animal's lungs was calculated according to the procedure described in the protocol. Pigs were also assessed for the isolation of PRRSV in serum and lung lavage fluid, clinical observations/scores, serology, mortality, average daily gain (ADG), and rectal temperature.

Results

A general description of lung pathology and the percentage of pathology in each lung lobe were recorded on the Necropsy Report Record. Total percent lung pathology was determined for each pig by summation of percent lung pathology for each lung lobe. Individual lung lesion scores are included in the appendix. The summary statistics are listed in the Table 24. The lung scores were analyzed using SAS in the mixed procedure using Type 3 Tests and the difference of least squared means; treatment and room were confounded due to housing constraints. There were statistically significant lower lung scores in the both vaccinated groups when compared to the challenge control group. No histopathology was submitted.

TABLE 24

Lung Score summary statistics with a scatter plot of individual values.

| % Lung Scores | Average | Min | Max | StdDev | Back-transformed LSM | p-val vs diluent group for LSM |
|---|---|---|---|---|---|---|
| Diluent | 52.9 | 11.3 | 100.0 | 25.1 | 54.7 | |
| INGELVAC PRRS ® MLV | 37.4 | 0.6 | 90.5 | 28.1 | 33.9 | 0.0452 |
| W96117#9 p42 | 35.5 | 0.1 | 72.0 | 22.1 | 32.7 | 0.0181 |

After the lungs were evaluated for pathology, a lung lavage sample was collected from each set of lungs by the Investigator or designee. Lung lavage samples were tested for PRRSV by PCR, qPCR and VI. Based on the qPCR all of the BAL samples were positive for the challenge virus. There were no statistical differences of quantity of virus detected in the BALs.

Blood was collected on D0, D7, 14, 22, D28, and D36. Serum was harvested from each tube and transferred to cryovials for retention and to HMC for testing. Serum samples at BIVI-Ames were held at 2-8° C. until testing and −70±10° C. for retention.

Figure 6:
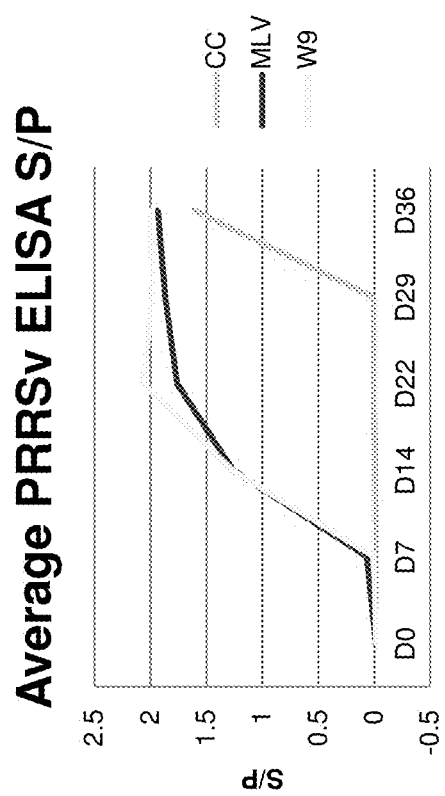
FIG. 6 is a graph of the average PRRSV ELISA S/P from Example 3.

Serum samples were for PRRSV antibodies using a commercial available test (IDEXX® PRRS ELISA). ELISA results were recorded as Sample-to-Positive (S/P) ratios. An S/P ratio of ≥0.4 is considered positive. Results are shown in FIG. 6.

Figure 7:
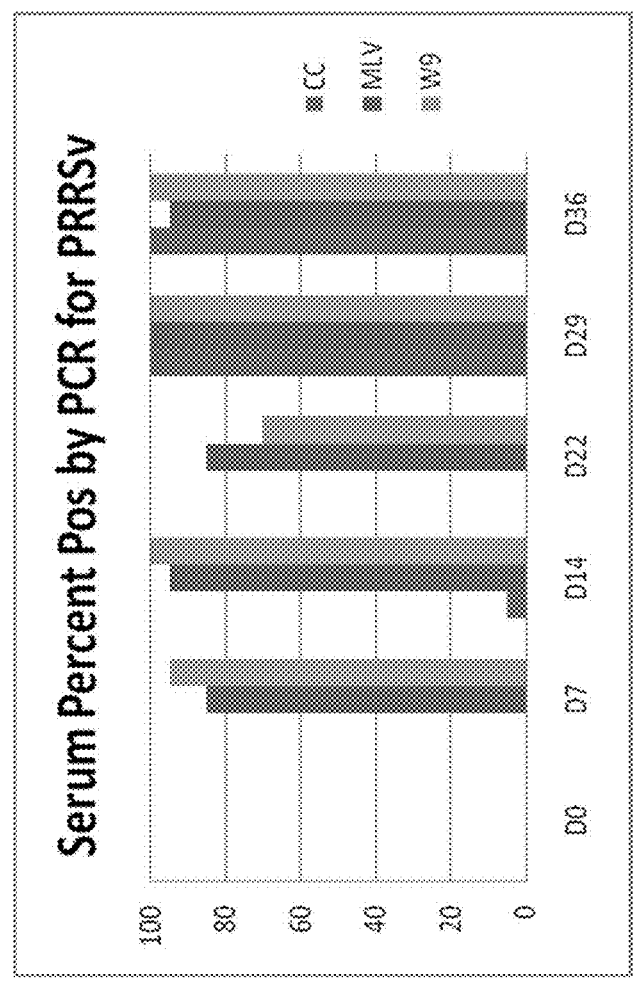
FIG. 7 is a graph showing percent positive by PCR for PPRSV from Example 3.

Viremia for PRRSV as tested by PCR and qPCR. Results were reported as positive or negative which used generic primers for any PRRS virus. A single occurrence of viremia at any time point following vaccination classified a pig as positive for viremia. Relative copy numbers of PRRS virus was determined by qPCR testing that used primers specifically designed to detect the challenge 144 PRRS virus without detecting either vaccine virus. The quantitative data were analyzed using SAS in the mixed procedure using Type 3 Tests and the difference of least squared means; treatment and room were confounded due to housing constraints. On day 29 the W96117#9 p42 vaccinate groups had significantly less virus in the serum than the challenge control group (p-value=<0.0001). On day 36, the group vaccinated with INGELVAC PRRS®MLV has significantly less viremia than the challenge control group (p-value=0.0089). The results are shown in FIG. 7.

Clinical Observations

Figure 8:
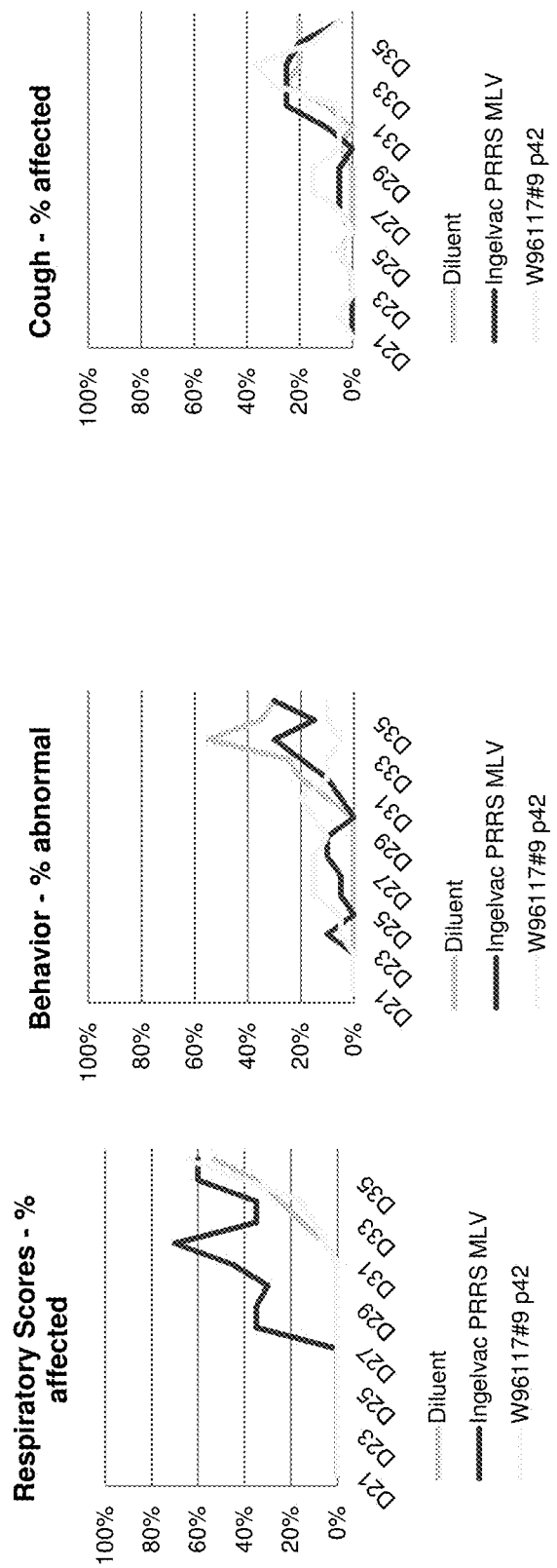
FIG. 8 shows graphs of respiratory scores, behavior scores and cough scores by percentage affected from Example 3.

Pigs were observed for overall health and clinical signs associated with PRRS disease by the Investigator or designee daily from one day prior to challenge (D27) to the day of necropsy (D36). Specifically, pigs were examined each day for respiration, behavior, and cough with each category rated 0 for normal and 1 for abnormal. The results are shown in FIG. 8.

Figure 9:
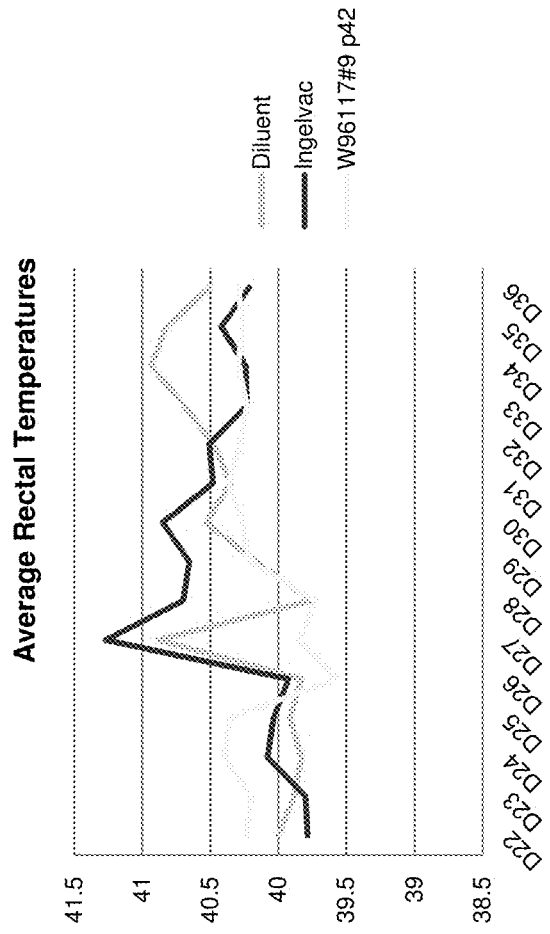
FIG. 9 shows average rectal temperatures from Example 3.

Rectal temperatures were taken daily, from D22 through D36. The data were analyzed using JMP8.0 student's t test. When comparing the temperature response of the group vaccinated with the W96117#9 p42 vaccine, the average temperatures were significantly higher on days 22-25 when compared to the challenge controls and significantly lower on days 26, 33-35. When comparing the group vaccinated with, there were significantly higher average temperatures than the challenge control pigs on days 24 and 29; the average temperatures were significantly lower on days 22, 33-35. In this study one pig in the challenge control group was euthanized on day 35 due to morbidity. The results are shown in FIG. 9.

Figure 10:
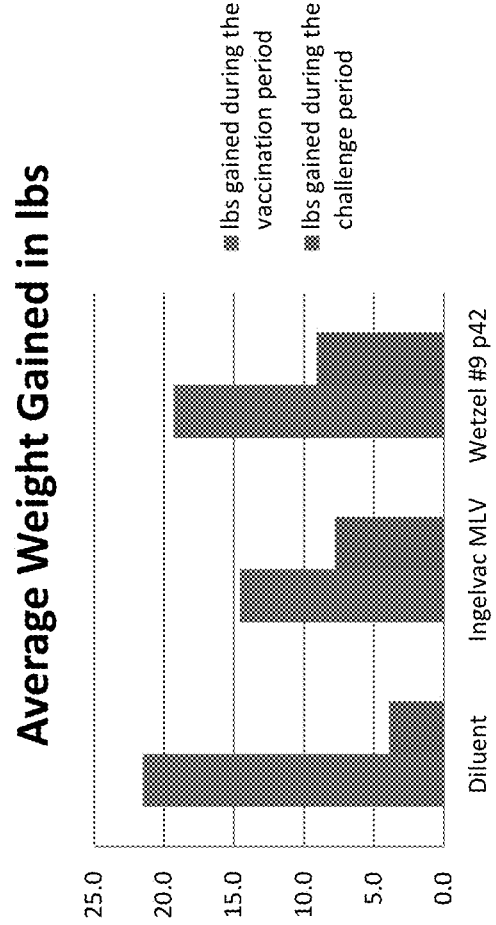
FIG. 10 shows average weight gain (in pounds) from Example 3.

Animals were weighed on Day 0, 22 and 36. The total average weight gain during the vaccination period and during the challenge period was calculated. The weight gain data were analyzed using SAS in the mixed procedure using Type 3 Tests and the difference of least squared means; treatment and room were confounded due to housing constraints. The group vaccinated with INGELVAC PRRS® MLV had statistically lower gain during the vaccination period (p-value=<0.0001) and statistically higher gain during the challenge period (p-value=0.0039) when compared to the challenge control group. The W96117#9 p42 group has significantly higher gain than the challenge control group during the challenge period (p-value=<0.0001). The results are shown in FIG. 10.

Discussion:

The objective of this study was to evaluate the efficacy of INGELVAC PRRS® MLV and an experimental vaccine against a recent NA-PRRSV challenge isolate in a respiratory challenge model. The challenge isolate was highly virulent and created very high (up to 100% lung lesion score indicative of pneumonia) lung lesions and noticeable clinical disease, including weight loss and mortality.

Two vaccines were evaluated for efficacy in the presence of the virulent challenge. Typically, it is recommended to vaccinate pigs four weeks prior to the anticipated period of challenge. However, in this study, the pigs were challenged at 22 days post-vaccination. Both vaccines resulted in a statistically significant reduction of lung lesions with improved weight gain during the post-challenge period and reduction in viremia post-challenge.

Through the course of this study a specific semi-quantitative PCR was developed for the detection of the 144 challenge virus, specifically. With this tool, the serum viremia data could be specific for the challenge virus and not detect the vaccine virus. It was demonstrated that there was no detectable vaccine virus in the unvaccinated group during the challenge period after being moved into the room with a vaccinated animal.

Example 4

Nucleotide and Protein Sequences Encoded Thereby of the Wetzel Pre-Attenuated (p3 Wetzel (Nucleotide Sequence of SEQ ID NO:1)) and Wetzel Attenuated ((Nucleotide Sequence of SEQ ID NO:2))

Nucleotide Sequence

The goal of this study was to provide PRRSV full genome sequence for PRRSV isolates pre-attenuated Wetzel strain (p3) and post-attenuated vaccine Wetzel strain (p41). Genomic sequencing of pre- and post-attenuated vaccine strains can provide critical information to help understand the biological determinates of viral fitness and thresholds required for viral reversion. Note that although the PRRSV virus is a single-stranded RNA virus, DNA equivalents (wherein T is substituted for the U in the actual RNA viral sequence) are disclosed herein for consistency with NCBI GenBank usage.

Genomic Sequencing

A viral metagenomic approach was employed in which tissue culture materials for each of the PRRS viruses were subjected to viral particle protected nucleic acid extraction and 454-sequencing of randomly primed amplicons. In total, 6 strains were attempted: 1-4-4 (data not shown), passage 3 Wetzel (p3), p10 Wetzel, p20 Wetzel, p30 Wetzel, p40 Wetzel, and vaccine strain p41 Wetzel. Of the 7 attempted, sufficient sequencing was achieved for complete/near-complete genome analysis of 6 strains, in which p20 Wetzel failed. Table 25 indicates the number of sequences and average coverage depth for each of the isolates. A high percentage of PRRSV sequences were obtained and no other viruses were detected in any of the samples. Genomic sequences are listed below for p3 Wetzel and p41 Wetzel as sequence IDs land 2, respectively.

TABLE 25

Summary of Sequencing

| Strain | Average Seq. Length | Total # of Sequences | % of Sequence align to PRRSV | Avg coverage depth | Genome complete/near-complete |
|---|---|---|---|---|---|
| 1-4-4 challenge | 225 | 27299 | 90% | 375X | Near-complete |
| p3 Wetzel | 216 | 40182 | 90% | 520X | Complete |
| p10 Wetzel | 205 | 10214 | 87% | 123X | Near-complete |
| p20 Wetzel | 202 | 32 | 100% | N/A | N/A |
| p30 Wetzel | 216 | 11655 | 88% | 149X | Near-complete |
| p40 Wetzel | 219 | 7472 | 93% | 113X | Partial |
| p41 Wetzel | 207 | 48806 | 94% | 636X | Complete |

Components of Attenuation

Detailed analysis of those positions which were modified or polymorphic at each passage tested during the attenuation was conducted; based on the sequencing data, no large scale deletions were identified in the vaccine strain. Summarized in Table 26, 33 point mutations were identified between p3 and p41, the majority (19/33) were either silent or polymorphic.

TABLE 26

Summary of p3 vs p41 changes

| Ref. Position | Gene | Nuc. Change | Polymorphic/ Substitution | Amino acid change |
|---|---|---|---|---|
| 931 | ORF1a | C > T | Sub. | Silent |
| 936 | ORF1a | G > GT | Poly. | R252R/L |
| 938 | ORF1a | G > CG | Poly. | V253L/V |
| 1147 | ORF1a | T > C | Sub. | Silent |
| 2047 | ORF1a | T > C | Sub. | Silent |
| 2137 | ORF1a | C > T | Sub. | Silent |
| 2916 | ORF1a | A > G | Sub. | Y912C |
| 3011 | ORF1a | C > T | Sub. | Silent |
| 3151 | ORF1a | T > CT | Poly. | Silent |
| 3450 | ORF1a | C > T | Sub. | A1090V |
| 3896 | ORF1a | T > C | Sub. | Silent |
| 5626 | ORF1a | C > T | Sub. | Silent |
| 5713 | ORF1a | C > T | Sub. | Silent |
| 5797 | ORF1a | C > T | Sub. | Silent |
| 6449 | ORF1a | A > T | Sub. | T2090S |
| 6769 | ORF1a | T > A | Sub. | Silent |
| 6947 | ORF1a | A > C | Sub. | K2256Q |
| 7345 | ORF1b | A > G | Sub. | T16A |
| 7602 | ORF1b | C > T | Sub. | Silent |
| 8364 | ORF1b | T > A | Sub. | Silent |
| 8379 | ORF1b | C > T | Sub. | Silent |
| 9957 | ORF1b | G > A | Sub. | Silent |
| 10361 | ORF1b | A > G | Sub. | D1021G |
| 10894 | ORF1b | C > T | Sub. | R1199W |
| 11976 | ORF2a | A > G | Sub. | K102R |
| 12693 | ORF3 | C > T | Sub. | Silent |
| 12721 | ORF3 | T > C | Sub. | F143L |
| 12722 | ORF3 | T > GT | Poly. | F143F/C |
| 12968 | ORF3 | C > T | Sub. | A225V |
| 13398 | ORF5 | A > T | Sub. | K4N |
| 13876 | ORF5 | G > A | Sub. | G164R |
| 13964 | ORF5 | C > T | Sub. | S193L |
| 14098 | ORF6 | T > C | Sub. | L42S |

Protein Sequences:

From Wang et al. (22) (internal references deleted; expressly incorporated by reference herein): PRRSV is a small, enveloped, single positive-stranded RNA virus including a genome of about 15 kb, encoding nine ORFs. The PRRSV genome is comprised of two polymerase genes, ORF1a and 1b, and seven structural genes, ORF2a, 2b, 3, 4, 5, 6, and 7. ORF1a and ORF1b constitutes approximately 75% of the viral genome, and are characterized by a process of ribosomal frame shifting translated into a large polyprotein; which by self-cleavage gives rise to the non-structural proteins (NSPs) including the RNA-dependent RNA polymerase. Open reading frames 2a, 3, 4 and 5 all encode glycosylated proteins, designated GP2a, GP3, GP4, and GP5, respectively. The newly defined ORF2b encodes the smallest protein of the virus particle designated GP2b. ORF7 encodes the non-glycosylated nucleocapsid protein (N), constituting 20-40% of the protein content of the virion. ORF6 encodes the likewise non-glycosylated matrix protein (M)."

Polypeptides encoded by the nucleotide sequences of SEQ ID NOs: 1 and 2 were identified, and are set forth as follows:

| | p3 Wetzel protein sequences encoded by SEQ ID NO: 1 |
|---|---|
| Protein/ Seq ID NO | SEQUENCE |
| ORF1a/ SEQ ID NO: 3 | MSGILDRCTCTPNARVFVADGQVYCTRCLSARTLLPLNLQVSELGVLGLFYRPEEPL<br>RWTLPRAFPTVECSPAGACWLSAIFPIARMTSGNLNFQQRIVRVAAEIYRVGQLTPTV<br>LKNLQVYERGCRWYPIVGPVPGVAVYANSLHVSDKPFPGATHVLTNLPLPQRPKPE<br>DFCPFECAMAVVYDIGHDAVMYVAKERVSWAPRGGEKGKFETVPEELRLVAEQLF<br>TSFPPHHVVDMSKFIFTAPDCGASMRVERQYGCLPAGTVPDGNCWWSLFSSLPPEV<br>QCREIRRATQFGYQTKHGVAGKYLQRRLQANGLRAVVDSNGPIVIQYFSVKESWIR<br>HVKLAGEPCYPGFEDLLRIRVEPNTLPLSDKGDKVFRFGGHKWYGAGKRARRSRAG<br>AATTVAGHASPVRETQQAKKHEAASANKAELLERYSPPAEGNCGWHCISAIVNRM<br>VNSKFETALPEKVRPPEDWATDEDLVNTIQILRLPAALDRNGVCASAKYVLKLEGEH<br>WTVSVTPGMPPSLLPLECVQGCCEHKGSLRSPDAVEVSGFDPASLDRLAGVMHLPSS<br>AIPAALAELSGDPDRPVSPATTAWTVSQFYARHSGGEHPDQKYLRKIISLCEVIESCC<br>CSQNKINLVTPEEVKTKIDQYLSGAASLEECLARLEKARPPSVLDTSFDWDVVLPGV<br>GAAVRAAKLPLANQCHAPVTVVTQRPSLKFQPRKAESVKSLPESRPLPAPRRKIRSR<br>CGSLTSLDGNFPDSWEDLAGGPFHFPTLPEPTTRPGEPVPVPAPRKTVPRLVSSLIVSV<br>PVPAPRRGIRQAEGMNLVAVTPACQDELLDLSESSQAEHGAPSLALPRSEDALAVGR<br>REAEEVLSEISGMPDDIRLVPVSSSSSLSSVEITRPKYSAQAIIDSGGPCCGHLQEVKEK<br>YLNVMREACDATKLDDPATREWLSRMWDRVDMLTWRNTSIFQAPFTLADKFKLLP<br>KMILETPPPYPCGFVMMPRTPAPSVGAESDLTVGSVATEDVPRILGKVQGVCKTTVH<br>EPLAPFADGPTDGQPAREPRTQTPPAGTGGVGLVLDSEGSPELTDSPPPNGTDASGG<br>GPLYTVKKKAERCFDQLSRRVPDIVSHLPVFFSRLFKSDGHYAPGDWGFAAFTLLCL<br>FLCYSYPAFGVVPLLGVFSGSSRRVRMGVFGCWLAFAVSLFKPAPDPVGTACEFDSP<br>ECRDILHSFELLQPWDPVRSLVVGPVGLGLAILGRLLGGARYVWLFLLRLGIVSDCIL<br>AGAYVLSQGRCKKCWGSCIRTAPSEVAFNVFPPFTRATRSSLIDLCDRFCAPKGMDPIF<br>LATGWRGCWAGQSPIEQPTEKPIAFAQLDEKKITAKTVVAQPYDPNQAVKCLRVLQ<br>AGGAMVAEAIPKVVKVSAIPFRAPPFFPVGVKVDPECRVVVDSDTFTTALRSGYSTTN<br>LILGVGDFAQLNGLKIRQISKPSGGGPHIMAALHVACSMALHMLVGIYVTTVGSCGS<br>GTNDPWCTNPFAVPVYGPGSLCTSRLCISQHGLTLPLTALVAGFGIQEVALVVLIFVS<br>IGGMAHRLSCKADVLCILLAIASYVWLPLTWLLCVFPCWLRWFSLHPLTVTWLVFF<br>LISVNMPSGVLALVLLISLWLLGRYTNVAGLVTPYDIHHYTNGPRGVAALATAPDGT<br>YLAAVRRAALTGRTMLFTPSQLGSLLEGAFRTQKPTLNTVNVVGSSMGSGGVFTID<br>GKIKCVTAAHILTGNSARVSGVGFNQMLDFDVKGDFAIADCPDWQGVAPKSQFCED<br>GWTGRAYWLTSSGVEPGVIGRGFAFCFTACGDSGSPVITEAGELVGVHTGSNKQGG<br>GIVTRPSGQFCNVTPTKLSELSEFFAGPRVPLGDVKVGNHIIKDTNEVPSDLCALLAA<br>KPELEGGLSTVQLLCVFFLLWRMMGHAWTPLVAVGFFVLNEILPAVLVRSVFSFGM<br>FALSWFTPWSAQILMIRLLTAALNRNRWSLAFYSLGALTGFAADLAINQGHSLHVA<br>MNFSTYAFLPRAMAVTSPVPTIACGVVHLLAIVLYLFKYRSLHTVLVGDGAFSAAFF<br>LRYFAEGKLREGVSQSCGMNHESLTGAIAIRLDDEDLDFLIKLTDFKCFVSASNMRN<br>AAGQFIEAAYAKALRVELAQLVQVDKVRGVLAKLEAFADTATPQLSPGDIVVALGH<br>TPVGSIFDLKVGSTKHTLQAIETRVLAGSRMTVARVVDPTPAPPPVPVPIPLPPKVLE<br>NGPRAWEDEDRLNKKRRRKMEAVGIYVMDGKKYQKFWDKNSGDVFYEEVHDNT<br>DAWECLRTDDPADLDPEKGTLCGHLTIENRPYHVYASPSGRKFLVPANPESGKAQW<br>EAARLSIEQALGMMNVDGELTAKEVEKLKRIIDKLQGLTKEQCLNY |
| ORF1b/ SEQ ID NO: 4 | GAVFKLLAASGLTRCGRGGLVITETAVKIVRFHSRTFTLGPVNLKVASEVELKDAVE<br>HNQHPIARPVDGGVVLLRSAVPSLIDVLISGADASPQLLAHHGPGNTGIDGTLWDFE<br>SVATKEEVTLSAQIIQACGIRRGDAPEIGLPYKLHPVRGNPERVKGVLKNTRFGDIPY<br>KTPSDTGSPVHAAACLTPNATPVTDGRSVLATTMPSGFELYVPTIPASVLDYLDSRPD<br>CPKQLTEHGCEDAALRDLSKYDLSTQGFVLPGVLRLVRKYLFAHVGKCPPVHRPST<br>YPAKNSMAGINGNRFPTKDIQSIPEIDVLCAQAVRENWQTVTPCTLKKQYCGKKKT<br>RTILGTNNFIALAHRAALSGVTQGFMKKAFNSPIALGKNKFKELQTPVLGRCLEADL<br>ASCDRSTPAIVRWFAAHLLYELACAEEHLPSYVLNCCHDLLVTQSGAVTKRGGLSS<br>GDPITSVSNTIYSLVIYAQHMVLSYFKSGHPHGLLFLQDQLKFEDMLKVQPLIVYSDD<br>LVLYAESPTMPNYHWWVEHLNLMLGFQTDPKKTTITDSPSFLGCRIMNGCQLVPNR<br>DRILAALAYHMKANNVSEYYASAAAILMDSCACLEYDPEWFEELVVGMAQCARKD<br>GYSFPGPPFFLSMWEKLRSNYEGKRSRVCGYCGASAPYATSCGLDVCVYHTHFHQH<br>CPVIIWCGHPAGSGSCDDCKSPTGKDTNPLDEVLKQVPYKPPRTVLMHVEQGLTPLD<br>PGRYQTRRGLVAVRRGIRGNEVDLPDGDYASTALLPTCKEINMVAVASNVLRSRFII<br>GPPGAGKTHWLLQQVQDGDVIYTPTHQTMLDMIKALGTCRFNVPAGTTLQFPAPSR<br>TGPWVRILAGGWCPGKNSFLDEAAYCNHLDVLRLLSKTTLTCLGDFKQLHPVGFDS<br>HCYVFDIMPQTQLKTIWRFGQNICDAIQPDYRDKLMSMVNTTRVTYVEKPVKYGQV<br>LTPYHRDREDGAITIDSSQGATFDVVTLHLPTKDSLNKQRALVAITRARHAIFVYDPY<br>RQLQSLFDLPAKSTPVNLAVHRDGQLIVLDRNNKECTVAQALGNGDKFRATDKRV<br>VDSLRAICADLEGSSSPLPKVAHNLGFYFSPDLTQFAKLPIELAPHWPVVTTQNNEN<br>WPDRLVASLRPIHKYSRACIGAGYMVGPSVFLGTPGVVSYYLTKFVKGEAQVLPET<br>VFSTGRIEVDCREYLDDREREVAASLPHAFIGDVKGTTVGGCHHVTSKYLPRFLPKE<br>SVAVVGVSSPGKAAKAVCTLTDVYLPDLEAYLHPVTQSKCWKMMLDFKEVRLMV<br>WKDKTAYFQLEGRHFTWYQLASFASYIRVPVNSTVYLDPCMGPALCNRKVVGSPH<br>WGADLAVTPYDYGARKILSSAYHGEMPPGYKILACAEFSLDDPVRYKHTWGFESDT<br>AYLYEFTGNGEDWEDYNDAFRARQKGKIYKATATSLKFHFPPGHIVEPTLGLN |
| GP2/ SEQ ID NO: 5 | MRWEPHRAFLTKLVNFLLMPSRSSWCLLLISSYFWPFCSASPSPVGWWSFASDWFSP<br>RYSVRALPFTLSNYRRSYEAYLSQCQVDIPAWGTKHPLGMIWHHKVSTLIDEMVSR<br>RMYRTMEQAGQAAWKQVVTEATLSRISSLDVVAHFQHLAAIEAETCKYLASRLPM<br>LHNLRLTGSNVTIVYNSSLDRVFAVPFPTSSSRPKLHDFRQWLIAVHSSIFSSVAASCTL<br>FVVLWLRLPIIRTVFGFRWLGAIFLSSSQ | p3 Wetzel protein sequences encoded by SEQ ID NO: 1

| Protein/Seq ID NO | SEQUENCE |
|---|---|
| GP3/ SEQ ID NO: 6 | MANSCAFLHILLCCGFLYPFRRTVVAASNNTYCFWFPLVRGNFSFELTVNYTVCPPC LTRQAASEIYEPSRSLWCRIGQDRCTESDHDELGFLVPPGLSNEGHLISVYAWLAFLS FSYTSQFHPEIFGIGNVSEVYVDIKHQFICAVHDGQNTTLPRHDNITAVYQTYYQHQV DGGNWFPHLEWLRPFFSSWLVLNVSWFLRRSPASRVSVRVFQTSKPTPPQLQALLSSK TSAVLGMATRPLRRLAKAANAVRR |
| GP4/ SEQ ID NO: 7 | MAASLLFFLVGFECFMVSQAFACKPCFSSSLSDIKTNTTAAAGFAVLQDISCLRHGDS SSEATRKSRQCRTAIGTPVYITVTANVTDENYLHSSDLLMLSSCLFYASEMSEKGFK VIFGNVSGIVAVCVNFTSYVQHVKEFTRRSLVVDHVRLLHFMTPETMRWATVLACL FAILLAI |
| GP5/ SEQ ID NO: 8 | MLGKCLTAGCCSQLLFLWCIVPFCFVALVNANNSSSSHLQLIYNLTICELNGTDWLN RKFDWAVETFVIFPVLTHIVSYGALTTSHFLDTVGLVTVSTAGYYHRRYVLSSIYAV CALAALICFAIRLTKNCMSWRYSCTRYTNFLLDTKGKLYRWRSPVIIEKGGKIEVNG HLIDLKRVVLDGSAATPVTKVSAEQWGRP |
| M/ SEQ ID NO: 9 | MGTSLDDFCNDSTAPQKVLLAFSITYTPIMIYALKVSRGRLLGLLHLLIFLNCAFTFG YMTFAHFRSTNKVALTMGAVVALLWGVYSAIETWRFITSRCRLCLLGRRYILAPAH HVESVAGFHPITASDNHAFVVRRPGSTTVNGTLVPGLKSLVLGGRRAVKRGVVNLV KYAK |
| N/ SEQ ID NO: 10 | MPNNNGKQQKRKKGDGQPVNQLCQMLGRIIAQQNQPRGKGPGKRNKKKSPEKPHF PLATEDDVRHHFTPSERQLCLSSIQTAFNQGAGTCTLSDSGRVSYAVEFSLPTHHTVR LIRATTSPSA | p41 attenuated Wetzel protein sequences encoded by SEQ ID NO:2 which differ from the p3 sequences

| Protein/Seq ID NO | SEQUENCE (changes from p3 bolded and underlined) |
|---|---|
| ORF1a/ SEQ ID NO: 11 | MSGILDRCTCTPNARVFVADGQVYCTRCLSARTLLPLNLQVSELGVLGLFYR PEEPLRWTLPRAFPTVECSPAGACWLSAIFPIARMTSGNLNFQQRIVRVAAEI YRVGQLTPTVLKNLQVYERGCRWYPIVGPVPGVAVYANSLHVSDKPFPGAT HVLTNLPLPQRPKPEDFCPFECAMAVVYDIGHDAVMYVAKERVSWAPRGGE KGKFETVPEELRLVAEQLFTSFPPHHVVDMSKFIFTAPDCGASMRVERQYGC LPAGTVPDGNCWWSLFSSLPPEVQCREIRRATQFGYQTKHGVAGKYLQRRL QANGLRAVVDSNGPIVIQYFSVKESWIRHVKLAGEPCYPGFEDLLRIRVEPNT LPLSDKGDKVFRFGGHKWYGAGKRARRSRAGAATTVAGHASPVRETQQAK KHEAASANKAELLERYSPPAEGNCGWHCISAIVNRMVNSKFETALPEKVRPP EDWATDEDLVNTIQILRLPAALDRNGVCASAKYVLKLEGEHWTVSVTPGMP PSLLPLECVQGCCEHKGSLRSPDAVEVSGFDPASLDRLAGVMHLPSSAIPAAL AELSGDPDRPVSPATTAWTVSQFYARHSGGEHPDQKYLRKIISLCEVIESCCC SQNKINLVTPEEVKTKIDQYLSGAASLEECLARLEKARPPSVLDTSFDWDVV LPGVGAAVRAAKLPLANQCHAPVTVVTQRPSLKFQPRKAESVKSLPESRPLP APRRKIRSRCGSLTSLDGNFPDSWEDLAGGPFHFPTLPEPTTRPGEPVPVPAPR KTVPRLVSSLIVSVPVPAPRRGIRQAEGMNLVAVTPACQDELLDLSESSQAEH GAPSLALPRSEDALAVGRREAEEVLSEISGMPDDIRLVPSSSSSLSSVEITRPK YSAQAIIDSGGPCCGHLQEVKEKCLNVMREACDATKLDDPATREWLSRMW DRVDMLTWRNTSIFQAPFTLADKFKLLPKMILETPPPYPCGFVMMPRTPAPS VGAESDLTVGSVATEDVPRILGKVQGVCKTTVHEPLAPFADGPTDGQPAREP RTQTPPAGTGGVGLVLDSEGSPELTDSPPPNGTDASGGGPLYTVKKKVERCF DQLSRRVFDIVSHLPVFFSRLFKSDGHYAPGDWGFAAFTLLCLFLCYSYPAFG VVPLLGVFSGSSRRVRMGVFGCWLAFAVSLFKPAPDPVGTACEFDSPECRDI LHSFELLQPWDPVRSLVVGPVGLGLAILGRLLGGARYVWLFLLRLGIVSDCIL AGAYVLSQGRCKKCWGSCIRTAPSEVAFNVFPPFTRATRSSLIDLCDRFCAPK GMDPIFLATGWRGCWAGQSPIEQPTEKPIAFAQLDEKKITAKTVVAQPYDPN QAVKCLRVLQAGGAMVAEAIPKVVKVSAIPFRAPFFPVGVKVDPECRVVVD SDTFTTALRSGYSTTNLILGVGDFAQLNGLKIRQISKPSGGGPHIMAALHVAC SMALHMLVGIYVTTVGSCGSGTNDPWCTNPFAVPVYGPGSLCTSRLCISQHG LTLPLTALVAGFGIQEVALVVLIFVSIGGMAHRLSCKADVLCILLAIASYVWL PLTWLLCVFPCWLRWFSLHPLTVTWLVFFLISVNMPSGVLALVLLISLWLLG RYTNVAGLVTPYDIHHYTNGPRGVAALATAPDGTYLAAVRRAALTGRTMLF TPSQLGSLLEGAFRTQKPTLNTVNVVGSSMGSGGVFTIDGKIKCVTAAHILTG NSARVSGVGFNQMLDFDVKGDFAIADCPDWQGVAPKSQFCEDGWTGRAY WLTSSGVEPGVIGRGFAFCFTACGDSGSPVITEAGELVGVHTGSNKQGGGIV TRPSGQFCNVTPTKLSELSEFFAGPRVPLGDVKVGNHIIKDTNEVPSDLCALL AAKPELEGGLSTVQLLCVFFLLWRMMGHAWTPLVAVGFFVLNEILPAVLVR |

| Protein/ Seq ID NO | SEQUENCE (changes from p3 bolded and underlined) |
|---|---|
| | SVFSFGMFALSWFTPWSAQILMIRLLTAALNRNRWSLAFYSLGALTGFAADL AINQGHSLHVAMNFSTYAFLPRAMAVTSPVPTIACGVVHLLAIVLYLFKYRS LHTVLVGDGAFSAAFFLRYFAEGKLREGVSQSCGMNHESLTGAIAIRLDDED LDFLIKLSDFKCFVSASNMRNAAGQFIEAAYAKALRVELAQLVQVDKVRGV LAKLEAFADTATPQLSPGDIVVALGHTPVGSIFDLKVGSTKHTLQAIETRVLA GSRMTVARVVDPTPAPPPVPVPIPLPPKVLENGPRAWEDEDRLNKKRRRKME AVGIYVMDGKKYQKFWDQNSGDVFYEEVHDNTDAWECLRTDDPADLDPE KGTLCGHLTIENRPYHVYASPSGRKFLVPANPESGKAQWEAARLSIEQALGM MNVDGELTAKEVEKLKRIIDKLQGLTKEQCLNY |
| ORF1b/ SEQ ID NO: 12 | GAVFKLLAASGLTRCGRGGLVITETAVKIVRFHSRTFTLGPVNLKVASEVEL KDAVEHNQHPIARPVDGGVVLLRSAVPSLIDVLISGADASPQLLAHHGPGNT GIDGTLWDFESVATKEEVTLSAQIIQACGIRRGDAPEIGLPYKLHPVRGNPER VKGVLKNTRFGDIPYKTPSDTGSPVHAAACLTPNATPVTDGRSVLATTMPSG FELYVPTIPASVLDYLDSRPDCPKQLTEHGCEDAALRDLSKYDLSTQGFVLPG VLRLRVKYLFAHVGKCPPVHRPSTYPAKNSMAGINGNRFPTKDIQSIPEIDVL CAQAVRENWQTVTPCTLKKQYCGKKKTRTILGTNNFIALAHRAALSGVTQG FMKKAFNSPIALGKNKFKELQTPVLGRCLEADLASCDRSTPAIVRWFAAHLL YELACAEEHLPSYVLNCCHDLLVTQSGAVTKRGGLSSGDPITSVSNTIYSLVI YAQHMVLSYFKSGHPHGLLFLQDQLKFEDMLKVQPLIVYSDDLVLYAESPT MPNYHWWVEHLNLMLGFQTDPKKTTITDSPSFLGCRIMNGCQLVPNRDRIL AALAYHMKANNVSEYYASAAAILMDSCACLEYDPEWFEELVVGMAQCAR KDGYSFPGPPFFLSMWEKLRSNYEGKRSVCGYCGASAPYATSCGLDVCVY HTHFHQHCPVIIWCGHPAGSGSCDDCKSPTGKDTNPLDEVLKQVPYKPPRTV LMHVEQGLTPLDPGRYQTRRGLVAVRRGIRGNEVDLPDGDYASTALLPTCK EINMVAVASNVLRSRFIIGPPGAGKTHWLLQQVQDGDVIYTPTHQTMLDMIK ALGTCRFNVPAGTTLQFPAPSRTGPWVRILAGGWCPGKNSFLDEAAYCNHL DVLRLLSKTTLTCLGDPFKQLHPVGFDSHCYVPDIMPQTQLKTIWRFGQNICD AIQPDYRDKLMSMVNTTRVTYVEKPVKYGQVLTPYHRDREDGAITIDSSQG ATFDVVTLHLPTKDSLNKQRALVAITRARHAIFVYDPYRQLQSLFGLPAKSTP VNLAVHRDGQLIVLDRNNKECTVAQALGNGDKFRATDKRVVDSLRAICADL EGSSSPLPKVAHNLGFYFSPDLTQFAKLPIELAPHWPVVTTQNNENWPDRLV ASLRPIHKYSRACIGAGYMVGPSVFLGTPGVVSYYLTKFVKGEAQVLPETVF STGRIEVDCREYLDDWEREVAASLPHAFIGDVKGTTVGGCHHVTSKYLPRFL PKESVAVVGVSSPGKAAKAVCTLTDVYLPDLEAYLHPVTQSKCWKMMLDF KEVRLMVWKDKTAYFQLEGRHFTWYQLASFASYIRVPVNSTVYLDPCMGP ALCNRKVVGSPHWGADLAVTPYDYGARKILSSAYHGEMPPGYKILACAEFS LDDPVRYKHTWGFESDTAYLYEFTGNGEDWEDYNDAFRARQKGKIYKATA TSLKFHFPPGHIVEPTLGLN |
| GP2/ SEQ ID NO: 13 | MRWEPHRAFLTKLVNFLLMPSRSSWCLLLISSYFWPFCSASPSPVGWWSFAS DWFSPRYSVRALPFTLSNYRRSYEAYLSQCQVDIPAWGTKHPLGMIWHHRV STLIDEMVSRRMYRTMEQAGQAAWKQVVTEATLSRISSLDVVAHFQHLAAI EAETCKYLASRLPMLHNLRLTGSNVTIVYNSSLDRVFAVFPTSSSRPKLHDR QWLIAVHSSIFSSVAASCTLFVVLWLRLPIIRTVFGFRWLGAIFLSSSQ |
| GP3/ SEQ ID NO: 14 | MANSCAFLHILLCCGFLYPFRRTVVAASNNTYCFWFPLVRGNFSFELTVNYT VCPPCLTRQAASEIYEPSRSLWCRIGQDRCTESDHDELGFLVPPGLSNEGHLIS VYAWLAFLSFSYTSQFHPEIFGIGNVSEVYVDIKHQLICAVHDGQNTTLPRHD NITAVYQTYYQHQVDGGNWFHLEWLRPFFSSWLVLNVSWFLRRSPASRVSV RVFQTSKPTPPQLQVLLSSKTSAVLGMATRPLRRLAKAANAVRR |
| GP4 | Amino acid sequence is identical to p3 GP4 (SEQ ID NO:

(4) Kapusinszky B, Molnar Z, Szomor K, Berencs G. Molecular characterization of poliovirus isolates from children who contracted vaccine-associated paralytic poliomyelitis (VAPP) following administration of monovalent type 3 oral poliovirus vaccine in the 1960s in Hungary. FEMS Immunol Med Microbiol 2010; (58) 211-217.

(5) Madsen K G, Hansen C M, Madsen E S, Strandbygaard B, Botner A, Sorensen K J. Sequence analysis of porcine reproductive and respiratory syndrome virus of the American type collected from Danish swine herds. Arch Virol 1998; 143(9):1683-700.

(6) Opriessnig T, Halbur P G, Yoon K J, Pogranichniy R M, Harmon K M, Evans R, et al. Comparison of molecular and biological characteristics of a modified live porcine reproductive and respiratory syndrome virus (PRRSV) vaccine (ingelvac PRRS MLV), the parent strain of the vaccine (ATCC VR2332), ATCC VR2385, and two recent field isolates of PRRSV. J Virol 2002 December; 76(23): 11837-44.

(7) Yoshii M, Okinaga T, Miyazaki A, Kato K, Ikeda H, Tsunemitsu H. Genetic polymorphism of the nsp2 gene in North American type—porcine reproductive and respiratory syndrome virus. Arch Virol 2008; 153(7):1323-34.

(8) de Lima M, Pattnaik A K, Flores E F, Osorio F A. Serologic marker candidates identified among B-cell linear epitopes of Nsp2 and structural proteins of a North American strain of porcine reproductive and respiratory syndrome virus. Virology 2006 Sep. 30; 353(2):410-21.

(9) Fang Y, Kim D Y, Ropp S, Steen P, Christopher-Hennings J, Nelson E A, et al. Heterogeneity in Nsp2 of European-like porcine reproductive and respiratory syndrome viruses isolated in the United States. Virus Res 2004 Mar. 15; 100(2):229-35.

(10) Fang Y, Schneider P, Zhang W P, Faaberg K S, Nelson E A, Rowland R R. Diversity and evolution of a newly emerged North American Type 1 porcine arterivirus: analysis of isolates collected between 1999 and 2004. Arch Virol 2007; 152(5):1009-17.

(11) Gao Z Q, Guo X, Yang H C. Genomic characterization of two Chinese isolates of porcine respiratory and reproductive syndrome virus. Arch Virol 2004 July; 149(7): 1341-51.

(12) Han J, Wang Y, Faaberg K S. Complete genome analysis of RFLP 184 isolates of porcine reproductive and respiratory syndrome virus. Virus Res 2006 December; 122(1-2):175-82.

(13) Li Y, Wang X, Bo K, Tang B, Yang B, Jiang W, et al. Emergence of a highly pathogenic porcine reproductive and respiratory syndrome virus in the Mid-Eastern region of China. Vet J 2007 November; 174(3):577-84.

(14) Ropp S L, Wees C E, Fang Y, Nelson E A, Rossow K D, Bien M, et al. Characterization of emerging European-like porcine reproductive and respiratory syndrome virus isolates in the United States. J Virol 2004 April; 78(7): 3684-703.

(15) Tian K, Yu X, Zhao T, Feng Y, Cao Z, Wang C, et al. Emergence of fatal PRRSV variants: unparalleled outbreaks of atypical PRRS in China and molecular dissection of the unique hallmark. PLoS One 2007; 2(6):e526.

(16) Han J, Liu G, Wang Y, Faaberg K S. Identification of nonessential regions of the nsp2 replicase protein of porcine reproductive and respiratory syndrome virus strain VR-2332 for replication in cell culture. J Virol 2007 September; 81(18):9878-90.

(17) Johnson W, Roof M, Vaughn E, Christopher-Hennings J, Johnson C R, Murtaugh M P. Pathogenic and humoral immune responses to porcine reproductive and respiratory syndrome virus (PRRSV) are related to viral load in acute infection. Vet Immunol Immunopathol 2004 Dec. 8; 102 (3):233-47.

(18) Reed L J, Muench H. A simple method of estimating fifty percent end-points. Amer J Hyg 1938; 27:493-7.

(19) Halbur P G, Miller L D, Paul P S, Meng X J, Huffman E L, Andrews J J. Immunohistochemical identification of porcine reproductive and respiratory syndrome virus (PRRSV) antigen in the heart and lymphoid system of three-week-old colostrum-deprived pigs. Vet Pathol 1995 March; 32(2):200-4.

(20) Mengeling W L, Lager K M, Vorwald A C. Clinical effects of porcine reproductive and respiratory syndrome virus on pigs during the early postnatal interval. Am J Vet Res 1998 January;59(1):52-5.

(21) Wesley R D, Mengeling W L, Lager K M, Vorwald A C, Roof M B. Evidence for divergence of restriction fragment length polymorphism patterns following in vitro replication of porcine reproductive and respiratory syndrome virus. Am J Vet Res 1999 April; 60(4):463-7.

(22) Wang C, Wu B, Amer S, Luo J, Zhang H, Guo J, Dong G, Zhao B, and He H. Phylogenetic analysis and molecular characteristics of seven variant Chinese field isolates of PRRSV. BMC Microbiol. 2010; 10: 146.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

The invention claimed is:

1. An immunogenic composition of Porcine Reproductive and Respiratory Syndrome Virus (PRRSV), comprising at least one of
   a) a composition comprising SEQ ID NO:2 (attenuated Wetzel p41); or
   b) a polypeptide selected from the group consisting of
      i) SEQ ID NO:9 (M protein of Wetzel p3 and of Wetzel p41),
      ii) SEQ ID NO:10 (N protein of Wetzel p3and of Wetzel p41),
      iii) SEQ ID NO:11 (ORF1a protein of Wetzel p41),
      iv) SEQ ID NO:12 ORF1b protein of Wetzel p41),
      v) SEQ ID NO:13 (GP2 protein of Wetzel p41),
      vi) SEQ ID NO:14 (GP3 protein of Wetzel p41), and
      vii) SEQ ID NO:15 (GP5 protein of Wetzel p41).

2. An isolated Porcine Reproductive and Respiratory Syndrome Virus (PRRSV), comprising
   a) SEQ ID NO:2, or
   b) a nucleic acid sequence 97% identical to SEQ ID NO:2, which encodes a polypeptide selected from the group consisting of SEQ ID NO: 11, SEQ ID NO:12, SEQ ID NO:13, SEQ ID NO:14 and SEQ ID NO:15.

3. The PRRSV of claim 2, comprising an attenuated, non-virulent form of a PRRSV.

4. A vaccine for generating an immune response by a virulent PRRSV, comprising a killed or attenuated form of a PRRSV of claim 2.

5. A method of generating an immune response in a mammal, comprising administering an immunologically-effective amount of a PRRSV of claim 2.

6. A method of generating an immune response in a mammal, comprising administering an immunologically-effective amount of a vaccine of claim 4.

7. The method of claim 6, wherein the mammal is a swine.

8. The method of claim 6, wherein the vaccine provides protective immunity to a disease caused by PRRSV infection.

* * * * *

SEQUENCE LISTING

```
<160> NUMBER OF SEQ ID NOS: 19

<210> SEQ ID NO 1
<211> LENGTH: 14963
<212> TYPE: DNA
<213> ORGANISM: Porcine reproductive and respiratory syndrome virus

<400> SEQUENCE: 1
gggtgttggc tctatgccac gacatttgta ttgtcaggag ctgtgaccac tggcacagcc      60
```

```
caaaacttgc tgcacgggaa caccctcctg tgacggcctc cttcagggaa gtttaggggt    120
ttgtccctaa caccttgttt ccggagttgc actgctttac ggtctctcca ctccttttaac   180 catgtctggg attcttgatc ggtgcacgtg taccccccaat gccagggtgt tgtggcaga    240 cggccaggtc tactgcacac gatgtctcag tgcacggacc ctccttcccc tgaatctcca    300
agtctctgaa cttggggtgt tgggcttgtt ctacaggccc gaagagccac tccggtggac    360
gttgccgcgc gcattcccca ctgttgagtg ctcccctgct ggagcttgtt ggctttctgc    420 gattttttcca attgcacgaa tgaccagtgg aaacctgaac ttccaacaaa ggatagtacg   480
ggttgcagct gagatttaca gagtcggcca actcacccccc acagtcttga agaacctaca   540
agtctatgaa cggggttgcc gctggtaccc catcgtcgga cctgtccctg gagttgccgt    600
ttacgctaac tccctacatg tgagtgataa acctttcccg ggggctactc acgtgctaac    660
caacctgccg ctcccgcaga gacctaagcc tgaagatttt tgccccttttg agtgtgcgat   720 ggctgtcgtc tatgacattg gtcatgacgc tgttatgtat gtggccaaag agagggtctc    780
ctgggctccg cgtggtggag aaaagggaaa attcgaaact gttccagagg agttgaggtt    840
ggttgcagag caactttttta cctccttccc gcctcaccac gtggtagaca tgtcgaagtt    900
catcttcaca gcccctgatt gtggagcttc catgcgggtc gaacgccagt atggctgcct    960
ccccgctggc actgtccctg acggtaattg ctggtggagc ttgtttagct cactcccacc   1020
ggaagttcag tgtagagaaa ttcgccgcgc cacccaattt ggctaccaaa ccaagcatgg   1080
cgttgctgga aagtacctac agcggaggct gcaagccaat ggtctccgag cagtggttga   1140
ctcaaatgga cctatcgtca tacagtattt ctccgttaag gagagctgga tccgccacgt   1200
gaaactggcg ggagagccct gctatcccgg gtttgaggat ctcctcagga taagagtcga   1260
gcccaacacg ttgccattgt ccgacaaggg cgacaaagtc ttccggtttg gcgggcacaa   1320
gtggtacggc gctgggaaga gggcaaggag atcacgtgca ggtgctgcca ctacagttgc   1380
cggtcacgcc tcgcctgttc gcgaaactca acaggccaag aagcacgagg ctgctagcgc   1440
caacaaggct gagctccttg agcgctactc cccgcctgct gaagggaact gcggctggca   1500
ctgcatctct gccattgtca accgaatggt aaattccaag tttgaaactg cccttcctga   1560
aaaagtgaga cccccagaag attgggccac tgatgaggat cttgtgaaca ctatccaaat   1620
tctcaggctc cctgcggcct tggacaggaa cggcgtctgc gcaagcgcca agtacgtcct   1680
taaactggag ggtgaacatt ggactgtttc agtgactccc ggaatgcctc cttccttgct   1740 ccccctttgaa tgcgttcaag gttgttgtga gcacaagggc agtcttcgtt ctccagatgc   1800
ggtcgaagtt tccggattcg accctgccag ccttgatcga ctcgccgggg tgatgcatct   1860
gcccagcagt gccatcccag ccgccctggc tgagttgtct ggcgaccctg atcgtccagt   1920
ttccccggcc accactgcgt ggactgtctc gcagtttat gctcgccata gtggcggaga    1980
gcatcctgac caaaagtact taagaaaaat catcagcctc tgcgaggtga tcgagagctg   2040
ctgctgttcc cagaataaaa tcaacctggt cactccggaa gaggttaaaa caaaaattga   2100
ccaatacctc agtggtgcag caagtcttga agaatgcttg gccaggcttg agaaggctcg   2160
cccgccaagc gtgttggaca cctcctttga ttgggatgtt gtgctccctg gtgttggggc   2220
ggctgttcga gcagcgaaac tgcccctcgc caatcagtgt cacgctccag tcactgttgt   2280
gacccaaagg ccttcgttga aatttcagcc tcgaaaagcg gaatctgtca agagcttacc   2340
agagagcagg cctcttcctg ccccgcgcag gaagattagg tccaggtgtg gtagtctgac   2400
```

```
ttcattggac ggcaacttcc ctgacagctg ggaagacttg gccggtggtc ccttccattt    2460
cccgacccta cctgagccga cgacacgtcc gggtgagcct gtgcctgtcc ctgcaccgcg    2520
caagactgtg ccccgattgg tgtcgtcact gatagtgtca gtccctgtgc ccgcaccacg    2580
acgtgggatt cgacaggcgg agggaatgaa tttggtggca gtgactccag cgtgccagga    2640
cgagctcctc gatttatctg aatcctcgca ggctgagcat ggggctccct ccttggcatt    2700
gccgcggagt gaggatgccc tggcggtggg gagacgagaa gctgaagaag ttctgagcga    2760
aatctcgggc atgccagatg acattagatt ggtgcccgtg tcatcaagca gctccctgtc    2820
aagcgtagag attacacgcc caaagtactc agctcaagcc atcattgact caggtgggcc    2880
ctgttgtggg cacctccaag aggtaaaaga gaaataccct aatgtgatgc gtgaggcatg    2940
tgatgcgacc aagcttgatg accctgccac acgagaatgg ctttcccgta tgtgggacag    3000
ggtagacatg ctaacctggc gcaacacgtc catttttcag gcgcctttca ctttggctga    3060
caagttcaag ctcctcccga agatgatact cgaaacaccg ccgccctacc cttgcgggtt    3120
tgtaatgatg ccccgcacac ctgcaccttc tgtgggtgcg gagagcgacc tcaccgttgg    3180
ttcagttgct actgaggatg ttccgcgcat tctcgggaag gtgcaaggtg tttgcaaaac    3240
aaccgtccat gaaccttag caccttttcgc agatggaccg acagatggcc aacctgctag    3300
agaaccccga acacaaactc ctcccgcagg cacaggtggc gttggcttag ttttggattc    3360
tgaaggatcg ccggagctca ctgattcgcc gcctccaaac ggtacagacg cgagcggagg    3420
gggaccgtta tacacagtca agaagaaggc tgagaggtgc tttgaccagc tgagccgacg    3480
ggtttttgac atcgtctccc atctccctgt tttcttctca cgccttttca gtctgacggg    3540
tcattatgct ccgggtgatt ggggttttgc agctttact ttattgtgcc tctttctgtg    3600
ttacagttac ccggcgttcg gtgtggttcc cctattgggt gtattttctg ggtcttctcg    3660
gcgcgtccgc atggggtttt tggttgttg gttggctttc gctgttagtt tgttcaagcc    3720
tgctcccgac ccagtcggta ctgcttgtga gtttgactcg ccagagtgta gagacatcct    3780
tcattctttt gagcttctgc aaccttggga ccctgttcgc agccttgtgg tgggccccgt    3840
cggtctcggt cttgccattc ttggcaggtt actgggcggg gcacgctacg tctggttgtt    3900
tttgcttagg cttggcatcg tttcagactg tatcttggct ggagcctatg tgctttcgca    3960
aggtaggtgt aaaaagtgtt ggggatcttg tataagaact gctcccagtg aggtcgcctt    4020
caatgtgttt cccttcacac gcgcaaccag atcgtcactt attgacctgt gcgaccggtt    4080
ctgcgcgccc aaaggcatgg accccatctt cctcgctact ggatggcgtg gatgctgggc    4140
cggtcagagc cccattgagc aacccactga gaaacccatt gcgttcgccc agttggatga    4200
gaagaaaatc actgctaaaa ctgtggttgc ccagccttat gacccaacc aagctgtgaa    4260
gtgcttacga gtcctgcagg cgggcgggc gatggtggct gaggcgattc caaaagtagt    4320
caaagtttct gctatcccat ttcgagctcc cttcttccct gtcggagtga agttgatcc    4380
tgaatgcagg gtcgtggttg actctgacac cttcacaact gctctccggt ccggctactc    4440
caccacaaac ctcattcttg gtgtgggga ttttgcccag ctgaatgggt tgaaaatcag    4500
gcaaatttcc aagccttcgg gaggaggtcc acacatcatg gcggccttac atgtcgcttg    4560
ctcgatggct ttgcacatgc tcgttgggat ttacgtcact acggtgggtt cttgtggttc    4620
tggcactaac gacccgtggt gcactaaccc gttgccgtc cctgtctacg gacctggctc    4680
tctttgcacc tccaggttgt gcatctccca gcatggcctt actctgccct taacagcgct    4740
tgtggcgggg tttggcattc aggaagttgc cttggtggtt ttaatctttg tttccatcgg    4800
```

```
aggtatggct cacagattaa gttgcaaggc tgatgtactg tgtattctgc ttgcgattgc   4860
cagctatgtt tggttacccc tcacctggtt gctctgtgtg tttccttgct ggttacgttg   4920
gttttctttg catcccctca ccgttacatg gttggtgttt ttcttgattt ctgtaaacat   4980
gccctcagga gtcttggcct tggtgttgtt aatctctctc tggctccttg gccgctatac   5040
caatgtcgca ggtcttgtca ctccttatga cattcaccat tacaccaacg gccccgtgg    5100 cgttgccgcc ttggccactg caccggatgg gacctacttg gctgctgtcc gccgcgctgc   5160
gctgactggt cgtaccatgc tgtttacccc gtcccagctt gggtcactcc ttgagggtgc   5220
ctttagaacc caaaagccta cactgaatac cgtcaatgtg gtcgggtcct ctatgggctc   5280
cggcggggtg ttcaccattg acgggaaaat caagtgcgtg acagcagcgc atattctcac   5340
aggcaactct gccagggtct ccggggtcgg cttcaatcaa atgttggatt cgatgtgaa    5400 aggggatttt gccatagccg attgtccgga ttggcaagga gtcgctccca agtcccagtt   5460
ctgtgaggat gggtggactg gccgcgctta ttggctaaca tcctctggcg tcgaacccgg   5520
cgtcatcggg aggggatttg ccttttgttt caccgcgtgc ggcgattccg ggtccccagt   5580
gatcaccgag gccggagaac ttgtcggtgt ccacacggga tcaaacaaac aaggaggagg   5640
cattgtcacg cgcccttcag gccagttttg taatgtgaca cccaccaaat taagtgaatt   5700
gagtgaattc ttcgctggac ccagggtccc gcttggcgat gtgaaggtcg gcaaccacat   5760
aatcaaagac acaaatgagg tgccctcaga tctttgcgcc ttgctcgctg ccaaacccga   5820
gttggaagga ggtctctcca ccgttcaact tttgtgcgtg ttttttcctcc tatggagaat   5880 gatgggacat gcctggacgc ctttggttgc tgttggtttt ttcgttttga cgaaatcct    5940 cccagcggtt ctggtccgga gtgttttctc ctttggaatg ttcgcactgt cttggttcac   6000
accgtggtct gcacaaattc taatgatcag gcttctaaca gcagctctta acagaaacag   6060
atggtcactt gccttttaca gccttggtgc actaactgga tttgctgcag accttgcaat   6120
taatcagggg cactcgctgc acgtggccat gaattttagc acctatgcat tcctacctcg   6180
tgcaatggcc gtgacctcac cagtcccaac gattgcgtgt ggtgttgtgc acttgcttgc   6240
tattgttttg tacttgttca agtaccgcag cctgcatacc gtcttggtcg gcgatggagc   6300
gttttccgca gctttctttt tgcgatactt tgcggaggga aaactgaggg aaggggtgtc   6360
gcagtcttgc ggcatgaatc atgagtcact gactggtgcc atcgccatca gactcgacga   6420
cgaggacctg gatttcctta taaaactgac tgattttaag tgctttgttt ccgcgtccaa   6480
catgaggaat gcggcaggcc agttcatcga ggccgcttat gccaaagcac ttagggtgga   6540
acttgctcag ttagtgcagg ttgacaaggt ccgtggtgtc ttagctaagc ttgaagcatt   6600
tgctgacact gcgacgcccc aactctcacc tggcgacatt gttgttgctc ttggccatac   6660
gcctgttggc agtatcttcg acttgaaagt gggcagcacc aagcataccc tacaagccat   6720
cgagaccaga gtcctcgctg gtccagaat gaccgtggcg cgcgtcgttg atccgactcc    6780
cgcacctcca cccgtgcccg tgcccattcc tctcccgccg aaagttttag agaacggccc   6840
ccgtgcctgg gaggacgagg accgtctgaa caaaaagagg cggcgcaaaa tggaagccgt   6900
tggcatttat gtcatggacg gaaaaagta ccaaaaattt gggataaga attctggtga    6960 tgtgttctat gaggaagtcc acgataacac agacgcgtgg gaatgcctca gaactgacga   7020
ccctgccgac ttggatcctg agaagggac tttgtgtggg cacctcacca tagagaatag   7080
accttaccat gtttacgcct ccccttccgg taggaagttc ctggtccctg caacccgaga   7140
```

```
gagtgggaaa gcccagtggg aagctgcaag gctttccata gagcaggccc ttggcatgat    7200
gaacgtcgac ggcgagttga ccgccaagga ggtagagaaa ctgaagagaa taattgacaa    7260
actccagggc ctgactaagg agcagtgttt aaactactag ccgccagcgg cttgacccgc    7320
tgtggtcgcg gcggcttggt tattactgag acagcggtga aaatagtcag attccacagt    7380 cggacctta  ccctggggcc tgtgaatttg aaagtggcta gcgaggttga gttgaaagac    7440
gccgtcgagc acaaccaaca cccaattgca agaccagttg acggtggcgt tgtgctcctg    7500
cgctctgcag ttccttcgct catagacgtc ttgatctccg gggccgacgc atcccctcag    7560
ttactcgccc atcatgggcc aggaaacacc gggattgatg gcacgctctg ggattttgag    7620
tccgtagcca ctaaagagga agtcacactt agtgcacaga taatacaggc ttgtggcatt    7680
aggcgcggcg atgctcctga gatcggcctc ccttacaaac tgcaccctgt taggggcaac    7740
cctgaacgtg taaaaggggt tttgaagaac acaaggtttg gggacatacc ttacaagacc    7800
cctagtgaca ctgggagccc tgtacatgcg gccgcctgtc ttacgcctaa tgccaccccg    7860
gtgactgacg ggcgctccgt cttggccacg accatgccct ccgggtttga gttgtatgtg    7920
ccgaccattc cagcatctgt ccttgattac cttgattcca ggccagactg ccctaaacag    7980
ttgacggagc acgggtgtga agatgctgca ttgagagatc tctccaaata tgacttgtcc    8040
acccaaggtt ttgttttgcc cggggtcctc cgcctcgtac ggaaatattt atttgcccac    8100
gtgggcaagt gccgcctgt  ccatcggccc tccacctacc cggccaagaa ttccatggct    8160
ggaataaacg ggaataggtt cccaaccaag gacattcaga gcattcctga gatcgacgtt    8220
ctatgtgcac aggctgtacg agagaactgg caaactgtta ccccttgcac cctcaagaag    8280
cagtattgcg ggaagaagaa aaccaggacc atactcggta ccaataactt tatcgcgctg    8340
gcccaccggg cagcgctgag tggtgtcacc cagggcttca tgaaaaaggc atttaactcg    8400
cccattgccc tcgggaagaa taaattcaag gagctacaaa ctccggtcct gggcaggtgc    8460
cttgaggctg atcttgcatc ttgcgatcga tccactcccg cgattgtccg ctggtttgcc    8520
gcccatctcc tttatgaact tgcctgcgct gaagagcacc taccgtcata tgtgctgaac    8580
tgctgtcatg acctattggt cacgcaatcc ggtgcggtga ctaagagagg tggcctgtca    8640
tctggtgatc cgatcacctc tgtgtccaac accatttaca gtctggtgat ttacgcgcag    8700
cacatggtgc tcagttactt taaaagtggt cacccacatg gtctcttgtt ccttcaggac    8760
cagctaaagt ttgaggacat gctcaaggtt caaccctga  ttgtctactc ggacgatctt    8820
gtgctgtatg ccgagtctcc caccatgcca aactaccatt ggtgggttga gcacctgaat    8880
ttgatgttag ggtttcagac ggacccgaag aaaacaacca ttactgactc gccgtctttc    8940
ctgggctgca ggataatgaa tgggtgtcag ctagtcccaa accgtgacag gattctcgca    9000
gctcttgcct accacatgaa ggcgaataat gtttctgagt actacgcctc cgccgctgca    9060
atactcatgg acagttgtgc ttgtctggag tacgaccctg aatggtttga agaacttgtg    9120
gtaggaatgg cgcaatgcgc tcgcaaggac ggctatagct cccccggccc gccgttcttc    9180
ctatccatgt gggagaaact caggtctaat tatgagggga agaggtcaag ggtgtgtggg    9240
tactgcggag cttcagcccc gtatgccact tcctgtggtc ttgatgtctg tgtttaccac    9300
actcacttcc accagcattg tccagtcata atctggtgtg gccaccggggc gggttctggg    9360 tcctgtgatg attgcaaatc tcccacaggg aaagatacaa acccctgga  tgaggtctta    9420 aaacaagtcc catataagcc tccacggact gtcctcatgc atgtggagca gggcctcacc    9480 cccccttgacc caggcagata tcagacccgt cgtgggttgg ttgccgttag cgcgggatc    9540
```

```
aggggaaatg aagtcgacct accagatggt gattatgcca gcaccgcgtt actcccaact    9600
tgtaaagaga tcaacatggt cgctgttgct tccaatgtat tgcgcagtag atttatcatc    9660
ggtccacccg gtgctggaaa aacacactgg ctccttcaac aggttcagga tggtgatgtc    9720
atttatacac cgacccacca gaccatgctc gacatgatta aagctttggg acgtgtcga    9780
tttaacgttc cggcaggtac aacgctgcaa ttccccgccc cttcccgcac tggcccgtgg    9840
gttcgcatcc tggctggcgg gtggtgtcct ggcaaaaatt cattcctgga cgaagctgcg    9900
tattgcaacc atcttgatgt cttgaggctc cttagcaaaa ctactctcac ctgtttggga    9960
gacttcaaac aactccaccc ggtgggtttt gattctcact gctatgtctt tgacatcatg   10020
cctcaaactc aactgaagac tatctggagg tttggacaga atatctgtga tgccattcaa   10080
ccagattaca gggacaagct tatgtccatg gtcaacacaa ctcgtgtaac ctatgtggaa   10140
aagcccgtca aatatgggca agtcctcacc ccttaccata gggaccgaga ggatggcgcc   10200
attaccattg actccagtca aggtgccaca tttgatgtgg ttacactgca tttgcccacg   10260
aaagattcac tcaacaaaca aagggccctt gttgctatca ccagggcaag acatgccatc   10320
tttgtgtatg acccatatag gcaactgcag agcttatttg atcttcctgc aaaaagcacg   10380
cccgtcaacc tggccgtgca ccgcgatggg caactgattg tgctagacag aaataataaa   10440
gaatgcacgg ttgcccaggc tctgggcaat ggtgacaaat tcagagctac agataagcgc   10500
gttgtagatt ctcttcgcgc catttgtgct gacctggaag ggtcgagctc gccgcttccc   10560
aaggttgcac ataacttggg gtttatattc tcacctgatt tgacacagtt tgccaagctt   10620
ccaatagaac ttgcaccaca ttggccagtg gtgacgaccc aaaataatga gaactggcct   10680
gatcgactgg ttgccagcct acgccccatt cacaaatata gccgtgcatg tatcggtgcc   10740
ggctatatgg tgggcccctc ggtgttttta ggcacccctg gggtagtatc atactatctc   10800
acaaaatttg tcaaggcga ggctcaggtg cttccagaaa cggtcttcag cactggccga   10860
attgaggtgg actgccgaga gtaccttgat gatcgggagc gggaagtcgc agcgtccctc   10920
ccgcatgcct ttatcggcga cgtcaaaggc actactgtgg gagggtgtca ccatgtcacc   10980
tctaaatatc tcccgcgctt cctccccaag gaatcagtcg cggtggtcgg ggtttcaagc   11040
cccgggaaag ccgcaaaagc agtgtgcaca ttgacggatg tgtacctccc agaccttgag   11100
gcctacctcc atcctgtgac ccagtccaag tgctggaaaa tgatgttgga ctttaaagaa   11160
gttcgactga tggtttggaa ggacaagacg gcctatttcc aactcgaagg tcgtcatttc   11220
acctggtatc agcttgctag ctttgcttcg tacatccgtg ttcctgtaaa ttccacggtg   11280
tacctggacc cctgcatggg ccccgccctt tgcaacagga aagtcgttgg gtcccctcat   11340
tggggagctg acctcgcagt cacccccttat gattatggag ctagaaaaat tttgtccagt   11400
gcatatcatg gtgagatgcc tcctgggtac aagattctgg cgtgcgcaga gttctcgcta   11460
gacgacccag tcagatacaa gcatacttgg ggttcgagt cggatacagc gtacttgtac   11520
gagttcactg gaaacggcga ggactgggag gattacaacg acgcgtttcg tgcgcgacag   11580
aaaggaaaaa tttataaggc cactgccacc agcctgaagt ccatttccc tccgggtcac   11640
atcgttgaac caactttggg cctgaactga atgagatgg gagccgcaca gagccttttt   11700
gacaaaattg gtcaactttt tgttgatgcc ttcacggagt tcttggtgtc tattgttgat   11760
atcatcatat ttttggccat tttgttcggc ttcaccatcg ccggttggct ggtggtcttt   11820
tgcatcagat tggtttttctc cgcgatactc cgtgcgcgcc ctaccgttca ctctgagcaa   11880
```

-continued

```
ttacagaaga tcctatgagg cctacctctc ccagtgccag gtggacattc ctgcctgggg    11940
gactaaacac cctttgggga tgatctggca ccacaaggtg tcgaccctaa ttgatgaaat    12000
ggtgtcgcgt cggatgtacc gcaccatgga acaagcaggg caggctgcct ggaaacaggt    12060
ggtgaccgag gcaacgctgt ctcgtattag tagtttggat gtggtggctc atttccagca    12120
tcttgccgcc atagaagccg agacttgtaa atacttggcc tcccggctgc caatgctaca    12180
caacctgcgc ttgacagggt caaatgtaac catagtgtat aatagctccc tggaccgggt    12240
gtttgctgtt ttcccgacct ccagttccgg gccaaagctt catgattttc ggcaatggct    12300
aatagctgtg cattcctcca tattctcctc tgttgcggct tcttgtaccc ttttcgtcgt    12360
actgtggttg cggcttccaa taatacgtac tgttttggt ttccgctggt tagggggcaat    12420 ttttctttcg agctcacagt gaattacacg gtatgtcctc cctgcctcac ccggcaagcg    12480
gcttcagaga tctacgaacc cagcagatct ctttggtgta ggatagggca agatcgatgt    12540
acagagagcg atcacgatga gctaggtttc ctggtgccgc ctggcctctc taacgaaggc    12600
catttaatta gtgtctacgc ctggctggcg ttcctatcct tcagttacac gtcgcagttc    12660
catcccgaaa tattcggcat agggaatgtg agcgaggtct atgtcgacat caagcaccaa    12720
tttatttgtg ctgttcatga tgggcagaac accaccttgc ctcgccatga caacatcacg    12780
gccgtgtacc agacgtatta tcaacaccag gttgatggcg gcaactggtt tcacctggaa    12840
tggctgcgtc ccttctttc ttcttggttg gttttgaatg tttcatggtt tctcaggcgt    12900
tcgcctgcaa gccgtgtttc agttcgagtc tttcagacat caaaaccaac accaccgcag    12960
ctgcaggctt tgctgtcctc caagacatca gctgtcttag gcatggcgac tcgtcctctg    13020
aggcgactcg caaaagccgc caatgccgta cggcgatagg gacgcccgta tacattactg    13080
tcacagccaa cgtgacagat gagaattatt tgcattcctc tgaccttctc atgctttctt    13140
cttgcctttt ctacgcttct gagatgagtg aaaagggatt caaggtgata tttggcaatg    13200
tgtcaggcat cgtggctgtt tgtgtcaact tcaccagcta tgtccaacat gttaaggaat    13260
ttacccgacg ctccttggta gtcgatcatg tacgactact acatttcatg cacctgaga    13320 ctatgaggtg ggcaacagtt ttagcctgtc ttttgccat cctattggca atttgaatgt    13380
tcaggtatgt tggggaaatg cttgaccgcg ggctgttgct cgcagttgct ttttttgtgg    13440
tgtatcgtgc cgttctgttt tgttgcgctc gtcaacgcca acaacagcag cagctcccat    13500
ttacagttaa tttataacct gacgatatgt gagctgaatg gcacagattg gctaaataga    13560
aaattcgact gggcagtgga gacctttgtc atctttccag tattgactca catcgtctcc    13620
tatggtgccc tcaccaccag ccatttcctt gacacagtcg gtttggtcac cgtgtccacc    13680
gccggatact accacaggcg gtatgtcctg agtagcattt acgctgtctg cgccctggcc    13740
gcgctgattt gcttcgccat caggctgaca aaaaactgca tgtcctggcg ctactcatgc    13800
actagatata ctaattttct tctagacacc aagggcaaac tctatcgttg gcggtctccc    13860
gtcattatag agaaagggg aaaaatcgag gttaacggtc acttgatcga cctcaagaga    13920
gttgtgcttg atggttccgc agcaacccct gtaaccaaag tttcagcgga acaatgggga    13980
cgtccttaga tgacttttgc aatgacagca cggctccaca aaaggtgctt ttggcgtttt    14040
ccattaccta tacgccaata atgatatatg ccctgaaggt aagtcgcggc cgattgttag    14100
ggcttctaca ccttttgatt ttcttgaatt gtgcttttac cttcgggtac atgacattcg    14160
cgcattttcg cagcacgaac aaggtcgcgc tcactatggg agcagtagtt gcactccttt    14220 gggggggtgta ttcagccata gaaacctgga gattcatcac ctccagatgc cggttgtgct    14280
```

-continued

```
tgctaggccg caggtacatt ctggcccctg cccaccacgt tgaaagtgtc gcaggctttc      14340
atccgataac ggcaagtgat aaccacgcat ttgtcgttcg gcgtcccggc tccactacag      14400
tcaacggcac attggtgccc gggttgaaaa gcctcgtgtt gggtggcaga agagctgtta      14460
aacgaggagt ggtgaacctt gtcaaatatg ccaataaca acggcaagca gcagaaaaga      14520
aaaaggggga tggccagcca gtcaatcagc tgtgccagat gctgggcagg atcatcgccc      14580
agcaaaacca gcccagaggt aagggaccgg gaaaaaggaa taagaagaaa agcccggaga      14640
agccccattt tcctctggcg actgaagatg acgttagaca tcacttcacc cctagtgagc      14700
gacaactgtg tctgtcgtca atccaaactg cctttaacca aggcgctgga acttgcaccc      14760
tgtcagactc gggtagggtg agttatgcag tggagtttag tttgcctacg catcatactg      14820
tgcgcctgat tcgtgccaca acatcaccct cagcatgatg agctggcatt cttgagacat      14880
cccagtgttt gaattggaag tgtgtgtggt gaatggcact gattgacatt gtgcctctaa      14940
gtcacctatt caattagggc gac                                              14963
```

<210> SEQ ID NO 2
<211> LENGTH: 14963
<212> TYPE: DNA
<213> ORGANISM: Porcine reproductive and respiratory syndrome virus

<400> SEQUENCE: 2

```
gggtgttggc tctatgccac gacatttgta ttgtcaggag ctgtgaccac tggcacagcc        60
caaaacttgc tgcacgggaa caccctcctg tgacggcctc cttcaggaa gtttaggggt       120 ttgtccctaa caccttgttt ccggagttgc actgctttac ggtctctcca ctcctttaac       180
catgtctggg attcttgatc ggtgcacgtg taccccaat gccagggtgt tgtgtggcaga       240 cggccaggtc tactgcacac gatgtctcag tgcacggacc ctccttcccc tgaatctcca       300
agtctctgaa cttggggtgt tgggcttgtt ctacaggccc gaagagccac tccggtggac       360
gttgccgcgc gcattcccca ctgttgagtg ctcccctgct ggagcttgtt ggctttctgc       420 gattttttcca attgcacgaa tgaccagtgg aaacctgaac ttccaacaaa ggatagtacg       480
ggttgcagct gagatttaca gagtcggcca actcaccccc acagtcttga agaacctaca       540
agtctatgaa cggggttgcc gctggtaccc catcgtcgga cctgtccctg gagttgccgt       600
ttacgctaac tccctacatg tgagtgataa acctttcccg ggggctactc acgtgctaac       660
caacctgccg ctcccgcaga gacctaagcc tgaagatttt tgccccttttg agtgtgcgat       720 ggctgtcgtc tatgacattg gtcatgacgc tgttatgtat gtggccaaag agagggtctc       780
ctgggctccg cgtggtggag aaaagggaaa attcgaaact gttccagagg agttgaggtt       840
ggttgcagag caacttttta cctccttccc gcctcaccac gtggtagaca tgtcgaagtt       900
catcttcaca gcccctgatt gtggagcttc tatgcgggtc gaacgccagt atggctgcct       960 cccgctggc actgtccctg acggtaattg ctggtggagc ttgtttagct cactcccacc      1020
ggaagttcag tgtagagaaa ttcgccgcgc cacccaattt ggctaccaaa ccaagcatgg      1080
cgttgctggc aagtacctac agcggaggct gcaagccaat ggtctccgag cagtggttga      1140
ctcaaacgga cctatcgtca tacagtattt ctccgttaag agagctggaa tccgccacgt      1200
gaaactggcg ggagagccct gctatccggg gtttgaggat ctcctcagga taagagtcga      1260
gcccaacacg ttgccattgt ccgacaaggg cgacaaagtc ttccgggtttg gcgggacaa      1320 gtggtacggc gctgggaaga gggcaaggag atcacgtgca ggtgctgcca ctacagttgc      1380
```

```
cggtcacgcc tcgcctgttc gcgaaactca acaggccaag aagcacgagg ctgctagcgc    1440
caacaaggct gagctccttg agcgctactc cccgcctgct gaagggaact gcggctggca    1500
ctgcatctct gccattgtca accgaatggt aaattccaag tttgaaactg cccttcctga    1560
aaaagtgaga ccccccagaag attgggccac tgatgaggat cttgtgaaca ctatccaaat    1620
tctcaggctc cctgcggcct tggacaggaa cggcgtctgc gcaagcgcca agtacgtcct    1680
taaactggag ggtgaacatt ggactgtttc agtgactccc ggaatgcctc cttccttgct    1740
cccccttgaa tgcgttcaag gttgttgtga gcacaagggc agtcttcgtt ctccagatgc    1800
ggtcgaagtt tccggattcg accctgccag ccttgatcga ctcgccgggg tgatgcatct    1860
gcccagcagt gccatcccag ccgccctggc tgagttgtct ggcgaccctg atcgtccagt    1920
ttccccggcc accactgcgt ggactgtctc gcagttttat gctcgccata gtggcggaga    1980
gcatcctgac caaaagtact taagaaaaat catcagcctc tgcgaggtga tcgagagctg    2040
ctgctgctcc cagaataaaa tcaacctggt cactccggaa gaggttaaaa caaaaattga    2100
ccaatacctc agtggtgcag caagtcttga agaatgtttg gccaggcttg agaaggctcg    2160
cccgccaagc gtgttggaca cctcctttga ttgggatgtt gtgctccctg gtgttggggc    2220
ggctgttcga gcagcgaaac tgcccctcgc caatcagtgt cacgctccag tcactgttgt    2280
gacccaaagg ccttcgttga aatttcagcc tcgaaaagcg gaatctgtca agagcttacc    2340
agagagcagg cctcttcctg ccccgcgcag gaagattagg tccaggtgtg gtagtctgac    2400
ttcattggac ggcaacttcc ctgacagctg ggaagacttg gccggtggtc ccttccattt    2460
cccgacccta cctgagccga cgacacgtcc gggtgagcct gtgcctgtcc ctgcaccgcg    2520
caagactgtg ccccgattgg tgtcgtcact gatagtgtca gtccctgtgc ccgcaccacg    2580
acgtgggatt cgacaggcgg agggaatgaa tttggtggca gtgactccag cgtgccagga    2640
cgagctcctc gatttatctg aatcctcgca ggctgagcat ggggctccct ccttggcatt    2700
gccgcggagt gaggatgccc tggcggtggg gagacgagaa gctgaagaag ttctgagcga    2760
aatctcgggc atgccagatg acattagatt ggtgcccgtg tcatcaagca gctccctgtc    2820
aagcgtagag attacacgcc caaagtactc agctcaagcc atcattgact caggtgggcc    2880
ctgttgtggg cacctccaag aggtaaaaga gaaatgcctc aatgtgatgc gtgaggcatg    2940
tgatgcgacc aagcttgatg accctgccac acgagaatgg ctttcccgta tgtgggacag    3000
ggtagacatg ttaacctggc gcaacacgtc catttttcag gcgcctttca ctttggctga    3060
caagttcaag ctcctcccga agatgatact cgaaacaccg ccgccctacc cttgcgggtt    3120
tgtaatgatg ccccgcacac ctgcaccttc tgtgggtgcg gagagcgacc tcaccgttgg    3180
ttcagttgct actgaggatg ttccgcgcat tctcggaaag gtgcaaggtg tttgcaaaac    3240
aaccgtccat gaacccttag caccttcgc agatggaccg acagatggcc aacctgctag    3300
agaaccccga acacaaactc ctcccgcagg cacaggtggc gttggcttag ttttggattc    3360
tgaaggatcg ccggagctca ctgattcgcc gcctccaaac ggtacagacg cgagcggagg    3420
gggaccgtta tacacagtca agaagaaggt tgagaggtgc tttgaccagc tgagccgacg    3480 ggttttgac atcgtctccc atctccctgt tttcttctca cgccttttca agtctgacgg    3540
tcattatgct ccgggtgatt ggggttttgc agcttttact ttattgtgcc tctttctgtg    3600
ttacagttac ccggcgttcg gtgtggttcc cctattgggt gtattttctg ggtcttctcg    3660
gcgcgtccgc atgggggttt ttggttgttg gttggctttc gctgttagtt tgttcaagcc    3720
tgctcccgac ccagtcggta ctgcttgtga gtttgactcg ccagagtgta gagacatcct    3780
```

```
tcattcttt  gagcttctgc  aaccttggga  ccctgttcgc  agccttgtgg  tgggcccgt   3840
cggtctcggt  cttgccattc  ttggcaggtt  actgggcggg  gcacgctacg  tctggctgtt  3900
tttgcttagg  cttggcatcg  tttcagactg  tatcttggct  ggagcctatg  tgctttcgca  3960
aggtaggtgt  aaaaagtgtt  ggggatcttg  tataagaact  gctcccagtg  aggtcgcctt  4020
caatgtgttt  cccttcacac  gcgcaaccag  atcgtcactt  attgacctgt  gcgaccggtt  4080
ctgcgcgccc  aaaggcatgg  accccatctt  cctcgctact  ggatggcgtg  gatgctgggc  4140
cggtcagagc  cccattgagc  aacccactga  gaaacccatt  gcgttcgccc  agttggatga  4200
gaagaaaatc  actgctaaaa  ctgtggttgc  ccagccttat  gaccccaacc  aagctgtgaa  4260
gtgcttacga  gtcctgcagg  cgggcgnggc  gatggtggct  gaggcgattc  caaaagtagt  4320
caaagtttct  gctatcccat  ttcgagctcc  cttcttccct  gtcggagtga  aagttgatcc  4380
tgaatgcagg  gtcgtggttg  actctgacac  cttcacaact  gctctccggt  ccggctactc  4440
caccacaaac  ctcattcttg  gtgtggggga  ttttgcccag  ctgaatgggt  tgaaaatcag  4500
gcaaatttcc  aagccttcgg  gaggaggtcc  acacatcatg  gcggccttac  atgtcgcttg  4560
ctcgatggct  ttgcacatgc  tcgttgggat  ttacgtcact  acggtggggtt  cttgtggttc  4620
tggcactaac  gacccgtggt  gcactaaccc  gtttgccgtc  cctgtctacg  gacctggctc  4680
tctttgcacc  tccaggttgt  gcatctccca  gcatggcctt  actctgccct  taacagcgct  4740
tgtggcgggg  tttggcattc  aggaagttgc  cttggtggtt  ttaatctttg  tttccatcgg  4800
aggtatggct  cacagattaa  gttgcaaggc  tgatgtactg  tgtattctgc  ttgcgattgc  4860
cagctatgtt  tggttacccc  tcacctggtt  gctctgtgtg  tttccttgct  ggttacgttg  4920
gttttctttg  catcccctca  ccgttacatg  gttggtgttt  tcttgatttt  ctgtaaacat  4980
gccctcagga  gtcttggcct  tggtgttgtt  aatctctctc  tggctccttg  gccgctatac  5040
caatgtcgca  ggtcttgtca  ctccttatga  cattcaccat  tacaccaacg  gcccccgtgg  5100
cgttgccgcc  ttggccactg  caccggatgg  gacctacttg  gctgctgtcc  gccgcgctgc  5160
gctgactggt  cgtaccatgc  tgtttacccc  gtcccagctt  gggtcactcc  ttgagggtgc  5220
ctttagaacc  caaaagccta  cactgaatac  cgtcaatgtg  gtcgggtcct  ctatgggctc  5280
cggcggggtg  ttcaccattg  acgggaaaat  caagtgcgtg  acagcagcgc  atattctcac  5340
aggcaactct  gccagggtct  ccggggtcgg  cttcaatcaa  atgttggatt  tcgatgtgaa  5400
aggggatttt  gccatagccg  attgtccgga  ttggcaagga  gtcgctccca  agtcccagtt  5460
ctgtgaggat  gggtggactg  gccgcgctta  ttggctaaca  tcctctggcg  tcgaacccgg  5520
cgtcatcggg  agggggatttg  ccttttgttt  caccgcgtgc  ggcgattccg  ggtccccagt  5580
gatcaccgag  gccggagaac  ttgtcggtgt  ccacacggga  tcaaataaac  aaggaggagg  5640
cattgtcacg  cgcccttcag  gccagttttg  taatgtgaca  cccaccaaat  taagtgaatt  5700
gagtgaattc  tttgctggac  ccagggtccc  gcttggcgat  gtgaaggtcg  gcaaccacat  5760
aatcaaagac  acaaatgagg  tgccctcaga  tctttgtgcc  ttgctcgctg  ccaaacccga  5820
gttggaagga  ggtctctcca  ccgttcaact  tttgtgcgtg  ttttcctcc  tatggagaat  5880
gatgggacat  gcctggacgc  ctttggttgc  tgttggtttt  tcgttttga  acgaaatcct  5940
cccagcggtt  ctggtccgga  gtgttttctc  ctttggaatg  ttcgcactgt  cttggttcac  6000
accgtggtct  gcacaaattc  taatgatcag  gcttctaaca  gcagctctta  acagaaacag  6060
atggtcactt  gcctttaca  gccttggtgc  actaactgga  tttgctgcag  accttgcaat  6120
```

```
taatcagggg cactcgctgc acgtggccat gaattttagc acctatgcat tcctacctcg    6180
tgcaatggcc gtgacctcac cagtcccaac gattgcgtgt ggtgttgtgc acttgcttgc    6240
tattgttttg tacttgttca agtaccgcag cctgcatacc gtcttggtcg gcgatggagc    6300
gttttccgca gctttctttt tgcgatactt tgcggaggga aaactgaggg aaggggtgtc    6360
gcagtcttgc ggcatgaatc atgagtcact gactggtgcc atcgccatca gactcgacga    6420
cgaggacctg gatttcctta taaaactgtc tgattttaag tgctttgttt ccgcgtccaa    6480
catgaggaat gcggcaggcc agttcatcga ggccgcttat gccaaagcac ttagggtgga    6540
acttgctcag ttagtgcagg ttgacaaggt ccgtggtgtc ttagctaagc ttgaagcatt    6600
tgctgacact gcgacgcccc aactctcacc tggcgacatt gttgttgctc ttggccatac    6660
gcctgttggc agtatcttcg acttgaaagt gggcagcacc aagcataccc tacaagccat    6720
cgagaccaga gtcctcgctg gtccagaat gaccgtggcg cgcgtcgtag atccgactcc    6780
cgcacctcca cccgtgcccg tgcccattcc tctcccgccg aaagttttag agaacggccc    6840
ccgtgcctgg gaggacgagg accgtctgaa caaaaagagg cggcgcaaaa tggaagccgt    6900
tggcatttat gtcatggacg ggaaaaagta ccaaaaattt tgggatcaga attctggtga    6960
tgtgttctat gaggaagtcc acgataacac agacgcgtgg gaatgcctca gaactgacga    7020
ccctgccgac ttggatcctg agaagggac tttgtgtggg cacctcacca tagagaatag    7080
accttaccat gtttacgcct ccccttccgg taggaagttc ctggtccctg ccaacccaga    7140
gagtgggaaa gcccagtggg aagctgcaag gctttccata gagcaggccc ttggcatgat    7200
gaacgtcgac ggcgagttga ccgccaagga ggtagagaaa ctgaagagaa taattgacaa    7260
actccagggc ctgactaagg agcagtgttt aaactactag ccgccagcgg cttgacccgc    7320
tgtggtcgcg gcggcttggt tattgctgag acagcggtga aaatagtcag attccacagt    7380
cggaccttta ccctggggcc tgtgaatttg aaagtggcta gcgaggttga gttgaaagac    7440
gccgtcgagc acaaccaaca cccaattgca agaccagttg acgtggcgt tgtgctcctg    7500
cgctctgcag ttccttcgct catagacgtc ttgatctccg gggccgacgc atcccctcag    7560
ttactcgccc atcatgggcc aggaaacacc gggattgatg gtacgctctg ggattttgag    7620
tccgtagcca ctaaagagga agtcacactt agtgcacaga taatacaggc ttgtggcatt    7680
aggcgcggcg atgctcctga gatcggcctc ccttacaaac tgcaccctgt taggggcaac    7740
cctgaacgtg taaaaggggt tttgaagaac acaaggtttg gggacatacc ttacaagacc    7800
cctagtgaca ctgggagccc tgtacatgcg gccgcctgtc ttacgcctaa tgccaccccg    7860
gtgactgacg ggcgctccgt cttggccacg accatgccct ccgggtttga gttgtatgtg    7920
ccgaccattc cagcatctgt ccttgattac cttgattcca ggccagactg ccctaaacag    7980
ttgacggagc acgggtgtga agatgctgca ttgagagatc tctccaaata tgacttgtcc    8040
acccaaggtt ttgttttgcc cggggtcctc cgcctcgtac ggaaatattt atttgcccac    8100
gtgggcaagt gcccgcctgt ccatcggccc tccacctacc cggccaagaa ttccatggct    8160
ggaataaacg ggaataggtt cccaaccaag acattcaga gcattcctga gatcgacgtt    8220
ctatgtgcac aggctgtacg agagaactgg caaactgtta cccttgcac cctcaagaag    8280
cagtattgcg ggaagaagaa aaccaggacc atactcggta ccaataactt tatcgcgctg    8340
gcccaccggg cagcgctgag tggagtcacc cagggcttta tgaaaaggc atttaactcg    8400
cccattgccc tcgggaagaa taaattcaag gagctacaaa ctccggtcct gggcaggtgc    8460
cttgaggctg atcttgcatc ttgcgatcga tccactcccg cgattgtccg ctggtttgcc    8520
```

```
gcccatctcc tttatgaact tgcctgcgct gaagagcacc taccgtcata tgtgctgaac    8580
tgctgtcatg acctattggt cacgcaatcc ggtgcggtga ctaagagagg tggcctgtca    8640
tctggtgatc cgatcacctc tgtgtccaac accatttaca gtctggtgat ttacgcgcag    8700
cacatggtgc tcagttactt taaaagtggt cacccacatg gtctcttgtt ccttcaggac    8760
cagctaaagt ttgaggacat gctcaaggtt caaccctga ttgtctactc ggacgatctt     8820
gtgctgtatg ccgagtctcc caccatgcca aactaccatt ggtgggttga gcacctgaat    8880
ttgatgttag ggtttcagac ggacccgaag aaaacaacca ttactgactc gccgtctttc    8940
ctgggctgca ggataatgaa tgggtgtcag ctagtcccaa accgtgacag gattctcgca    9000
gctcttgcct accacatgaa ggcgaataat gtttctgagt actacgcctc cgccgctgca    9060
atactcatgg acagttgtgc ttgtctggag tacgaccctg aatggtttga agaacttgtg    9120
gtaggaatgg cgcaatgcgc tcgcaaggac ggctatagct tccccggccc gccgttcttc    9180
ctatccatgt gggagaaact caggtctaat tatgagggga agaggtcaag ggtgtgtggg    9240
tactgcggag cttcagcccc gtatgccact tcctgtggtc ttgatgtctg tgtttaccac    9300
actcacttcc accagcattg tccagtcata atctggtgtg gccacccggc gggttctggg    9360
tcctgtgatg attgcaaatc tcccacaggg aaagatacaa acccctggaa tgaggtctta    9420
aaacaagtcc catataagcc tccacggact gtcctcatgc atgtggagca gggcctcacc    9480 cccttgacc caggcagata tcagacccgt cgtgggttgg ttgccgttag gcgcgggatc     9540 agggaaatg aagtcgacct accagatggt gattatgcca gcaccgcgtt actcccaact      9600
tgtaaagaga tcaacatggt cgctgttgct tccaatgtat tgcgcagtag atttatcatc    9660
ggtccacccg gtgctggaaa aacacactgg ctccttcaac aggttcagga tggtgatgtc    9720
atttatacac cgacccacca gaccatgctc gacatgatta agctttggg acgtgtcga      9780 tttaacgttc cggcaggtac aacgctgcaa ttccccgccc cttccgcac tggcccgtgg      9840 gttcgcatcc tggctggcgg gtggtgtcct ggcaaaaatt cattcctgga cgaagctgcg    9900
tattgcaacc atcttgatgt cttgaggctc cttagcaaaa ctactctcac ctgtttagga    9960
gacttcaaac aactccaccc ggtgggtttt gattctcact gctatgtctt tgacatcatg   10020
cctcaaactc aactgaagac tatctggagg tttggacaga atatctgtga tgccattcaa   10080
ccagattaca gggacaagct tatgtccatg gtcaacacac tcgtgtaac ctatgtgaa     10140 aagcccgtca aatatgggca agtcctcacc ccttaccata gggaccgaga ggatggcgcc   10200
attaccattg actccagtca aggtgccaca tttgatgtgg ttacactgca tttgcccacg   10260
aaagattcac tcaacaaaca aagggccctt gttgctatca ccagggcaag acatgccatc   10320
tttgtgtatg acccatatag gcaactgcag agcttatttg gtcttcctgc aaaaagcacg   10380
cccgtcaacc tggccgtgca ccgcgatggg caactgattg tgctagacag aaataataaa   10440
gaatgcacgg ttgcccaggc tctgggcaat ggtgacaaat tcagagctac agataagcgc   10500
gttgtagatt ctcttcgcgc catttgtgct gacctggaag ggtcgagctc gccgcttccc   10560
aaggttgcac ataacttggg gtttttattc tcacctgatt tgacacagtt tgccaagctt   10620
ccaatagaac ttgcaccaca ttggccagtg gtgacgaccc aaaataatga gaactggcct   10680
gatcgactgg ttgccagcct acgccccatt cacaaatata gccgtgcatg tatcggtgcc   10740
ggctatatgg tgggcccctc ggtgttttta ggcaccctg gggtagtatc atactatctc    10800
acaaaatttg tcaaaggcga ggctcaggtg cttccagaaa cggtcttcag cactggccga   10860
```

```
attgaggtgg actgccgaga gtaccttgat gattgggagc gggaagtcgc agcgtccctc    10920
ccgcatgcct ttatcggcga cgtcaaaggc actactgtgg gagggtgtca ccatgtcacc    10980
tctaaatatc tcccgcgctt cctccccaag gaatcagtcg cggtggtcgg ggtttcaagc    11040
cccgggaaag ccgcaaaagc agtgtgcaca ttgacggatg tgtacctccc agaccttgag    11100
gcctacctcc atcctgtgac ccagtccaag tgctggaaaa tgatgttgga ctttaaagaa    11160
gttcgactga tggtttggaa ggacaagacg gcctatttcc aactcgaagg tcgtcatttc    11220
acctggtatc agcttgctag cttttgcttcg tacatccgtg ttcctgtaaa ttccacggtg    11280
tacctggacc cctgcatggg ccccgcccctt tgcaacagga aagtcgttgg gtcccctcat    11340
tggggagctg acctcgcagt caccccttat gattatggag ctagaaaaat tttgtccagt    11400
gcatatcatg gtgagatgcc tcctgggtac aagattctgg cgtgcgcaga gttctcgcta    11460
gacgacccag tcagatacaa gcatacttgg gggttcgagt cggatacagc gtacttgtac    11520
gagttcactg gaaacggcga ggactgggag gattacaacg acgcgtttcg tgcgcgacag    11580
aaaggaaaaa tttataaggc cactgccacc agcctgaagt tccatttccc tccgggtcac    11640
atcgttgaac caactttggg cctgaactga aatgagatgg gagccgcaca gagcctttttt    11700
gacaaaattg gtcaacttttt tgttgatgcc ttcacggagt tcttggtgtc tattgttgat    11760
atcatcatat ttttggccat tttgttcggc ttcaccatcg ccggttggct ggtggtcttt    11820
tgcatcagat tggtttttctc cgcgatactc cgtgcgcgcc ctaccgttca ctctgagcaa    11880
ttacagaaga tcctatgagg cctacctctc ccagtgccag gtggacattc ctgcctgggg    11940
gactaaacac cctttgggga tgatctggca ccacagggtg tcgaccctaa ttgatgaaat    12000
ggtgtcgcgt cggatgtacc gcaccatgga acaagcaggg caggctgcct ggaaacaggt    12060
ggtgaccgag gcaacgctgt ctcgtattag tagtttggat gtggtggctc atttccagca    12120
tcttgccgcc atagaagccg agacttgtaa atacttggcc tcccggctgc aatgctaca     12180
caacctgcgc ttgacagggt caaatgtaac catagtgtat aatagctccc tggacccgggt    12240
gtttgctgtt ttcccgacct ccagttcccg gccaaagctt catgattttc ggcaatggct    12300
aatagctgtg cattcctcca tattctcctc tgttgcggct tcttgtaccc ttttcgtcgt    12360
actgtggttg cggcttccaa taatacgtac tgttttggt ttccgctggt tagggggcaat    12420
tttttctttcg agctcacagt gaattacacg gtatgtcctc cctgcctcac ccggcaagcg    12480
gcttcagaga tctacgaacc cagcagatct cttttggtgta ggatagggca agatcgatgt    12540
acagagagcg atcacgatga gctaggtttc ctggtgccgc ctggcctctc taacgaaggc    12600
catttaatta gtgtctacgc ctggctggcg ttcctatcct tcagttacac gtcgcagttc    12660
catcccgaaa tattcggcat agggaatgtg agtgaggtct atgtcgacat caagcaccaa    12720
cttatttgtg ctgttcatga tgggcagaac accaccttgc ctcgccatga acatcacg      12780
gccgtgtacc agacgtatta tcaacaccag gttgatggcg gcaactggtt tcacctggaa    12840
tggctgcgtc ccttcttttc ttcttggttg gtttttgaatg tttcatggtt tctcaggcgt    12900
tcgcctgcaa gccgtgtttc agttcgagtc tttcagacat caaaaccaac accaccgcag    12960
ctgcaggttt tgctgtcctc caagacatca gctgtcttag gcatggcgac tcgtcctctg    13020
aggcgactcg caaaagccgc caatgccgta cggcgatagg gacgcccgta tacattactg    13080
tcacagccaa cgtgacagat gagaattatt tgcattcctc tgaccttctc atgctttctt    13140
cttgcctttt ctacgcttct gagatgagtg aaaagggatt caaggtgata tttggcaatg    13200
tgtcaggcat cgtggctgtt tgtgtcaact tcaccagcta tgtccaacat gttaaggaat    13260
```

-continued

```
ttacccgacg ctccttggta gtcgatcatg tacgactact acatttcatg acacctgaga    13320
ctatgaggtg ggcaacagtt ttagcctgtc tttttgccat cctattggca atttgaatgt    13380
tcaggtatgt tggggaattg cttgaccgcg ggctgttgct cgcagttgct ttttttgtgg    13440
tgtatcgtgc cgttctgttt tgttgcgctc gtcaacgcca acaacagcag cagctcccat    13500
ttacagttaa tttataacct gacgatatgt gagctgaatg gcacagattg gctaaataga    13560
aaattcgact gggcagtgga gacctttgtc atctttccag tattgactca catcgtctcc    13620
tatggtgccc tcaccaccag ccatttcctt gacacagtcg gtttggtcac cgtgtccacc    13680
gccggatact accacaggcg gtatgtcctg agtagcattt acgctgtctg cgccctggcc    13740
gcgctgattt gcttcgccat caggctgaca aaaaactgca tgtcctggcg ctactcatgc    13800
actagatata ctaattttct tctagacacc aagggcaaac tctatcgttg gcggtctccc    13860
gtcattatag agaaaagggg aaaaatcgag gttaacggtc acttgatcga cctcaagaga    13920
gttgtgcttg atggttccgc agcaacccct gtaaccaaag ttttagcgga acaatgggga    13980
cgtccttaga tgactttgtc aatgacagca cggctccaca aaaggtgctt ttggcgtttt    14040
ccattaccta tacgccaata atgatatatg ccctgaaggt aagtcgcggc cgattgtcag    14100
ggcttctaca ccttttgatt ttcttgaatt gtgcttttac cttcgggtac atgacattcg    14160
cgcattttcg cagcacgaac aaggtcgcgc tcactatggg agcagtagtt gcactccttt    14220 gggggtgta ttcagccata gaaacctgga gattcatcac ctccagatgc cggttgtgct    14280
tgctaggccg caggtacatt ctggcccctg cccaccacgt tgaaagtgtc gcaggctttc    14340
atccgataac ggcaagtgat aaccacgcat tgtcgttcg gcgtcccggc tccactacag    14400
tcaacggcac attggtgccc gggttgaaaa gcctcgtgtt gggtggcaga agagctgtta    14460
aacgaggagt ggtgaacctt gtcaaatatg ccaataaca acggcaagca gcagaaaaga    14520 aaaagggga tggccagcca gtcaatcagc tgtgccagat gctgggcagg atcatcgccc    14580
agcaaaacca gcccagaggt aagggaccgg gaaaaggaa taagaagaaa gcccggaga    14640 agccccattt tcctctggcg actgaagatg acgttagaca tcacttcacc cctagtgagc    14700
gacaactgtg tctgtcgtca atccaaactg cctttaacca aggcgctgga acttgcaccc    14760
tgtcagactc gggtagggtg agttatgcag tggagtttag tttgcctacg catcatactg    14820
tgcgcctgat tcgtgccaca acatcaccct cagcatgatg agctggcatt cttgagacat    14880
cccagtgttt gaattggaag tgtgtgtggt gaatggcact gattgacatt gtgcctctaa    14940
gtcacctatt caattagggc gac    14963
```

<210> SEQ ID NO 3
<211> LENGTH: 2372
<212> TYPE: PRT
<213> ORGANISM: Porcine reproductive and respiratory syndrome virus

<400> SEQUENCE: 3

```
Met Ser Gly Ile Leu Asp Arg Cys Thr Cys Thr Pro Asn Ala Arg Val
1               5                   10                  15

Phe Val Ala Asp Gly Gln Val Tyr Cys Thr Arg Cys Leu Ser Ala Arg
            20                  25                  30

Thr Leu Leu Pro Leu Asn Leu Gln Val Ser Glu Leu Gly Val Leu Gly
        35                  40                  45

Leu Phe Tyr Arg Pro Glu Glu Pro Leu Arg Trp Thr Leu Pro Arg Ala
    50                  55                  60
```

-continued

```
Phe Pro Thr Val Glu Cys Ser Pro Ala Gly Ala Cys Trp Leu Ser Ala
 65                  70                  75                  80

Ile Phe Pro Ile Ala Arg Met Thr Ser Gly Asn Leu Asn Phe Gln Gln
                 85                  90                  95

Arg Ile Val Arg Val Ala Ala Glu Ile Tyr Arg Val Gly Gln Leu Thr
            100                 105                 110

Pro Thr Val Leu Lys Asn Leu Gln Val Tyr Glu Arg Gly Cys Arg Trp
            115                 120                 125

Tyr Pro Ile Val Gly Pro Pro Gly Val Ala Val Tyr Ala Asn Ser
    130                 135                 140

Leu His Val Ser Asp Lys Pro Phe Pro Gly Ala Thr His Val Leu Thr
145                 150                 155                 160

Asn Leu Pro Leu Pro Gln Arg Pro Lys Pro Glu Asp Phe Cys Pro Phe
                165                 170                 175

Glu Cys Ala Met Ala Val Val Tyr Asp Ile Gly His Asp Ala Val Met
                180                 185                 190

Tyr Val Ala Lys Glu Arg Val Ser Trp Ala Pro Arg Gly Gly Glu Lys
            195                 200                 205

Gly Lys Phe Glu Thr Val Pro Glu Glu Leu Arg Leu Val Ala Glu Gln
    210                 215                 220

Leu Phe Thr Ser Phe Pro Pro His His Val Val Asp Met Ser Lys Phe
225                 230                 235                 240

Ile Phe Thr Ala Pro Asp Cys Gly Ala Ser Met Arg Val Glu Arg Gln
                245                 250                 255

Tyr Gly Cys Leu Pro Ala Gly Thr Val Pro Asp Gly Asn Cys Trp Trp
            260                 265                 270

Ser Leu Phe Ser Ser Leu Pro Pro Glu Val Gln Cys Arg Glu Ile Arg
    275                 280                 285

Arg Ala Thr Gln Phe Gly Tyr Gln Thr Lys His Gly Val Ala Gly Lys
290                 295                 300

Tyr Leu Gln Arg Leu Gln Ala Asn Gly Leu Arg Ala Val Val Asp
305                 310                 315                 320

Ser Asn Gly Pro Ile Val Ile Gln Tyr Phe Ser Val Lys Glu Ser Trp
                325                 330                 335

Ile Arg His Val Lys Leu Ala Gly Glu Pro Cys Tyr Pro Gly Phe Glu
                340                 345                 350

Asp Leu Leu Arg Ile Arg Val Glu Pro Asn Thr Leu Pro Leu Ser Asp
            355                 360                 365

Lys Gly Asp Lys Val Phe Arg Phe Gly His Lys Trp Tyr Gly Ala
    370                 375                 380

Gly Lys Arg Ala Arg Ser Arg Ala Gly Ala Ala Thr Thr Val Ala
385                 390                 395                 400

Gly His Ala Ser Pro Val Arg Glu Thr Gln Ala Lys His Glu
                405                 410                 415

Ala Ala Ser Ala Asn Lys Ala Glu Leu Leu Glu Arg Tyr Ser Pro Pro
                420                 425                 430

Ala Glu Gly Asn Cys Gly Trp His Cys Ile Ser Ala Ile Val Asn Arg
            435                 440                 445

Met Val Asn Ser Lys Phe Glu Thr Ala Leu Pro Glu Lys Val Arg Pro
    450                 455                 460

Pro Glu Asp Trp Ala Thr Asp Glu Asp Leu Val Asn Thr Ile Gln Ile
465                 470                 475                 480

Leu Arg Leu Pro Ala Ala Leu Asp Arg Asn Gly Val Cys Ala Ser Ala
```

```
            485                 490                 495
Lys Tyr Val Leu Lys Leu Glu Gly Glu His Trp Thr Val Ser Val Thr
                500                 505                 510

Pro Gly Met Pro Pro Ser Leu Leu Pro Leu Glu Cys Val Gln Gly Cys
            515                 520                 525

Cys Glu His Lys Gly Ser Leu Arg Ser Pro Asp Ala Val Glu Val Ser
        530                 535                 540

Gly Phe Asp Pro Ala Ser Leu Asp Arg Leu Ala Gly Val Met His Leu
545                 550                 555                 560

Pro Ser Ser Ala Ile Pro Ala Ala Leu Ala Glu Leu Ser Gly Asp Pro
                565                 570                 575

Asp Arg Pro Val Ser Pro Ala Thr Thr Ala Trp Thr Val Ser Gln Phe
            580                 585                 590

Tyr Ala Arg His Ser Gly Gly Glu His Pro Asp Gln Lys Tyr Leu Arg
            595                 600                 605

Lys Ile Ile Ser Leu Cys Glu Val Ile Glu Ser Cys Cys Cys Ser Gln
        610                 615                 620

Asn Lys Ile Asn Leu Val Thr Pro Glu Glu Val Lys Thr Lys Ile Asp
625                 630                 635                 640

Gln Tyr Leu Ser Gly Ala Ala Ser Leu Glu Glu Cys Leu Ala Arg Leu
                645                 650                 655

Glu Lys Ala Arg Pro Pro Ser Val Leu Asp Thr Ser Phe Asp Trp Asp
            660                 665                 670

Val Val Leu Pro Gly Val Gly Ala Ala Val Arg Ala Ala Lys Leu Pro
        675                 680                 685

Leu Ala Asn Gln Cys His Ala Pro Val Thr Val Thr Gln Arg Pro
690                 695                 700

Ser Leu Lys Phe Gln Pro Arg Lys Ala Glu Val Lys Ser Leu Pro
705                 710                 715                 720

Glu Ser Arg Pro Leu Pro Ala Pro Arg Lys Ile Arg Ser Arg Cys
                725                 730                 735

Gly Ser Leu Thr Ser Leu Asp Gly Asn Phe Pro Asp Ser Trp Glu Asp
            740                 745                 750

Leu Ala Gly Gly Pro Phe His Phe Pro Thr Leu Pro Glu Pro Thr Thr
        755                 760                 765

Arg Pro Gly Glu Pro Val Pro Val Pro Ala Pro Arg Lys Thr Val Pro
        770                 775                 780

Arg Leu Val Ser Ser Leu Ile Val Ser Val Pro Val Pro Ala Pro Arg
785                 790                 795                 800

Arg Gly Ile Arg Gln Ala Glu Gly Met Asn Leu Val Ala Val Thr Pro
                805                 810                 815

Ala Cys Gln Asp Glu Leu Leu Asp Leu Ser Glu Ser Ser Gln Ala Glu
            820                 825                 830

His Gly Ala Pro Ser Leu Ala Leu Pro Arg Ser Glu Asp Ala Leu Ala
            835                 840                 845

Val Gly Arg Arg Glu Ala Glu Glu Val Leu Ser Glu Ile Ser Gly Met
        850                 855                 860

Pro Asp Asp Ile Arg Leu Val Pro Val Ser Ser Ser Ser Ser Leu Ser
865                 870                 875                 880

Ser Val Glu Ile Thr Arg Pro Lys Tyr Ser Ala Gln Ala Ile Ile Asp
                885                 890                 895

Ser Gly Gly Pro Cys Cys Gly His Leu Gln Glu Val Lys Glu Lys Tyr
            900                 905                 910
```

-continued

Leu Asn Val Met Arg Glu Ala Cys Asp Ala Thr Lys Leu Asp Asp Pro
        915                 920                 925

Ala Thr Arg Glu Trp Leu Ser Arg Met Trp Asp Arg Val Asp Met Leu
930                 935                 940

Thr Trp Arg Asn Thr Ser Ile Phe Gln Ala Pro Phe Thr Leu Ala Asp
945                 950                 955                 960

Lys Phe Lys Leu Leu Pro Lys Met Ile Leu Glu Thr Pro Pro Pro Tyr
                965                 970                 975

Pro Cys Gly Phe Val Met Met Pro Arg Thr Pro Ala Pro Ser Val Gly
            980                 985                 990

Ala Glu Ser Asp Leu Thr Val Gly Ser Val Ala Thr Glu Asp Val Pro
        995                 1000                1005

Arg Ile Leu Gly Lys Val Gln Gly Val Cys Lys Thr Thr Val His
    1010                1015                1020

Glu Pro Leu Ala Pro Phe Ala Asp Gly Pro Thr Asp Gly Gln Pro
    1025                1030                1035

Ala Arg Glu Pro Arg Thr Gln Thr Pro Ala Gly Thr Gly Gly
    1040                1045                1050

Val Gly Leu Val Leu Asp Ser Glu Gly Ser Pro Glu Leu Thr Asp
    1055                1060                1065

Ser Pro Pro Pro Asn Gly Thr Asp Ala Ser Gly Gly Pro Leu
    1070                1075                1080

Tyr Thr Val Lys Lys Lys Ala Glu Arg Cys Phe Asp Gln Leu Ser
    1085                1090                1095

Arg Arg Val Phe Asp Ile Val Ser His Leu Pro Val Phe Phe Ser
    1100                1105                1110

Arg Leu Phe Lys Ser Asp Gly His Tyr Ala Pro Gly Asp Trp Gly
    1115                1120                1125

Phe Ala Ala Phe Thr Leu Leu Cys Leu Phe Leu Cys Tyr Ser Tyr
    1130                1135                1140

Pro Ala Phe Gly Val Val Pro Leu Leu Gly Val Phe Ser Gly Ser
    1145                1150                1155

Ser Arg Arg Val Arg Met Gly Val Phe Gly Cys Trp Leu Ala Phe
    1160                1165                1170

Ala Val Ser Leu Phe Lys Pro Ala Pro Asp Pro Val Gly Thr Ala
    1175                1180                1185

Cys Glu Phe Asp Ser Pro Glu Cys Arg Asp Ile Leu His Ser Phe
    1190                1195                1200

Glu Leu Leu Gln Pro Trp Asp Pro Val Arg Ser Leu Val Val Gly
    1205                1210                1215

Pro Val Gly Leu Gly Leu Ala Ile Leu Gly Arg Leu Leu Gly Gly
    1220                1225                1230

Ala Arg Tyr Val Trp Leu Phe Leu Leu Arg Leu Gly Ile Val Ser
    1235                1240                1245

Asp Cys Ile Leu Ala Gly Ala Tyr Val Leu Ser Gln Gly Arg Cys
    1250                1255                1260

Lys Lys Cys Trp Gly Ser Cys Ile Arg Thr Ala Pro Ser Glu Val
    1265                1270                1275

Ala Phe Asn Val Phe Pro Phe Thr Arg Ala Thr Arg Ser Ser Leu
    1280                1285                1290

Ile Asp Leu Cys Asp Arg Phe Cys Ala Pro Lys Gly Met Asp Pro
    1295                1300                1305

-continued

```
Ile Phe Leu Ala Thr Gly Trp Arg Gly Cys Trp Ala Gly Gln Ser
1310                1315                1320

Pro Ile Glu Gln Pro Thr Glu Lys Pro Ile Ala Phe Ala Gln Leu
1325                1330                1335

Asp Glu Lys Lys Ile Thr Ala Lys Thr Val Val Ala Gln Pro Tyr
1340                1345                1350

Asp Pro Asn Gln Ala Val Lys Cys Leu Arg Val Leu Gln Ala Gly
1355                1360                1365

Gly Ala Met Val Ala Glu Ala Ile Pro Lys Val Val Lys Val Ser
1370                1375                1380

Ala Ile Pro Phe Arg Ala Pro Phe Phe Pro Val Gly Val Lys Val
1385                1390                1395

Asp Pro Glu Cys Arg Val Val Val Asp Ser Asp Thr Phe Thr Thr
1400                1405                1410

Ala Leu Arg Ser Gly Tyr Ser Thr Thr Asn Leu Ile Leu Gly Val
1415                1420                1425

Gly Asp Phe Ala Gln Leu Asn Gly Leu Lys Ile Arg Gln Ile Ser
1430                1435                1440

Lys Pro Ser Gly Gly Pro His Ile Met Ala Ala Leu His Val
1445                1450                1455

Ala Cys Ser Met Ala Leu His Met Leu Val Gly Ile Tyr Val Thr
1460                1465                1470

Thr Val Gly Ser Cys Gly Ser Gly Thr Asn Asp Pro Trp Cys Thr
1475                1480                1485

Asn Pro Phe Ala Val Pro Val Tyr Gly Pro Gly Ser Leu Cys Thr
1490                1495                1500

Ser Arg Leu Cys Ile Ser Gln His Gly Leu Thr Leu Pro Leu Thr
1505                1510                1515

Ala Leu Val Ala Gly Phe Gly Ile Gln Glu Val Ala Leu Val Val
1520                1525                1530

Leu Ile Phe Val Ser Ile Gly Gly Met Ala His Arg Leu Ser Cys
1535                1540                1545

Lys Ala Asp Val Leu Cys Ile Leu Leu Ala Ile Ala Ser Tyr Val
1550                1555                1560

Trp Leu Pro Leu Thr Trp Leu Leu Cys Val Phe Pro Cys Trp Leu
1565                1570                1575

Arg Trp Phe Ser Leu His Pro Leu Thr Val Thr Trp Leu Val Phe
1580                1585                1590

Phe Leu Ile Ser Val Asn Met Pro Ser Gly Val Leu Ala Leu Val
1595                1600                1605

Leu Leu Ile Ser Leu Trp Leu Leu Gly Arg Tyr Thr Asn Val Ala
1610                1615                1620

Gly Leu Val Thr Pro Tyr Asp Ile His His Tyr Thr Asn Gly Pro
1625                1630                1635

Arg Gly Val Ala Ala Leu Ala Thr Ala Pro Asp Gly Thr Tyr Leu
1640                1645                1650

Ala Ala Val Arg Arg Ala Ala Leu Thr Gly Arg Thr Met Leu Phe
1655                1660                1665

Thr Pro Ser Gln Leu Gly Ser Leu Leu Glu Gly Ala Phe Arg Thr
1670                1675                1680

Gln Lys Pro Thr Leu Asn Thr Val Asn Val Val Gly Ser Ser Met
1685                1690                1695

Gly Ser Gly Gly Val Phe Thr Ile Asp Gly Lys Ile Lys Cys Val
```

-continued

```
            1700                1705                1710
Thr Ala Ala His Ile Leu Thr Gly Asn Ser Ala Arg Val Ser Gly
            1715                1720                1725

Val Gly Phe Asn Gln Met Leu Asp Phe Asp Val Lys Gly Asp Phe
            1730                1735                1740

Ala Ile Ala Asp Cys Pro Asp Trp Gln Gly Val Ala Pro Lys Ser
            1745                1750                1755

Gln Phe Cys Glu Asp Gly Trp Thr Gly Arg Ala Tyr Trp Leu Thr
            1760                1765                1770

Ser Ser Gly Val Glu Pro Gly Val Ile Gly Arg Gly Phe Ala Phe
            1775                1780                1785

Cys Phe Thr Ala Cys Gly Asp Ser Gly Ser Pro Val Ile Thr Glu
            1790                1795                1800

Ala Gly Glu Leu Val Gly Val His Thr Gly Ser Asn Lys Gln Gly
            1805                1810                1815

Gly Gly Ile Val Thr Arg Pro Ser Gly Gln Phe Cys Asn Val Thr
            1820                1825                1830

Pro Thr Lys Leu Ser Glu Leu Ser Glu Phe Phe Ala Gly Pro Arg
            1835                1840                1845

Val Pro Leu Gly Asp Val Lys Val Gly Asn His Ile Ile Lys Asp
            1850                1855                1860

Thr Asn Glu Val Pro Ser Asp Leu Cys Ala Leu Leu Ala Ala Lys
            1865                1870                1875

Pro Glu Leu Glu Gly Gly Leu Ser Thr Val Gln Leu Leu Cys Val
            1880                1885                1890

Phe Phe Leu Leu Trp Arg Met Met Gly His Ala Trp Thr Pro Leu
            1895                1900                1905

Val Ala Val Gly Phe Phe Val Leu Asn Glu Ile Leu Pro Ala Val
            1910                1915                1920

Leu Val Arg Ser Val Phe Ser Phe Gly Met Phe Ala Leu Ser Trp
            1925                1930                1935

Phe Thr Pro Trp Ser Ala Gln Ile Leu Met Ile Arg Leu Leu Thr
            1940                1945                1950

Ala Ala Leu Asn Arg Asn Arg Trp Ser Leu Ala Phe Tyr Ser Leu
            1955                1960                1965

Gly Ala Leu Thr Gly Phe Ala Ala Asp Leu Ala Ile Asn Gln Gly
            1970                1975                1980

His Ser Leu His Val Ala Met Asn Phe Ser Thr Tyr Ala Phe Leu
            1985                1990                1995

Pro Arg Ala Met Ala Val Thr Ser Pro Val Pro Thr Ile Ala Cys
            2000                2005                2010

Gly Val His Leu Leu Ala Ile Val Leu Tyr Leu Phe Lys Tyr
            2015                2020                2025

Arg Ser Leu His Thr Val Leu Val Gly Asp Gly Ala Phe Ser Ala
            2030                2035                2040

Ala Phe Phe Leu Arg Tyr Phe Ala Glu Gly Lys Leu Arg Glu Gly
            2045                2050                2055

Val Ser Gln Ser Cys Gly Met Asn His Glu Ser Leu Thr Gly Ala
            2060                2065                2070

Ile Ala Ile Arg Leu Asp Asp Glu Asp Leu Asp Phe Leu Ile Lys
            2075                2080                2085

Leu Thr Asp Phe Lys Cys Phe Val Ser Ala Ser Asn Met Arg Asn
            2090                2095                2100
```

-continued

```
Ala Ala Gly Gln Phe Ile Glu Ala Ala Tyr Ala Lys Ala Leu Arg
        2105                2110                2115

Val Glu Leu Ala Gln Leu Val Gln Val Asp Lys Val Arg Gly Val
    2120                2125                2130

Leu Ala Lys Leu Glu Ala Phe Ala Asp Thr Ala Thr Pro Gln Leu
        2135                2140                2145

Ser Pro Gly Asp Ile Val Val Ala Leu Gly His Thr Pro Val Gly
        2150                2155                2160

Ser Ile Phe Asp Leu Lys Val Gly Ser Thr Lys His Thr Leu Gln
        2165                2170                2175

Ala Ile Glu Thr Arg Val Leu Ala Gly Ser Arg Met Thr Val Ala
        2180                2185                2190

Arg Val Val Asp Pro Thr Pro Ala Pro Pro Val Pro Val Pro
        2195                2200                2205

Ile Pro Leu Pro Pro Lys Val Leu Glu Asn Gly Pro Arg Ala Trp
        2210                2215                2220

Glu Asp Glu Asp Arg Leu Asn Lys Lys Arg Arg Arg Lys Met Glu
        2225                2230                2235

Ala Val Gly Ile Tyr Val Met Asp Gly Lys Lys Tyr Gln Lys Phe
        2240                2245                2250

Trp Asp Lys Asn Ser Gly Asp Val Phe Tyr Glu Glu Val His Asp
        2255                2260                2265

Asn Thr Asp Ala Trp Glu Cys Leu Arg Thr Asp Asp Pro Ala Asp
        2270                2275                2280

Leu Asp Pro Glu Lys Gly Thr Leu Cys Gly His Leu Thr Ile Glu
        2285                2290                2295

Asn Arg Pro Tyr His Val Tyr Ala Ser Pro Ser Gly Arg Lys Phe
        2300                2305                2310

Leu Val Pro Ala Asn Pro Glu Ser Gly Lys Ala Gln Trp Glu Ala
        2315                2320                2325

Ala Arg Leu Ser Ile Glu Gln Ala Leu Gly Met Met Asn Val Asp
        2330                2335                2340

Gly Glu Leu Thr Ala Lys Glu Val Glu Lys Leu Lys Arg Ile Ile
        2345                2350                2355

Asp Lys Leu Gln Gly Leu Thr Lys Glu Gln Cys Leu Asn Tyr
        2360                2365                2370

<210> SEQ ID NO 4
<211> LENGTH: 1463
<212> TYPE: PRT
<213> ORGANISM: Porcine reproductive and respiratory syndrome virus

<400> SEQUENCE: 4

Gly Ala Val Phe Lys Leu Leu Ala Ala Ser Gly Leu Thr Arg Cys Gly
1               5                   10                  15

Arg Gly Gly Leu Val Ile Thr Glu Thr Ala Val Lys Ile Val Arg Phe
                20                  25                  30

His Ser Arg Thr Phe Thr Leu Gly Pro Val Asn Leu Lys Val Ala Ser
            35                  40                  45

Glu Val Glu Leu Lys Asp Ala Val Glu His Asn Gln His Pro Ile Ala
        50                  55                  60

Arg Pro Val Asp Gly Gly Val Val Leu Leu Arg Ser Ala Val Pro Ser
65                  70                  75                  80

Leu Ile Asp Val Leu Ile Ser Gly Ala Asp Ala Ser Pro Gln Leu Leu
```

```
            85                  90                  95
Ala His His Gly Pro Gly Asn Thr Gly Ile Asp Gly Thr Leu Trp Asp
            100                 105                 110

Phe Glu Ser Val Ala Thr Lys Glu Glu Val Thr Leu Ser Ala Gln Ile
            115                 120                 125

Ile Gln Ala Cys Gly Ile Arg Arg Gly Asp Ala Pro Glu Ile Gly Leu
            130                 135                 140

Pro Tyr Lys Leu His Pro Val Arg Gly Asn Pro Glu Arg Val Lys Gly
145                 150                 155                 160

Val Leu Lys Asn Thr Arg Phe Gly Asp Ile Pro Tyr Lys Thr Pro Ser
                165                 170                 175

Asp Thr Gly Ser Pro Val His Ala Ala Cys Leu Thr Pro Asn Ala
                180                 185                 190

Thr Pro Val Thr Asp Gly Arg Ser Val Leu Ala Thr Thr Met Pro Ser
            195                 200                 205

Gly Phe Glu Leu Tyr Val Pro Thr Ile Pro Ala Ser Val Leu Asp Tyr
            210                 215                 220

Leu Asp Ser Arg Pro Asp Cys Pro Lys Gln Leu Thr Glu His Gly Cys
225                 230                 235                 240

Glu Asp Ala Ala Leu Arg Asp Leu Ser Lys Tyr Asp Leu Ser Thr Gln
                245                 250                 255

Gly Phe Val Leu Pro Gly Val Leu Arg Leu Val Arg Lys Tyr Leu Phe
                260                 265                 270

Ala His Val Gly Lys Cys Pro Pro Val His Arg Pro Ser Thr Tyr Pro
                275                 280                 285

Ala Lys Asn Ser Met Ala Gly Ile Asn Gly Asn Arg Phe Pro Thr Lys
            290                 295                 300

Asp Ile Gln Ser Ile Pro Glu Ile Asp Val Leu Cys Ala Gln Ala Val
305                 310                 315                 320

Arg Glu Asn Trp Gln Thr Val Thr Pro Cys Thr Leu Lys Lys Gln Tyr
                325                 330                 335

Cys Gly Lys Lys Lys Thr Arg Thr Ile Leu Gly Thr Asn Asn Phe Ile
            340                 345                 350

Ala Leu Ala His Arg Ala Ala Leu Ser Gly Val Thr Gln Gly Phe Met
            355                 360                 365

Lys Lys Ala Phe Asn Ser Pro Ile Ala Leu Gly Lys Asn Lys Phe Lys
            370                 375                 380

Glu Leu Gln Thr Pro Val Leu Gly Arg Cys Leu Glu Ala Asp Leu Ala
385                 390                 395                 400

Ser Cys Asp Arg Ser Thr Pro Ala Ile Val Arg Trp Phe Ala Ala His
                405                 410                 415

Leu Leu Tyr Glu Leu Ala Cys Ala Glu His Leu Pro Ser Tyr Val
            420                 425                 430

Leu Asn Cys Cys His Asp Leu Leu Val Thr Gln Ser Gly Ala Val Thr
            435                 440                 445

Lys Arg Gly Gly Leu Ser Ser Gly Asp Pro Ile Thr Ser Val Ser Asn
            450                 455                 460

Thr Ile Tyr Ser Leu Val Ile Tyr Ala Gln His Met Val Leu Ser Tyr
465                 470                 475                 480

Phe Lys Ser Gly His Pro His Gly Leu Leu Phe Leu Gln Asp Gln Leu
                485                 490                 495

Lys Phe Glu Asp Met Leu Lys Val Gln Pro Leu Ile Val Tyr Ser Asp
            500                 505                 510
```

Asp Leu Val Leu Tyr Ala Glu Ser Pro Thr Met Pro Asn Tyr His Trp
            515                 520                 525

Trp Val Glu His Leu Asn Leu Met Leu Gly Phe Gln Thr Asp Pro Lys
    530                 535                 540

Lys Thr Thr Ile Thr Asp Ser Pro Ser Phe Leu Gly Cys Arg Ile Met
545                 550                 555                 560

Asn Gly Cys Gln Leu Val Pro Asn Arg Asp Arg Ile Leu Ala Ala Leu
                565                 570                 575

Ala Tyr His Met Lys Ala Asn Asn Val Ser Glu Tyr Tyr Ala Ser Ala
            580                 585                 590

Ala Ala Ile Leu Met Asp Ser Cys Ala Cys Leu Glu Tyr Asp Pro Glu
            595                 600                 605

Trp Phe Glu Glu Leu Val Val Gly Met Ala Gln Cys Ala Arg Lys Asp
    610                 615                 620

Gly Tyr Ser Phe Pro Gly Pro Pro Phe Phe Leu Ser Met Trp Glu Lys
625                 630                 635                 640

Leu Arg Ser Asn Tyr Glu Gly Lys Arg Ser Arg Val Cys Gly Tyr Cys
                645                 650                 655

Gly Ala Ser Ala Pro Tyr Ala Thr Ser Cys Gly Leu Asp Val Cys Val
            660                 665                 670

Tyr His Thr His Phe His Gln His Cys Pro Val Ile Ile Trp Cys Gly
            675                 680                 685

His Pro Ala Gly Ser Gly Ser Cys Asp Asp Cys Lys Ser Pro Thr Gly
    690                 695                 700

Lys Asp Thr Asn Pro Leu Asp Glu Val Leu Lys Gln Val Pro Tyr Lys
705                 710                 715                 720

Pro Pro Arg Thr Val Leu Met His Val Glu Gln Gly Leu Thr Pro Leu
                725                 730                 735

Asp Pro Gly Arg Tyr Gln Thr Arg Arg Gly Leu Val Ala Val Arg Arg
            740                 745                 750

Gly Ile Arg Gly Asn Glu Val Asp Leu Pro Asp Gly Asp Tyr Ala Ser
            755                 760                 765

Thr Ala Leu Leu Pro Thr Cys Lys Glu Ile Asn Met Val Ala Val Ala
    770                 775                 780

Ser Asn Val Leu Arg Ser Arg Phe Ile Ile Gly Pro Pro Gly Ala Gly
785                 790                 795                 800

Lys Thr His Trp Leu Leu Gln Gln Val Gln Asp Gly Asp Val Ile Tyr
                805                 810                 815

Thr Pro Thr His Gln Thr Met Leu Asp Met Ile Lys Ala Leu Gly Thr
            820                 825                 830

Cys Arg Phe Asn Val Pro Ala Gly Thr Thr Leu Gln Phe Pro Ala Pro
            835                 840                 845

Ser Arg Thr Gly Pro Trp Val Arg Ile Leu Ala Gly Gly Trp Cys Pro
    850                 855                 860

Gly Lys Asn Ser Phe Leu Asp Glu Ala Ala Tyr Cys Asn His Leu Asp
865                 870                 875                 880

Val Leu Arg Leu Leu Ser Lys Thr Thr Leu Thr Cys Leu Gly Asp Phe
                885                 890                 895

Lys Gln Leu His Pro Val Gly Phe Asp Ser His Cys Tyr Val Phe Asp
            900                 905                 910

Ile Met Pro Gln Thr Gln Leu Lys Thr Ile Trp Arg Phe Gly Gln Asn
            915                 920                 925

```
Ile Cys Asp Ala Ile Gln Pro Asp Tyr Arg Asp Lys Leu Met Ser Met
930                 935                 940
Val Asn Thr Thr Arg Val Thr Tyr Val Glu Lys Pro Val Lys Tyr Gly
945                 950                 955                 960
Gln Val Leu Thr Pro Tyr His Arg Asp Arg Glu Asp Gly Ala Ile Thr
                965                 970                 975
Ile Asp Ser Ser Gln Gly Ala Thr Phe Asp Val Val Thr Leu His Leu
            980                 985                 990
Pro Thr Lys Asp Ser Leu Asn Lys Gln Arg Ala Leu Val Ala Ile Thr
        995                 1000                1005
Arg Ala Arg His Ala Ile Phe Val Tyr Asp Pro Tyr Arg Gln Leu
    1010                1015                1020
Gln Ser Leu Phe Asp Leu Pro Ala Lys Ser Thr Pro Val Asn Leu
    1025                1030                1035
Ala Val His Arg Asp Gly Gln Leu Ile Val Leu Asp Arg Asn Asn
    1040                1045                1050
Lys Glu Cys Thr Val Ala Gln Ala Leu Gly Asn Gly Asp Lys Phe
    1055                1060                1065
Arg Ala Thr Asp Lys Arg Val Val Asp Ser Leu Arg Ala Ile Cys
    1070                1075                1080
Ala Asp Leu Glu Gly Ser Ser Ser Pro Leu Pro Lys Val Ala His
    1085                1090                1095
Asn Leu Gly Phe Tyr Phe Ser Pro Asp Leu Thr Gln Phe Ala Lys
    1100                1105                1110
Leu Pro Ile Glu Leu Ala Pro His Trp Pro Val Val Thr Thr Gln
    1115                1120                1125
Asn Asn Glu Asn Trp Pro Asp Arg Leu Val Ala Ser Leu Arg Pro
    1130                1135                1140
Ile His Lys Tyr Ser Arg Ala Cys Ile Gly Ala Gly Tyr Met Val
    1145                1150                1155
Gly Pro Ser Val Phe Leu Gly Thr Pro Gly Val Val Ser Tyr Tyr
    1160                1165                1170
Leu Thr Lys Phe Val Lys Gly Glu Ala Gln Val Leu Pro Glu Thr
    1175                1180                1185
Val Phe Ser Thr Gly Arg Ile Glu Val Asp Cys Arg Glu Tyr Leu
    1190                1195                1200
Asp Asp Arg Glu Arg Glu Val Ala Ala Ser Leu Pro His Ala Phe
    1205                1210                1215
Ile Gly Asp Val Lys Gly Thr Val Gly Gly Cys His His Val
    1220                1225                1230
Thr Ser Lys Tyr Leu Pro Arg Phe Leu Pro Lys Glu Ser Val Ala
    1235                1240                1245
Val Val Gly Val Ser Ser Pro Gly Lys Ala Ala Lys Ala Val Cys
    1250                1255                1260
Thr Leu Thr Asp Val Tyr Leu Pro Asp Leu Glu Ala Tyr Leu His
    1265                1270                1275
Pro Val Thr Gln Ser Lys Cys Trp Lys Met Met Leu Asp Phe Lys
    1280                1285                1290
Glu Val Arg Leu Met Val Trp Lys Asp Lys Thr Ala Tyr Phe Gln
    1295                1300                1305
Leu Glu Gly Arg His Phe Thr Trp Tyr Gln Leu Ala Ser Phe Ala
    1310                1315                1320
Ser Tyr Ile Arg Val Pro Val Asn Ser Thr Val Tyr Leu Asp Pro
```

```
                    1325                1330                1335

Cys Met Gly Pro Ala Leu Cys Asn Arg Lys Val Val Gly Ser Pro
    1340                1345                1350

His Trp Gly Ala Asp Leu Ala Val Thr Pro Tyr Asp Tyr Gly Ala
    1355                1360                1365

Arg Lys Ile Leu Ser Ser Ala Tyr His Gly Glu Met Pro Pro Gly
    1370                1375                1380

Tyr Lys Ile Leu Ala Cys Ala Glu Phe Ser Leu Asp Asp Pro Val
    1385                1390                1395

Arg Tyr Lys His Thr Trp Gly Phe Glu Ser Asp Thr Ala Tyr Leu
    1400                1405                1410

Tyr Glu Phe Thr Gly Asn Gly Glu Asp Trp Glu Asp Tyr Asn Asp
    1415                1420                1425

Ala Phe Arg Ala Arg Gln Lys Gly Lys Ile Tyr Lys Ala Thr Ala
    1430                1435                1440

Thr Ser Leu Lys Phe His Phe Pro Pro Gly His Ile Val Glu Pro
    1445                1450                1455

Thr Leu Gly Leu Asn
    1460

<210> SEQ ID NO 5
<211> LENGTH: 256
<212> TYPE: PRT
<213> ORGANISM: Porcine reproductive and respiratory syndrome virus

<400> SEQUENCE: 5

Met Arg Trp Glu Pro His Arg Ala Phe Leu Thr Lys Leu Val Asn Phe
1               5                   10                  15

Leu Leu Met Pro Ser Arg Ser Ser Trp Cys Leu Leu Leu Ile Ser Ser
                20                  25                  30

Tyr Phe Trp Pro Phe Cys Ser Ala Ser Pro Ser Pro Val Gly Trp Trp
            35                  40                  45

Ser Phe Ala Ser Asp Trp Phe Ser Pro Arg Tyr Ser Val Arg Ala Leu
        50                  55                  60

Pro Phe Thr Leu Ser Asn Tyr Arg Arg Ser Tyr Glu Ala Tyr Leu Ser
65                  70                  75                  80

Gln Cys Gln Val Asp Ile Pro Ala Trp Gly Thr Lys His Pro Leu Gly
                85                  90                  95

Met Ile Trp His His Lys Val Ser Thr Leu Ile Asp Glu Met Val Ser
            100                 105                 110

Arg Arg Met Tyr Arg Thr Met Glu Gln Ala Gly Gln Ala Ala Trp Lys
        115                 120                 125

Gln Val Val Thr Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Leu Thr Gly
                165                 170                 175

Ser Asn Val Thr Ile Val Tyr Asn Ser Ser Leu Asp Arg Val Phe Ala
            180                 185                 190

Val Phe Pro Thr Ser Ser Ser Arg Pro Lys Leu His Asp Phe Arg Gln
        195                 200                 205

Trp Leu Ile Ala Val His Ser Ser Ile Phe Ser Ser Val Ala Ala Ser
    210                 215                 220
```

```
Cys Thr Leu Phe Val Val Leu Trp Leu Arg Leu Pro Ile Ile Arg Thr
225                 230                 235                 240

Val Phe Gly Phe Arg Trp Leu Gly Ala Ile Phe Leu Ser Ser Ser Gln
                245                 250                 255

<210> SEQ ID NO 6
<211> LENGTH: 254
<212> TYPE: PRT
<213> ORGANISM: Porcine reproductive and respiratory syndrome virus

<400> SEQUENCE: 6

Met Ala Asn Ser Cys Ala Phe Leu His Ile Leu Leu Cys Cys Gly Phe
1               5                   10                  15

Leu Tyr Pro Phe Arg Arg Thr Val Ala Ala Ser Asn Asn Thr Tyr
                20                  25                  30

Cys Phe Trp Phe Pro Leu Val Arg Gly Asn Phe Ser Phe Glu Leu Thr
                35                  40                  45

Val Asn Tyr Thr Val Cys Pro Pro Cys Leu Thr Arg Gln Ala Ala Ser
        50                  55                  60

Glu Ile Tyr Glu Pro Ser Arg Ser Leu Trp Cys Arg Ile Gly Gln Asp
65                  70                  75                  80

Arg Cys Thr Glu Ser Asp His Asp Glu Leu Gly Phe Leu Val Pro Pro
                85                  90                  95

Gly Leu Ser Asn Glu Gly His Leu Ile Ser Val Tyr Ala Trp Leu Ala
                100                 105                 110

Phe Leu Ser Phe Ser Tyr Thr Ser Gln Phe His Pro Glu Ile Phe Gly
                115                 120                 125

Ile Gly Asn Val Ser Glu Val Tyr Val Asp Ile Lys His Gln Phe Ile
        130                 135                 140

Cys Ala Val His Asp Gly Gln Asn Thr Thr Leu Pro Arg His Asp Asn
145                 150                 155                 160

Ile Thr Ala Val Tyr Gln Thr Tyr Tyr Gln His Gln Val Asp Gly Gly
                165                 170                 175

Asn Trp Phe His Leu Glu Trp Leu Arg Pro Phe Phe Ser Ser Trp Leu
                180                 185                 190

Val Leu Asn Val Ser Trp Phe Leu Arg Arg Ser Pro Ala Ser Arg Val
        195                 200                 205

Ser Val Arg Val Phe Gln Thr Ser Lys Pro Thr Pro Pro Gln Leu Gln
        210                 215                 220

Ala Leu Leu Ser Ser Lys Thr Ser Ala Val Leu Gly Met Ala Thr Arg
225                 230                 235                 240

Pro Leu Arg Arg Leu Ala Lys Ala Ala Asn Ala Val Arg Arg
                245                 250

<210> SEQ ID NO 7
<211> LENGTH: 178
<212> TYPE: PRT
<213> ORGANISM: Porcine reproductive and respiratory syndrome virus

<400> SEQUENCE: 7

Met Ala Ala Ser Leu Leu Phe Phe Leu Val Gly Phe Glu Cys Phe Met
1               5                   10                  15

Val Ser Gln Ala Phe Ala Cys Lys Pro Cys Phe Ser Ser Ser Leu Ser
                20                  25                  30

Asp Ile Lys Thr Asn Thr Thr Ala Ala Ala Gly Phe Ala Val Leu Gln
                35                  40                  45
```

```
Asp Ile Ser Cys Leu Arg His Gly Asp Ser Ser Glu Ala Thr Arg
    50                  55                  60

Lys Ser Arg Gln Cys Arg Thr Ala Ile Gly Thr Pro Val Tyr Ile Thr
 65                  70                  75                  80

Val Thr Ala Asn Val Thr Asp Glu Asn Tyr Leu His Ser Ser Asp Leu
                 85                  90                  95

Leu Met Leu Ser Ser Cys Leu Phe Tyr Ala Ser Glu Met Ser Glu Lys
                100                 105                 110

Gly Phe Lys Val Ile Phe Gly Asn Val Ser Gly Ile Val Ala Val Cys
            115                 120                 125

Val Asn Phe Thr Ser Tyr Val Gln His Val Lys Glu Phe Thr Arg Arg
            130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile

<210> SEQ ID NO 8
<211> LENGTH: 200
<212> TYPE: PRT
<213> ORGANISM: Porcine reproductive and respiratory syndrome virus

<400> SEQUENCE: 8

Met Leu Gly Lys Cys Leu Thr Ala Gly Cys Cys Ser Gln Leu Leu Phe
 1               5                  10                  15

Leu Trp Cys Ile Val Pro Phe Cys Phe Val Ala Leu Val Asn Ala Asn
                20                  25                  30

Asn Ser Ser Ser Ser His Leu Gln Leu Ile Tyr Asn Leu Thr Ile Cys
            35                  40                  45

Glu Leu Asn Gly Thr Asp Trp Leu Asn Arg Lys Phe Asp Trp Ala Val
    50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Tyr Tyr His Arg Arg Tyr Val Leu Ser Ser Ile Tyr
                100                 105                 110

Ala Val Cys Ala Leu Ala Ala Leu Ile Cys Phe Ala Ile Arg Leu Thr
            115                 120                 125

Lys Asn Cys Met Ser Trp Arg Tyr Ser Cys Thr Arg Tyr Thr Asn Phe
            130                 135                 140

Leu Leu Asp Thr Lys Gly Lys Leu Tyr Arg Trp Arg Ser Pro Val Ile
145                 150                 155                 160

Ile Glu Lys Gly Gly Lys Ile Glu Val Asn Gly His Leu Ile Asp Leu
                165                 170                 175

Lys Arg Val Val Leu Asp Gly Ser Ala Ala Thr Pro Val Thr Lys Val
                180                 185                 190

Ser Ala Glu Gln Trp Gly Arg Pro
            195                 200

<210> SEQ ID NO 9
<211> LENGTH: 174
<212> TYPE: PRT
<213> ORGANISM: Porcine reproductive and respiratory syndrome virus
```

-continued

```
<400> SEQUENCE: 9

Met Gly Thr Ser Leu Asp Asp Phe Cys Asn Asp Ser Thr Ala Pro Gln
1               5                   10                  15

Lys Val Leu Leu Ala Phe Ser Ile Thr Tyr Thr Pro Ile Met Ile Tyr
            20                  25                  30

Ala Leu Lys Val Ser Arg Gly Arg Leu Leu Gly Leu Leu His Leu Leu
        35                  40                  45

Ile Phe Leu Asn Cys Ala Phe Thr Phe Gly Tyr Met Thr Phe Ala His
    50                  55                  60

Phe Arg Ser Thr Asn Lys Val Ala Leu Thr Met Gly Ala Val Val Ala
65                  70                  75                  80

Leu Leu Trp Gly Val Tyr Ser Ala Ile Glu Thr Trp Arg Phe Ile Thr
                85                  90                  95

Ser Arg Cys Arg Leu Cys Leu Leu Gly Arg Arg Tyr Ile Leu Ala Pro
            100                 105                 110

Ala His His Val Glu Ser Val Ala Gly Phe His Pro Ile Thr Ala Ser
        115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Arg
145                 150                 155                 160

Ala Val Lys Arg Gly Val Val Asn Leu Val Lys Tyr Ala Lys
                165                 170

<210> SEQ ID NO 10
<211> LENGTH: 123
<212> TYPE: PRT
<213> ORGANISM: Porcine reproductive and respiratory syndrome virus

<400> SEQUENCE: 10

Met Pro Asn Asn Asn Gly Lys Gln Gln Lys Arg Lys Lys Gly Asp Gly
1               5                   10                  15

Gln Pro Val Asn Gln Leu Cys Gln Met Leu Gly Arg Ile Ile Ala Gln
            20                  25                  30

Gln Asn Gln Pro Arg Gly Lys Gly Pro Gly Lys Arg Asn Lys Lys Lys
        35                  40                  45

Ser Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Val Ser Tyr Ala Val Glu Phe Ser Leu Pro Thr His His Thr Val
            100                 105                 110

Arg Leu Ile Arg Ala Thr Thr Ser Pro Ser Ala
        115                 120

<210> SEQ ID NO 11
<211> LENGTH: 2372
<212> TYPE: PRT
<213> ORGANISM: Porcine reproductive and respiratory syndrome virus

<400> SEQUENCE: 11

Met Ser Gly Ile Leu Asp Arg Cys Thr Cys Thr Pro Asn Ala Arg Val
1               5                   10                  15

Phe Val Ala Asp Gly Gln Val Tyr Cys Thr Arg Cys Leu Ser Ala Arg
```

```
                  20                  25                  30
Thr Leu Leu Pro Leu Asn Leu Gln Val Ser Glu Leu Gly Val Leu Gly
             35                  40                  45
Leu Phe Tyr Arg Pro Glu Glu Pro Leu Arg Trp Thr Leu Pro Arg Ala
 50                  55                  60
Phe Pro Thr Val Glu Cys Ser Pro Ala Gly Ala Cys Trp Leu Ser Ala
 65                  70                  75                  80
Ile Phe Pro Ile Ala Arg Met Thr Ser Gly Asn Leu Asn Phe Gln Gln
                 85                  90                  95
Arg Ile Val Arg Val Ala Ala Glu Ile Tyr Arg Val Gly Gln Leu Thr
                100                 105                 110
Pro Thr Val Leu Lys Asn Leu Gln Val Tyr Glu Arg Gly Cys Arg Trp
                115                 120                 125
Tyr Pro Ile Val Gly Pro Val Pro Gly Val Ala Val Tyr Ala Asn Ser
                130                 135                 140
Leu His Val Ser Asp Lys Pro Phe Pro Gly Ala Thr His Val Leu Thr
145                 150                 155                 160
Asn Leu Pro Leu Pro Gln Arg Pro Lys Pro Glu Asp Phe Cys Pro Phe
                165                 170                 175
Glu Cys Ala Met Ala Val Val Tyr Asp Ile Gly His Asp Ala Val Met
                180                 185                 190
Tyr Val Ala Lys Glu Arg Val Ser Trp Ala Pro Arg Gly Gly Glu Lys
                195                 200                 205
Gly Lys Phe Glu Thr Val Pro Glu Glu Leu Arg Leu Val Ala Glu Gln
                210                 215                 220
Leu Phe Thr Ser Phe Pro Pro His His Val Val Asp Met Ser Lys Phe
225                 230                 235                 240
Ile Phe Thr Ala Pro Asp Cys Gly Ala Ser Met Arg Val Glu Arg Gln
                245                 250                 255
Tyr Gly Cys Leu Pro Ala Gly Thr Val Pro Asp Gly Asn Cys Trp Trp
                260                 265                 270
Ser Leu Phe Ser Ser Leu Pro Pro Glu Val Gln Cys Arg Glu Ile Arg
                275                 280                 285
Arg Ala Thr Gln Phe Gly Tyr Gln Thr Lys His Gly Val Ala Gly Lys
                290                 295                 300
Tyr Leu Gln Arg Arg Leu Gln Ala Asn Gly Leu Arg Ala Val Val Asp
305                 310                 315                 320
Ser Asn Gly Pro Ile Val Ile Gln Tyr Phe Ser Val Lys Glu Ser Trp
                325                 330                 335
Ile Arg His Val Lys Leu Ala Gly Glu Pro Cys Tyr Pro Gly Phe Glu
                340                 345                 350
Asp Leu Leu Arg Ile Arg Val Glu Pro Asn Thr Leu Pro Leu Ser Asp
                355                 360                 365
Lys Gly Asp Lys Val Phe Arg Phe Gly Gly His Lys Trp Tyr Gly Ala
                370                 375                 380
Gly Lys Arg Ala Arg Arg Ser Arg Ala Gly Ala Ala Thr Val Ala
385                 390                 395                 400
Gly His Ala Ser Pro Val Arg Glu Thr Gln Gln Ala Lys Lys His Glu
                405                 410                 415
Ala Ala Ser Ala Asn Lys Ala Glu Leu Leu Glu Arg Tyr Ser Pro Pro
                420                 425                 430
Ala Glu Gly Asn Cys Gly Trp His Cys Ile Ser Ala Ile Val Asn Arg
                435                 440                 445
```

-continued

```
Met Val Asn Ser Lys Phe Glu Thr Ala Leu Pro Lys Val Arg Pro
    450                 455                 460

Pro Glu Asp Trp Ala Thr Asp Glu Asp Leu Val Asn Thr Ile Gln Ile
465                 470                 475                 480

Leu Arg Leu Pro Ala Ala Leu Asp Arg Asn Gly Val Cys Ala Ser Ala
                485                 490                 495

Lys Tyr Val Leu Lys Leu Glu Gly His Trp Thr Val Ser Val Thr
                500                 505                 510

Pro Gly Met Pro Pro Ser Leu Leu Pro Leu Glu Cys Val Gln Gly Cys
            515                 520                 525

Cys Glu His Lys Gly Ser Leu Arg Ser Pro Asp Ala Val Glu Val Ser
    530                 535                 540

Gly Phe Asp Pro Ala Ser Leu Asp Arg Leu Ala Gly Val Met His Leu
545                 550                 555                 560

Pro Ser Ser Ala Ile Pro Ala Ala Leu Ala Glu Leu Ser Gly Asp Pro
                565                 570                 575

Asp Arg Pro Val Ser Pro Ala Thr Thr Ala Trp Thr Val Ser Gln Phe
            580                 585                 590

Tyr Ala Arg His Ser Gly Gly Glu His Pro Asp Gln Lys Tyr Leu Arg
            595                 600                 605

Lys Ile Ile Ser Leu Cys Glu Val Ile Glu Ser Cys Cys Cys Ser Gln
610                 615                 620

Asn Lys Ile Asn Leu Val Thr Pro Glu Glu Val Lys Thr Lys Ile Asp
625                 630                 635                 640

Gln Tyr Leu Ser Gly Ala Ala Ser Leu Glu Glu Cys Leu Ala Arg Leu
                645                 650                 655

Glu Lys Ala Arg Pro Pro Ser Val Leu Asp Thr Ser Phe Asp Trp Asp
            660                 665                 670

Val Val Leu Pro Gly Val Gly Ala Ala Val Arg Ala Ala Lys Leu Pro
            675                 680                 685

Leu Ala Asn Gln Cys His Ala Pro Val Thr Val Thr Gln Arg Pro
690                 695                 700

Ser Leu Lys Phe Gln Pro Arg Lys Ala Glu Ser Val Lys Ser Leu Pro
705                 710                 715                 720

Glu Ser Arg Pro Leu Pro Ala Pro Arg Arg Lys Ile Arg Ser Arg Cys
                725                 730                 735

Gly Ser Leu Thr Ser Leu Asp Gly Asn Phe Pro Asp Ser Trp Glu Asp
                740                 745                 750

Leu Ala Gly Gly Pro Phe His Phe Pro Thr Leu Pro Glu Pro Thr Thr
            755                 760                 765

Arg Pro Gly Glu Pro Val Pro Val Pro Ala Pro Arg Lys Thr Val Pro
770                 775                 780

Arg Leu Val Ser Ser Leu Ile Val Ser Val Pro Val Pro Ala Pro Arg
785                 790                 795                 800

Arg Gly Ile Arg Gln Ala Glu Gly Met Asn Leu Val Ala Val Thr Pro
                805                 810                 815

Ala Cys Gln Asp Glu Leu Leu Asp Leu Ser Glu Ser Ser Gln Ala Glu
            820                 825                 830

His Gly Ala Pro Ser Leu Ala Leu Pro Arg Ser Glu Asp Ala Leu Ala
            835                 840                 845

Val Gly Arg Arg Glu Ala Glu Glu Val Leu Ser Glu Ile Ser Gly Met
850                 855                 860
```

```
Pro Asp Asp Ile Arg Leu Val Pro Val Ser Ser Ser Ser Leu Ser
865                 870                 875                 880

Ser Val Glu Ile Thr Arg Pro Lys Tyr Ser Ala Gln Ala Ile Ile Asp
            885                 890                 895

Ser Gly Gly Pro Cys Cys Gly His Leu Gln Glu Val Lys Glu Lys Cys
            900                 905                 910

Leu Asn Val Met Arg Glu Ala Cys Asp Ala Thr Lys Leu Asp Asp Pro
            915                 920                 925

Ala Thr Arg Glu Trp Leu Ser Arg Met Trp Asp Arg Val Asp Met Leu
    930                 935                 940

Thr Trp Arg Asn Thr Ser Ile Phe Gln Ala Pro Phe Thr Leu Ala Asp
945                 950                 955                 960

Lys Phe Lys Leu Leu Pro Lys Met Ile Leu Glu Thr Pro Pro Tyr
                965                 970                 975

Pro Cys Gly Phe Val Met Met Pro Arg Thr Pro Ala Pro Ser Val Gly
            980                 985                 990

Ala Glu Ser Asp Leu Thr Val Gly Ser Val Ala Thr Glu Asp Val Pro
            995                 1000                1005

Arg Ile Leu Gly Lys Val Gln Gly Val Cys Lys Thr Thr Val His
    1010                1015                1020

Glu Pro Leu Ala Pro Phe Ala Asp Gly Pro Thr Asp Gly Gln Pro
    1025                1030                1035

Ala Arg Glu Pro Arg Thr Gln Thr Pro Ala Gly Thr Gly Gly
    1040                1045                1050

Val Gly Leu Val Leu Asp Ser Glu Gly Ser Pro Glu Leu Thr Asp
    1055                1060                1065

Ser Pro Pro Pro Asn Gly Thr Asp Ala Ser Gly Gly Gly Pro Leu
    1070                1075                1080

Tyr Thr Val Lys Lys Lys Val Glu Arg Cys Phe Asp Gln Leu Ser
    1085                1090                1095

Arg Arg Val Phe Asp Ile Val Ser His Leu Pro Val Phe Phe Ser
    1100                1105                1110

Arg Leu Phe Lys Ser Asp Gly His Tyr Ala Pro Gly Asp Trp Gly
    1115                1120                1125

Phe Ala Ala Phe Thr Leu Leu Cys Leu Phe Leu Cys Tyr Ser Tyr
    1130                1135                1140

Pro Ala Phe Gly Val Val Pro Leu Leu Gly Val Phe Ser Gly Ser
    1145                1150                1155

Ser Arg Arg Val Arg Met Gly Val Phe Gly Cys Trp Leu Ala Phe
    1160                1165                1170

Ala Val Ser Leu Phe Lys Pro Ala Pro Asp Pro Val Gly Thr Ala
    1175                1180                1185

Cys Glu Phe Asp Ser Pro Glu Cys Arg Asp Ile Leu His Ser Phe
    1190                1195                1200

Glu Leu Leu Gln Pro Trp Asp Pro Val Arg Ser Leu Val Val Gly
    1205                1210                1215

Pro Val Gly Leu Gly Leu Ala Ile Leu Gly Arg Leu Leu Gly Gly
    1220                1225                1230

Ala Arg Tyr Val Trp Leu Phe Leu Leu Arg Leu Gly Ile Val Ser
    1235                1240                1245

Asp Cys Ile Leu Ala Gly Ala Tyr Val Leu Ser Gln Gly Arg Cys
    1250                1255                1260

Lys Lys Cys Trp Gly Ser Cys Ile Arg Thr Ala Pro Ser Glu Val
```

```
                1265                1270                1275

Ala  Phe  Asn  Val  Phe  Pro  Phe  Thr  Arg  Ala  Thr  Arg  Ser  Ser  Leu
               1280                1285                1290

Ile  Asp  Leu  Cys  Asp  Arg  Phe  Cys  Ala  Pro  Lys  Gly  Met  Asp  Pro
               1295                1300                1305

Ile  Phe  Leu  Ala  Thr  Gly  Trp  Arg  Gly  Cys  Trp  Ala  Gly  Gln  Ser
               1310                1315                1320

Pro  Ile  Glu  Gln  Pro  Thr  Glu  Lys  Pro  Ile  Ala  Phe  Ala  Gln  Leu
               1325                1330                1335

Asp  Glu  Lys  Lys  Ile  Thr  Ala  Lys  Thr  Val  Val  Ala  Gln  Pro  Tyr
               1340                1345                1350

Asp  Pro  Asn  Gln  Ala  Val  Lys  Cys  Leu  Arg  Val  Leu  Gln  Ala  Gly
               1355                1360                1365

Gly  Ala  Met  Val  Ala  Glu  Ala  Ile  Pro  Lys  Val  Val  Lys  Val  Ser
               1370                1375                1380

Ala  Ile  Pro  Phe  Arg  Ala  Pro  Phe  Phe  Pro  Val  Gly  Val  Lys  Val
               1385                1390                1395

Asp  Pro  Glu  Cys  Arg  Val  Val  Asp  Ser  Asp  Thr  Phe  Thr  Thr
               1400                1405                1410

Ala  Leu  Arg  Ser  Gly  Tyr  Ser  Thr  Thr  Asn  Leu  Ile  Leu  Gly  Val
               1415                1420                1425

Gly  Asp  Phe  Ala  Gln  Leu  Asn  Gly  Leu  Lys  Ile  Arg  Gln  Ile  Ser
               1430                1435                1440

Lys  Pro  Ser  Gly  Gly  Pro  His  Ile  Met  Ala  Ala  Leu  His  Val
               1445                1450                1455

Ala  Cys  Ser  Met  Ala  Leu  His  Met  Leu  Val  Gly  Ile  Tyr  Val  Thr
               1460                1465                1470

Thr  Val  Gly  Ser  Cys  Gly  Ser  Gly  Thr  Asn  Asp  Pro  Trp  Cys  Thr
               1475                1480                1485

Asn  Pro  Phe  Ala  Val  Pro  Val  Tyr  Gly  Pro  Gly  Ser  Leu  Cys  Thr
               1490                1495                1500

Ser  Arg  Leu  Cys  Ile  Ser  Gln  His  Gly  Leu  Thr  Leu  Pro  Leu  Thr
               1505                1510                1515

Ala  Leu  Val  Ala  Gly  Phe  Gly  Ile  Gln  Glu  Val  Ala  Leu  Val  Val
               1520                1525                1530

Leu  Ile  Phe  Val  Ser  Ile  Gly  Gly  Met  Ala  His  Arg  Leu  Ser  Cys
               1535                1540                1545

Lys  Ala  Asp  Val  Leu  Cys  Ile  Leu  Leu  Ala  Ile  Ala  Ser  Tyr  Val
               1550                1555                1560

Trp  Leu  Pro  Leu  Thr  Trp  Leu  Leu  Cys  Val  Phe  Pro  Cys  Trp  Leu
               1565                1570                1575

Arg  Trp  Phe  Ser  Leu  His  Pro  Leu  Thr  Val  Thr  Trp  Leu  Val  Phe
               1580                1585                1590

Phe  Leu  Ile  Ser  Val  Asn  Met  Pro  Ser  Gly  Val  Leu  Ala  Leu  Val
               1595                1600                1605

Leu  Leu  Ile  Ser  Leu  Trp  Leu  Leu  Gly  Arg  Tyr  Thr  Asn  Val  Ala
               1610                1615                1620

Gly  Leu  Val  Thr  Pro  Tyr  Asp  Ile  His  His  Tyr  Thr  Asn  Gly  Pro
               1625                1630                1635

Arg  Gly  Val  Ala  Ala  Leu  Ala  Thr  Ala  Pro  Asp  Gly  Thr  Tyr  Leu
               1640                1645                1650

Ala  Ala  Val  Arg  Arg  Ala  Ala  Leu  Thr  Gly  Arg  Thr  Met  Leu  Phe
               1655                1660                1665
```

```
Thr Pro Ser Gln Leu Gly Ser Leu Leu Glu Gly Ala Phe Arg Thr
    1670            1675                1680

Gln Lys Pro Thr Leu Asn Thr Val Asn Val Val Gly Ser Ser Met
    1685            1690                1695

Gly Ser Gly Gly Val Phe Thr Ile Asp Gly Lys Ile Lys Cys Val
    1700            1705                1710

Thr Ala Ala His Ile Leu Thr Gly Asn Ser Ala Arg Val Ser Gly
    1715            1720                1725

Val Gly Phe Asn Gln Met Leu Asp Phe Asp Val Lys Gly Asp Phe
    1730            1735                1740

Ala Ile Ala Asp Cys Pro Asp Trp Gln Gly Val Ala Pro Lys Ser
    1745            1750                1755

Gln Phe Cys Glu Asp Gly Trp Thr Gly Arg Ala Tyr Trp Leu Thr
    1760            1765                1770

Ser Ser Gly Val Glu Pro Gly Val Ile Gly Arg Gly Phe Ala Phe
    1775            1780                1785

Cys Phe Thr Ala Cys Gly Asp Ser Gly Ser Pro Val Ile Thr Glu
    1790            1795                1800

Ala Gly Glu Leu Val Gly Val His Thr Gly Ser Asn Lys Gln Gly
    1805            1810                1815

Gly Gly Ile Val Thr Arg Pro Ser Gly Gln Phe Cys Asn Val Thr
    1820            1825                1830

Pro Thr Lys Leu Ser Glu Leu Ser Glu Phe Phe Ala Gly Pro Arg
    1835            1840                1845

Val Pro Leu Gly Asp Val Lys Val Gly Asn His Ile Ile Lys Asp
    1850            1855                1860

Thr Asn Glu Val Pro Ser Asp Leu Cys Ala Leu Leu Ala Ala Lys
    1865            1870                1875

Pro Glu Leu Glu Gly Gly Leu Ser Thr Val Gln Leu Leu Cys Val
    1880            1885                1890

Phe Phe Leu Leu Trp Arg Met Met Gly His Ala Trp Thr Pro Leu
    1895            1900                1905

Val Ala Val Gly Phe Phe Val Leu Asn Glu Ile Leu Pro Ala Val
    1910            1915                1920

Leu Val Arg Ser Val Phe Ser Phe Gly Met Phe Ala Leu Ser Trp
    1925            1930                1935

Phe Thr Pro Trp Ser Ala Gln Ile Leu Met Ile Arg Leu Leu Thr
    1940            1945                1950

Ala Ala Leu Asn Arg Asn Arg Trp Ser Leu Ala Phe Tyr Ser Leu
    1955            1960                1965

Gly Ala Leu Thr Gly Phe Ala Ala Asp Leu Ala Ile Asn Gln Gly
    1970            1975                1980

His Ser Leu His Val Ala Met Asn Phe Ser Thr Tyr Ala Phe Leu
    1985            1990                1995

Pro Arg Ala Met Ala Val Thr Ser Pro Val Pro Thr Ile Ala Cys
    2000            2005                2010

Gly Val Val His Leu Leu Ala Ile Val Leu Tyr Leu Phe Lys Tyr
    2015            2020                2025

Arg Ser Leu His Thr Val Leu Val Gly Asp Gly Ala Phe Ser Ala
    2030            2035                2040

Ala Phe Phe Leu Arg Tyr Phe Ala Glu Gly Lys Leu Arg Glu Gly
    2045            2050                2055
```

```
Val Ser Gln Ser Cys Gly Met Asn His Glu Ser Leu Thr Gly Ala
    2060            2065                2070

Ile Ala Ile Arg Leu Asp Asp Glu Asp Leu Asp Phe Leu Ile Lys
    2075            2080                2085

Leu Ser Asp Phe Lys Cys Phe Val Ser Ala Ser Asn Met Arg Asn
    2090            2095                2100

Ala Ala Gly Gln Phe Ile Glu Ala Ala Tyr Ala Lys Ala Leu Arg
    2105            2110                2115

Val Glu Leu Ala Gln Leu Val Gln Val Asp Lys Val Arg Gly Val
    2120            2125                2130

Leu Ala Lys Leu Glu Ala Phe Ala Asp Thr Ala Thr Pro Gln Leu
    2135            2140                2145

Ser Pro Gly Asp Ile Val Val Ala Leu Gly His Thr Pro Val Gly
    2150            2155                2160

Ser Ile Phe Asp Leu Lys Val Gly Ser Thr Lys His Thr Leu Gln
    2165            2170                2175

Ala Ile Glu Thr Arg Val Leu Ala Gly Ser Arg Met Thr Val Ala
    2180            2185                2190

Arg Val Val Asp Pro Thr Pro Ala Pro Pro Val Pro Val Pro
    2195            2200                2205

Ile Pro Leu Pro Pro Lys Val Leu Glu Asn Gly Pro Arg Ala Trp
    2210            2215                2220

Glu Asp Glu Asp Arg Leu Asn Lys Lys Arg Arg Arg Lys Met Glu
    2225            2230                2235

Ala Val Gly Ile Tyr Val Met Asp Gly Lys Lys Tyr Gln Lys Phe
    2240            2245                2250

Trp Asp Gln Asn Ser Gly Asp Val Phe Tyr Glu Glu Val His Asp
    2255            2260                2265

Asn Thr Asp Ala Trp Glu Cys Leu Arg Thr Asp Asp Pro Ala Asp
    2270            2275                2280

Leu Asp Pro Glu Lys Gly Thr Leu Cys Gly His Leu Thr Ile Glu
    2285            2290                2295

Asn Arg Pro Tyr His Val Tyr Ala Ser Pro Ser Gly Arg Lys Phe
    2300            2305                2310

Leu Val Pro Ala Asn Pro Glu Ser Gly Lys Ala Gln Trp Glu Ala
    2315            2320                2325

Ala Arg Leu Ser Ile Glu Gln Ala Leu Gly Met Met Asn Val Asp
    2330            2335                2340

Gly Glu Leu Thr Ala Lys Glu Val Glu Lys Leu Lys Arg Ile Ile
    2345            2350                2355

Asp Lys Leu Gln Gly Leu Thr Lys Glu Gln Cys Leu Asn Tyr
    2360            2365                2370

<210> SEQ ID NO 12
<211> LENGTH: 1463
<212> TYPE: PRT
<213> ORGANISM: Porcine reproductive and respiratory syndrome virus

<400> SEQUENCE: 12

Gly Ala Val Phe Lys Leu Leu Ala Ala Ser Gly Leu Thr Arg Cys Gly
1               5                   10                  15

Arg Gly Gly Leu Val Ile Thr Glu Thr Ala Val Lys Ile Val Arg Phe
                20                  25                  30

His Ser Arg Thr Phe Thr Leu Gly Pro Val Asn Leu Lys Val Ala Ser
            35                  40                  45
```

-continued

Glu Val Glu Leu Lys Asp Ala Val Glu His Asn Gln His Pro Ile Ala
        50                  55                  60

Arg Pro Val Asp Gly Gly Val Val Leu Leu Arg Ser Ala Val Pro Ser
65                  70                  75                  80

Leu Ile Asp Val Leu Ile Ser Gly Ala Asp Ala Ser Pro Gln Leu Leu
                85                  90                  95

Ala His His Gly Pro Gly Asn Thr Gly Ile Asp Gly Thr Leu Trp Asp
            100                 105                 110

Phe Glu Ser Val Ala Thr Lys Glu Glu Val Thr Leu Ser Ala Gln Ile
        115                 120                 125

Ile Gln Ala Cys Gly Ile Arg Arg Gly Asp Ala Pro Glu Ile Gly Leu
    130                 135                 140

Pro Tyr Lys Leu His Pro Val Arg Gly Asn Pro Glu Arg Val Lys Gly
145                 150                 155                 160

Val Leu Lys Asn Thr Arg Phe Gly Asp Ile Pro Tyr Lys Thr Pro Ser
                165                 170                 175

Asp Thr Gly Ser Pro Val His Ala Ala Cys Leu Thr Pro Asn Ala
            180                 185                 190

Thr Pro Val Thr Asp Gly Arg Ser Val Leu Ala Thr Thr Met Pro Ser
        195                 200                 205

Gly Phe Glu Leu Tyr Val Pro Thr Ile Pro Ala Ser Val Leu Asp Tyr
    210                 215                 220

Leu Asp Ser Arg Pro Asp Cys Pro Lys Gln Leu Thr Glu His Gly Cys
225                 230                 235                 240

Glu Asp Ala Ala Leu Arg Asp Leu Ser Lys Tyr Asp Leu Ser Thr Gln
                245                 250                 255

Gly Phe Val Leu Pro Gly Val Leu Arg Leu Val Arg Lys Tyr Leu Phe
            260                 265                 270

Ala His Val Gly Lys Cys Pro Val His Arg Pro Ser Thr Tyr Pro
        275                 280                 285

Ala Lys Asn Ser Met Ala Gly Ile Asn Gly Asn Arg Phe Pro Thr Lys
    290                 295                 300

Asp Ile Gln Ser Ile Pro Glu Ile Asp Val Leu Cys Ala Gln Ala Val
305                 310                 315                 320

Arg Glu Asn Trp Gln Thr Val Thr Pro Cys Thr Leu Lys Lys Gln Tyr
                325                 330                 335

Cys Gly Lys Lys Lys Thr Arg Thr Ile Leu Gly Thr Asn Asn Phe Ile
            340                 345                 350

Ala Leu Ala His Arg Ala Ala Leu Ser Gly Val Thr Gln Gly Phe Met
        355                 360                 365

Lys Lys Ala Phe Asn Ser Pro Ile Ala Leu Gly Lys Asn Lys Phe Lys
    370                 375                 380

Glu Leu Gln Thr Pro Val Leu Gly Arg Cys Leu Glu Ala Asp Leu Ala
385                 390                 395                 400

Ser Cys Asp Arg Ser Thr Pro Ala Ile Val Arg Trp Phe Ala Ala His
                405                 410                 415

Leu Leu Tyr Glu Leu Ala Cys Ala Glu Glu His Leu Pro Ser Tyr Val
            420                 425                 430

Leu Asn Cys Cys His Asp Leu Leu Val Thr Gln Ser Gly Ala Val Thr
        435                 440                 445

Lys Arg Gly Gly Leu Ser Ser Gly Asp Pro Ile Thr Ser Val Ser Asn
    450                 455                 460

```
Thr Ile Tyr Ser Leu Val Ile Tyr Ala Gln His Met Val Leu Ser Tyr
465                 470                 475                 480

Phe Lys Ser Gly His Pro His Gly Leu Leu Phe Leu Gln Asp Gln Leu
                485                 490                 495

Lys Phe Glu Asp Met Leu Lys Val Gln Pro Leu Ile Val Tyr Ser Asp
            500                 505                 510

Asp Leu Val Leu Tyr Ala Glu Ser Pro Thr Met Pro Asn Tyr His Trp
        515                 520                 525

Trp Val Glu His Leu Asn Leu Met Leu Gly Phe Gln Thr Asp Pro Lys
    530                 535                 540

Lys Thr Thr Ile Thr Asp Ser Pro Ser Phe Leu Gly Cys Arg Ile Met
545                 550                 555                 560

Asn Gly Cys Gln Leu Val Pro Asn Arg Asp Arg Ile Leu Ala Ala Leu
                565                 570                 575

Ala Tyr His Met Lys Ala Asn Asn Val Ser Glu Tyr Tyr Ala Ser Ala
            580                 585                 590

Ala Ala Ile Leu Met Asp Ser Cys Ala Cys Leu Glu Tyr Asp Pro Glu
        595                 600                 605

Trp Phe Glu Glu Leu Val Val Gly Met Ala Gln Cys Ala Arg Lys Asp
    610                 615                 620

Gly Tyr Ser Phe Pro Gly Pro Pro Phe Phe Leu Ser Met Trp Glu Lys
625                 630                 635                 640

Leu Arg Ser Asn Tyr Glu Gly Lys Arg Ser Arg Val Cys Gly Tyr Cys
                645                 650                 655

Gly Ala Ser Ala Pro Tyr Ala Thr Ser Cys Gly Leu Asp Val Cys Val
            660                 665                 670

Tyr His Thr His Phe His Gln His Cys Pro Val Ile Ile Trp Cys Gly
        675                 680                 685

His Pro Ala Gly Ser Gly Ser Cys Asp Asp Cys Lys Ser Pro Thr Gly
    690                 695                 700

Lys Asp Thr Asn Pro Leu Asp Glu Val Leu Lys Gln Val Pro Tyr Lys
705                 710                 715                 720

Pro Pro Arg Thr Val Leu Met His Val Glu Gln Gly Leu Thr Pro Leu
                725                 730                 735

Asp Pro Gly Arg Tyr Gln Thr Arg Arg Gly Leu Val Ala Val Arg Arg
            740                 745                 750

Gly Ile Arg Gly Asn Glu Val Asp Leu Pro Asp Gly Asp Tyr Ala Ser
        755                 760                 765

Thr Ala Leu Leu Pro Thr Cys Lys Glu Ile Asn Met Val Ala Val Ala
    770                 775                 780

Ser Asn Val Leu Arg Ser Arg Phe Ile Ile Gly Pro Pro Gly Ala Gly
785                 790                 795                 800

Lys Thr His Trp Leu Leu Gln Gln Val Gln Asp Gly Asp Val Ile Tyr
                805                 810                 815

Thr Pro Thr His Gln Thr Met Leu Asp Met Ile Lys Ala Leu Gly Thr
            820                 825                 830

Cys Arg Phe Asn Val Pro Ala Gly Thr Thr Leu Gln Phe Pro Ala Pro
        835                 840                 845

Ser Arg Thr Gly Pro Trp Val Arg Ile Leu Ala Gly Gly Trp Cys Pro
    850                 855                 860

Gly Lys Asn Ser Phe Leu Asp Glu Ala Ala Tyr Cys Asn His Leu Asp
865                 870                 875                 880

Val Leu Arg Leu Leu Ser Lys Thr Thr Leu Thr Cys Leu Gly Asp Phe
```

```
                885                 890                 895
Lys Gln Leu His Pro Val Gly Phe Asp Ser His Cys Tyr Val Phe Asp
                    900                 905                 910
Ile Met Pro Gln Thr Gln Leu Lys Thr Ile Trp Arg Phe Gly Gln Asn
                    915                 920                 925
Ile Cys Asp Ala Ile Gln Pro Asp Tyr Arg Asp Lys Leu Met Ser Met
                930                 935                 940
Val Asn Thr Thr Arg Val Thr Tyr Val Glu Lys Pro Val Lys Tyr Gly
945                 950                 955                 960
Gln Val Leu Thr Pro Tyr His Arg Asp Arg Glu Asp Gly Ala Ile Thr
                965                 970                 975
Ile Asp Ser Ser Gln Gly Ala Thr Phe Asp Val Val Thr Leu His Leu
                980                 985                 990
Pro Thr Lys Asp Ser Leu Asn Lys  Gln Arg Ala Leu Val  Ala Ile Thr
                995                 1000                1005
Arg Ala  Arg His Ala Ile Phe  Val Tyr Asp Pro Tyr  Arg Gln Leu
1010                 1015                1020
Gln Ser  Leu Phe Gly Leu Pro  Ala Lys Ser Thr Pro  Val Asn Leu
1025                 1030                1035
Ala Val  His Arg Asp Gly Gln  Leu Ile Val Leu Asp  Arg Asn Asn
1040                 1045                1050
Lys Glu  Cys Thr Val Ala Gln  Ala Leu Gly Asn Gly  Asp Lys Phe
1055                 1060                1065
Arg Ala  Thr Asp Lys Arg Val  Val Asp Ser Leu Arg  Ala Ile Cys
1070                 1075                1080
Ala Asp  Leu Glu Gly Ser Ser  Ser Pro Leu Pro Lys  Val Ala His
1085                 1090                1095
Asn Leu  Gly Phe Tyr Phe Ser  Pro Asp Leu Thr Gln  Phe Ala Lys
1100                 1105                1110
Leu Pro  Ile Glu Leu Ala Pro  His Trp Pro Val Val  Thr Thr Gln
1115                 1120                1125
Asn Asn  Glu Asn Trp Pro Asp  Arg Leu Val Ala Ser  Leu Arg Pro
1130                 1135                1140
Ile His  Lys Tyr Ser Arg Ala  Cys Ile Gly Ala Gly  Tyr Met Val
1145                 1150                1155
Gly Pro  Ser Val Phe Leu Gly  Thr Pro Gly Val Val  Ser Tyr Tyr
1160                 1165                1170
Leu Thr  Lys Phe Val Lys Gly  Glu Ala Gln Val Leu  Pro Glu Thr
1175                 1180                1185
Val Phe  Ser Thr Gly Arg Ile  Glu Val Asp Cys Arg  Glu Tyr Leu
1190                 1195                1200
Asp Asp  Trp Glu Arg Glu Val  Ala Ala Ser Leu Pro  His Ala Phe
1205                 1210                1215
Ile Gly  Asp Val Lys Gly Thr  Thr Val Gly Gly Cys  His His Val
1220                 1225                1230
Thr Ser  Lys Tyr Leu Pro Arg  Phe Leu Pro Lys Glu  Ser Val Ala
1235                 1240                1245
Val Val  Gly Val Ser Ser Pro  Gly Lys Ala Ala Lys  Ala Val Cys
1250                 1255                1260
Thr Leu  Thr Asp Val Tyr Leu  Pro Asp Leu Glu Ala  Tyr Leu His
1265                 1270                1275
Pro Val  Thr Gln Ser Lys Cys  Trp Lys Met Met Leu  Asp Phe Lys
1280                 1285                1290
```

Glu Val Arg Leu Met Val Trp Lys Asp Lys Thr Ala Tyr Phe Gln
    1295                1300                1305

Leu Glu Gly Arg His Phe Thr Trp Tyr Gln Leu Ala Ser Phe Ala
    1310                1315                1320

Ser Tyr Ile Arg Val Pro Val Asn Ser Thr Val Tyr Leu Asp Pro
    1325                1330                1335

Cys Met Gly Pro Ala Leu Cys Asn Arg Lys Val Gly Ser Pro
    1340                1345                1350

His Trp Gly Ala Asp Leu Ala Val Thr Pro Tyr Asp Tyr Gly Ala
    1355                1360                1365

Arg Lys Ile Leu Ser Ser Ala Tyr His Gly Glu Met Pro Pro Gly
    1370                1375                1380

Tyr Lys Ile Leu Ala Cys Ala Glu Phe Ser Leu Asp Asp Pro Val
    1385                1390                1395

Arg Tyr Lys His Thr Trp Gly Phe Glu Ser Asp Thr Ala Tyr Leu
    1400                1405                1410

Tyr Glu Phe Thr Gly Asn Gly Glu Asp Trp Glu Asp Tyr Asn Asp
    1415                1420                1425

Ala Phe Arg Ala Arg Gln Lys Gly Lys Ile Tyr Lys Ala Thr Ala
    1430                1435                1440

Thr Ser Leu Lys Phe His Phe Pro Pro Gly His Ile Val Glu Pro
    1445                1450                1455

Thr Leu Gly Leu Asn
    1460

<210> SEQ ID NO 13
<211> LENGTH: 256
<212> TYPE: PRT
<213> ORGANISM: Porcine reproductive and respiratory syndrome virus

<400> SEQUENCE: 13

Met Arg Trp Glu Pro His Arg Ala Phe Leu Thr Lys Leu Val Asn Phe
1               5                   10                  15

Leu Leu Met Pro Ser Arg Ser Ser Trp Cys Leu Leu Leu Ile Ser Ser
                20                  25                  30

Tyr Phe Trp Pro Phe Cys Ser Ala Ser Pro Ser Pro Val Gly Trp Trp
            35                  40                  45

Ser Phe Ala Ser Asp Trp Phe Ser Pro Arg Tyr Ser Val Arg Ala Leu
        50                  55                  60

Pro Phe Thr Leu Ser Asn Tyr Arg Arg Ser Tyr Glu Ala Tyr Leu Ser
65                  70                  75                  80

Gln Cys Gln Val Asp Ile Pro Ala Trp Gly Thr Lys His Pro Leu Gly
                85                  90                  95

Met Ile Trp His His Arg Val Ser Thr Leu Ile Asp Glu Met Val Ser
            100                 105                 110

Arg Arg Met Tyr Arg Thr Met Glu Gln Ala Gly Gln Ala Ala Trp Lys
        115                 120                 125

Gln Val Val Thr Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Leu Thr Gly
                165                 170                 175

Ser Asn Val Thr Ile Val Tyr Asn Ser Ser Leu Asp Arg Val Phe Ala

```
                180                 185                 190
Val Phe Pro Thr Ser Ser Arg Pro Lys Leu His Asp Phe Arg Gln
                195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Leu Pro Ile Ile Arg Thr
225                 230                 235                 240

Val Phe Gly Phe Arg Trp Leu Gly Ala Ile Phe Leu Ser Ser Ser Gln
                245                 250                 255

<210> SEQ ID NO 14
<211> LENGTH: 254
<212> TYPE: PRT
<213> ORGANISM: Porcine reproductive and respiratory syndrome virus

<400> SEQUENCE: 14

Met Ala Asn Ser Cys Ala Phe Leu His Ile Leu Leu Cys Cys Gly Phe
1               5                   10                  15

Leu Tyr Pro Phe Arg Arg Thr Val Ala Ala Ser Asn Asn Thr Tyr
                20                  25                  30

Cys Phe Trp Phe Pro Leu Val Arg Gly Asn Phe Ser Phe Glu Leu Thr
            35                  40                  45

Val Asn Tyr Thr Val Cys Pro Pro Cys Leu Thr Arg Gln Ala Ala Ser
        50                  55                  60

Glu Ile Tyr Glu Pro Ser Arg Ser Leu Trp Cys Arg Ile Gly Gln Asp
65                  70                  75                  80

Arg Cys Thr Glu Ser Asp His Asp Glu Leu Gly Phe Leu Val Pro Pro
                85                  90                  95

Gly Leu Ser Asn Glu Gly His Leu Ile Ser Val Tyr Ala Trp Leu Ala
                100                 105                 110

Phe Leu Ser Phe Ser Tyr Thr Ser Gln Phe His Pro Glu Ile Phe Gly
            115                 120                 125

Ile Gly Asn Val Ser Glu Val Tyr Val Asp Ile Lys His Gln Leu Ile
        130                 135                 140

Cys Ala Val His Asp Gly Gln Asn Thr Thr Leu Pro Arg His Asp Asn
145                 150                 155                 160

Ile Thr Ala Val Tyr Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Ser Arg Val
        195                 200                 205

Ser Val Arg Val Phe Gln Thr Ser Lys Pro Thr Pro Pro Gln Leu Gln
    210                 215                 220

Val Leu Leu Ser Ser Lys Thr Ser Ala Val Leu Gly Met Ala Thr Arg
225                 230                 235                 240

Pro Leu Arg Arg Leu Ala Lys Ala Ala Asn Ala Val Arg Arg
                245                 250

<210> SEQ ID NO 15
<211> LENGTH: 200
<212> TYPE: PRT
<213> ORGANISM: Porcine reproductive and respiratory syndrome virus

<400> SEQUENCE: 15

Met Leu Gly Asn Cys Leu Thr Ala Gly Cys Cys Ser Gln Leu Leu Phe
```

```
            1               5                  10                 15
Leu Trp Cys Ile Val Pro Phe Cys Phe Val Ala Leu Val Asn Ala Asn
                20                  25                 30

Asn Ser Ser Ser His Leu Gln Leu Ile Tyr Asn Leu Thr Ile Cys
            35                  40                 45

Glu Leu Asn Gly Thr Asp Trp Leu Asn Arg Lys Phe Asp Trp Ala Val
 50                  55                 60

Glu Thr Phe Val Ile Phe Pro Val Leu Thr His Ile Val Ser Tyr Gly
 65                  70                 75                 80

Ala Leu Thr Thr Ser His Phe Leu Asp Thr Val Gly Leu Val Thr Val
                85                  90                 95

Ser Thr Ala Gly Tyr Tyr His Arg Arg Tyr Val Leu Ser Ser Ile Tyr
                100                 105                110

Ala Val Cys Ala Leu Ala Ala Leu Ile Cys Phe Ala Ile Arg Leu Thr
            115                 120                125

Lys Asn Cys Met Ser Trp Arg Tyr Ser Cys Thr Arg Tyr Thr Asn Phe
            130                 135                140

Leu Leu Asp Thr Lys Gly Lys Leu Tyr Arg Trp Arg Ser Pro Val Ile
145                  150                 155                160

Ile Glu Lys Arg Gly Lys Ile Glu Val Asn Gly His Leu Ile Asp Leu
                165                 170                175

Lys Arg Val Val Leu Asp Gly Ser Ala Ala Thr Pro Val Thr Lys Val
            180                 185                190

Leu Ala Glu Gln Trp Gly Arg Pro
        195                 200

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctgcggcctt rgacaggaac gg                                              22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgtchaccck atcccacatg cg                                              22

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtacggcgat agggacacc                                                  19

<210> SEQ ID NO 19
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccagaatgta cttgcggcc                                                  19
```